US010918728B2

(12) United States Patent
Levin

(10) Patent No.: US 10,918,728 B2
(45) Date of Patent: *Feb. 16, 2021

(54) COMPOSITIONS AND METHODS FOR INCREASING EFFICIENCY OF CARDIAC METABOLISM

(71) Applicant: IMBRIA PHARMACEUTICALS, INC., San Diego, CA (US)

(72) Inventor: Andrew D. Levin, Newton, MA (US)

(73) Assignee: IMBRIA PHARMACEUTICALS, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/722,754

(22) Filed: Dec. 20, 2019

(65) Prior Publication Data

US 2020/0138963 A1 May 7, 2020

Related U.S. Application Data

(63) Continuation of application No. 16/011,196, filed on Jun. 18, 2018, now Pat. No. 10,556,013.

(60) Provisional application No. 62/647,926, filed on Mar. 26, 2018, provisional application No. 62/637,434, filed on Mar. 2, 2018, provisional application No. 62/710,316, filed on Feb. 16, 2018, provisional application No. 62/524,237, filed on Jun. 23, 2017, provisional application No. 62/522,214, filed on Jun. 20, 2017.

(51) Int. Cl.
| | |
|---|---|
| *C07D 401/12* | (2006.01) |
| *A61K 31/496* | (2006.01) |
| *A61P 9/10* | (2006.01) |
| *A61P 9/04* | (2006.01) |
| *A61K 47/55* | (2017.01) |
| *A61K 31/495* | (2006.01) |
| *A61K 47/60* | (2017.01) |
| *A61P 3/00* | (2006.01) |

(52) U.S. Cl.
CPC ......... *A61K 47/551* (2017.08); *A61K 31/495* (2013.01); *A61K 47/55* (2017.08); *A61K 47/60* (2017.08); *C07D 401/12* (2013.01); *A61P 3/00* (2018.01)

(58) Field of Classification Search
CPC .. C07D 401/12; A61K 31/495; A61K 31/496; A61K 47/551; A61K 47/55; A61K 47/60
See application file for complete search history.

(56) References Cited

U.S. PATENT DOCUMENTS

| | | | |
|---|---|---|---|
| 4,100,285 A | 7/1978 | Murai et al. | |
| 4,166,452 A | 9/1979 | Generales, Jr. | |
| 4,256,108 A | 3/1981 | Theeuwes | |
| 4,265,874 A | 5/1981 | Bonsen et al. | |
| 4,574,156 A | 3/1986 | Morita et al. | |
| 4,845,099 A | 7/1989 | Ruger et al. | |
| 4,876,257 A | 10/1989 | Hajos et al. | |
| 4,885,300 A | 12/1989 | Press et al. | |
| 5,077,288 A | 12/1991 | Lavielle et al. | |
| 5,286,728 A | 2/1994 | Ferrini | |
| 5,340,809 A | 8/1994 | Gaudry et al. | |
| 5,380,726 A | 1/1995 | Ferrini | |
| 5,384,319 A | 1/1995 | Ferrini | |
| 5,397,780 A | 3/1995 | Mizuno et al. | |
| 5,399,557 A | 3/1995 | Mizuno et al. | |
| 5,401,743 A | 3/1995 | Rendenbach-Mueller et al. | |
| 5,428,038 A | 6/1995 | Chatterjee et al. | |
| 5,527,800 A | 6/1996 | Goto et al. | |
| 5,591,849 A | 1/1997 | Kato et al. | |
| 5,641,779 A | 6/1997 | Halazy et al. | |
| 5,770,735 A | 6/1998 | Emonds-Alt et al. | |
| 5,776,937 A | 7/1998 | Gante et al. | |
| 5,849,745 A | 12/1998 | Wierzbicki et al. | |
| 5,856,326 A | 1/1999 | Anthony et al. | |
| 5,962,448 A | 10/1999 | Mizuno et al. | |
| 5,977,111 A | 11/1999 | Mizuno et al. | |
| 6,087,346 A | 7/2000 | Glennon et al. | |
| 6,121,267 A | 9/2000 | Glase et al. | |
| 6,200,989 B1 | 3/2001 | De Cillis et al. | |
| 6,214,841 B1 | 4/2001 | Jackson et al. | |
| 6,271,223 B1 | 8/2001 | Mizuno et al. | |
| 6,331,623 B1 | 12/2001 | Mizuno et al. | |
| 6,528,529 B1 | 3/2003 | Brann et al. | |
| 6,562,978 B1 | 5/2003 | Imamura et al. | |
| 6,693,099 B2 | 2/2004 | Degenhardt et al. | |
| 7,638,531 B2 | 12/2009 | Mutahi et al. | |
| 7,666,866 B2 | 2/2010 | Franciskovich et al. | |
| 7,772,251 B2 | 8/2010 | Sturzebecher et al. | |
| 7,968,538 B2 | 6/2011 | Becker et al. | |

(Continued)

FOREIGN PATENT DOCUMENTS

| | | |
|---|---|---|
| CA | 2170615 A1 | 3/1995 |
| CA | 2186010 A1 | 9/1995 |

(Continued)

OTHER PUBLICATIONS

Bhosle et al., 2006, Mutual Prodrug Concept: Fundamentals and Applications, Indian Journal of Pharmaceutical Sciences, May-June, pp. 286-294.

Das, 1995, Essential Fatty Acid Metabolism in Patients with Essential Hypertension, Diabetes Mellitus and Coronary Heart Disease, Prostaglandins Leukotrienes and Essential Fatty Acids, 52, 387-391.

Kantor, 2000, The Antianginal Drug Trimetazidine Shifts Cardiac Energy Metabolism From Fatty Acid Oxidation to Glucose Oxidation by Inhibiting Mitochondrial Long-Chain 3-Ketoacyl Coenzyme A Thiolase, Circulation Research, 86:580-588.

Reddy, 2006, Lipid Metabolism and Liver Inflammation. II. Fatty liver disease and fatty acid oxidation, Am J Physiol Gastrointest Liver Physiol, 290: G852-G858.

Sabbah et al., 2005, Metabolic Therapy for Heart Disease: Impact of Trimetazidine, Heart Failure Reviews, 10, 281-288.

(Continued)

*Primary Examiner* — Irina Neagu
(74) *Attorney, Agent, or Firm* — Brown Rudnick LLP; Adam M. Schoen

(57) ABSTRACT

Compositions and methods for increasing efficiency of cardiac metabolism are provided.

4 Claims, 134 Drawing Sheets

(56) References Cited

U.S. PATENT DOCUMENTS

| | | |
|---|---|---|
| 8,202,901 B2 | 6/2012 | Lopaschuk et al. |
| 8,461,117 B2 | 6/2013 | Sufi et al. |
| 8,569,495 B2 | 10/2013 | Chassaing et al. |
| 8,697,661 B2 | 4/2014 | Kritikou |
| 9,096,538 B2 | 8/2015 | Nakamura et al. |
| 9,120,801 B2 | 9/2015 | Alisi et al. |
| 10,556,013 B2 * | 2/2020 | Levin .................. A61P 9/10 |
| 2003/0191182 A1 | 10/2003 | Lopaschuk et al. |
| 2003/0232877 A1 | 12/2003 | Sikorski et al. |
| 2004/0082564 A1 | 4/2004 | Arrhenius et al. |
| 2005/0004121 A1 | 1/2005 | Palani et al. |
| 2007/0004750 A1 | 1/2007 | Lorsbach et al. |
| 2008/0108618 A1 | 5/2008 | Brann et al. |
| 2009/0197891 A1 | 8/2009 | Lecanu et al. |
| 2010/0022530 A1 | 1/2010 | Schiemann et al. |
| 2011/0046370 A1 | 2/2011 | Sim et al. |
| 2011/0212072 A1 | 9/2011 | Henkel et al. |
| 2012/0214818 A1 | 8/2012 | Dudley |
| 2016/0060530 A1 | 3/2016 | Archetti et al. |
| 2016/0346397 A1 | 12/2016 | Milne et al. |
| 2017/0008950 A1 | 1/2017 | Capon |
| 2017/0105414 A1 | 4/2017 | Nakano et al. |
| 2018/0360975 A1 | 12/2018 | Levin |
| 2019/0084917 A1 | 3/2019 | Savourey et al. |

FOREIGN PATENT DOCUMENTS

| | | |
|---|---|---|
| CN | 101747292 B | 7/2011 |
| EP | 0251141 A1 | 1/1988 |
| EP | 615855 A1 | 9/1994 |
| EP | 661266 A1 | 7/1995 |
| EP | 749967 A1 | 12/1996 |
| EP | 1634598 A1 | 3/2006 |
| EP | 1886994 A1 | 2/2008 |
| EP | 2727916 A1 | 5/2014 |
| JP | 57131777 | 8/1982 |
| JP | 2000147773 A | 5/2000 |
| JP | 2006113343 A | 4/2006 |
| JP | 2015017236 A | 1/2015 |
| WO | 1995000165 A1 | 1/1995 |
| WO | 9626196 A2 | 8/1996 |
| WO | 9630054 A1 | 10/1996 |
| WO | 9630343 A1 | 10/1996 |
| WO | 9728141 A1 | 8/1997 |
| WO | 9746549 A1 | 12/1997 |
| WO | 9950247 A1 | 10/1999 |
| WO | 2001005763 A2 | 1/2001 |
| WO | 2002058698 A2 | 8/2002 |
| WO | 2002064576 A1 | 8/2002 |
| WO | 2006027223 A1 | 3/2006 |
| WO | 2006117686 A2 | 11/2006 |
| WO | 2006133784 A1 | 12/2006 |
| WO | 2007075629 A2 | 7/2007 |
| WO | 2007096251 A1 | 8/2007 |
| WO | 2008109991 A1 | 9/2008 |
| WO | 2009015485 A1 | 2/2009 |
| WO | 2009066315 A2 | 5/2009 |
| WO | 2009156479 A1 | 12/2009 |
| WO | 2011032099 A1 | 3/2011 |
| WO | 2012049101 A1 | 4/2012 |
| WO | 2015018660 A1 | 2/2015 |
| WO | 2016005576 A1 | 1/2016 |
| WO | 2016107603 A1 | 7/2016 |

OTHER PUBLICATIONS

Spiekerkoetter, 2010, Mitochondrial fatty acid oxidation disorders: clinical presentation of long-chain fatty acid oxidation defects before and after newborn screening, J Inherit Metab Dis, 33:527-532.

Cheng, 2006, Discovery of Potent and Orally Available Malonyl-CoA Decarboxylase Inhibitors as Cardioprotective Agents, J. Med. Chem. 49:4055-4058.

Cheng, 2006, Synthesis and structure-activity relationship of small-molecule malonyl coenzyme A decarboxylase inhibitors, J. Med. Chem. 49:1517-1525.

Fillmore, 2014, Malonyl CoA: A Promising Target for the Treatment of Cardiac Disease, Int. Union of Biochem. and Mol. Biol., 66(3):139-146.

Fillmore, 2014, Mitochondrial fatty acid oxidation alterations in heart failure, ischemic heart disease and diabetic cardiomyopathy, Brit. J. Pharmacol. 171:2080-2090.

Gibbs, 1995, Cardiac efficiency, Cardiovasc. Res. 30:627-634.

International Search Report and Written Opinion dated Nov. 5, 2018, for International Patent Application PCT/US2018/038067 with International filing date Jun. 18, 2018 (11 pages).

Leriche, 2012, Cleavable linkers in chemical biology, Bioorg. Med. Chem. 20:571-582.

Lopaschuk, 2010, Myocardial Fatty Acid Metabolism in Health and Disease, Phys. Rev. 90:207-258.

Morin, 1998, Evidence for the existence of [3H]-trimetazidine binding sites involved in the regulation of the mitochondrial permeability transition pore, Brit. J. Pharmacol. 123:1385-1394.

Pubchem, CID 2223657, Jul. 15, 2005, pp. 1-14.

Schipke, 1994, Cardiac efficiency, Basic Res. Cardiol. 89:207-40.

Trammell, 2016, Nicotinamide riboside is uniquely and orally bioavailable in mice and humans, Nat. Commun. 7:12948.

Translation of CN101747292, retrieved from Espacenet on Dec. 5, 2018 (44 pages).

Translation of JP2000147773 retrieved from Espacenet on Apr. 25, 2019 (30 pages).

Translation of JP2006113343 retrieved from Espacenet on Apr. 25, 2019 (39 pages).

Translation of JP2015017236 retrieved from Espacenet on Apr. 25, 2019 (34 pages).

Translation of WO2006133784 retrieved from Espacenet on May 10, 2019 (24 pages).

Translation of WO2012049101 retrieved from Espacenet on May 10, 2019 (23 pages).

Translation of WO2016107603 retrieved from Espacenet on Apr. 25, 2019 (113 pages).

Translation of WO9728141 retrieved from Espacenet on May 10, 2019 (96 pages).

Visser, 2008, Measuring cardiac efficiency: is it clinically useful? Heart Metab. 39:3-4.

Folmes, 2005, Fatty Acid Oxidation Inhibitors in the Management of Chronic Complications of Atherosclerosis, Current Atherosclerosis Reports 2005, 7, 63-70.

The Merck Manual List of Diseases https://merckmanuals.com/professional (accessed Jan. 17, 2020), 4 pages.

\* cited by examiner

Compounds

| Compound Id | Alert | OCR AC₅₀ (µM) | Reserve Capacity AC₅₀ (µM) | ECAR AC₅₀ (µM) | Mechanism |
|---|---|---|---|---|---|
| Nicotinamide | No (-) | NR | NR | NR | No effect |
| Trimetazidine + Nicotinamide | No (-) | NR | NR | NR | No effect |
| Succinate | Yes (+) | >100↑ | 97.1 | >100↑ | Other |
| CV-8816 | No (-) | NR | NR | >100↑ | No effect |
| CV-8814 | No (-) | NR | NR | >100↑ | No effect |
| Trimetazidine | No (-) | NR | NR | >100↑ | No effect |
| CV-8815 | No (-) | NR | NR | >100↑ | No effect |
| Succinate + Nicotinamide + Trimetazidine | Yes (+) | NR | >100↓ | >100↑ | Other |
| Trimetazidine analog 2 + Nicotinamide | No (-) | NR | NR | >100↑ | No effect |
| Trimetazidine analog 1 + Nicotinamide | No (-) | NR | NR | >100↑ | No effect |
| Trimetazidine analog 3 + Nicotinamide | No (-) | NR | NR | >100↑ | No effect |
| Succinate + Nicotinamide | No (-) | NR | NR | >100↑ | No effect |

$AC_{50}$ The concentration at which 50% maximum effect is observed for each cell health parameter.
† An $AC_{50}$ was calculated, but is greater than the maximum surviving concentration.
↑↓ Direction of response.
NR No response observed.

FIG. 1

Nicotinamide (CY0001765:26)

Assay Summary

Incubation time: 0h
Concentrations (μM): 0.1, 0.316, 1, 3.16, 10, 31.6, 100
Replicates per concentration: 2
Cell model: HepG2
Certified on: 2017-05-26

Data Summary

| Cell Health Parameter | ↑↓ | MEC (μM) | AC₅₀ (μM) | Potential Mechanism |
|---|---|---|---|---|
| OCR | | NR | NR | |
| Reserve Capacity | | NR | NR | |
| ECAR | | NR | NR | |

| Concentration (μM) | OCR | Reserve Capacity | ECAR | Potential Mechanism |
|---|---|---|---|---|
| 0.1 | No effect | No effect | No effect | No effect |
| 0.316 | No effect | No effect | No effect | No effect |
| 1 | No effect | No effect | No effect | No effect |
| 3.16 | No effect | No effect | No effect | No effect |
| 10 | No effect | No effect | No effect | No effect |
| 31.6 | No effect | No effect | No effect | No effect |
| 100 | No effect | No effect | No effect | No effect |

Alert: No (–)

FIG. 2

MEC Minimum effective concentration that significantly crosses vehicle control threshold.
$AC_{50}$ The concentration at which 50% maximum effect is observed for each cell health parameter.
† An $AC_{50}$ was calculated, but is greater than the maximum surviving concentration.
↑↓ Direction of response.
NR No response observed.
MR (%) Maximum % response.
Alert: Yes (+) if a feature deviates outside of the vehicle control this is flagged as a potential mitochondrial toxicant∗.
∗If the $AC_{50}$ values of all responding features are greater than 100x plasma total $C_{max}$ this is considered to have lower potential to exhibit mitochondrial toxicity *in vivo*. In the absence of $C_{max}$ data then this cut-off is 50µM (as described by Eakins *et al.*, (2016), *TIV*, 34, 161-170).

FIG. 2 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 3 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 3 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 4 (cont.)

Trimetazidine + Nicotinamide (Cyprotex 74497)

Assay Summary

Incubation time: 0h
Concentrations (µM): 0.1, 0.316, 1, 3.16, 10, 31.6, 100
Replicates per concentration: 2
Cell model: HepG2
Certified on: 2017-05-26

Data Summary

| Cell Health Parameter | ↑↓ | MEC (µM) | AC₅₀ (µM) | MR (%) |
|---|---|---|---|---|
| OCR | | NR | NR | |
| Reserve Capacity | | NR | NR | |
| ECAR | | NR | NR | |

| Concentration (µM) | OCR | Reserve Capacity | ECAR | Potential Mechanism |
|---|---|---|---|---|
| 0.1 | No effect | No effect | No effect | No effect |
| 0.316 | No effect | No effect | No effect | No effect |
| 1 | No effect | No effect | No effect | No effect |
| 3.16 | No effect | No effect | No effect | No effect |
| 10 | No effect | No effect | No effect | No effect |
| 31.6 | No effect | No effect | No effect | No effect |
| 100 | No effect | No effect | No effect | No effect |

| Alert | Mechanism |
|---|---|
| | No (-) |

FIG. 5

MEC Minimum effective concentration that significantly crosses vehicle control threshold.
$AC_{50}$ The concentration at which 50% maximum effect is observed for each cell health parameter.
† An $AC_{50}$ was calculated, but is greater than the maximum surviving concentration.
↑↓ Direction of response.
NR No response observed.
MR (%) Maximum % response.
Alert: Yes (+) if a feature deviates outside of the vehicle control this is flagged as a potential mitochondrial toxicant*.
*If the $AC_{50}$ values of all responding features are greater than 100x plasma total $C_{max}$ this is considered to have lower potential to exhibit mitochondrial toxicity *in vivo*. In the absence of $C_{max}$ data then this cut-off is 50µM (as described by Eakins *et al.*, (2016), *TIV*, 34, 161-170).

FIG. 5 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 6 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 6 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 7 (cont.)

Succinate (CYCMD15253)

Assay Summary

| | |
|---|---|
| Incubation time: | 6h |
| Concentrations (µM): | 0.1, 0.316, 1, 3.16, 10, 31.6, 100 |
| Replicates per concentration: | 2 |
| Cell model: | HepG2 |
| Certified on: | 2017-04-12 |

Data Summary

| Cell Health Parameter | ↑↓ | MEC (µM) | $AC_{50}$ (µM) | MR (%) |
|---|---|---|---|---|
| OCR | ↑ | 55.8 | >100† | 14 |
| Reserve Capacity | ↑ | 7.41 | 97.1 | 50 |
| ECAR | ↓ | 74.6 | >100† | 17 |

| Concentration (µM) | OCR | Reserve Capacity | ECAR | Potential Mechanism |
|---|---|---|---|---|
| 0.1 | No effect | No effect | No effect | No effect |
| 0.316 | No effect | No effect | No effect | No effect |
| 1 | No effect | No effect | No effect | No effect |
| 3.16 | No effect | No effect | No effect | No effect |
| 10 | No effect | ↑ | No effect | Other |
| 31.6 | No effect | ↑ | No effect | Other |
| 100 | ↑ | ↑ | ↓ | Other |

| Alert | Mechanism |
|---|---|
| Yes (+) | Other |

FIG. 8

MEC Minimum effective concentration that significantly crosses vehicle control threshold.
$AC_{50}$ The concentration at which 50% maximum effect is observed for each cell health parameter.
† An $AC_{50}$ was calculated, but is greater than the maximum surviving concentration.
↑↓ Direction of response.
NR No response observed.
MR (%) Maximum % response.
Alert: Yes (+) if a feature deviates outside of the vehicle control this is flagged as a potential mitochondrial toxicant*.
*If the $AC_{50}$ values of all responding features are greater than 100x plasma total $C_{max}$ this is considered to have lower potential to exhibit mitochondrial toxicity *in vivo*. In the absence of $C_{max}$ data then this cut-off is 50μM (as described by Eakins *et al.*, (2016), *TIV*, 34, 161-170).

FIG. 8 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 9 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 9 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 10 (cont.)

CV-9914 (CyO0017400l)

Assay Summary

| | |
|---|---|
| Incubation time: | 6h |
| Concentrations (µM): | 0.1, 0.316, 1, 3.16, 10, 31.6, 100 |
| Replicates per concentration: | 2 |
| Cell model: | HepG2 |
| Certified on: | 2017-04-12 |

Data Summary

| Cell Health Parameter | ↑↓ | MEC (µM) | AC$_{50}$ (µM) | MR (%) |
|---|---|---|---|---|
| OCR | | NR | NR | |
| Reserve Capacity | | NR | NR | |
| ECAR | ↓ | 9.74 | >100† | 16 |

| Concentration (µM) | OCR | Reserve Capacity | ECAR | Potential Mechanism |
|---|---|---|---|---|
| 0.1 | No effect | No effect | No effect | No effect |
| 0.316 | No effect | No effect | No effect | No effect |
| 1 | No effect | No effect | No effect | No effect |
| 3.16 | No effect | No effect | No effect | No effect |
| 10 | No effect | No effect | No effect | No effect |
| 31.6 | No effect | No effect | ↓ | No effect |
| 100 | No effect | No effect | ↓ | No effect |

| Alert | Mechanism |
|---|---|
| | No (-) |

FIG. 11

MEC Minimum effective concentration that significantly crosses vehicle control threshold.
$AC_{50}$ The concentration at which 50% maximum effect is observed for each cell health parameter.
† An $AC_{50}$ was calculated, but is greater than the maximum surviving concentration.
↑↓ Direction of response.
NR No response observed.
MR (%) Maximum % response.
Alert: Yes (+) if a feature deviates outside of the vehicle control this is flagged as a potential mitochondrial toxicant*.
*If the $AC_{50}$ values of all responding features are greater than 100x plasma total $C_{max}$ this is considered to have lower potential to exhibit mitochondrial toxicity *in vivo*. In the absence of $C_{max}$ data then this cut-off is 50µM (as described by Eakins *et al.*, (2016), *TIV*, 34, 161-170).

FIG. 11 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 12 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 12 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 13 (cont.)

Trimetazidine (CY000174A02)

Assay Summary

| | |
|---|---|
| Incubation time: | 0h |
| Concentrations (µM): | 0.1, 0.316, 1, 3.16, 10, 31.6, 100 |
| Replicates per concentration: | 2 |
| Cell model: | HepG2 |
| Certified on: | 2017-04-12 |

Data Summary

| Cell Health Parameter | ↑↓ | MEC (µM) | AC$_{50}$ (µM) | MR (%) |
|---|---|---|---|---|
| OCR | | NR | NR | |
| Reserve Capacity | | NR | NR | |
| ECAR | ↓ | 10.7 | >100↑ | 19 |

| Concentration (µM) | OCR | Reserve Capacity | ECAR | Potential Mechanism |
|---|---|---|---|---|
| 0.1 | No effect | No effect | No effect | No effect |
| 0.316 | No effect | No effect | No effect | No effect |
| 1 | No effect | No effect | No effect | No effect |
| 3.16 | No effect | No effect | No effect | No effect |
| 10 | No effect | No effect | No effect | No effect |
| 31.6 | No effect | No effect | ↓ | No effect |
| 100 | No effect | No effect | ↓ | No effect |

| Alert | Mechanism |
|---|---|
| | No (-) |

FIG. 14

MEC Minimum effective concentration that significantly crosses vehicle control threshold.
$AC_{50}$ The concentration at which 50% maximum effect is observed for each cell health parameter.
† An $AC_{50}$ was calculated, but is greater than the maximum surviving concentration.
↑↓ Direction of response.
NR No response observed.
MR (%) Maximum % response.
Alert: Yes (+) if a feature deviates outside of the vehicle control this is flagged as a potential mitochondrial toxicant∗.
∗If the $AC_{50}$ values of all responding features are greater than 100x plasma total $C_{max}$ this is considered to have lower potential to exhibit mitochondrial toxicity *in vivo*. In the absence of $C_{max}$ data then this cut-off is 50µM (as described by Eakins *et al.*, (2016), *TIV*, 34, 161-170).

FIG. 14 (cont.)

Green dashed lines Significant cut-off from vehicle control (used to calculate the MEC).
Filled blue diamonds Mean data points for each concentration (plus or minus standard deviation).
Blue × Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 15 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 15 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 16 (cont.)

Succinate + Nicotinamide + Trimetazidine (CV000175589)

Assay Summary

Incubation time: 0h
Concentrations (μM): 0.1, 0.316, 1, 3.16, 10, 31.6, 100
Replicates per concentration: 2
Cell model: HepG2
Certified on: 2017-05-26

Data Summary

| Cell Health Parameter | ↑↓ | MEC (μM) | $AC_{50}$ (μM) | MR (%) |
|---|---|---|---|---|
| OCR | | NR | NR | |
| Reserve Capacity | ↑ | 64.8 | >100 | 23 |
| ECAR | ↓ | 30.9 | >100 | 25 |

| Concentration (μM) | OCR | Reserve Capacity | ECAR | Potential Mechanism |
|---|---|---|---|---|
| 0.1 | No effect | No effect | No effect | No effect |
| 0.316 | No effect | No effect | No effect | No effect |
| 1 | No effect | No effect | No effect | No effect |
| 3.16 | No effect | No effect | No effect | No effect |
| 10 | No effect | No effect | No effect | No effect |
| 31.6 | No effect | ↑ | ↓ | Other |
| 100 | No effect | | | |

| Alert | Mechanism |
|---|---|
| Yes (+) | Other |

FIG. 17

MEC Minimum effective concentration that significantly crosses vehicle control threshold.
$AC_{50}$ The concentration at which 50% maximum effect is observed for each cell health parameter.
† An $AC_{50}$ was calculated, but is greater than the maximum surviving concentration.
↑↓ Direction of response.
NR No response observed.
MR (%) Maximum % response.
Alert: Yes (+) if a feature deviates outside of the vehicle control this is flagged as a potential mitochondrial toxicant*.
*If the $AC_{50}$ values of all responding features are greater than 100x plasma total $C_{max}$ this is considered to have lower potential to exhibit mitochondrial toxicity *in vivo*. In the absence of $C_{max}$ data then this cut-off is 50μM (as described by Eakins *et al.*, (2016), *TIV*, 34, 161-170).

FIG. 17 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 18 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 18 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 19 (cont.)

Trimetazidine analog 2 + Nicotinamide (CV00017659†)

Assay Summary

Incubation time: 0h
Concentrations (µM): 0.1, 0.316, 1, 3.16, 10, 31.6, 100
Replicates per concentration: 2
Cell model: HepG2
Certified on: 2017-05-26

Data Summary

| | ↑↓ | MEC (µM) | AC$_{50}$ (µM) | MR (%) |
|---|---|---|---|---|
| OCR | | NR | NR | |
| Reserve Capacity | | NR | NR | |
| ECAR | ↓ | 55.5 | >100† | 13 |

| Concentration (µM) | OCR | Reserve Capacity | ECAR | Potential Mechanism |
|---|---|---|---|---|
| 0.1 | No effect | No effect | No effect | No effect |
| 0.316 | No effect | No effect | No effect | No effect |
| 1 | No effect | No effect | No effect | No effect |
| 3.16 | No effect | No effect | No effect | No effect |
| 10 | No effect | No effect | No effect | No effect |
| 31.6 | No effect | No effect | No effect | No effect |
| 100 | No effect | No effect | ↓ | No effect |

Alert: No (-) Mechanism:

FIG. 20

MEC Minimum effective concentration that significantly crosses vehicle control threshold.
$AC_{50}$ The concentration at which 50% maximum effect is observed for each cell health parameter.
† An $AC_{50}$ was calculated, but is greater than the maximum surviving concentration.
↑↓ Direction of response.
NR No response observed.
MR (%) Maximum % response.
Alert: Yes (+) if a feature deviates outside of the vehicle control this is flagged as a potential mitochondrial toxicant*.
*If the $AC_{50}$ values of all responding features are greater than 100x plasma total $C_{max}$ this is considered to have lower potential to exhibit mitochondrial toxicity *in vivo*. In the absence of $C_{max}$ data then this cut-off is 50μM (as described by Eakins *et al.*, (2016), *TIV*, 34, 161-170).

FIG. 20 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 21 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 21 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 22 (cont.)

Trimetazidine analog 1 + Nicotinamide (CV000176590)

Assay Summary

Incubation time: 0h
Concentrations (μM): 0.1, 0.316, 1, 3.16, 10, 31.6, 100
Replicates per concentration: 2
Cell model: HepG2
Certified on: 2017-05-26

Data Summary

| Cell Health Parameter | | ↑↓ | MEC (μM) | AC$_{50}$ (μM) | MR (%) |
|---|---|---|---|---|---|
| OCR | | | NR | NR | |
| Reserve Capacity | | | NR | NR | |
| ECAR | | ↓ | 67.3 | >100 | 15 |

| Concentration (μM) | OCR | Reserve Capacity | ECAR | Potential Mechanism |
|---|---|---|---|---|
| 0.1 | No effect | No effect | No effect | No effect |
| 0.316 | No effect | No effect | No effect | No effect |
| 1 | No effect | No effect | No effect | No effect |
| 3.16 | No effect | No effect | No effect | No effect |
| 10 | No effect | No effect | No effect | No effect |
| 31.6 | No effect | No effect | No effect | No effect |
| 100 | No effect | No effect | ↓ | No effect |

| Alert | Mechanism |
|---|---|
| | No (-) |

FIG. 23

MEC Minimum effective concentration that significantly crosses vehicle control threshold.
$AC_{50}$ The concentration at which 50% maximum effect is observed for each cell health parameter.
† An $AC_{50}$ was calculated, but is greater than the maximum surviving concentration.
↑↓ Direction of response.
NR No response observed.
MR (%) Maximum % response.
Alert: Yes (+) if a feature deviates outside of the vehicle control this is flagged as a potential mitochondrial toxicant*.
*If the $AC_{50}$ values of all responding features are greater than 100x plasma total $C_{max}$ this is considered to have lower potential to exhibit mitochondrial toxicity *in vivo*. In the absence of $C_{max}$ data then this cut-off is 50µM (as described by Eakins *et al.*, (2016), *TIV*, 34, 161-170).

FIG. 23 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 24 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 24 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 25 (cont.)

Trimetazidine analog 3 + Nicotinamide (CY000176592)

Assay Summary

| | |
|---|---|
| Incubation time: | 0h |
| Concentrations (µM): | 0.1, 0.316, 1, 3.16, 10, 31.6, 100 |
| Replicates per concentration: | 2 |
| Cell model: | HepG2 |
| Certified on: | 2017-05-26 |

Data Summary

| | ↑↓ | MEC (µM) | AC50 (µM) | MR (%) |
|---|---|---|---|---|
| OCR | | NR | NR | |
| Reserve Capacity | | NR | NR | |
| ECAR | ↓ | 73.1 | >100↑ | 13 |

| Concentration (µM) | Cell Health Parameter | | | Potential Mechanism |
|---|---|---|---|---|
| | OCR | Reserve Capacity | ECAR | |
| 0.1 | No effect | No effect | No effect | No effect |
| 0.316 | No effect | No effect | No effect | No effect |
| 1 | No effect | No effect | No effect | No effect |
| 3.16 | No effect | No effect | No effect | No effect |
| 10 | No effect | No effect | No effect | No effect |
| 31.6 | No effect | No effect | No effect | No effect |
| 100 | No effect | No effect | ↓ | No effect |

| Alert | Mechanism |
|---|---|
| | No (-) |

FIG. 26

MEC Minimum effective concentration that significantly crosses vehicle control threshold.
$AC_{50}$ The concentration at which 50% maximum effect is observed for each cell health parameter.
† An $AC_{50}$ was calculated, but is greater than the maximum surviving concentration.
↑↓ Direction of response.
NR No response observed.
MR (%) Maximum % response.
Alert: Yes (+) if a feature deviates outside of the vehicle control this is flagged as a potential mitochondrial toxicant∗.
∗If the $AC_{50}$ values of all responding features are greater than 100x plasma total $C_{max}$, this is considered to have lower potential to exhibit mitochondrial toxicity *in vivo*. In the absence of $C_{max}$ data then this cut-off is 50µM (as described by Eakins *et al.*, (2016), *TIV*, 34, 161-170).

FIG. 26 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 27 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 27 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 28 (cont.)

Succinate + Nicotinamide (CyQUANT76639)

Assay Summary

| | |
|---|---|
| Incubation time: | 6h |
| Concentrations (µM): | 0.1, 0.316, 1, 3.16, 10, 31.6, 100 |
| Replicates per concentration: | 2 |
| Cell model: | HepG2 |
| Certified on: | 2017-05-26 |

Data Summary

| Cell Health Parameter | ↑↓ | MEC (µM) | AC₅₀ (µM) | MR (%) |
|---|---|---|---|---|
| OCR | | NR | NR | |
| Reserve Capacity | | NR | NR | |
| ECAR | ↑ | 89.8 | >100 ↑ | 14 |

| Concentration (µM) | OCR | Reserve Capacity | ECAR | Potential Mechanism |
|---|---|---|---|---|
| 0.1 | No effect | No effect | No effect | No effect |
| 0.316 | No effect | No effect | No effect | No effect |
| 1 | No effect | No effect | No effect | No effect |
| 3.16 | No effect | No effect | No effect | No effect |
| 10 | No effect | No effect | No effect | No effect |
| 31.6 | No effect | No effect | No effect | No effect |
| 100 | No effect | No effect | ↑ | No effect |

Mechanism

| Alert |
|---|
| No (-) |

FIG. 29

MEC Minimum effective concentration that significantly crosses vehicle control threshold.
$AC_{50}$ The concentration at which 50% maximum effect is observed for each cell health parameter.
† An $AC_{50}$ was calculated, but is greater than the maximum surviving concentration.
↑↓ Direction of response.
NR No response observed.
MR (%) Maximum % response.
Alert: Yes (+) if a feature deviates outside of the vehicle control this is flagged as a potential mitochondrial toxicant*.
*If the $AC_{50}$ values of all responding features are greater than 100x plasma total $C_{max}$, this is considered to have lower potential to exhibit mitochondrial toxicity *in vivo*. In the absence of $C_{max}$ data then this cut-off is 50µM (as described by Eakins *et al.*, (2016), *TIV*, 34, 161-170).

FIG. 29 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 30 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 30 (cont.)

Green dashed lines Significant cut-off from vehicle control (used to calculate the MEC).
Filled blue diamonds Mean data points for each concentration (plus or minus standard deviation).
Blue x Data points excluded from plot due to precipitate in well.
Open blue circles Data points excluded from plot due to data plateau, or other reasons. Points lying outside y-axis limits are annotated with small arrows.
Red solid lines Historical maximum and minimum responses, used to calculate $AC_{50}$.

NS Fit not statistically significant.
MR Maximum response (ratio of control).

FIG. 31 (cont.)

LVESD: Left Ventricular End-Systolic Diameter

COMPOSITIONS AND METHODS FOR INCREASING EFFICIENCY OF CARDIAC METABOLISM

This application is a continuation of U.S. patent application Ser. No. 16/011,196, which claims the benefit of, and priority to, U.S. Provisional Patent Application No. 62/647,926, filed Mar. 26, 2018, U.S. Provisional Patent Application No. 62/637,434, filed Mar. 2, 2018, U.S. Provisional Patent Application No. 62/710,316, filed Feb. 16, 2018, U.S. Provisional Patent Application No. 62/524,237, filed Jun. 23, 2017, and U.S. Provisional Patent Application No. 62/522,214, filed Jun. 20, 2017, the contents of each of which are incorporated by reference.

FIELD OF THE INVENTION

This application is related to compositions and methods for increasing the efficiency of cardiac metabolism.

BACKGROUND

Heart disease is the leading cause of death worldwide, accounting for 15 million deaths across the globe in 2015. In many forms of heart disease, decreased cardiac efficiency stems from changes in mitochondrial energy metabolism. Mitochondria are sub-cellular compartments in which metabolites derived from glucose and fatty acids are oxidized to produce high-energy molecules. Increasing fatty acid oxidation in the heart decreases glucose oxidation, and vice versa. Glucose oxidation is a more efficient source of energy, but in certain types of heart disease, such as heart failure, ischemic heart disease, and diabetic cardiomyopathies, fatty acid oxidation predominates in cardiac mitochondria. As a result, the pumping capacity of the heart is reduced.

Existing drugs that redress the balance between glucose oxidation and fatty acid oxidation in cardiac mitochondria have serious shortcomings. Foremost among them is that such drugs address only part of the problem: the reliance on fatty acid oxidation in lieu of glucose oxidation causes a 10% reduction in efficiency in energy production, but patients with heart disease often show a decrease in cardiac efficiency of up to 30%. Consequently, existing approaches to improve cardiac function by altering mitochondrial metabolism are unsatisfactory, and millions of people continue to die from heart disease each year.

SUMMARY

The invention provides compositions that stimulate cardiac glucose oxidation and mitochondrial respiration. The compositions include a compound that shifts cardiac metabolism from fatty acid oxidation to glucose oxidation, such as trimetazidine, and a compound that promotes mitochondrial respiration, such as succinate. The compositions may also include a molecule, such as nicotinic acid, that serves as a precursor for synthesis of nicotinamide adenine dinucleotide ($NAD^+$), which also facilitates mitochondrial respiration. Preferably, the compositions include compounds in which a trimetazidine derivative, succinate, and, optionally, a $NAD^+$ precursor are covalently linked in a single molecule. Such compounds can be metabolized in the body to allow the individual components to exert distinct biochemical effects to increase glucose oxidation relative to fatty acid oxidation and improve overall mitochondrial respiration in the heart. The invention also provides methods of altering cardiac metabolism by providing compounds of the invention.

Because the compositions concomitantly shift cardiac metabolism toward glucose oxidation and increase mitochondrial respiration, they are useful as therapeutic agents for treating heart diseases characterized by elevated fatty acid oxidation, such as heart failure, ischemic heart disease, and diabetic cardiomyopathies. By shifting cardiac metabolism from fatty acid oxidation to glucose oxidation, the compositions allow the use of a more efficient source of energy. In addition, the compositions stimulate metabolic pathways that are common to oxidation of both glucose and fatty acids and that may also be impaired in patients with heart disease. Some compositions of the invention include a compound that comprises trimetazidine covalently coupled to one or more activators of mitochondrial respiration.

Furthermore, trimetazidine can cause Parkinsonian symptoms for a portion of the population. Without being limited by any particular theory or mechanism of action, it is also believed that delivery of trimetazidine as a component of a larger molecule may improve its efficacy and mitigate its side effects.

In an aspect, the invention includes compounds represented by formula (I):

$$A\text{-}L\text{-}B \qquad (I),$$

in which A is a compound that shifts cardiac metabolism from fatty acid oxidation to glucose oxidation, L is a linker, and B is a compound that promotes mitochondrial respiration.

The compound that shifts cardiac metabolism from fatty acid oxidation to glucose oxidation may be trimetazidine, etomoxir, perhexiline, a PPAR agonist, a malonyl CoA decarboxylase inhibitor, or dichloroacetate.

The compound that promotes mitochondrial respiration may be an intermediate of the citric acid cycle or a molecule that can be metabolized to enter the citric acid cycle. For example, the compound may be succinate, fumarate, malate, oxaloacetate, citrate, isocitrate, α-ketoglutarate, pyruvate, acetone, acetoacetic acid, β-hydroxybutyric acid, β-ketopentanoate, or β-hydroxypentanoate.

The linker may be any suitable linker that can be cleaved in vivo. The linker may be an alkoxy group. The linker may be polyethylene glycol of any length. Preferably, the linker is represented by $(CH_2CH_2O)_x$, in which x=1-15.

The compound may include a $NAD^+$ precursor molecule covalently linked to another component of the compound. The $NAD^+$ precursor molecule may be nicotinic acid, nicotinamide, or nicotinamide riboside. The $NAD^+$ precursor molecule may be attached to the compound that shifts cardiac metabolism, the compound that promotes mitochondrial respiration, or the linker. The $NAD^+$ precursor molecule may be attached to another component via an additional linker. Preferably, the $NAD^+$ precursor molecule is attached to the compound that promotes mitochondrial respiration via a 1,3-propanediol linkage.

The compound of formula (I) may be represented by formula (II):

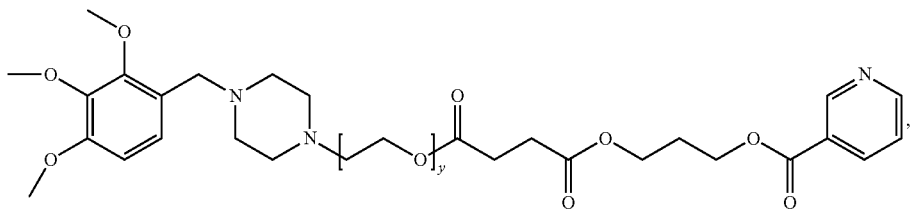

in which y=1-3.

The compound of formula (I) may be represented by formula (III):

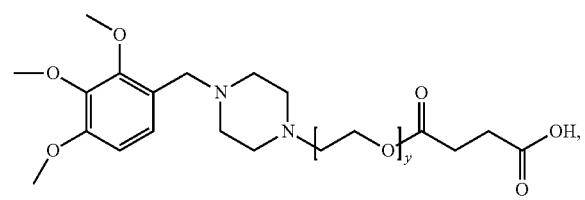

in which y=1-3.

In another aspect, the invention includes a compound represented by formula (IV):

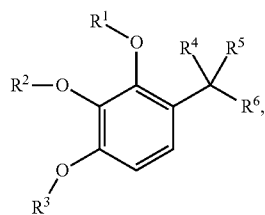

in which $R^1$, $R^2$, and $R^3$ are independently H or a ($C_1$-$C_4$) alkyl group; $R^4$ and $R^5$ together are =O, —O($CH_2$)$_m$O—, or —($CH_2$)$_m$—, in which m=2-4, or $R^4$ is H and $R^5$ is O$R^{14}$, S$R^{14}$, or ($CH_2CH_2O$)$_n$H, in which $R^{14}$ is H or a ($C_1$-$C_4$)alkyl group and n=1-15; and $R^6$ is a single or multi-ring structure optionally substituted at one or more ring positions by a heteroatom, in which each ring position optionally comprises one or more substituents.

One or more ring position of $R^6$ may include a substituent that includes a compound that promotes mitochondrial respiration, such as succinate, fumarate, malate, oxaloacetate, citrate, isocitrate, α-ketoglutarate, pyruvate, acetone, acetoacetic acid, β-hydroxybutyric acid, β-ketopentanoate, or β-hydroxypentanoate. The substituent may include a linker, such as ($CH_2CH_2O$)$_x$, in which x=1-15. The substituent may include a NAD$^+$ precursor molecule, such as nicotinic acid, nicotinamide, and nicotinamide riboside.

The substituent on a ring position of $R^6$ may be

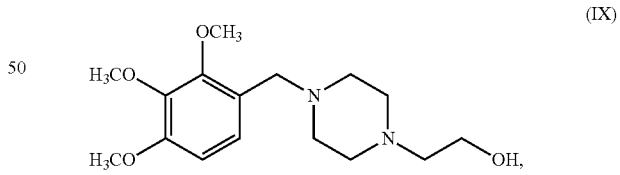

in which y=1-3.

The substituent on a ring position of $R^6$ may be

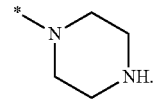

in which y=1-3.

$R^6$ may be

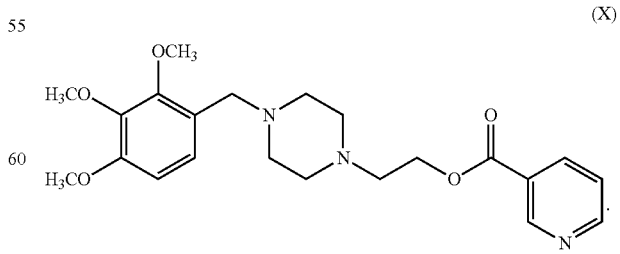

The compound of formula (IV) may have a structure represented formula (IX) or formula (X):

In another aspect, the invention includes compounds represented by formula (V):

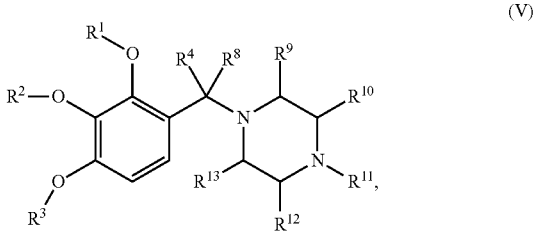

(V)

in which $R^1$, $R^2$, and $R^3$ are independently H or a ($C_1$-$C_4$) alkyl group; $R^4$ and $R^8$ together are =O, —O($CH_2$)$_m$O—, or —($CH_2$)$_m$—, in which m=2-4, or $R^4$ is H and $R^8$ is H, $OR^{14}$, $SR^{14}$, or $(CH_2CH_2O)_n$H, in which $R^{14}$ is H or a ($C_1$-$C_4$)alkyl group and n=1-15; $R^9$, $R^{10}$, $R^{12}$, and $R^{13}$ are independently H or $(CH_2CH_2O)_z$H, in which z=1-6; and $R^{11}$ comprises a compound that promotes mitochondrial respiration.

The compound that promotes mitochondrial respiration may be an intermediate of the citric acid cycle or a molecule that can be metabolized to enter the citric acid cycle. For example, the compound may be succinate, fumarate, malate, oxaloacetate, citrate, isocitrate, α-ketoglutarate, pyruvate, acetone, acetoacetic acid, β-hydroxybutyric acid, β-ketopentanoate, or β-hydroxypentanoate.

$R^{11}$ may include a linker, such as polyethylene glycol. For example, $R^{11}$ may include $(CH_2CH_2O)_x$, in which x=1-15.

$R^{11}$ may be

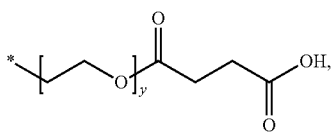

in which y=1-3.

$R^{11}$ may include a $NAD^+$ precursor molecule. For example, $R^{11}$ may include nicotinic acid, nicotinamide, or nicotinamide riboside.

$R^{11}$ may be

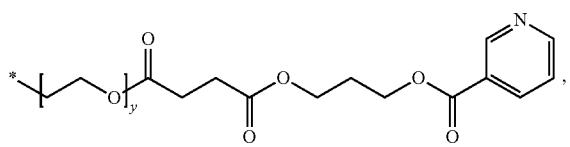

in which y=1-3.

In an aspect, the invention includes compounds represented by formula (VII):

A-C     (VII), in which A is a compound that shifts cardiac metabolism from fatty acid oxidation to glucose oxidation, and C is a $NAD^+$ precursor molecule. A and C may be covalently linked.

The compound that shifts cardiac metabolism from fatty acid oxidation to glucose oxidation may be trimetazidine, etomoxir, perhexiline, a PPAR agonist, a malonyl CoA decarboxylase inhibitor, or dichloroacetate.

The compound that shifts cardiac metabolism from fatty acid oxidation to glucose oxidation may be PEGylated with an ethylene glycol moiety. The compound that shifts cardiac metabolism from fatty acid oxidation to glucose oxidation may have multiple ethylene glycol moieties, such as one, two three, four, five, or more ethylene glycol moieties. The ethylene glycol moiety may be represented by $(CH_2CH_2O)_x$, in which x=1-15. The ethylene glycol moiety may form a covalent linkage between the compound that shifts cardiac metabolism from fatty acid oxidation to glucose oxidation and the $NAD^+$ precursor molecule. The ethylene glycol moiety may be separate from a covalent linkage between the compound that shifts cardiac metabolism from fatty acid oxidation to glucose oxidation and the $NAD^+$ precursor molecule. The compound that shifts cardiac metabolism from fatty acid oxidation to glucose oxidation may be a PEGylated form of trimetazidine.

The $NAD^+$ precursor molecule may be nicotinic acid, nicotinamide, or nicotinamide riboside.

The compound of formula (VII) may include nicotinic acid that is covalently linked to a PEGylated form of trimetazidine. The nicotinic acid may be covalently linked via the PEGylated moiety, i.e., via an ethylene glycol linkage. The nicotinic acid may be covalently linked via the trimetazidine moiety.

The compound of formula (VII) may have a structure represented by formula (X), as shown above.

In an aspect, the invention includes compounds represented by formula (VIII):

A-L-C     (VIII), in which A is a compound that shifts cardiac metabolism from fatty acid oxidation to glucose oxidation, L is a linker, and C is a $NAD^+$ precursor molecule. A may be covalently linked to L, and L may be covalently linked to C.

The compound that shifts cardiac metabolism from fatty acid oxidation to glucose oxidation, the linker, and the $NAD^+$ precursor molecule may be as described above in relation to compounds of other formulas.

The compound of formula (VIII) may have a structure represented by formula (X), as shown above.

Any of the compounds described above may include one or more atoms that are enriched for an isotope. For example, the compounds may have one or more hydrogen atoms replaced with deuterium or tritium. The isotopically enriched atom or atoms may be located at any position within the compound.

In an aspect, the invention includes compositions that include at least two of A, B, and C, in which A is a compound that shifts cardiac metabolism from fatty acid oxidation to glucose oxidation as described above, B is a compound that promotes mitochondrial respiration as described above, and C is a $NAD^+$ precursor molecule as described above. The compositions may include A, B, and C. Each of components A, B, and C may be provided as a separate molecule, or two or more of the components may be covalently linked in a single molecule. For example, components A and B may be covalently linked in a single molecule, and C may be provided as a separate molecule.

The compositions may include co-crystals of two or more separate molecules that include two or more of components A, B, and C. For example, a co-crystal may include (1) a compound of formula (I), (III), (IV), or (V) and (2) nicotinic acid, nicotinamide, or nicotinamide riboside. Preferably the co-crystal includes nicotinamide.

In an aspect, the invention includes methods of increasing efficiency of cardiac metabolism in a subject. The methods include providing a compound represented by formula (I), as described above. In the methods, the compound of formula (I) may include any of the features described above in relation to compounds of the invention.

In an aspect, the invention includes methods of increasing efficiency of cardiac metabolism in a subject. The methods include providing a compound that shifts cardiac metabolism from fatty acid oxidation to glucose oxidation, a compound that promotes mitochondrial respiration, and, optionally, a compound that is a $NAD^+$ precursor molecule.

The compound that shifts cardiac metabolism from fatty acid oxidation to glucose may be trimetazidine, etomoxir, perhexiline, a PPAR agonist, a malonyl CoA decarboxylase inhibitor, or dichloroacetate.

The compound that promotes mitochondrial respiration may be an intermediate of the citric acid cycle or a molecule that can be metabolized to enter the citric acid cycle, such as succinate, fumarate, malate, oxaloacetate, citrate, isocitrate, α-ketoglutarate, pyruvate, acetone, acetoacetic acid, β-hydroxybutyric acid, β-ketopentanoate, or β-hydroxypentanoate.

The $NAD^+$ precursor molecule may be nicotinic acid, nicotinamide, or nicotinamide riboside.

The compounds may be provided in any suitable manner. The compounds may be provided in a single composition. Alternatively, the compounds may not be provided in a single composition. For example, one or two of the compounds may be provided in a single composition, and another compound may be provided in a separate composition. Alternatively, each compound may be provided in a separate composition. The compounds may be provided simultaneously or sequentially. The compounds may be provided at different intervals, with different frequency, or in different quantities.

It is believed that any disease that may be treated using trimetazidine would benefit from compounds of the invention as described herein with more efficacious results and fewer side effects. Exemplary diseases are those that involve impaired mitochondrial function or altered fatty acid oxidation, such as heart failure diseases, cardiac dysfunction diseases, or muscle myopathy diseases. Exemplary methods involve providing a composition as described herein or any combination of a compound that shifts cardiac metabolism from fatty acid oxidation to glucose metabolism, a compound that promotes mitochondrial respiration, and/or optionally an $NAD^+$ precursor molecule.

BRIEF DESCRIPTION OF THE DRAWINGS

FIG. 1 is a table summarizing the effects of various compounds on mitochondrial function.

FIG. 2 is a table summarizing the effects of nicotinamide on various mitochondrial functional parameters.

FIG. 5 is a table summarizing the effects of a combination of trimetazidine and nicotinamide on various mitochondrial functional parameters.

FIG. 8 is a table summarizing the effects of succinate on various mitochondrial functional parameters.

FIG. 11 is a table summarizing the effects of compound CV-8814 on various mitochondrial functional parameters.

FIG. 14 is a table summarizing the effects of trimetazidine on various mitochondrial functional parameters.

FIG. 17 is a table summarizing the effects of a combination of succinate, nicotinamide, and trimetazidine on various mitochondrial functional parameters.

FIG. 20 is a table summarizing the effects of a combination of trimetazidine analog 2 and nicotinamide on various mitochondrial functional parameters.

FIG. 23 is a table summarizing the effects of a combination of trimetazidine analog 1 and nicotinamide on various mitochondrial functional parameters.

FIG. 26 is a table summarizing the effects of a combination of trimetazidine analog 3 and nicotinamide on various mitochondrial functional parameters.

FIG. 29 is a table summarizing the effects of a combination of succinate and nicotinamide on various mitochondrial functional parameters.

DETAILED DESCRIPTION

Figure 3:
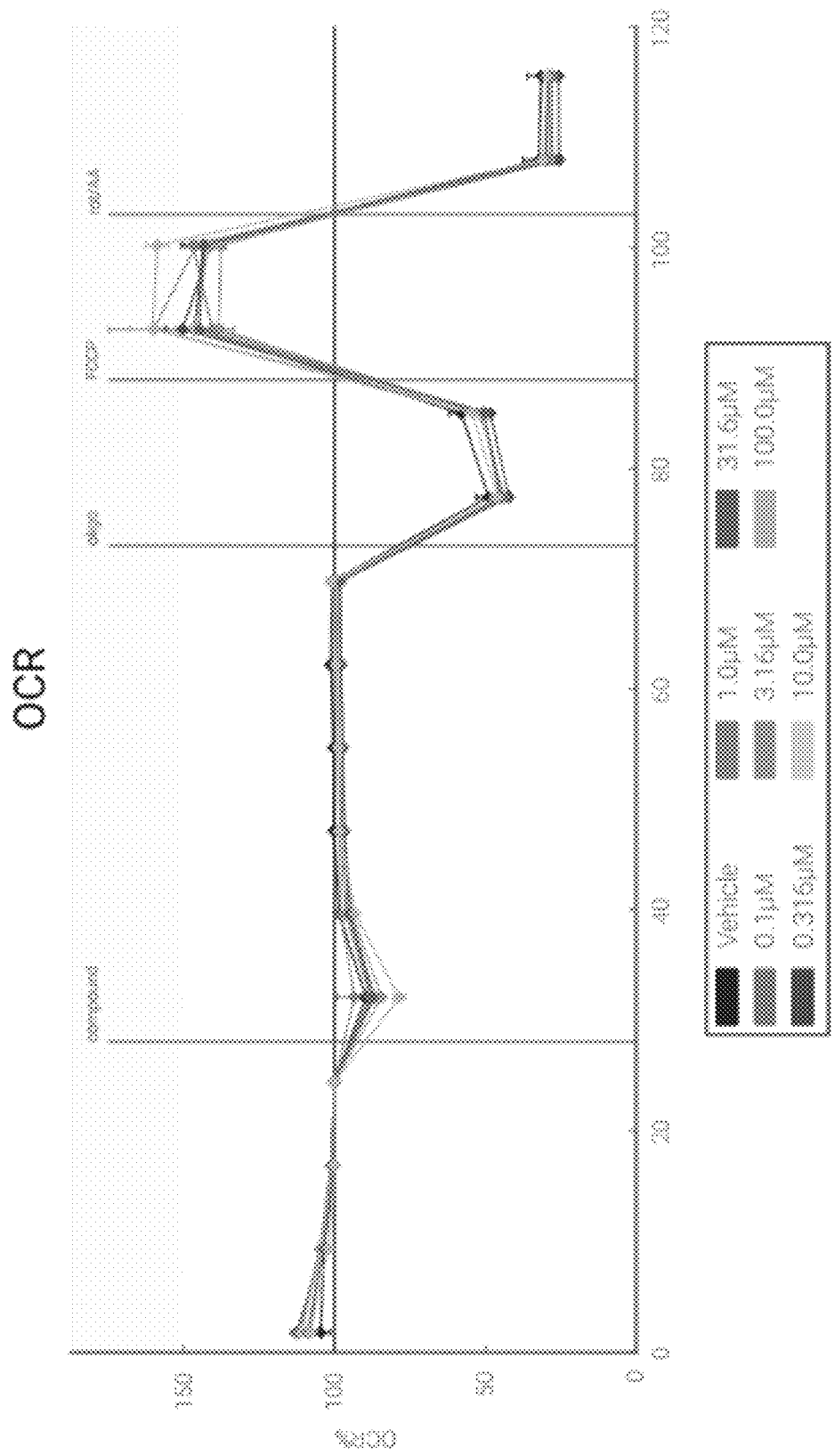
FIG. 3 is a series of graphs showing the effects of nicotinamide on oxygen consumption rate and reserve capacity.
Figure 3:
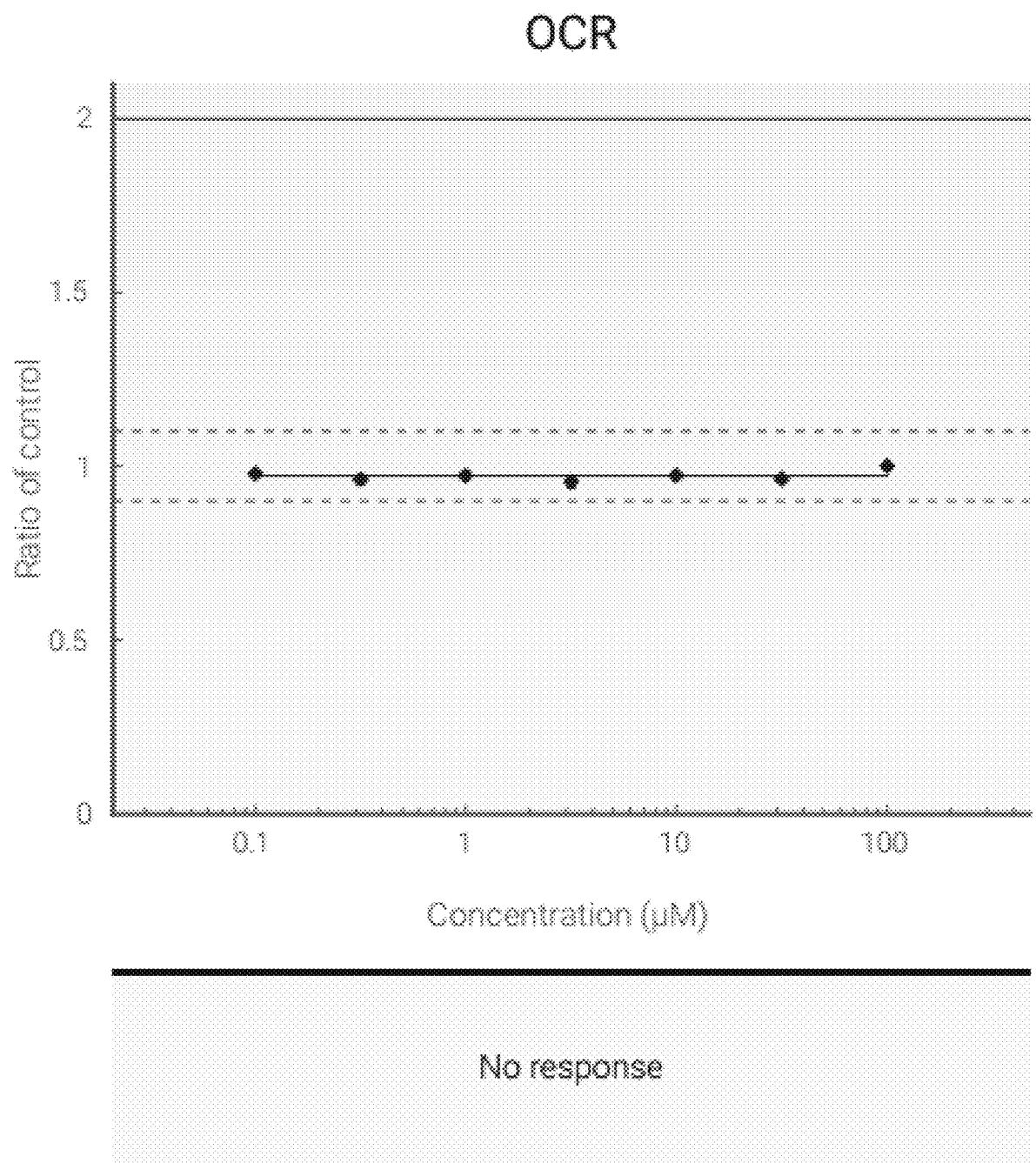
Figure 3:
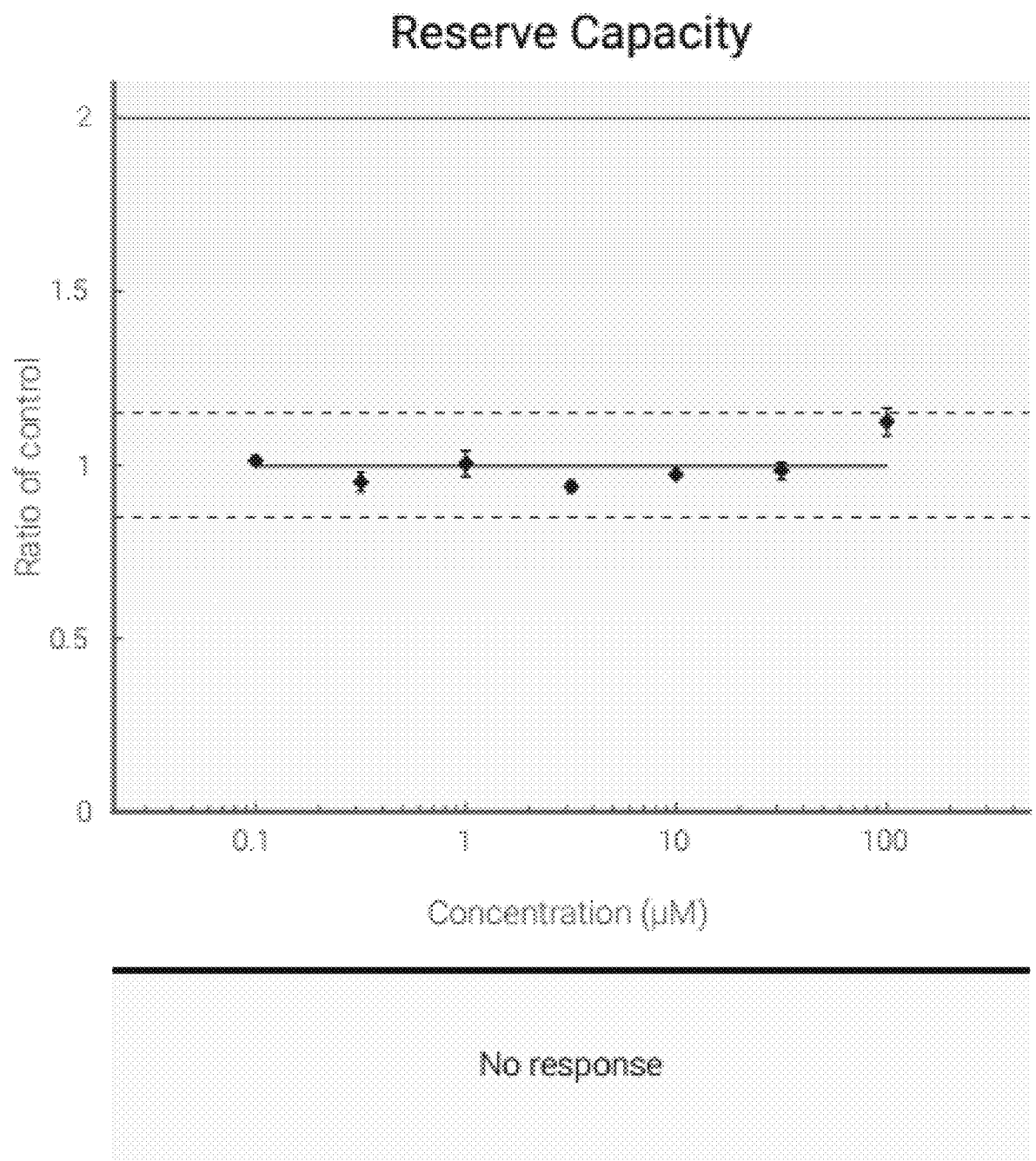

The invention provides compositions that increase the efficiency of cardiac metabolism by concomitantly shifting cardiac metabolism from fatty acid oxidation to glucose oxidation and increasing mitochondrial respiration. Glucose oxidation and fatty acid oxidation are energy-producing metabolic pathways that compete with each other for substrates. In glucose oxidation, glucose is broken down to pyruvate via glycolysis in the cytosol of the cell. Pyruvate then enters the mitochondria, where it is converted to acetyl coenzyme A (acetyl-CoA). In beta-oxidation of fatty acids, which occurs in the mitochondria, two-carbon units from long-chain fatty acids are sequentially converted to acetyl-CoA.

The remaining steps in energy production from oxidation of glucose or fatty acids are common to the two pathways. Acetyl-CoA is oxidized to carbon dioxide ($CO_2$) via the citric acid cycle, which results in the conversion of nicotinamide adenine dinucleotide ($NAD^+$) to its reduced form, NADH. NADH, in turn, drives the mitochondrial electron transport chain. The electron transport chain comprises a series of four mitochondrial membrane-bound complexes that transfer electrons via redox reactions and pump protons across the membrane to create a proton gradient. The redox reactions of the electron transport chain require molecular oxygen ($O_2$). Finally, the proton gradient enables another membrane-bound enzymatic complex to form high-energy ATP molecules, the source of energy for most cellular reactions.

In many types of heart disease, the overall efficiency of energy production by cardiac mitochondria is diminished. In part, this is due to an increased reliance on fatty acid oxidation over glucose oxidation in many types of heart disease. Glucose oxidation is a more efficient pathway for energy production, as measured by the number of ATP molecules produced per $O_2$ molecule consumed, than is fatty acid oxidation. However, other metabolic changes contribute to decreased cardiac efficiency in patients with heart disease. For example, overall mitochondrial oxidative metabolism can be impaired in heart failure, and energy production is decreased in ischemic heart disease due to a limited supply of oxygen. As indicated above, the final steps in ATP synthesis, which include several redox reactions and oxygen-driven proton transport, are common to both the glucose oxidation and fatty acid oxidation pathways. Thus, shifting the balance from fatty acid oxidation to glucose oxidation by itself is not enough in many circumstances to restore full cardiac efficiency because downstream processes are affected as well.

The invention provides compositions that improve cardiac efficiency by using multiple mechanisms to alter mitochondrial metabolism. By including a component that shifts cardiac metabolism from fatty acid oxidation to glucose oxidation and one or more other components that promote mitochondrial respiration, the compositions trigger a change in the pathway used to produce energy and concomitantly improve overall mitochondrial oxidative function. Consequently, the compositions of the invention are more effective at restoring cardiac capacity in patients with heart disease, such as heart failure, ischemic heart disease, and diabetic cardiomyopathies, than are compounds that only effect a shift to glucose oxidation.

In some embodiments, the compositions are compounds represented by formula (I):

A-L-B                            (I), in which A is a compound that shifts cardiac metabolism from fatty acid oxidation to glucose oxidation, L is a linker, and B is a compound that promotes mitochondrial respiration.

Component A may be any suitable compound that shifts cardiac metabolism from fatty acid oxidation to glucose oxidation. Such compounds can be classified based on their mechanism of action. See Fillmore, N., et al., Mitochondrial fatty acid oxidation alterations in heart failure, ischemic heart disease and diabetic cardiomyopathy, Brit. J. Pharmacol. 171:2080-2090 (2014), incorporated herein by reference.

One class of glucose-shifting compounds includes compounds that inhibit fatty acid oxidation directly. Compounds in this class include inhibitors of malonyl CoA decarboxylase (MCD), carnitine palmitoyl transferase 1 (CPT-1), or mitochondrial fatty acid oxidation. Mitochondrial fatty acid oxidation inhibitors include trimetazidine and other compounds described in WO 2002/064576, which is incorporated herein by reference. Trimetazidine binds to distinct sites on the inner and outer mitochondrial membranes and affects both ion permeability and metabolic function of mitochondria. Morin, D., et al., Evidence for the existence of [$^3$H]-trimetazidine binding sites involved in the regulation of the mitochondrial permeability transition pore, Brit. J. Pharmacol. 123:1385-1394 (1998), incorporated herein by reference. MCD inhibitors include CBM-301106, CBM-300864, CBM-301940, 5-(1,1,1,3,3,3-hexafluoro-2-hydroxypropan-2-yl)-4,5-dihydroisoxazole-3-carboxamides, methyl 5-(N-(4-(1,1,1,3,3,3-hexafluoro-2-hydroxypropan-2-yl)phenyl)morpholine-4-carboxamido) pentanoate, and other compounds described in Chung, J. F., et al., Discovery of Potent and Orally Available Malonyl-CoA Decarboxylase Inhibitors as Cardioprotective Agents, J. Med. Chem. 49:4055-4058 (2006); Cheng J. F. et al., Synthesis and structure-activity relationship of small-molecule malonyl coenzyme A decarboxylase inhibitors, J. Med. Chem. 49:1517-1525 (2006); US Publication No. 2004/0082564; and WO 2002/058698, which are incorporated herein by reference. CPT-1 inhibitors include oxfenicine, perhexiline, etomoxir, and other compounds described in WO 2015/018660, WO 2008/109991; WO 2009/015485; US Publication No. 2011/0212072; and WO 2009/156479, which are incorporated herein by reference.

Another class of glucose-shifting compounds includes compounds that stimulate glucose oxidation directly. Examples of such compounds are described in US Publication No. 2003/0191182; WO 2006/117686; U.S. Pat. No. 8,202,901, which are incorporated herein by reference.

Another class of glucose-shifting compounds includes compounds that decrease the level of circulating fatty acids that supply the heart. Examples of such compounds include agonists of PPARα and PPARγ, including fibrate drugs, such as clofibrate, gemfibrozil, ciprofibrate, bezafibrate, and fenofibrate, and thiazolidinediones, GW-9662, and other compounds described in U.S. Pat. No. 9,096,538, which is incorporated herein by reference.

Component L may be any suitable linker. Preferably, the linker can be cleaved in vivo to release components A and B. The linker may be an alkoxy group. The linker may be polyethylene glycol of any length. The linker may be represented by $(CH_2CH_2O)_x$, in which x=1-15 or $(CH_2CH_2O)_x$, in which x=1-3. Other suitable linkers include 1,3-propanediol, diazo linkers, phosphoramidite linkers, disulfide linkers, cleavable peptides, iminodiacetic acid linkers, thioether linkers, and other linkers described in Leriche, G., et al., Cleavable linkers in chemical biology, Bioorg. Med. Chem. 20:571-582 (2012); WO 1995000165; and U.S. Pat. No. 8,461,117, which are incorporated herein by reference.

Component B may be any compound that promotes mitochondrial respiration. For example, component B may be an intermediate of the citric acid cycle or a molecule that can be metabolized to enter the citric acid cycle, such as succinate, fumarate, malate, oxaloacetate, citrate, isocitrate, α-ketoglutarate, pyruvate, acetone, acetoacetic acid, β-hydroxybutyric acid, β-ketopentanoate, or β-hydroxypentanoate. Intermediates of the citric acid cycle may become depleted if these molecules are used for biosynthetic purposes, resulting in inefficient generation of ATP from the citric acid cycle. However, due to the anaplerotic effect, providing one intermediate of the citric acid cycle leads to restoration of all intermediates as the cycle turns. Thus, intermediates of the citric acid cycle can promote mitochondrial respiration.

The compound may include a $NAD^+$ precursor molecule. $NAD^+$ is an important oxidizing agent that acts as a coenzyme in multiple reactions of the citric acid cycle. In these reactions, $NAD^+$ is reduced to NADH. Conversely, NADH is oxidized back to $NAD^+$ when it donates electrons to mitochondrial electron transport chain. In humans, $NAD^+$ can be synthesized de novo from tryptophan, but not in quantities sufficient to meet metabolic demands. Consequently, $NAD^+$ is also synthesized via a salvage pathway, which uses precursors that must be supplied from the diet. Among the precursors used by the salvage pathway for $NAD^+$ synthesis are nicotinic acid, nicotinamide, and nicotinamide riboside. By providing a $NAD^+$ precursor, such as nicotinic acid, nicotinamide, or nicotinamide riboside, the compound facilitates $NAD^+$ synthesis.

The inclusion of a $NAD^+$ precursor in compounds of the invention allows the compounds to stimulate energy production in cardiac mitochondria in multiple ways. First, component A shifts cardiac metabolism from fatty acid oxidation to glucose oxidation, which is inherently more efficient. Next, component B ensures that the intermediates of the citric acid cycle are present at adequate levels and do not become depleted or limiting. As a result, glucose-derived acetyl CoA is efficiently oxidized. Finally, the NAD$^+$ precursor provides an essential coenzyme that cycles between oxidized and reduced forms to promote respiration. In the oxidized form, NAD$^+$ drives reactions of the citric acid cycle. In the reduced form, NADH promotes electron transport to create a proton gradient that enables ATP synthesis. Consequently, the chemical potential resulting from oxidation of acetyl CoA is efficiently converted to ATP that can be used for various cellular functions.

The NAD$^+$ precursor molecule may be covalently attached to the compound in any suitable manner. For example, it may linked to A, L, or B, and it may be attached directly or via another linker. Preferably, it is attached via a linker that can be cleaved in vivo. The NAD$^+$ precursor molecule may be attached via a 1,3-propanediol linkage.

The compound may be covalently attached to one or more molecules of polyethylene glycol (PEG), i.e., the compound may be PEGylated. In many instances, PEGylation of molecules reduces their immunogenicity, which prevents the molecules from being cleared from the body and allows them to remain in circulation longer. The compound may contain a PEG polymer of any size. For example, the PEG polymer may have from 1-500 (CH$_2$CH$_2$O) units. The PEG polymer may have any suitable geometry, such as a straight chain, branched chain, star configuration, or comb configuration. The compound may be PEGylated at any site. For example, the compound may be PEGylated on component A, component B, component L, or, if present, the NAD$^+$ precursor. The compound may be PEGylated at multiple sites. For a compound PEGylated at multiple sites, the various PEG polymers may be of the same or different size and of the same or different configuration.

The compound may be a PEGylated form of trimetazidine. For example, the compound may be represented by formula (VI):

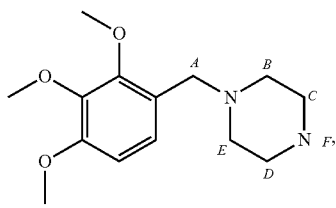

in which one or more of the carbon atoms at positions A, B, C, D, and E and/or the nitrogen atom at position F are substituted with —(CH$_2$CH$_2$O)$_n$H and n=1-15. The carbon atoms at positions A, B, C, D, and E may have two PEG substituents. In molecules that have multiple PEG chains, the different PEG chains may have the same or different length.

The compounds of formula (I) may be represented by formula (II):

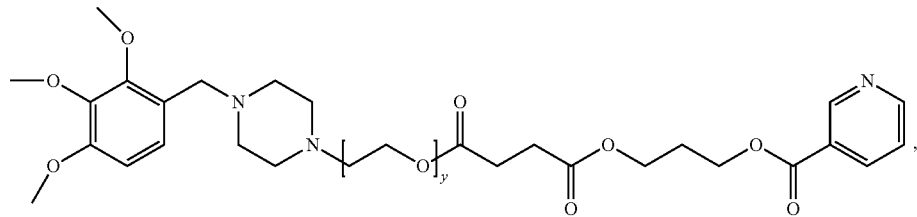

in which y=1-3.

The compounds of formula (I) may be represented by formula (III):

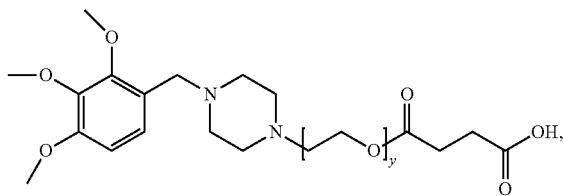

in which y=1-3.

The invention also provides compounds represented by formula (IV):

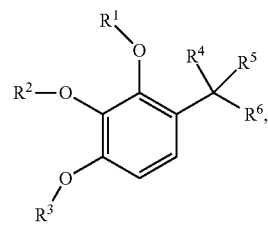

in which R$^1$, R$^2$, and R$^3$ are independently H or a (C$_1$-C$_4$) alkyl group; R$^4$ and R$^5$ together are =O, —O(CH$_2$)$_m$O—, or —(CH$_2$)$_m$—, in which m=2-4, or R$^4$ is H and R$^5$ is OR$^{14}$, SR$^{14}$, or (CH$_2$CH$_2$O)$_n$H, in which R$^{14}$ is H or a (C$_1$-C$_4$)alkyl group and n=1-15; and R$^6$ is a single or multi-ring structure optionally substituted at one or more ring positions by a heteroatom, in which each ring position optionally comprises one or more substituents.

R$^6$ may be a single or multi-ring structure of any size. For example, the structure may contain 3-22 atoms, not including hydrogen atoms bonded to atoms in ring positions. The structure may include one or more alkyl, alkenyl, or aromatic rings. The structure may include one or more heteroatoms, i.e., atoms other than carbon. For example, the heteroatom may be oxygen, nitrogen, or sulfur, or phosphorus.

One or more ring position of $R^6$ may include a substituent that includes a compound that promotes mitochondrial respiration, as described above in relation to component B of formula (I). The substituent may include a linker, as described above in relation to component L of formula (I). The substituent may include a NAD⁺ precursor molecule, as described above in relation to compounds of formula (I).

The substituent on a ring position of $R^6$ may be

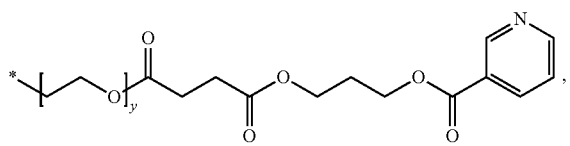

in which y=1-3.

The substituent on a ring position of $R^6$ may be

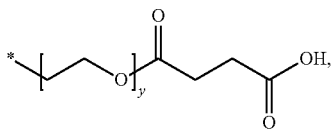

in which y=1-3.

$R^6$ may be

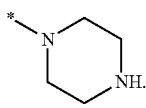

For some compounds of the invention that include trimetazidine prodrugs, analogs, deriviatives, it is advantageous to have the trimetazidine moiety substituted with a single ethylene glycol moiety. Thus, preferred compositions of the invention include compounds of formulas (I) and (VIII) that contain linkers in which x=1, compounds of formulas (II) and (III) in which y=1, compounds of formula (V) in which z=1, compounds of formula (VI) in which n=1, and compounds of formula (VII) in which A is linked to C via a single ethylene glycol moiety. Without wishing to be bound by theory, the attachment of a single ethylene glycol moiety to the trimetazidine moiety may improve the bioavailability of trimetazidine.

The compound of formula (IV) may have structure represented by formula (IX) or formula (X):

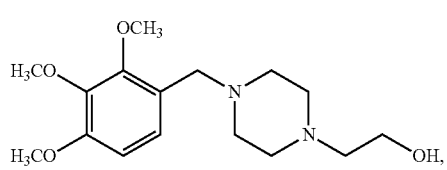

(IX)

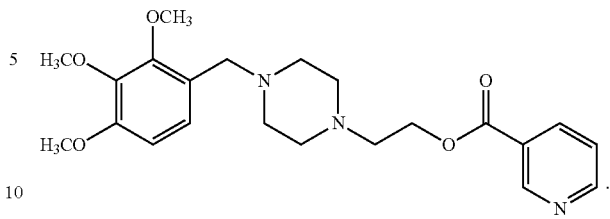

(X)

The invention also provides compounds represented by formula (V):

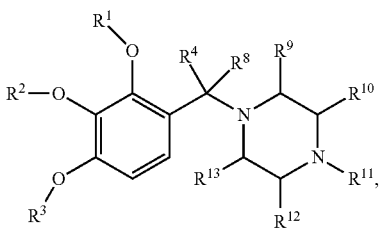

(V)

in which $R^1$, $R^2$, and $R^3$ are independently H or a ($C_1$-$C_4$) alkyl group; $R^4$ and $R^8$ together are =O, —O(CH$_2$)$_m$O—, or —(CH$_2$)$_m$—, in which m=2-4, or $R^4$ is H and $R^8$ is H, OR$^{14}$, SR$^{14}$, or (CH$_2$CH$_2$O)$_n$H, in which R$^{14}$ is H or a ($C_1$-$C_4$)alkyl group and n=1-15; $R^9$, $R^{10}$, $R^{12}$, and $R^{13}$ are independently H or (CH$_2$CH$_2$O)$_z$H, in which z=1-15; and $R^{11}$ comprises a compound that promotes mitochondrial respiration, as described above in relation to component B of formula (I). $R^{11}$ may include a linker, as described above in relation to component L of formula (I).

$R^{11}$ may be

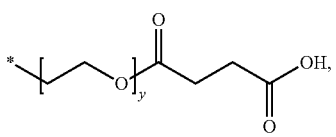

in which y=1-3.

$R^{11}$ may include a NAD⁺ precursor molecule, as described above in relation to compounds of formula (I).

$R^{11}$ may be

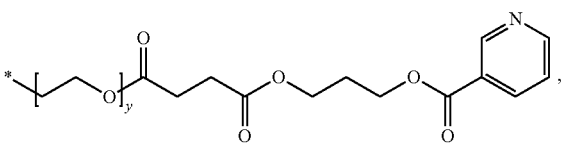

in which y=1-3.

In some embodiments described above, compounds of the invention include multiple active agents joined by linkers in a single molecule. It may be advantageous to deliver multiple active agents as components of a single molecule. Without wishing to be bound by a particular theory, there are several reasons why co-delivery of active agents in a single molecule may be advantageous. One possibility is that a single large molecule may have reduced side effects compared to the component agents. Free trimetazidine causes symptoms similar to those in Parkinson's disease in a fraction of patients. However, when trimetazidine is derivatized to include other components, such as succinate, the molecule is bulkier and may not be able to access sites where free trimetazidine can causes unintended effects. Trimetazidine derivatized as described above is also more hydrophilic and thus may be less likely to cross the blood-brain barrier to cause neurological effects. Another possibility is that modification of trimetazidine may alter its pharmacokinetic properties. Because the derivatized molecule is metabolized to produce the active agent, the active agent is released gradually. Consequently, levels of the active agent in the body may not reach peaks as high as when a comparable amount is administered in a single bolus. Another possibility is that less of each active agent, such as trimetazidine, is required because the compounds of the invention include multiple active agents. For example, trimetazidine shifts metabolism from fatty acid oxidation to glucose oxidation, and succinate improves mitochondrial respiration generally. Thus, a compound that provides both agents stimulates a larger increase in glucose-driven ATP production for a given amount of trimetazidine than does a compound that delivers trimetazidine alone.

The invention also provides compounds represented by formula (VII):

$$A\text{-}C \qquad (\text{VII}),$$

in which A is a compound that shifts cardiac metabolism from fatty acid oxidation to glucose oxidation, and C is a NAD$^+$ precursor molecule. A and C may be covalently linked.

The compound that shifts cardiac metabolism from fatty acid oxidation to glucose oxidation may be PEGylated with an ethylene glycol moiety. The compound that shifts cardiac metabolism from fatty acid oxidation to glucose oxidation may have multiple ethylene glycol moieties, such as one, two three, four, five, or more ethylene glycol moieties. The ethylene glycol moiety may be represented by $(CH_2CH_2O)_x$, in which x=1-15. The ethylene glycol moiety may form a covalent linkage between the compound that shifts cardiac metabolism from fatty acid oxidation to glucose oxidation and the NAD$^+$ precursor molecule. The ethylene glycol moiety may be separate from a covalent linkage between the compound that shifts cardiac metabolism from fatty acid oxidation to glucose oxidation and the NAD$^+$ precursor molecule.

The compound of formula (VII) may include nicotinic acid that is covalently linked to a PEGylated form of trimetazidine. The nicotinic acid may be covalently linked via a PEGylated moiety, i.e., via an ethylene glycol linkage. The nicotinic acid may be covalently linked via the trimetazidine moiety.

The invention also provides compounds represented by formula (VIII):

$$A\text{-}L\text{-}C \qquad (\text{VIII}),$$

in which A is a compound that shifts cardiac metabolism from fatty acid oxidation to glucose oxidation, L is a linker, and C is a NAD$^+$ precursor molecule. A may be covalently linked to L, and L may be covalently linked to C.

The compound that shifts cardiac metabolism from fatty acid oxidation to glucose oxidation, the linker, and the NAD$^+$ precursor molecule may be as described above in relation to compounds of other formulas.

The invention also provides compositions that include at least two of (1) a compound that shifts cardiac metabolism from fatty acid oxidation to glucose oxidation, (2) a compound that promotes mitochondrial respiration, and (3) a NAD$^+$ precursor molecule. The aforementioned components of the composition may be provided as separate molecules.

The compositions may include each of a (1) a compound that shifts cardiac metabolism from fatty acid oxidation to glucose oxidation, (2) a compound that promotes mitochondrial respiration, and (3) a NAD$^+$ precursor molecule. In such compositions, each of the three components may be provided as a separate molecule. Alternatively, in such compositions, two of the components may be covalently linked as part of single molecule, and the third component may be provided as a separate molecule. For example, the compound that shifts cardiac metabolism from fatty acid oxidation to glucose oxidation may be linked to the compound that promotes mitochondrial respiration, and the NAD$^+$ precursor may be provided as a separate molecule.

The compounds of the invention may be provided as co-crystals with other compounds. Co-crystals are crystalline materials composed of two or more different molecules in the same crystal lattice. The different molecules may be neutral and interact non-ionically within the lattice. Co-crystals of the invention may include one or more compounds of the invention with one or more other molecules that stimulate mitochondrial respiration or serve as NAD$^+$ precursors. For example, a co-crystal may include any of the following combinations: (1) a compound that shifts cardiac metabolism from fatty acid oxidation to glucose oxidation and (2) a NAD$^+$ precursor molecule; (1) a compound that promotes mitochondrial respiration and (2) a NAD$^+$ precursor molecule; (1) a compound that shifts cardiac metabolism from fatty acid oxidation to glucose oxidation and (2) a compound that promotes mitochondrial respiration; (1) a molecule comprising a compound that shifts cardiac metabolism from fatty acid oxidation to glucose oxidation covalently linked to a compound that promotes mitochondrial respiration and (2) a NAD$^+$ precursor molecule. In specific embodiments, a co-crystal may include (1) a compound of formula (I), (III), (IV), or (V) and (2) nicotinic acid, nicotinamide, or nicotinamide riboside.

The compounds may include one or more atoms that are enriched for an isotope. For example, the compounds may have one or more hydrogen atoms replaced with deuterium or tritium. Isotopic substitution or enrichment may occur at carbon, sulfur, or phosphorus, or other atoms. The compounds may be isotopically substituted or enriched for a given atom at one or more positions within the compound, or the compounds may be isotopically substituted or enriched at all instances of a given atom within the compound.

The invention provides pharmaceutical compositions containing one or more of the compounds described above. A pharmaceutical composition containing the compounds may be in a form suitable for oral use, for example, as tablets, troches, lozenges, fast-melts, aqueous or oily suspensions, dispersible powders or granules, emulsions, hard or soft capsules, syrups or elixirs. Compositions intended for oral use may be prepared according to any method known in the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the compounds in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration in the stomach and absorption lower down in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452 and 4,265,874, to form osmotic therapeutic tablets for control release. Preparation and administration of compounds is discussed in U.S. Pat. No. 6,214,841 and U.S. Pub. 2003/0232877, incorporated by reference herein in their entirety.

Formulations for oral use may also be presented as hard gelatin capsules in which the compounds are mixed with an inert solid diluent, for example calcium carbonate, calcium phosphate or kaolin, or as soft gelatin capsules in which the compounds are mixed with water or an oil medium, for example peanut oil, liquid paraffin or olive oil.

An alternative oral formulation, where control of gastrointestinal tract hydrolysis of the compound is sought, can be achieved using a controlled-release formulation, where a compound of the invention is encapsulated in an enteric coating.

Aqueous suspensions may contain the compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally occurring phosphatide, for example lecithin, or condensation products of an alkylene oxide with fatty acids, for example, polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the compounds in a vegetable oil, for example, *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compounds in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, such as glycerol, propylene glycol, sorbitol or sucrose. Such formulations may also contain a demulcent, a preservative, and agents for flavoring and/or coloring. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

The compounds of the invention are useful for improving cardiac efficiency. A variety of definitions of cardiac efficiency exist in the medical literature. See, e.g. Schipke, J. D. Cardiac efficiency, Basic Res. Cardiol. 89:207-40 (1994); and Gibbs, C. L. and Barclay, C. J. Cardiac efficiency, Cardiovasc. Res. 30:627-634 (1995), incorporated herein by reference. One definition of cardiac mechanical efficiency is the ratio of external cardiac power to cardiac energy expenditure by the left ventricle. See Lopaschuk G. D., et al., Myocardial Fatty Acid Metabolism in Health and Disease, Phys. Rev. 90:207-258 (2010), incorporated herein by reference. Another definition is the ratio between stroke work and oxygen consumption, which ranges from 20-25% in the normal human heart. Visser, F., Measuring cardiac efficiency: is it useful? Hear Metab. 39:3-4 (2008), incorporated herein by reference. Another definition is the ratio of the stroke volume to mean arterial blood pressure. Any suitable definition of cardiac efficiency may be used to measure the effects of compounds of the invention The invention also provides methods of altering cardiac metabolism in a subject to increase glucose oxidation relative to fatty acid oxidation. The methods may include providing a composition of the invention, such as any the compounds described above, including the compounds represented by formulas (I), (II), (III), (IV), or (V) or formulations thereof.

The methods may include providing a compound that shifts cardiac metabolism from fatty acid oxidation to glucose oxidation, as described above, and a compound that promotes mitochondrial respiration, as described above. The compounds may be provided as components of a single molecule, as separate molecules in a single composition, or as separate compositions.

The methods may also include providing a $NAD^+$ precursor molecule, as described above. In methods that involve providing a compound that shifts cardiac metabolism from fatty acid oxidation to glucose oxidation, a compound that promotes mitochondrial respiration, and a NAD+ precursor molecule, compounds may be provided as components of a single molecule, two different molecules, or three different molecules. The compounds may be provided in one, two, three, or any number of different compositions. The compounds may be provided together, separately, or in any combination. The compounds may be provided simultaneously or sequentially. The compounds may be provided at different intervals, with different frequency, in different quantities, or at different dosages.

The invention also provides methods of treating conditions by providing compositions of the invention. The condition may be heart disease, such as heart failure, ischemic heart disease, diabetic cardiomyopathy, rheumatic heart disease, valvular heart disease, aneurysm, atherosclerosis, high blood pressure (hypertension), peripheral arterial disease, angina, atherosclerosis, coronary artery disease, coronary heart disease, heart attack, atherosclerosis, cerebral vascular disease, stroke, transient ischemic attacks, atherosclerosis, cardiomyopathy, pericardial disease, valvular heart disease, or congenital heart disease.

EXAMPLES

Protocol

The effects of compounds of the invention on mitochondrial function were analyzed. HepG2 cells were dosed with test compound and in real time the extracellular oxygen levels and pH were measured using the XFe96 flux analyzer (Seahorse Biosciences). XFe Technology uses solid-state sensors to simultaneously measure both oxygen consumption rate (OCR) and extracellular acidification rate (ECAR) to determine effects on oxidative phosphorylation (OXPHOS) and glycolysis simultaneously. The cells were then subjected to sequential exposure to various inhibitors of mitochondrial function to assess cellular metabolism.

Data Interpretation.

A compound was identified as positive mitochondrial-active compound when it caused a change in oxygen consumption rate (OCR) or extracellular acidification rate (ECAR) in the absence of cytotoxicity. Cytotoxicity was determined when both OXPHOS (OCR) and glycolysis (ECAR) were inhibited.

Definition of Mitochondrial Parameters.

Oxygen consumption rate (OCR) is a measurement of oxygen content in extracellular media. Changes in OCR indicate effects on mitochondrial function and can be bi-directional. A decrease is due to an inhibition of mitochondrial respiration, while an increase may indicate an uncoupler, in which respiration is not linked to energy production.

$$OCR = \frac{\text{compound } OCR - \text{non mitochondrial } OCR}{\text{basal } OCR - \text{non mitochondrial } OCR}$$

Extracellular acidification rate (ECAR) is the measurement of extracellular proton concentration (pH). An increase in signal means an increase in rate in number of pH ions (thus decreasing pH value) and seen as an increase in glycolysis. ECAR is expressed as a fraction of basal control (rate prior to addition of compound).

$$ECAR = \frac{\text{compound } ECAR}{\text{basal } ECAR}$$

Reserve capacity is the measured ability of cells to respond to an increase in energy demand. A reduction indicates mitochondrial dysfunction. This measurement demonstrates how close to the bioenergetic limit the cell is.

$$\text{reserve capacity} = \frac{FCCP\ OCR - \text{non mitochondrial } OCR}{\text{basal } OCR - \text{non mitochondrial } OCR}$$

Mitochondrial Stress Test.

A series of compounds were added sequentially to the cells to assess a bioenergetics profile, effects of test compounds on parameters such as proton leak, and reserve capacity. This can be used to assist in understanding potential mechanisms of mitochondrial toxicity. The following compounds were added in order: (1) oligomycin, (2) FCCP, and (3) rotenone and antimycin A.

Oligomycin is a known inhibitor of ATP synthase and prevents the formation of ATP. Oligomycin treatment provides a measurement of the amount of oxygen consumption related to ATP production and ATP turnover. The addition of oligomycin results in a decrease in OCR under normal conditions, and residual OCR is related to the natural proton leak.

FCCP is a protonophore and is a known uncoupler of oxygen consumption from ATP production. FCCP treatment allows the maximum achievable transfer of electrons and oxygen consumption rate and provides a measurement of reserve capacity.

Rotenone and antimycin A are known inhibitors of complex I and III of the electron transport chain, respectively. Treatment with these compounds inhibits electron transport completely, and any residual oxygen consumption is due to non-mitochondrial activity via oxygen requiring enzymes.

Definition of Mechanisms.

An electron transport chain inhibitor is an inhibitor of mitochondrial respiration that causes an increase in glycolysis as an adaptive response (e.g. decrease OCR and increase in ECAR).

The inhibition of oxygen consumption may also be due to reduced substrate availability (e.g. glucose, fatty acids, glutamine, pyruvate), for example, via transporter inhibition. Compounds that reduce the availability of substrates are substrate inhibitors. A substrate inhibitor does not result in an increase in glycolysis (e.g. OCR decrease, no response in ECAR).

Compounds that inhibit the coupling of the oxidation process from ATP production are known as uncouplers. These result in an increase in mitochondrial respiration (OCR) but inhibition of ATP production.

FIG. 1 is a table summarizing the effects of various compounds on mitochondrial function.

FIG. 2 is a table summarizing the effects of nicotinamide on various mitochondrial functional parameters.

FIG. 3 is a series of graphs showing the effects of nicotinamide on oxygen consumption rate and reserve capacity.

Figure 4:
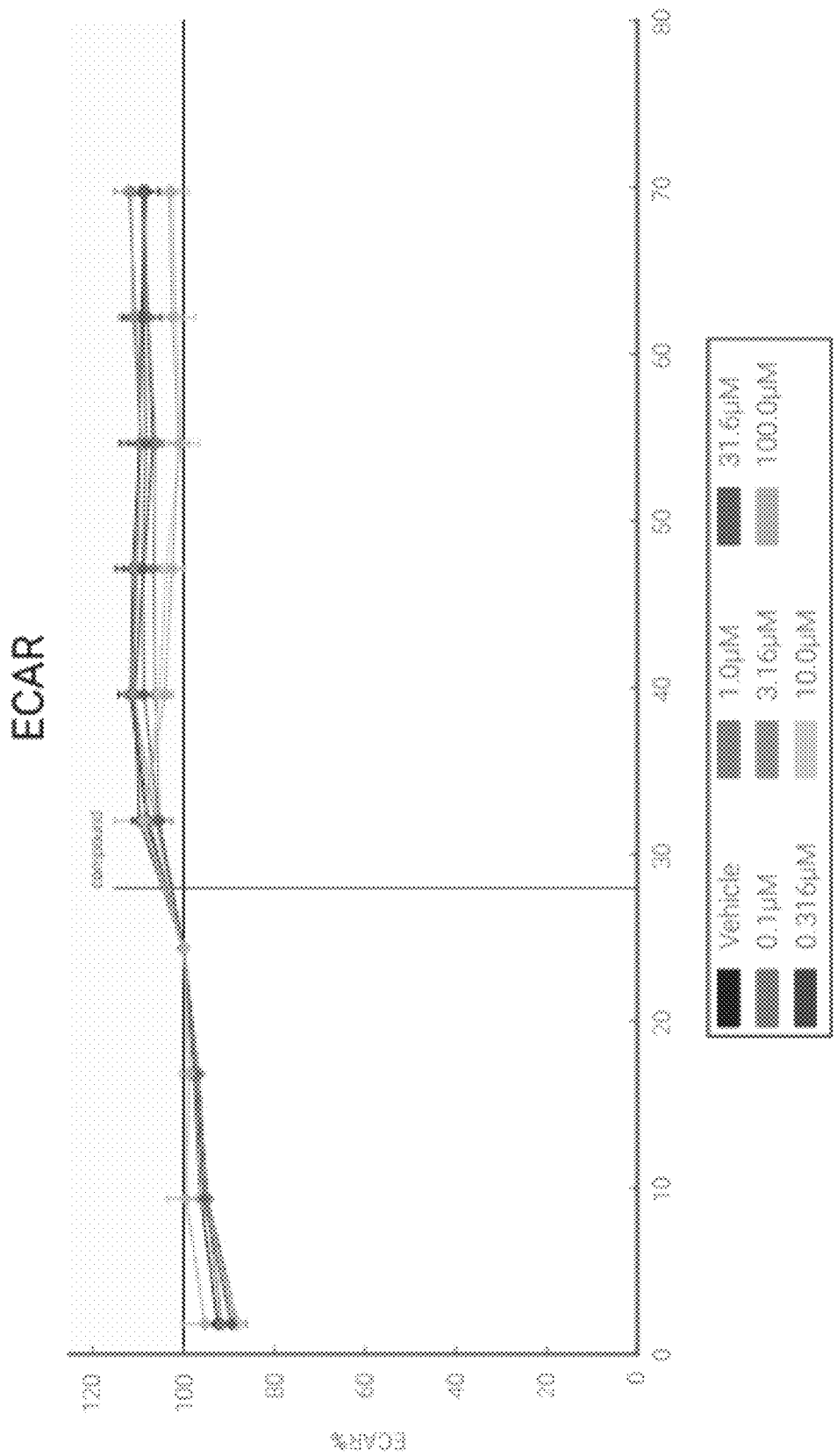
FIG. 4 is a series of graphs showing the effects of nicotinamide on extracellular acidification rate.
Figure 4:
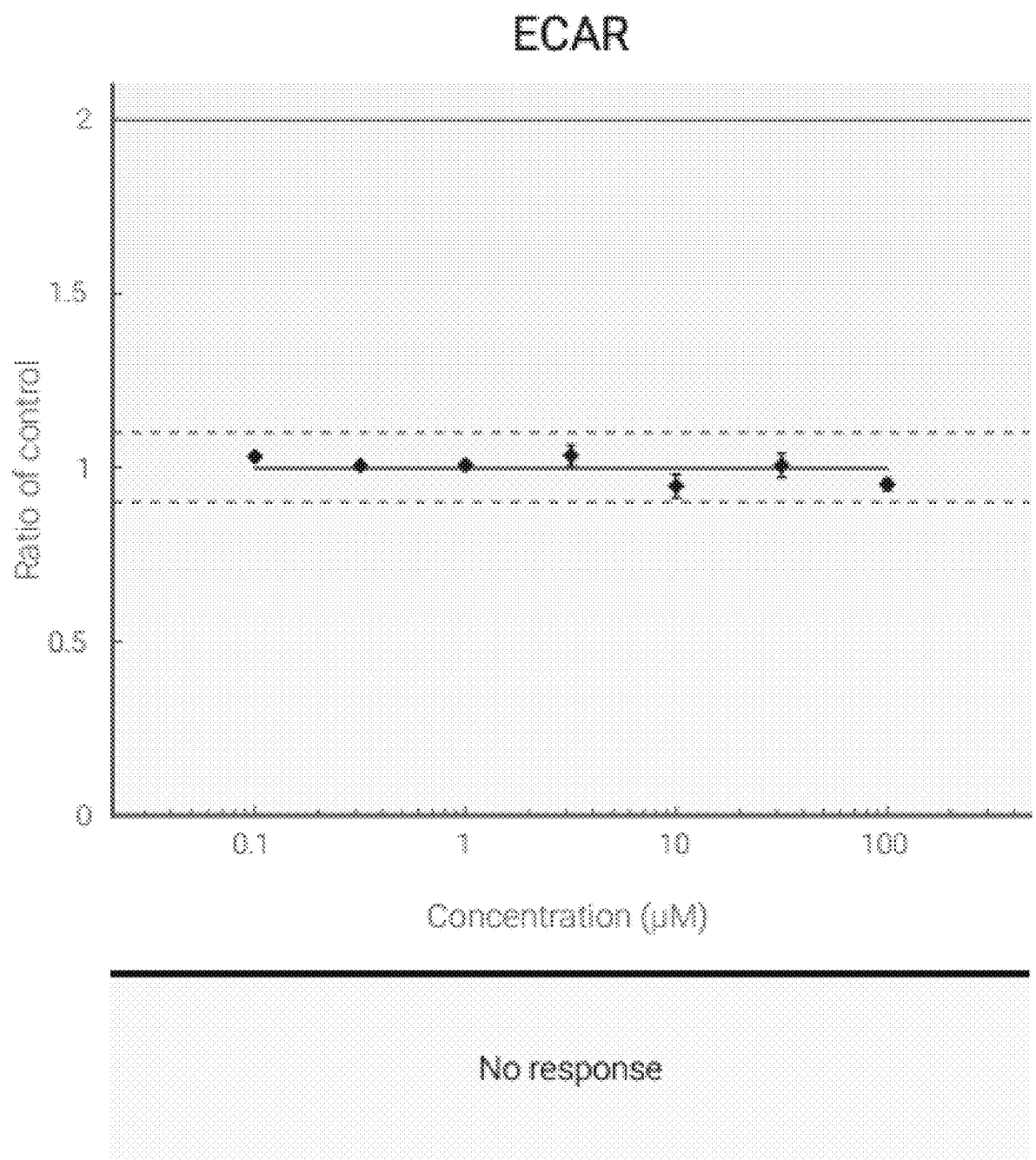

FIG. 4 is a series of graphs showing the effects of nicotinamide on extracellular acidification rate.

FIG. 5 is a table summarizing the effects of a combination of trimetazidine and nicotinamide on various mitochondrial functional parameters.

Figure 6:
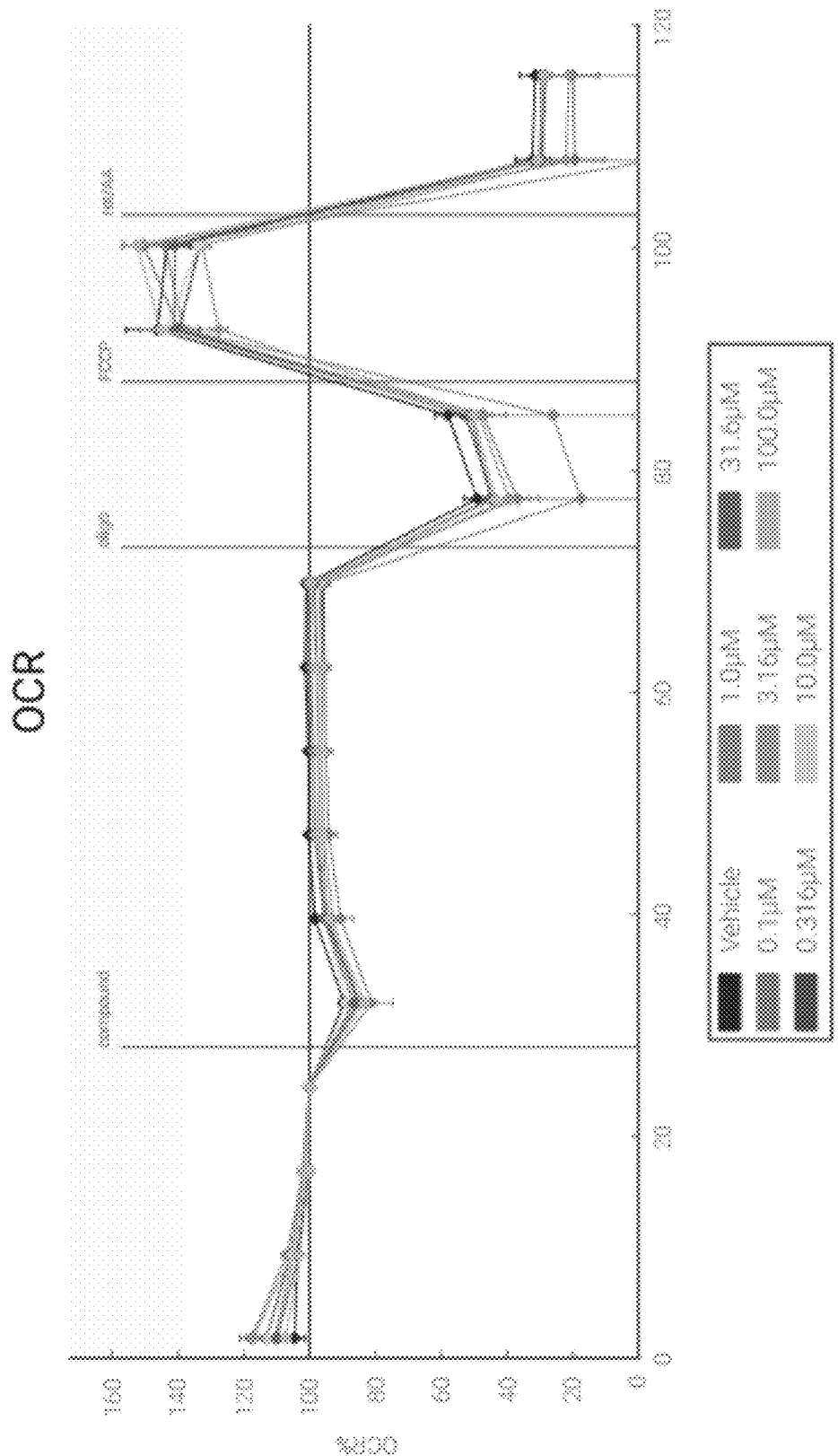
FIG. 6 is a series of graphs showing the effects of a combination of trimetazidine and nicotinamide on oxygen consumption rate and reserve capacity.
Figure 6:
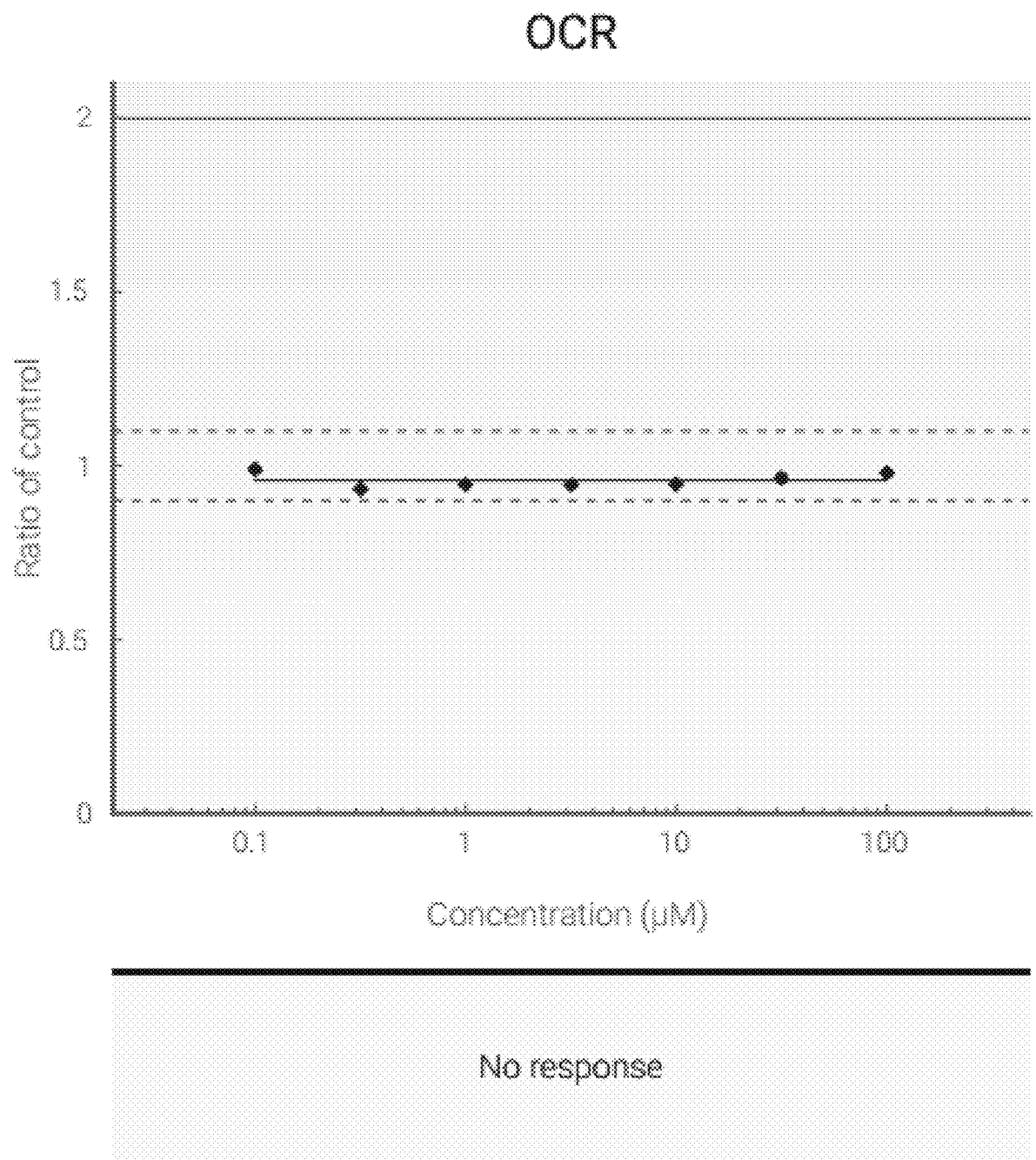
Figure 6:
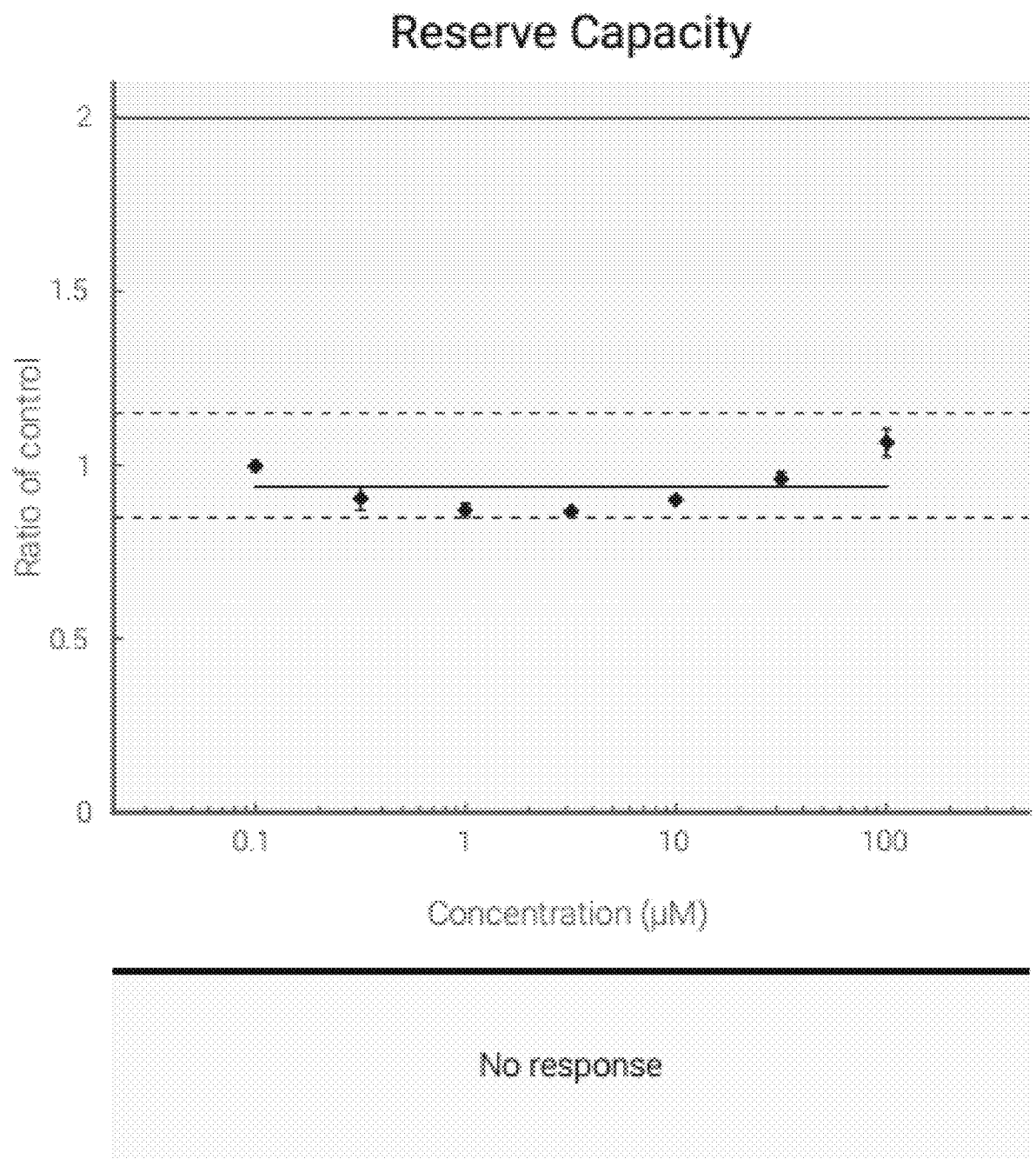

FIG. 6 is a series of graphs showing the effects of a combination of trimetazidine and nicotinamide on oxygen consumption rate and reserve capacity.

Figure 7:
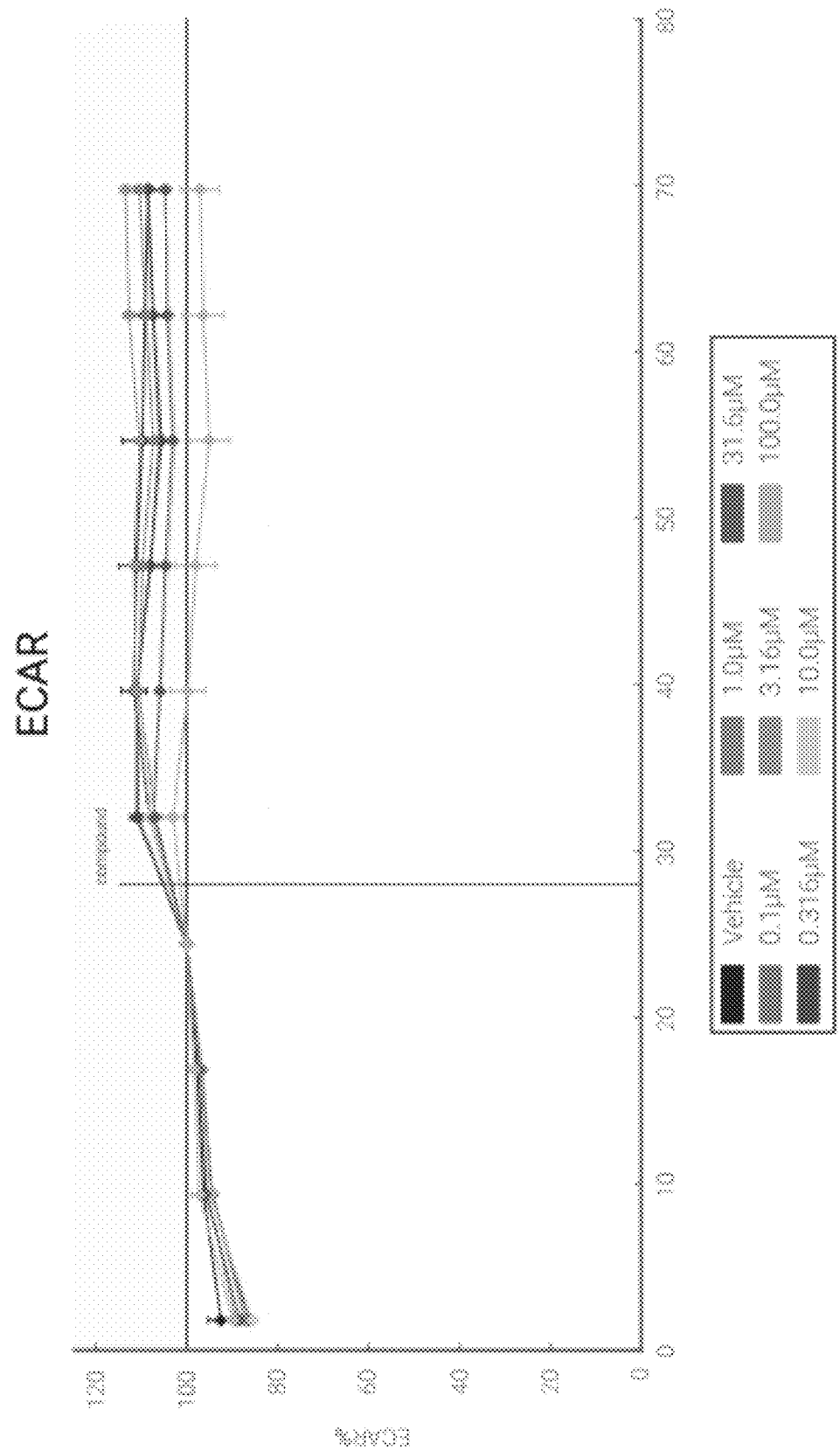
FIG. 7 is a series of graphs showing the effects of a combination of trimetazidine and nicotinamide on extracellular acidification rate.
Figure 7:
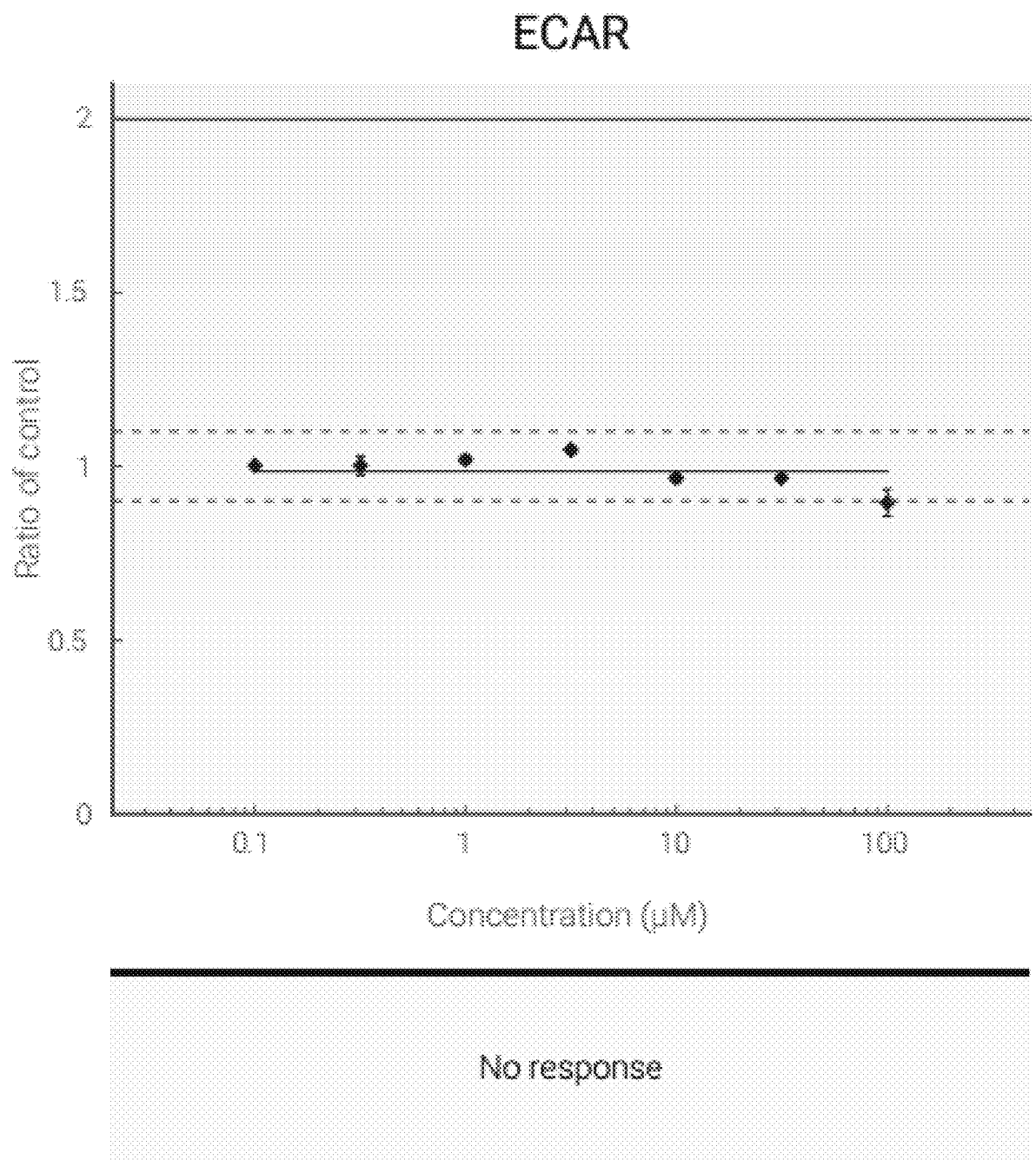

FIG. 7 is a series of graphs showing the effects of a combination of trimetazidine and nicotinamide on extracellular acidification rate.

FIG. 8 is a table summarizing the effects of succinate on various mitochondrial functional parameters.

Figure 9:
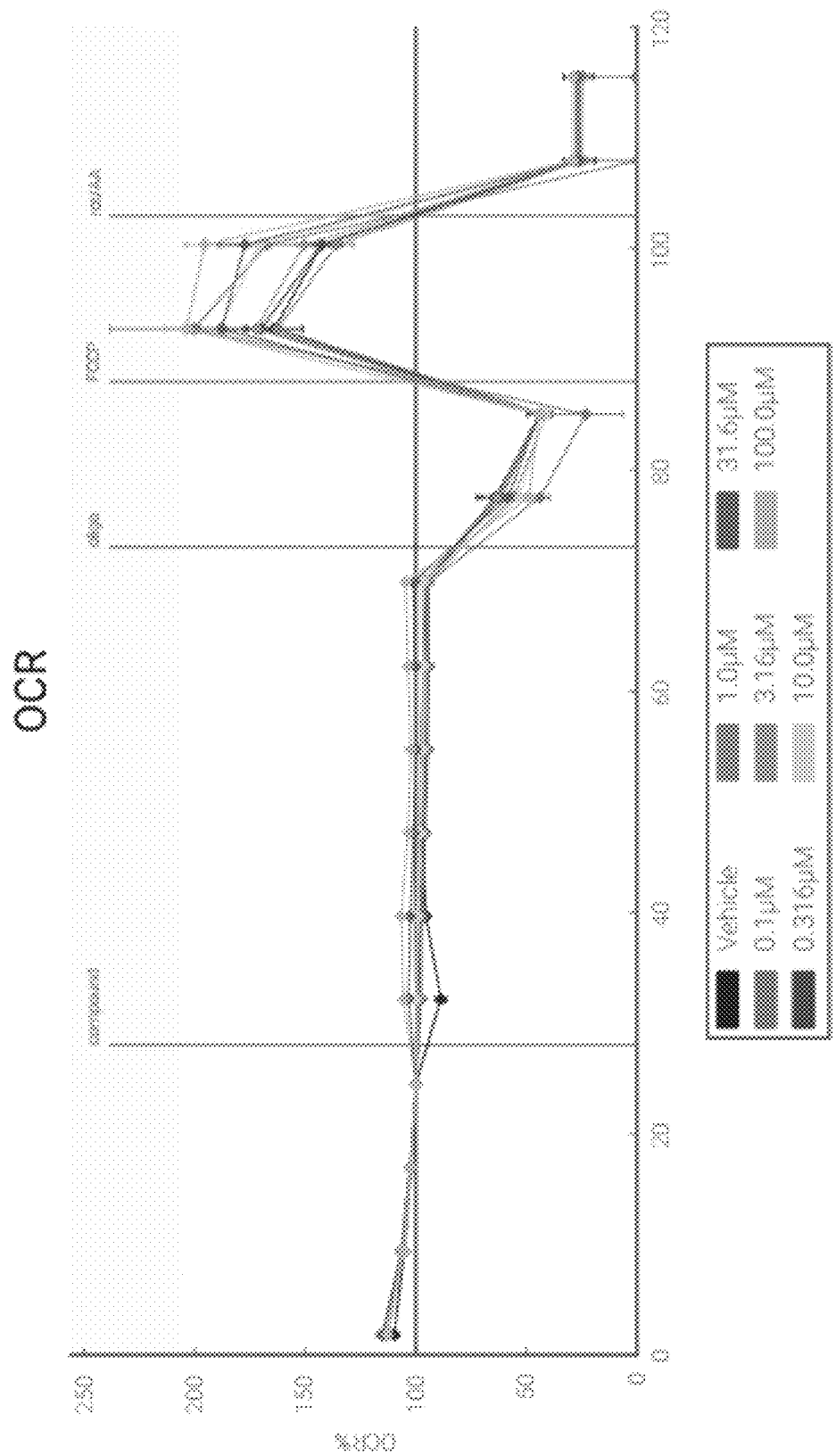
FIG. 9 is a series of graphs showing the effects of succinate on oxygen consumption rate and reserve capacity.
Figure 9:
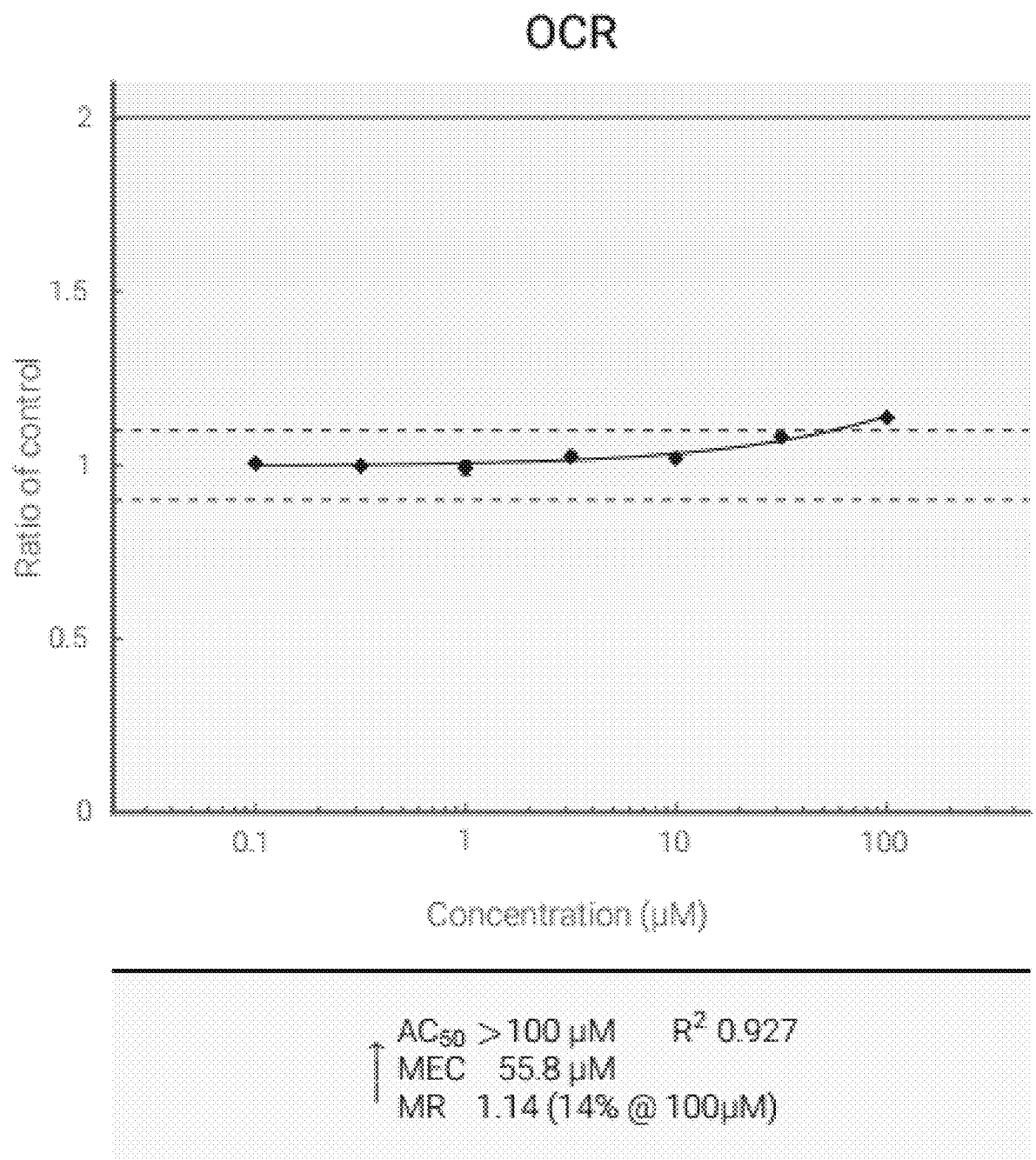
Figure 9:
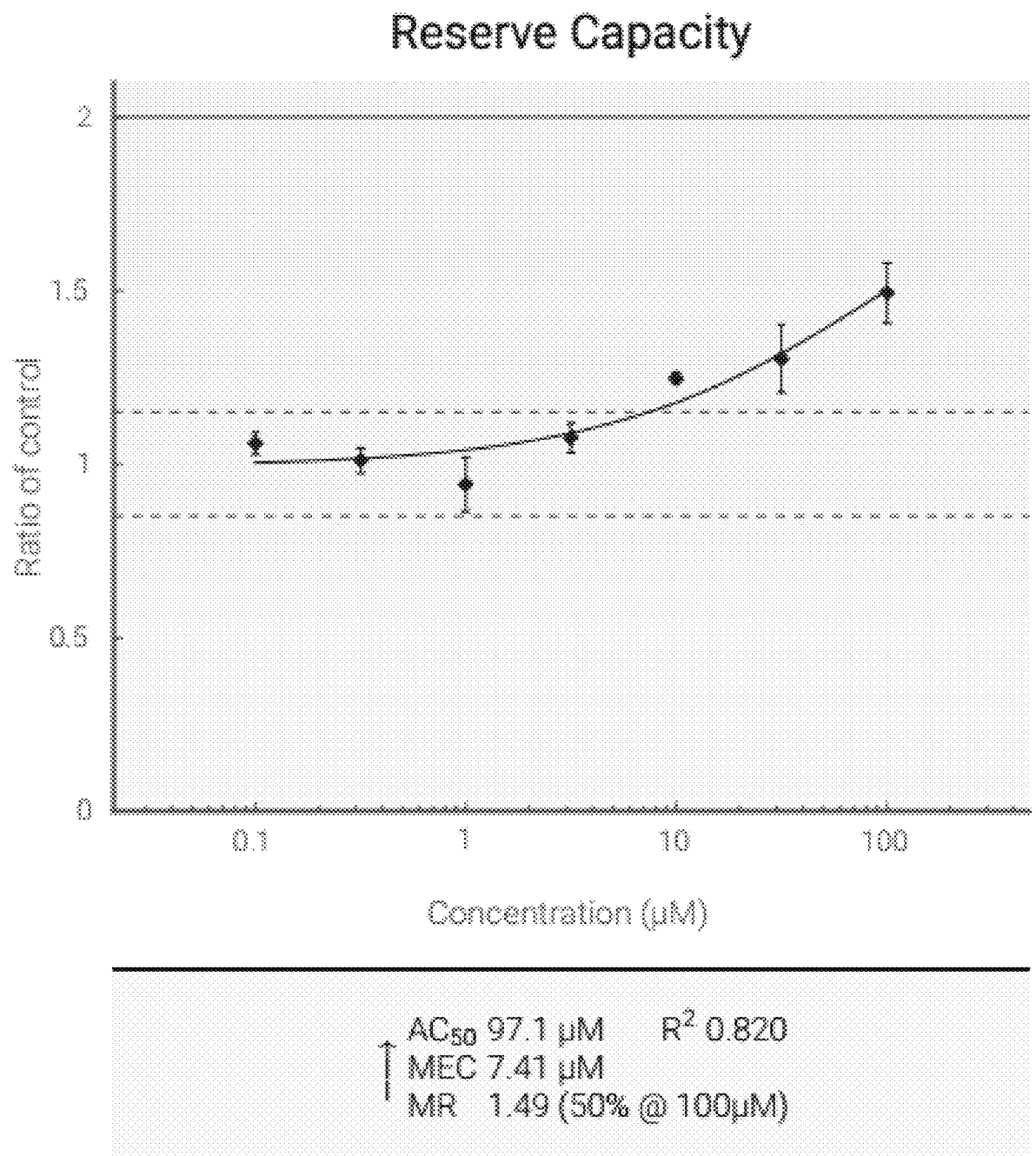

FIG. 9 is a series of graphs showing the effects of succinate on oxygen consumption rate and reserve capacity.

Figure 10:
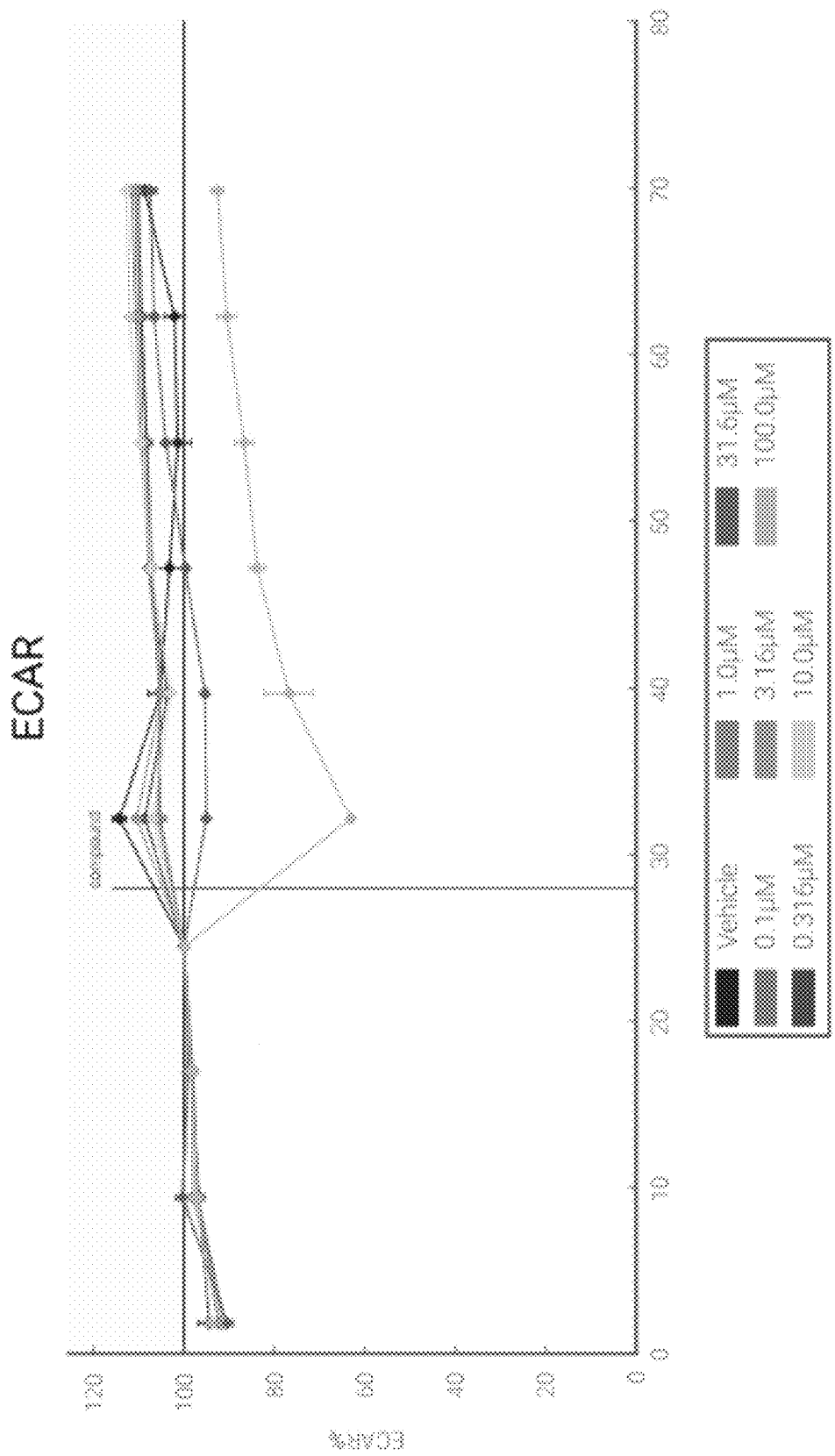
FIG. 10 is a series of graphs showing the effects of succinate on extracellular acidification rate.
Figure 10:
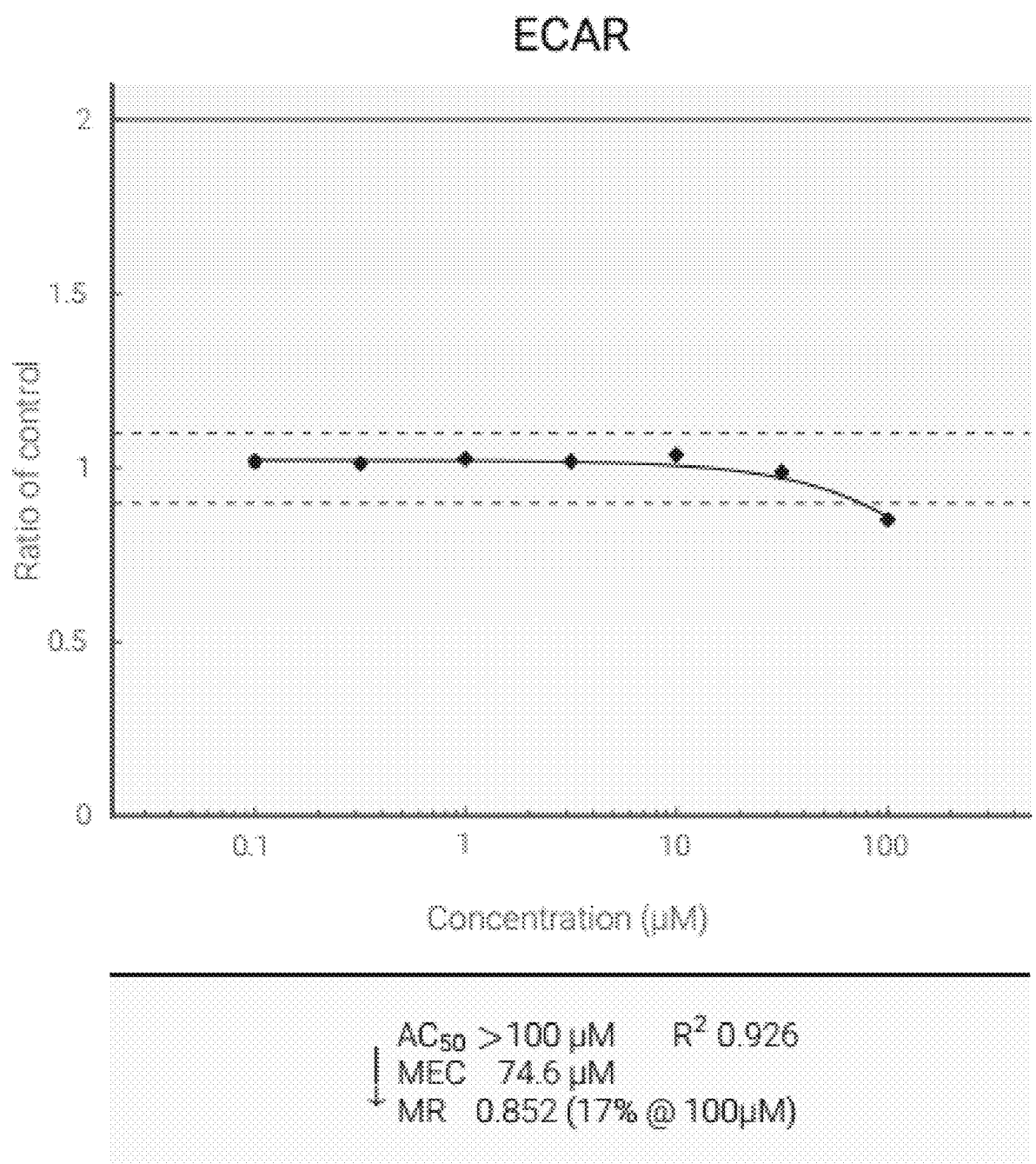

FIG. 10 is a series of graphs showing the effects of succinate on extracellular acidification rate.

FIG. 11 is a table summarizing the effects of compound CV-8814 on various mitochondrial functional parameters.

Figure 12:
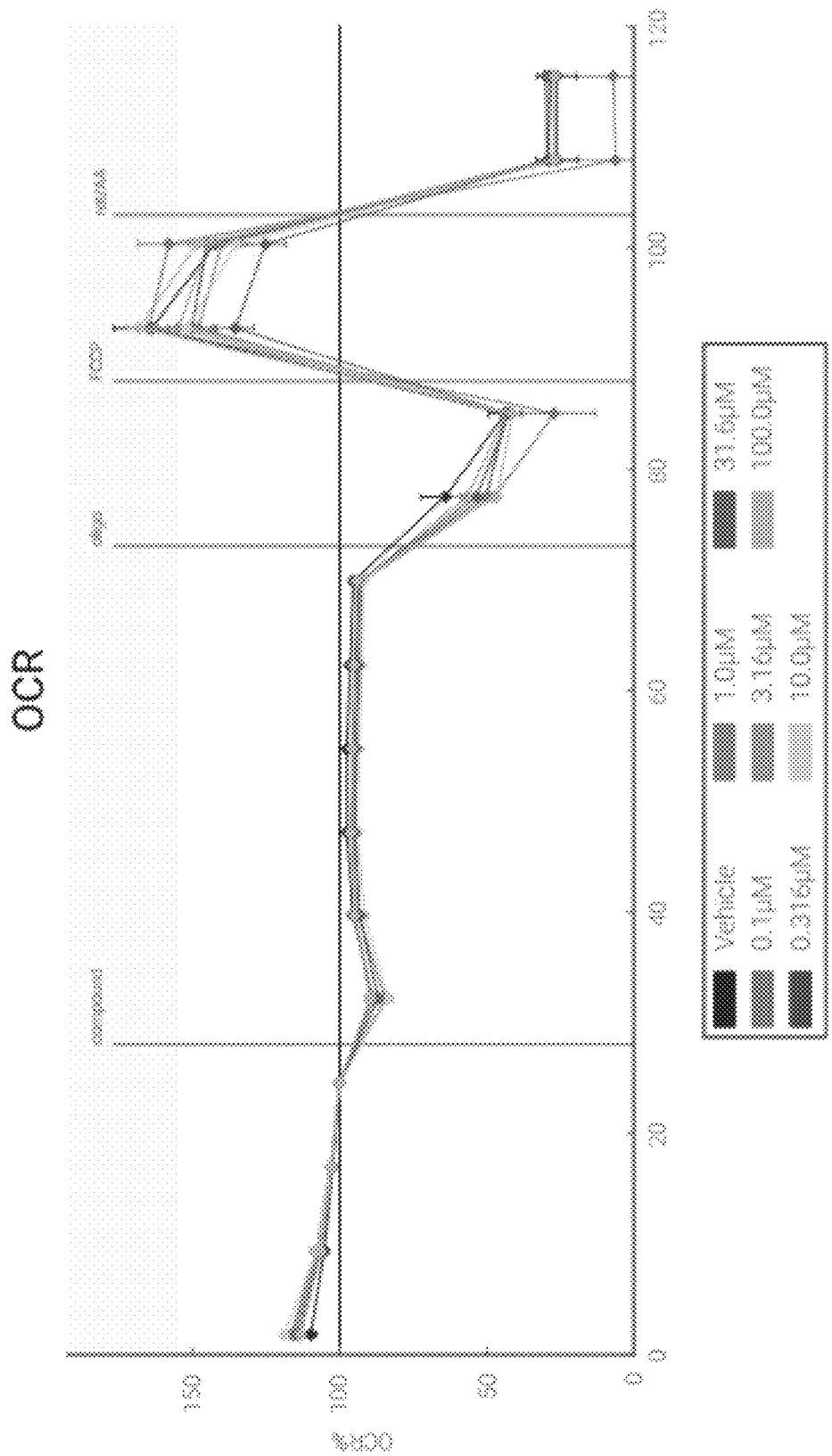
FIG. 12 is a series of graphs showing the effects of compound CV-8814 on oxygen consumption rate and reserve capacity.
Figure 12:
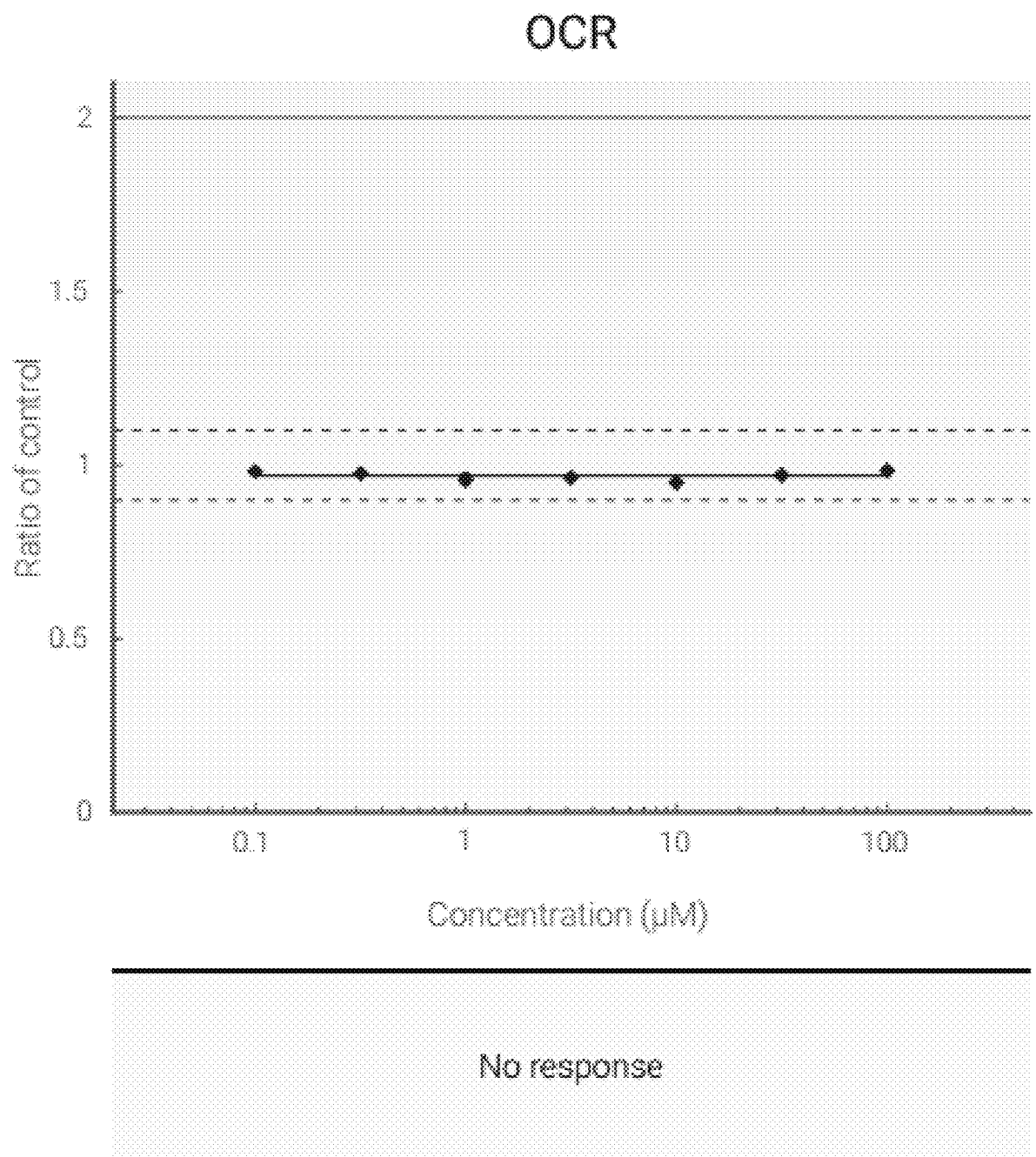
Figure 12:
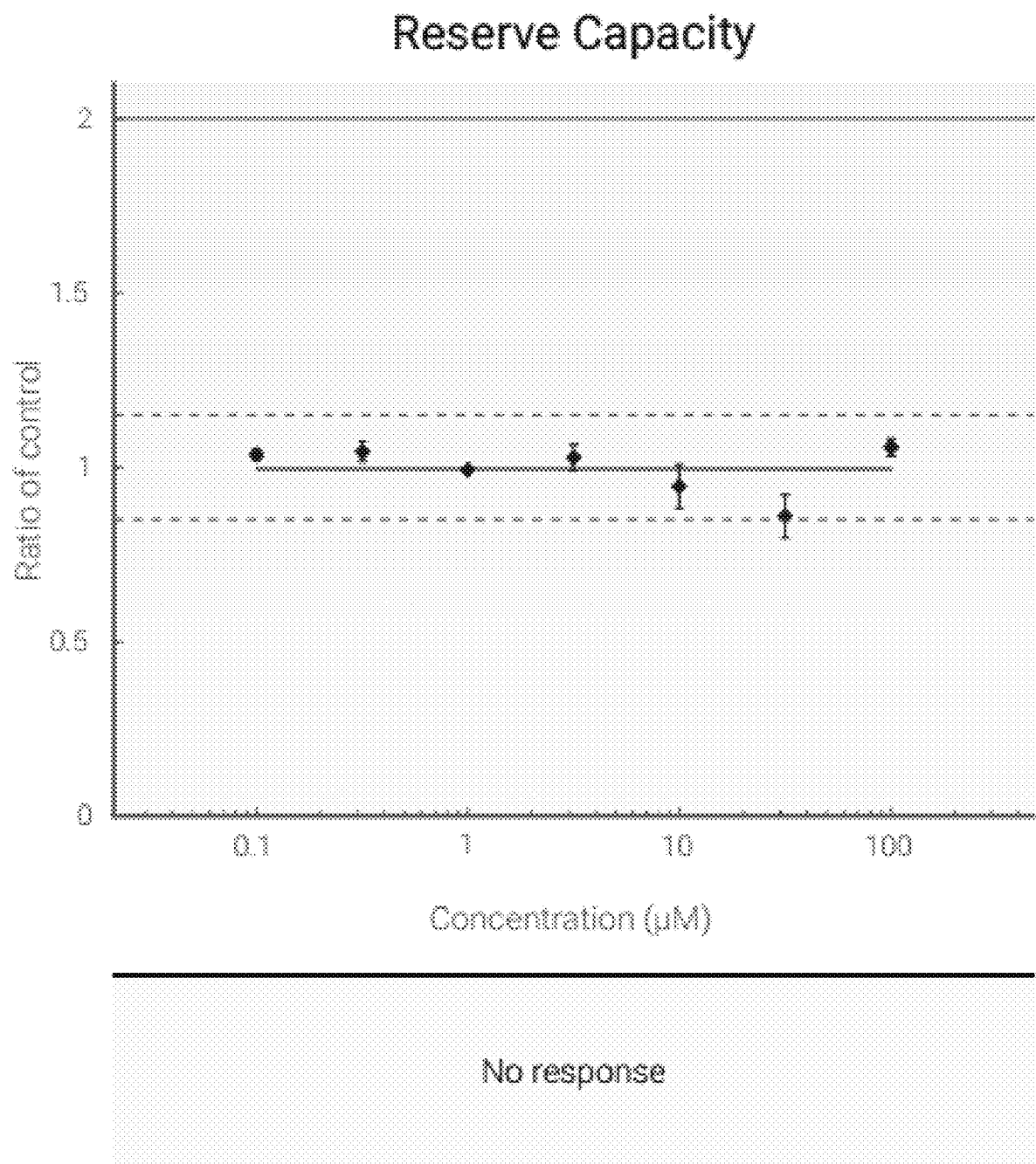

FIG. 12 is a series of graphs showing the effects of compound CV-8814 on oxygen consumption rate and reserve capacity.

Figure 13:
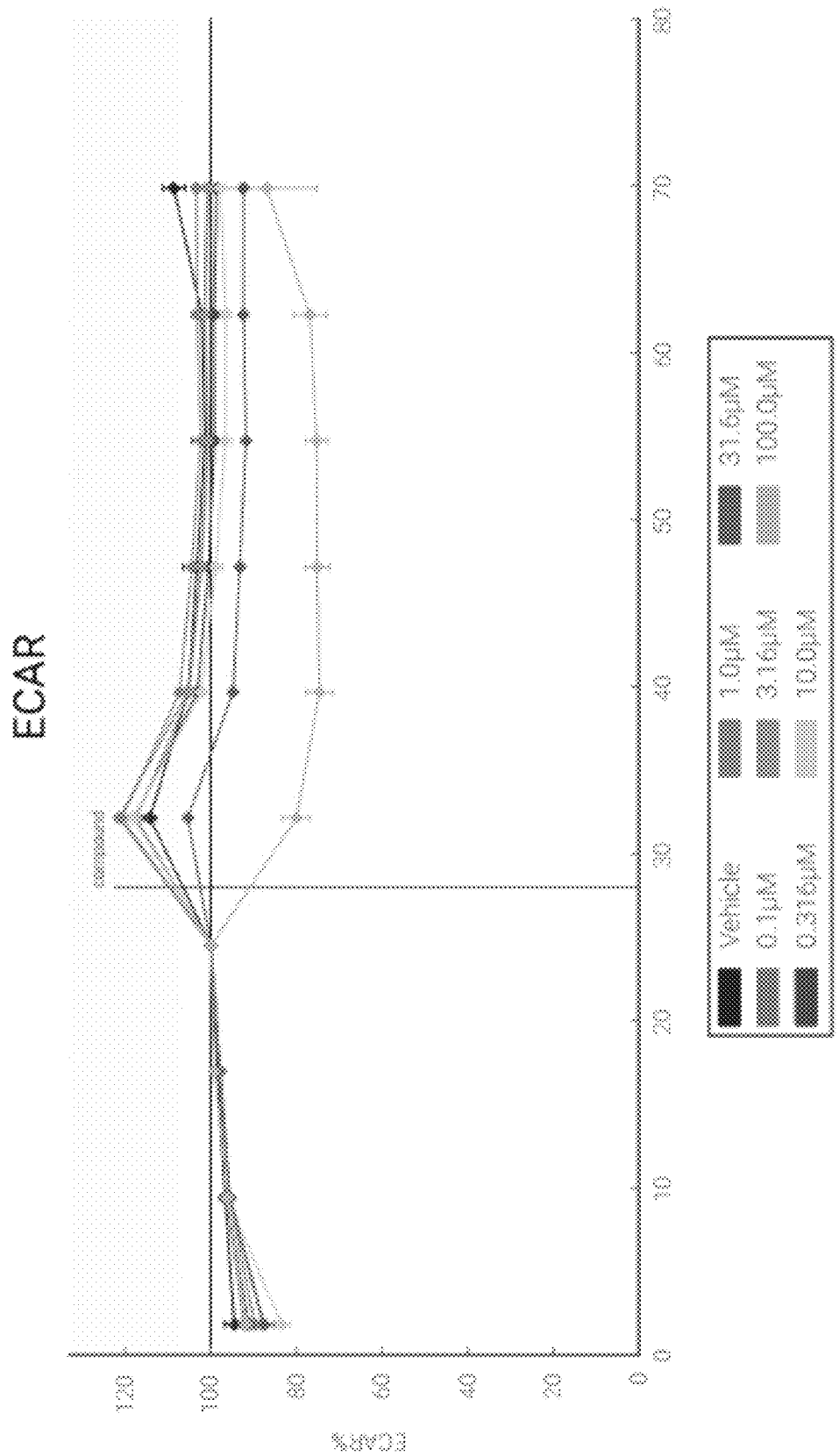
FIG. 13 is a series of graphs showing the effects of compound CV-8814 on extracellular acidification rate.
Figure 13:
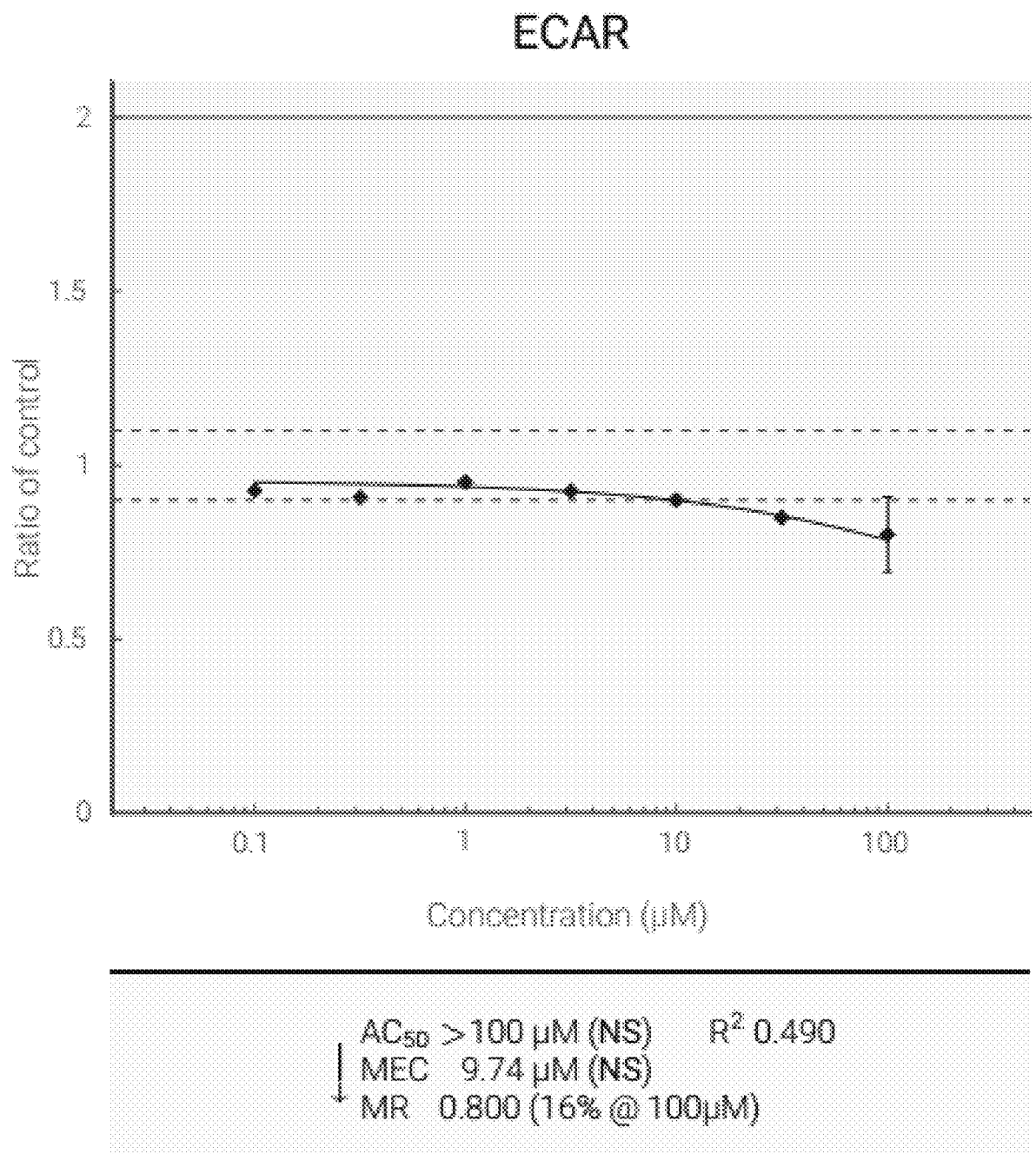

FIG. 13 is a series of graphs showing the effects of compound CV-8814 on extracellular acidification rate.

FIG. 14 is a table summarizing the effects of trimetazidine on various mitochondrial functional parameters.

Figure 15:
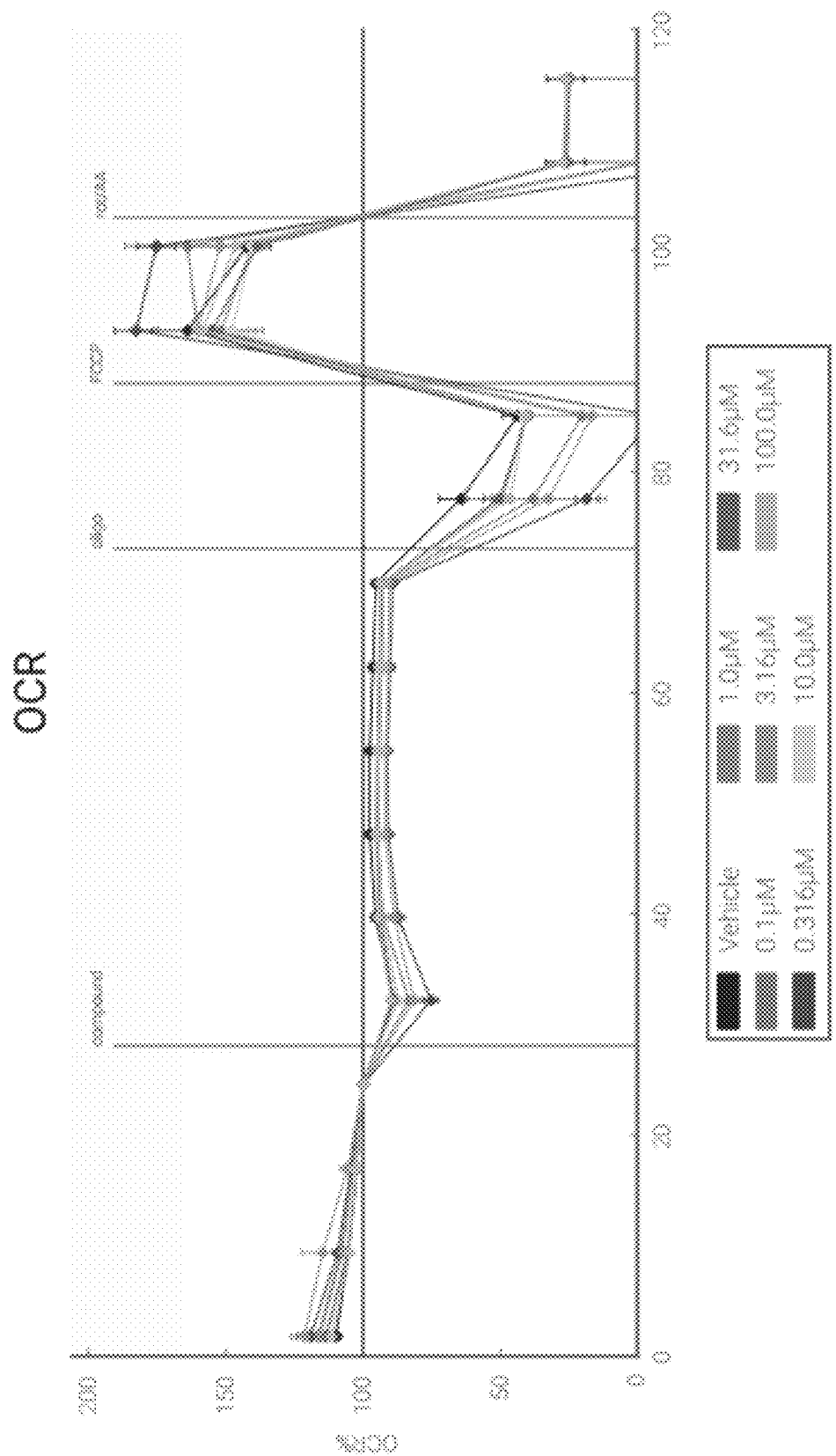
FIG. 15 is a series of graphs showing the effects of trimetazidine on oxygen consumption rate and reserve capacity.
Figure 15:
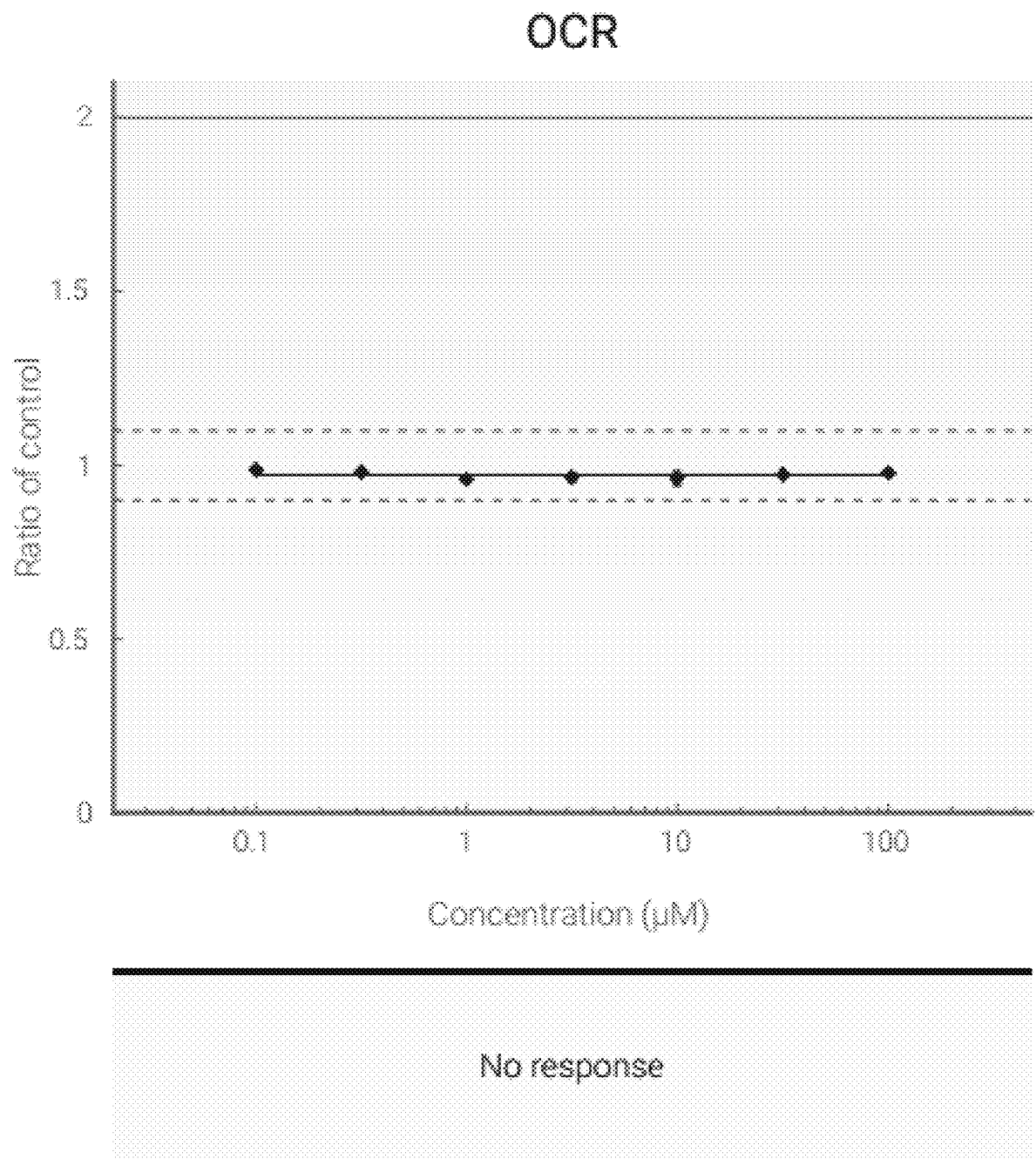
Figure 15:
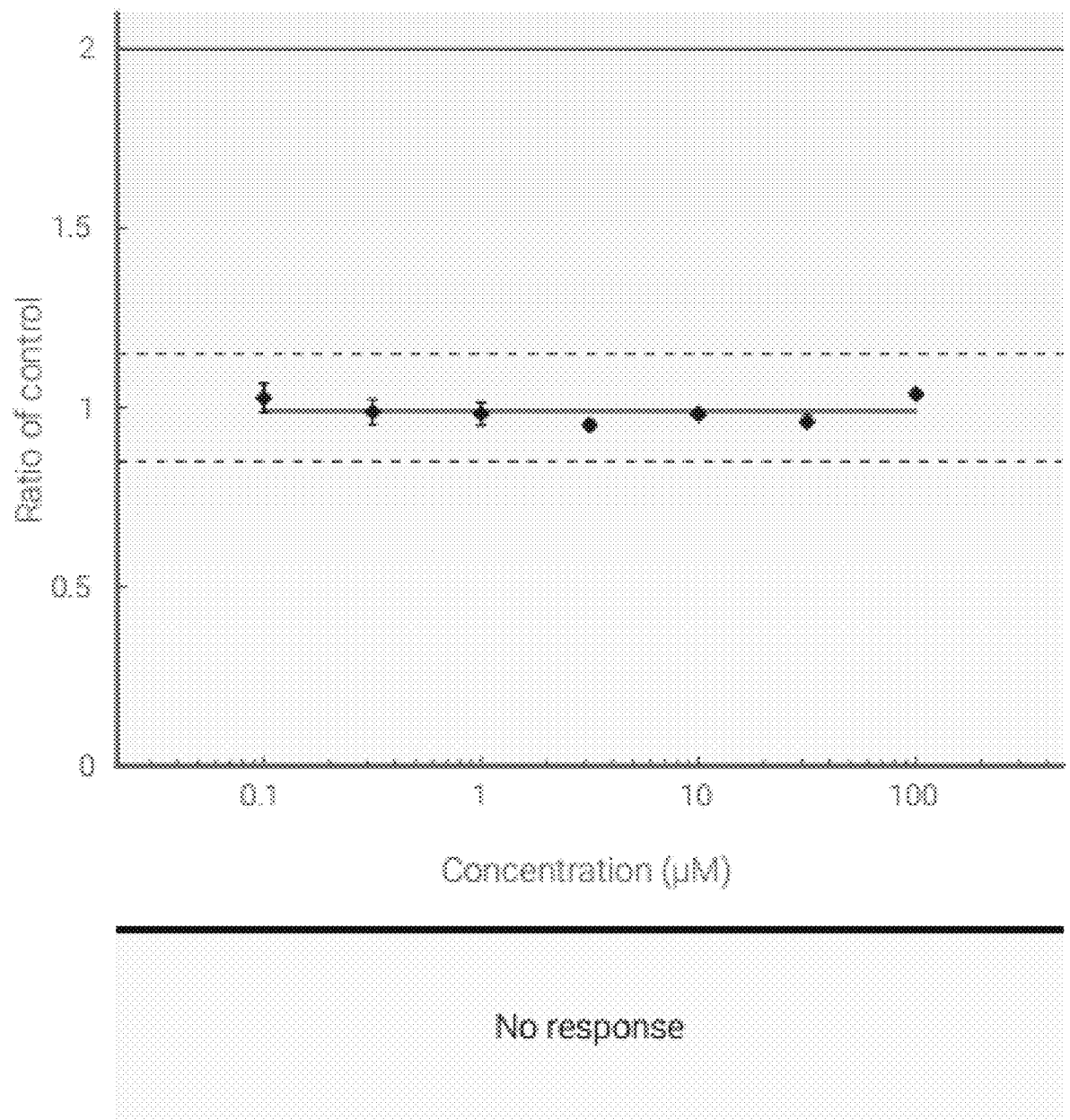

FIG. 15 is a series of graphs showing the effects of trimetazidine on oxygen consumption rate and reserve capacity.

Figure 16:
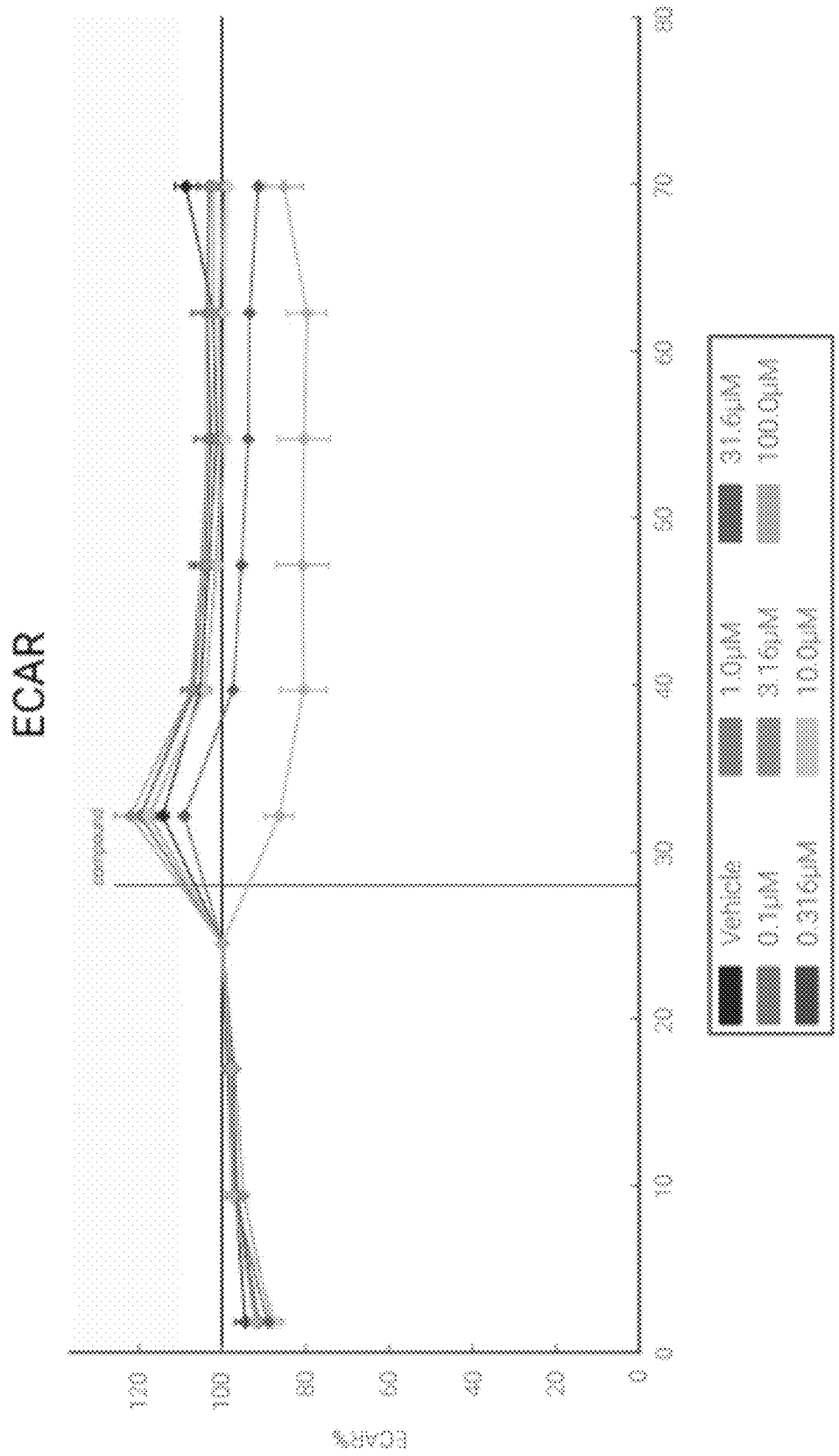
FIG. 16 is a series of graphs showing the effects of trimetazidine on extracellular acidification rate.
Figure 16:
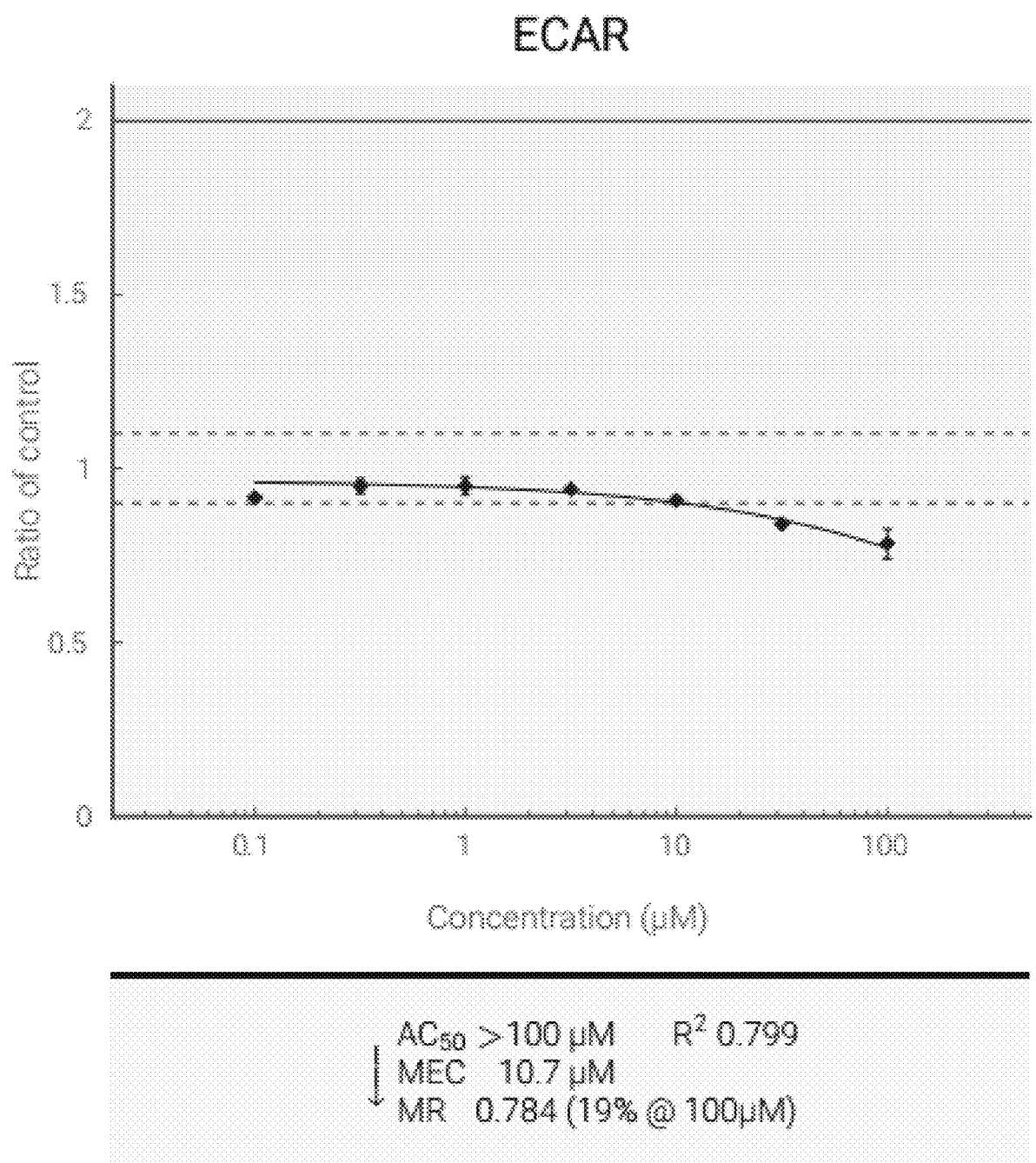

FIG. 16 is a series of graphs showing the effects of trimetazidine on extracellular acidification rate.

FIG. 17 is a table summarizing the effects of a combination of succinate, nicotinamide, and trimetazidine on various mitochondrial functional parameters.

Figure 18:
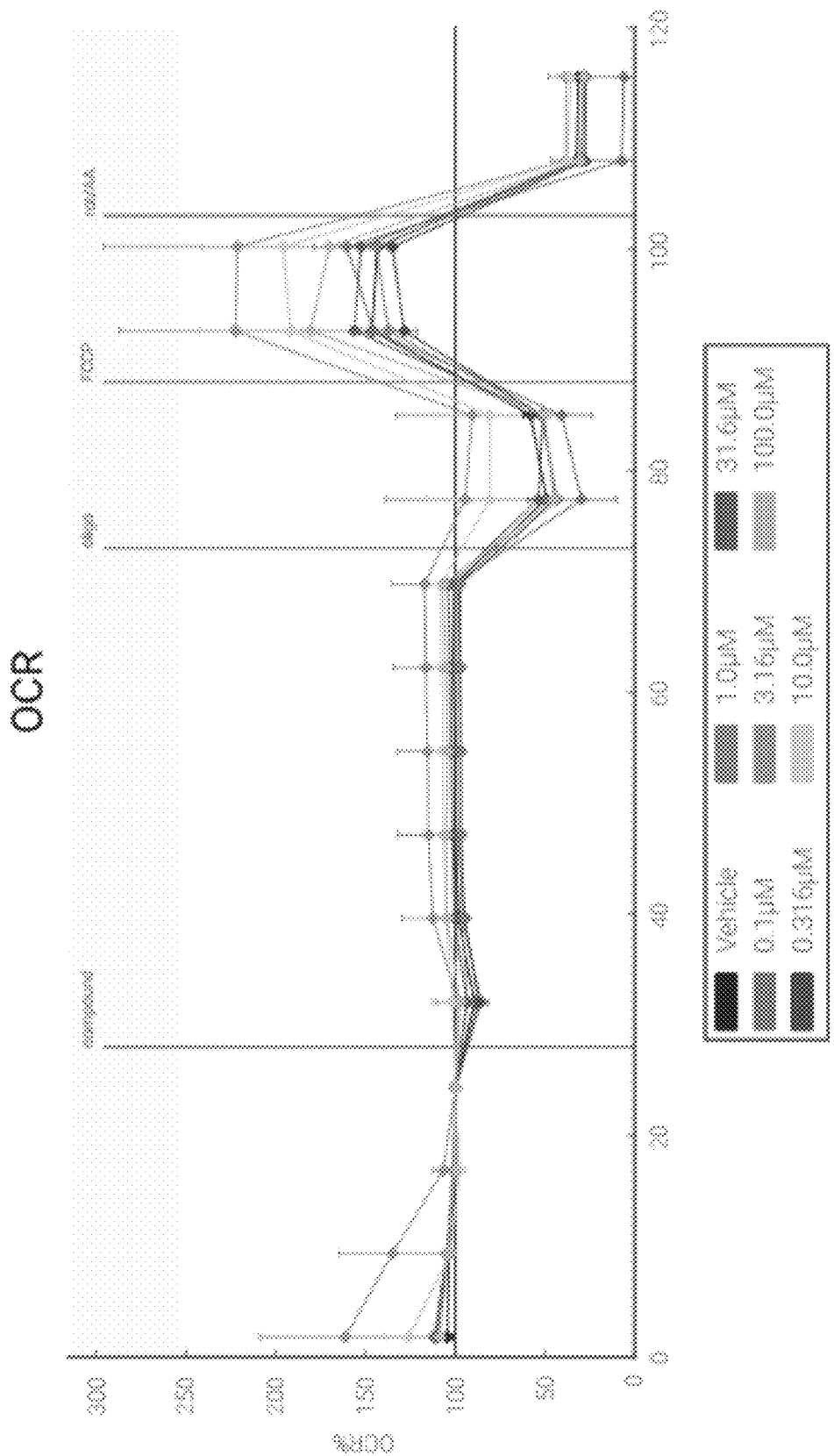
FIG. 18 is a series of graphs showing the effects of a combination of succinate, nicotinamide, and trimetazidine on oxygen consumption rate and reserve capacity.
Figure 18:
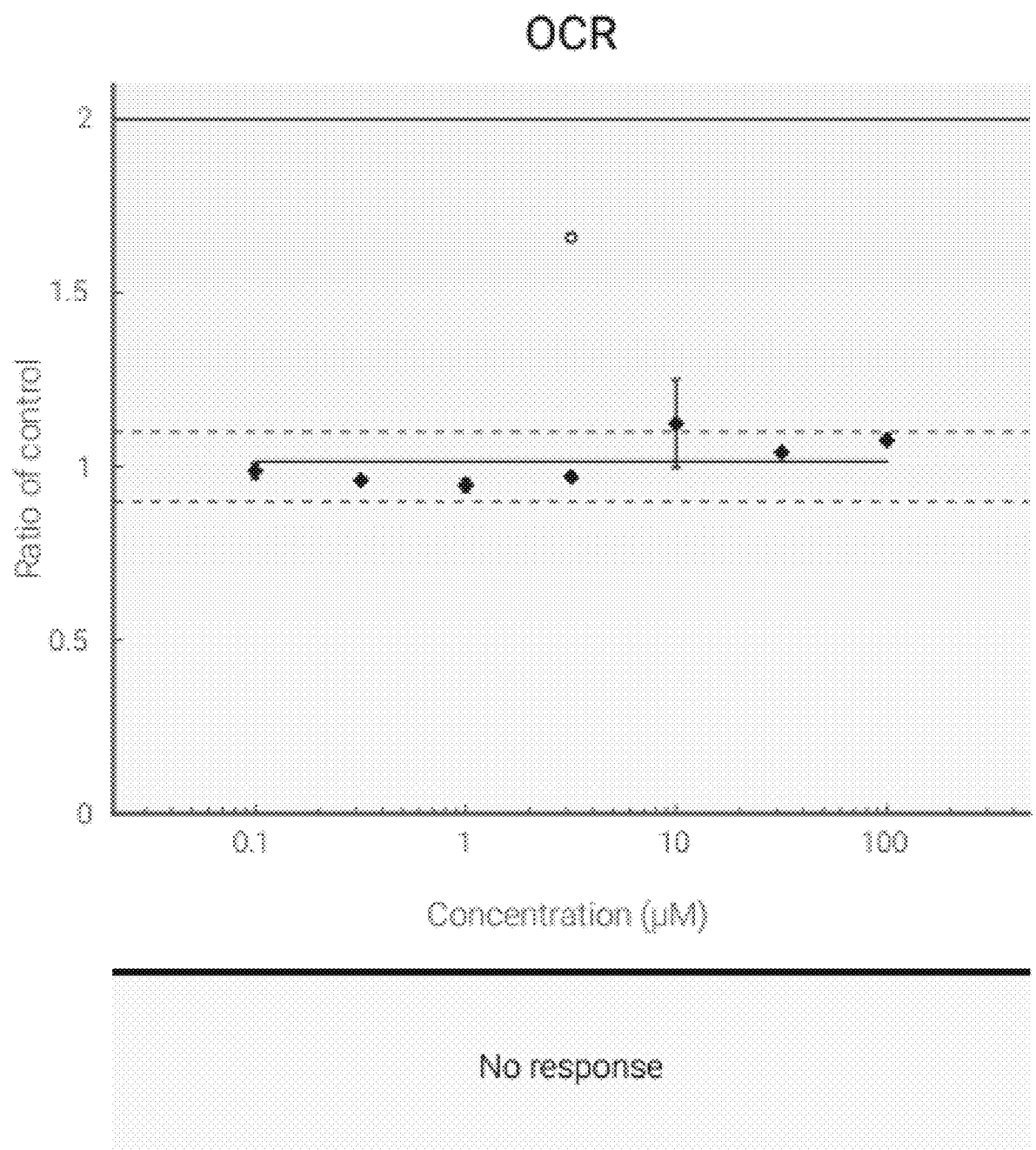
Figure 18:
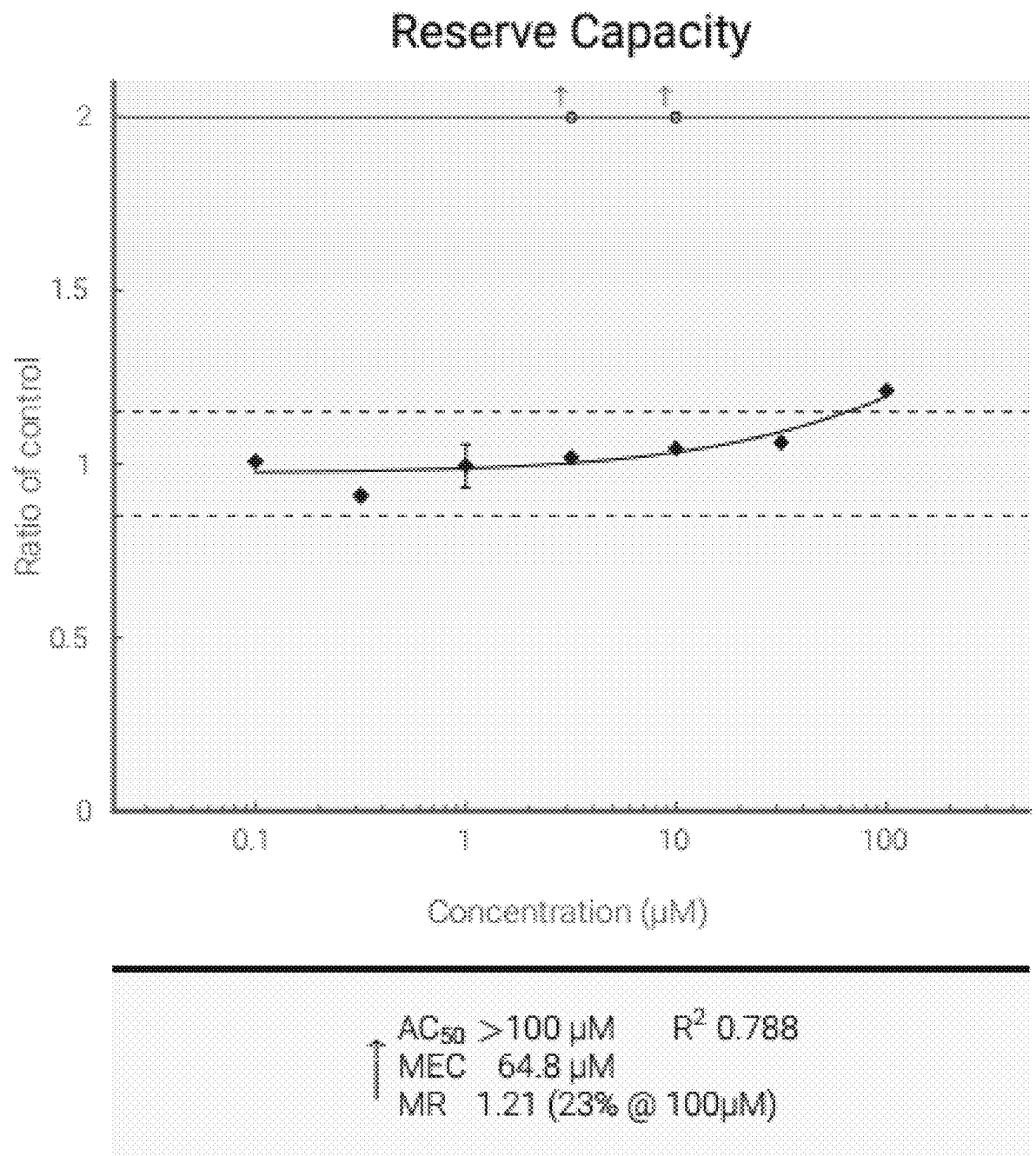

FIG. 18 is a series of graphs showing the effects of a combination of succinate, nicotinamide, and trimetazidine on oxygen consumption rate and reserve capacity.

Figure 19:
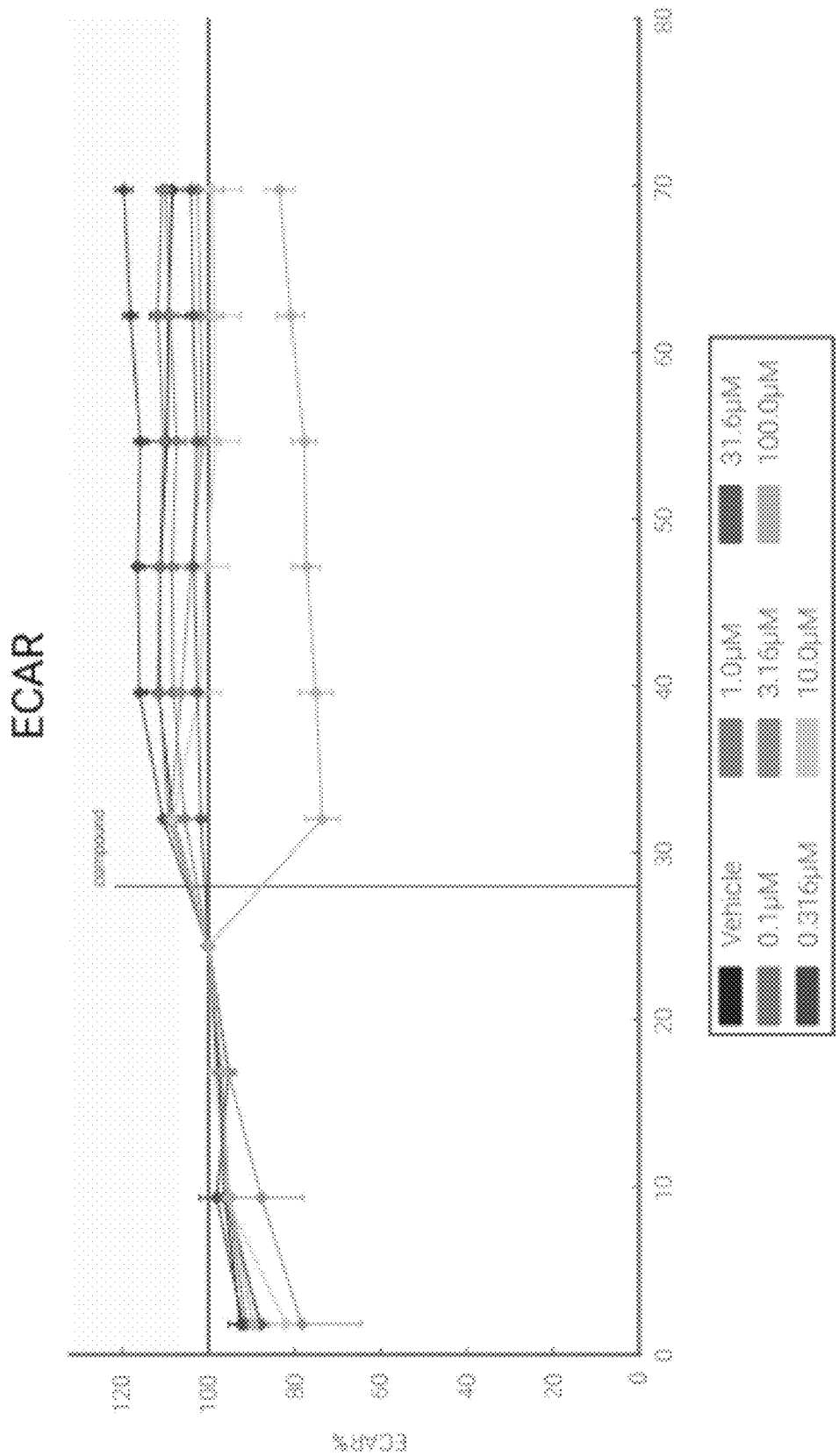
FIG. 19 is a series of graphs showing the effects of a combination of succinate, nicotinamide, and trimetazidine on extracellular acidification rate.
Figure 19:
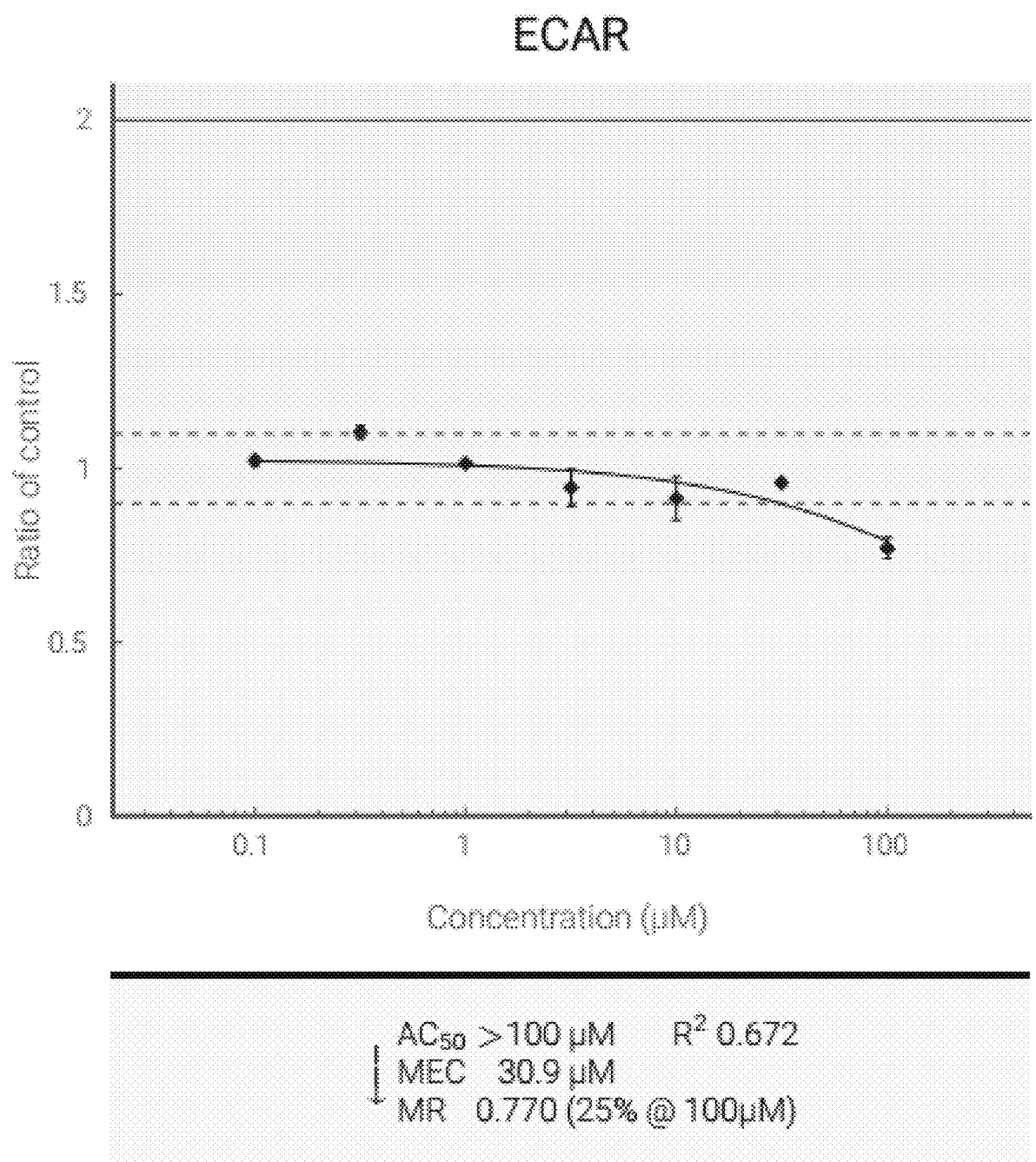

FIG. 19 is a series of graphs showing the effects of a combination of succinate, nicotinamide, and trimetazidine on extracellular acidification rate.

FIG. 20 is a table summarizing the effects of a combination of trimetazidine analog 2 and nicotinamide on various mitochondrial functional parameters.

Figure 21:
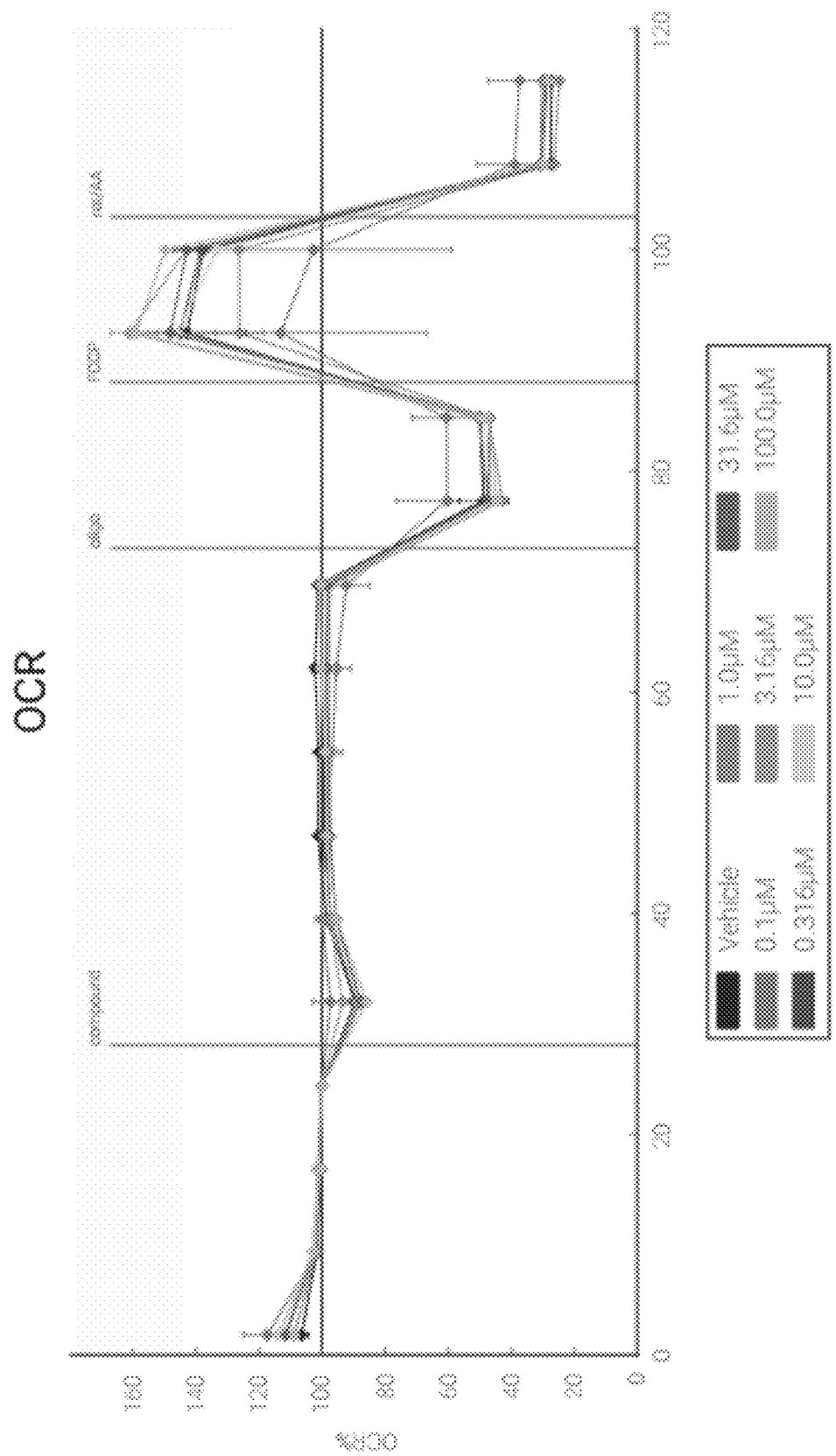
FIG. 21 is a series of graphs showing the effects of a combination of trimetazidine analog 2 and nicotinamide on oxygen consumption rate and reserve capacity.
Figure 21:
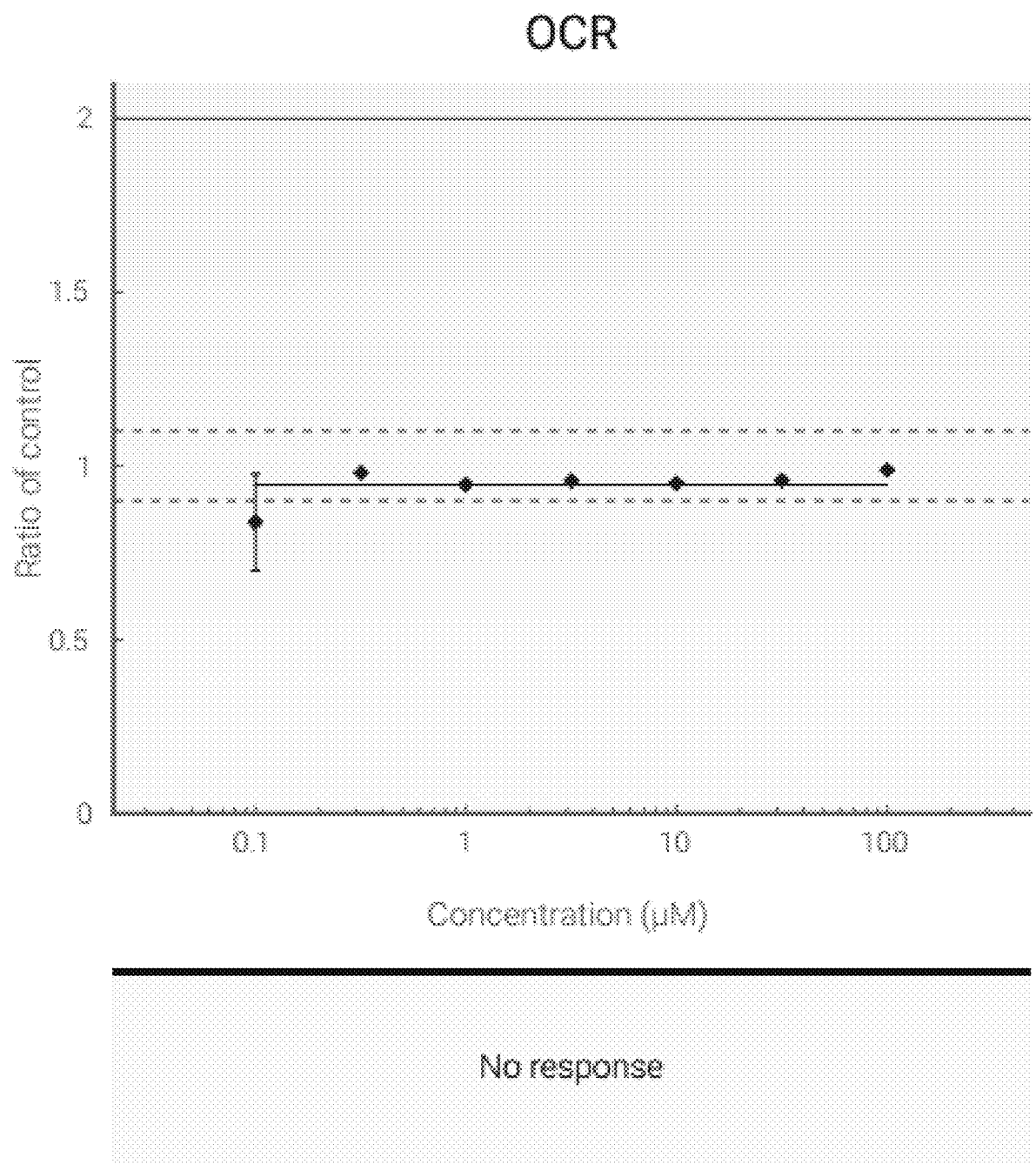
Figure 21:
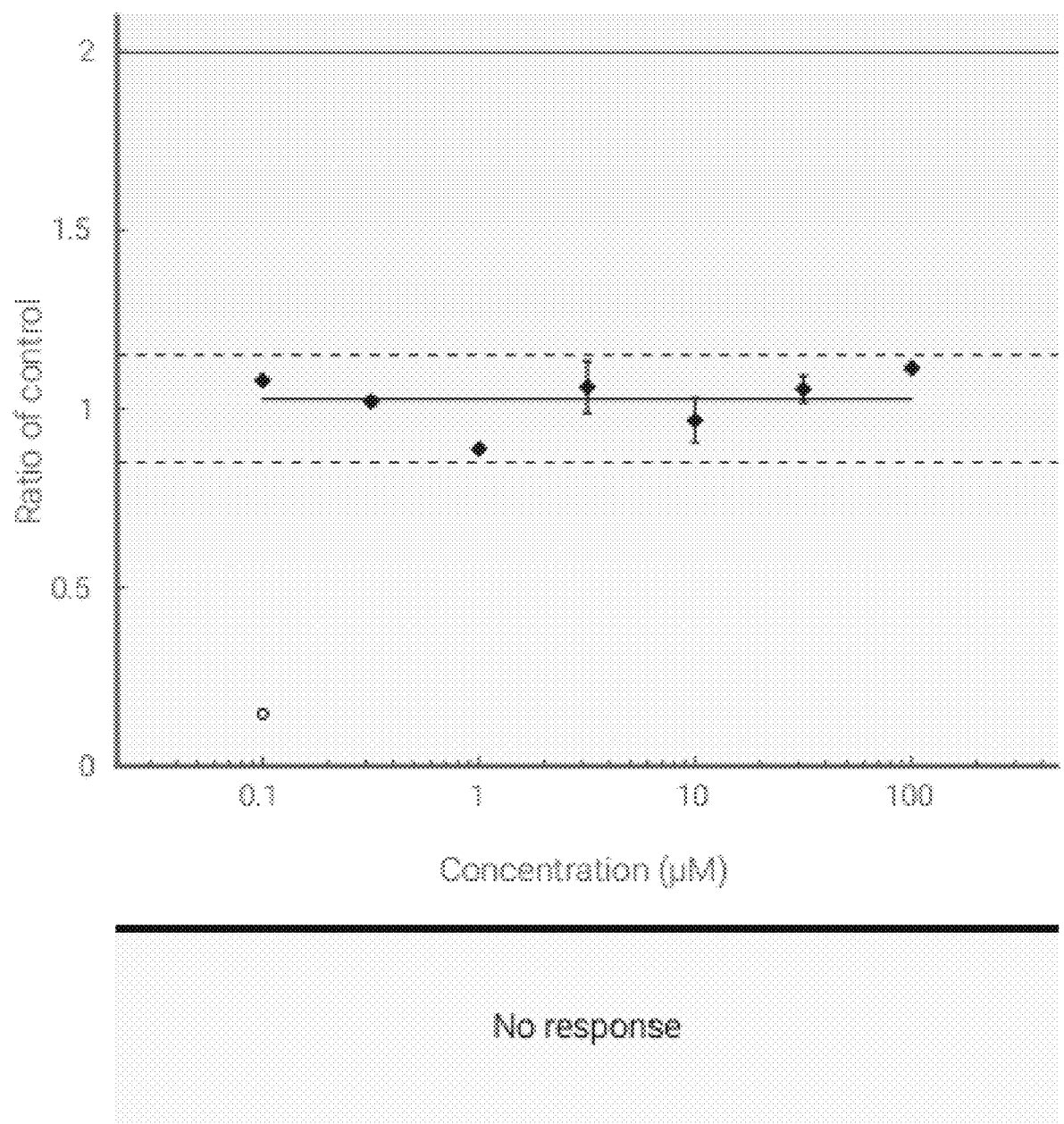

FIG. 21 is a series of graphs showing the effects of a combination of trimetazidine analog 2 and nicotinamide on oxygen consumption rate and reserve capacity.

Figure 22:
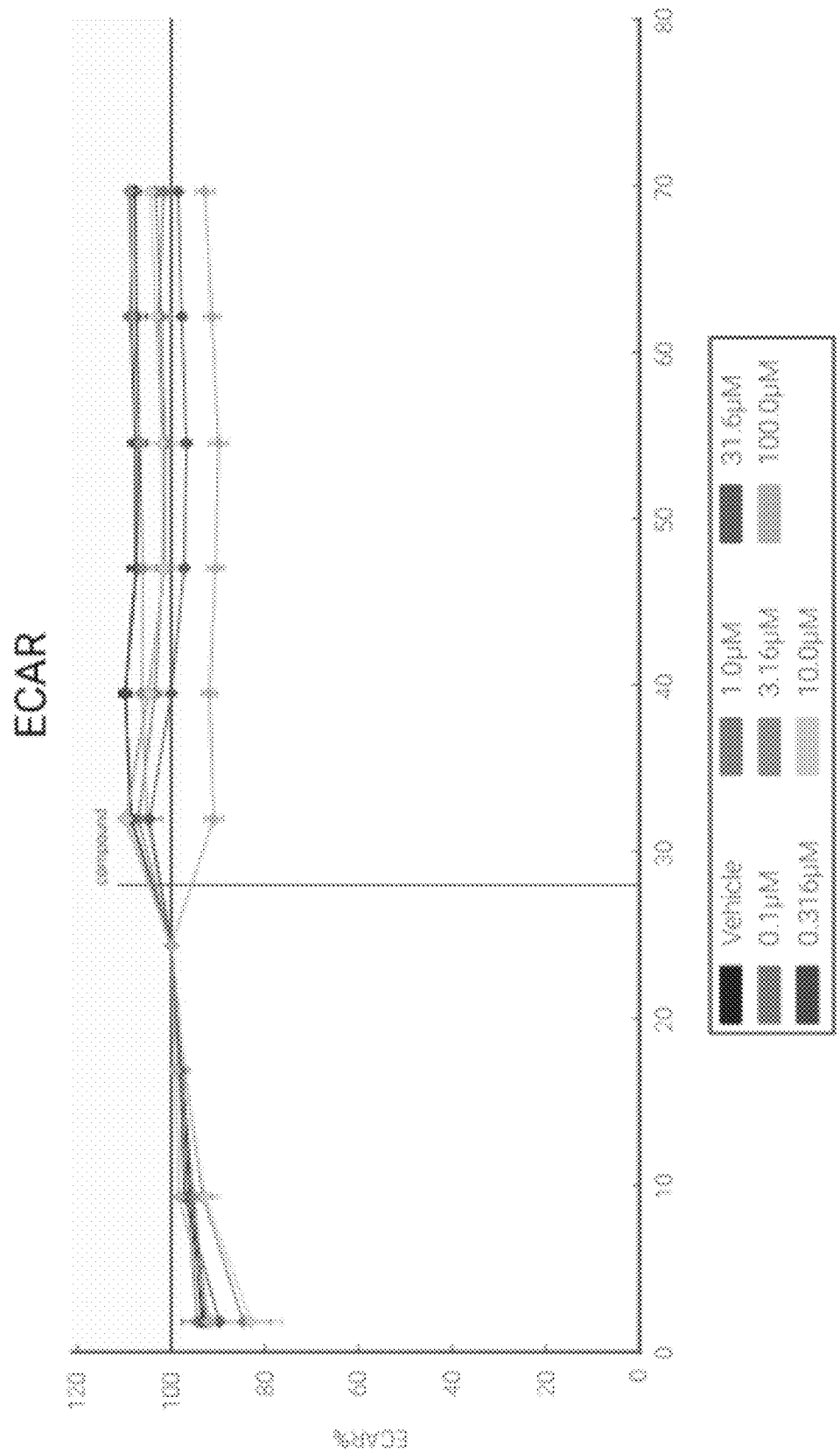
FIG. 22 is a series of graphs showing the effects a combination of trimetazidine analog 2 and nicotinamide on extracellular acidification rate.
Figure 22:
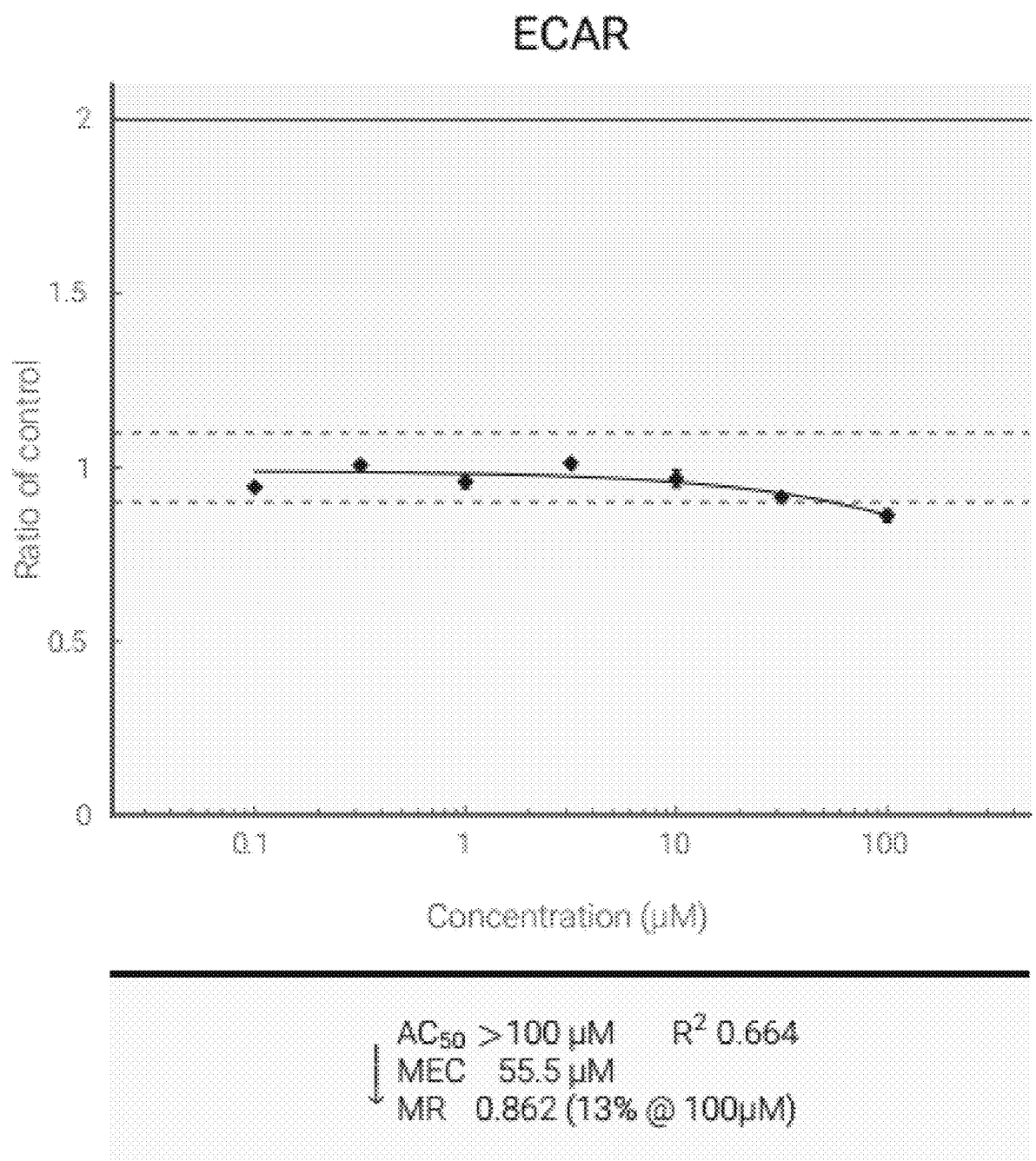

FIG. 22 is a series of graphs showing the effects a combination of trimetazidine analog 2 and nicotinamide on extracellular acidification rate.

FIG. 23 is a table summarizing the effects of a combination of trimetazidine analog 1 and nicotinamide on various mitochondrial functional parameters.

Figure 24:
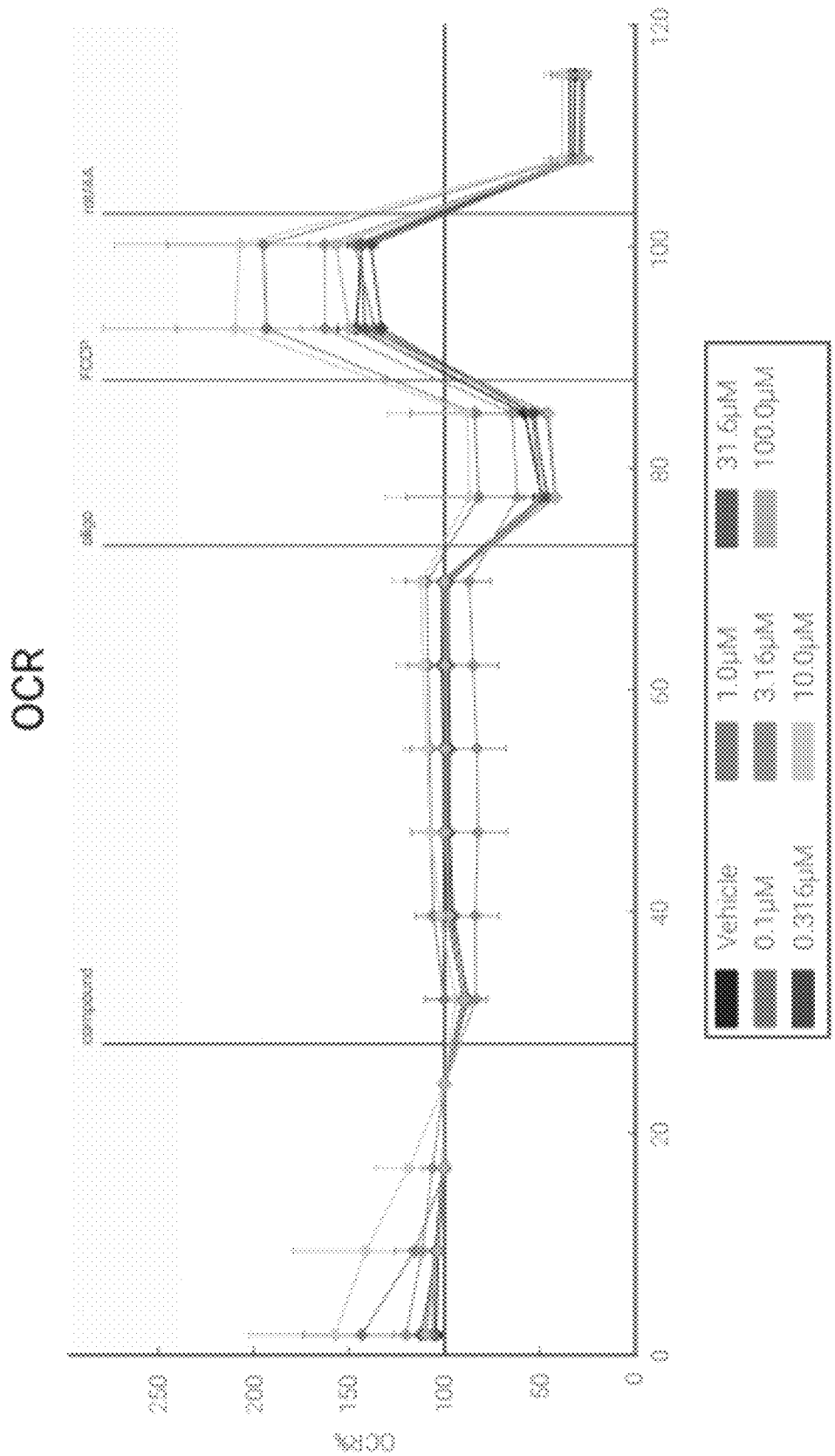
FIG. 24 is a series of graphs showing the effects of a combination of trimetazidine analog 1 and nicotinamide on oxygen consumption rate and reserve capacity.
Figure 24:
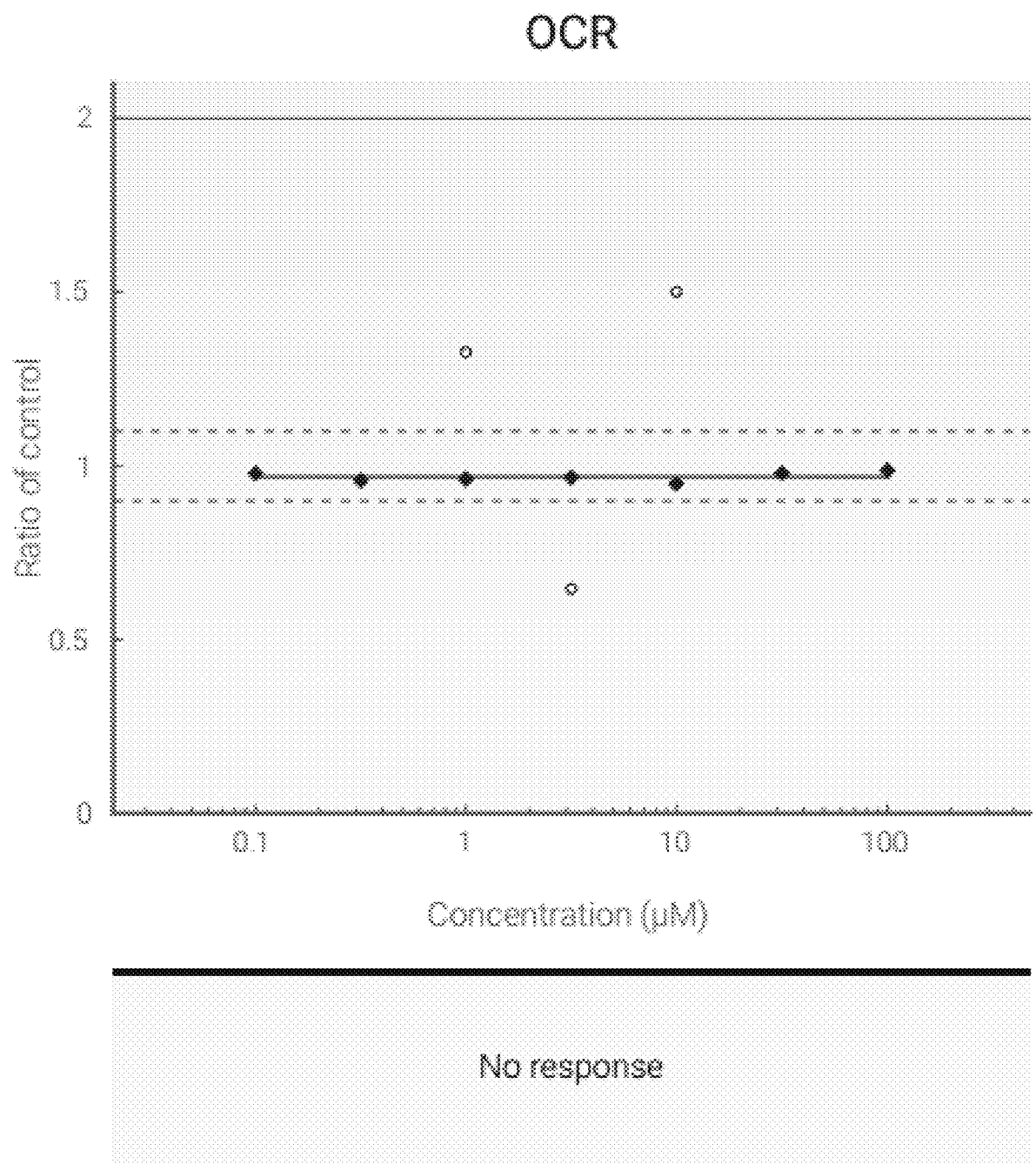
Figure 24:
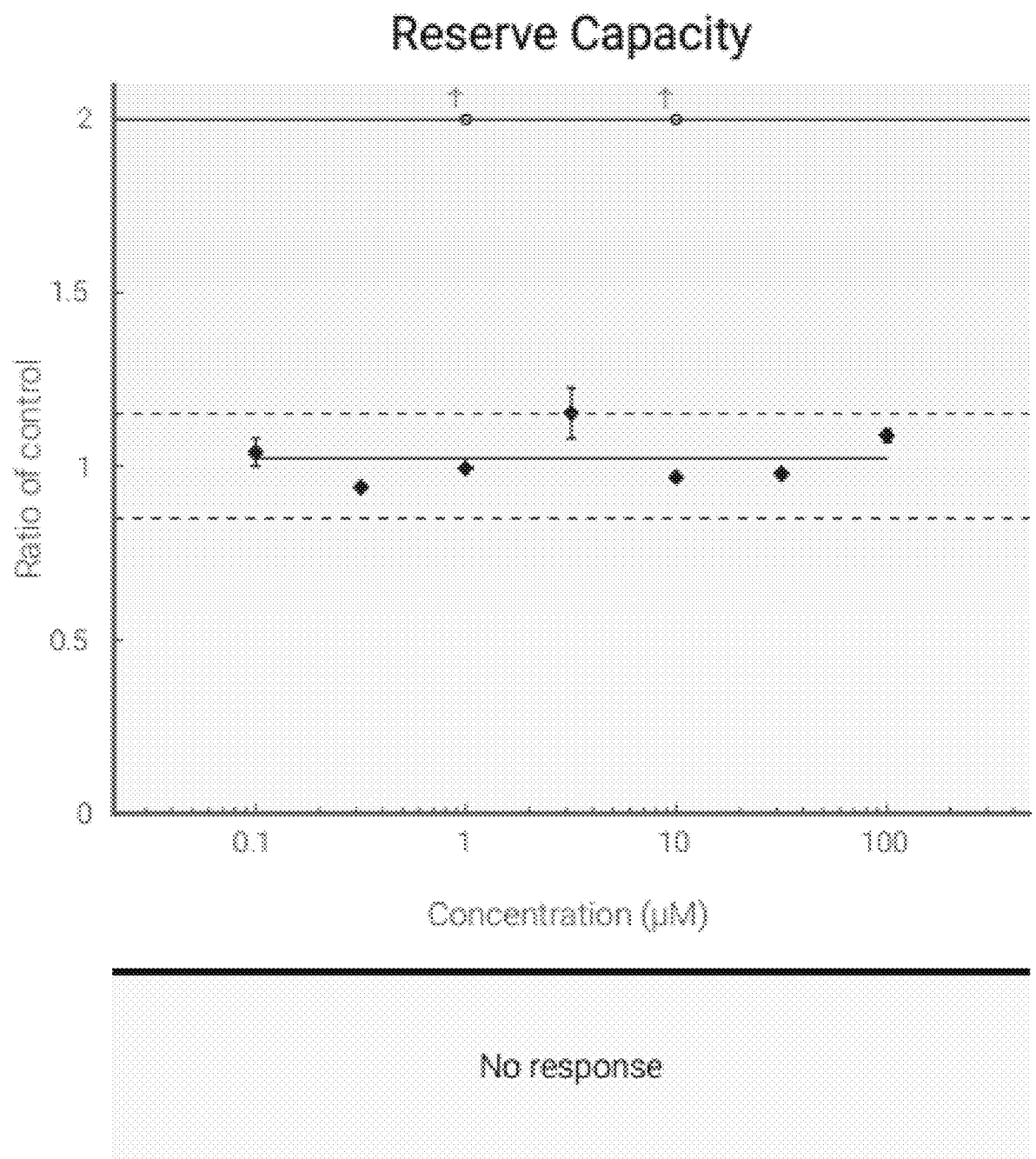

FIG. 24 is a series of graphs showing the effects of a combination of trimetazidine analog 1 and nicotinamide on oxygen consumption rate and reserve capacity.

Figure 25:
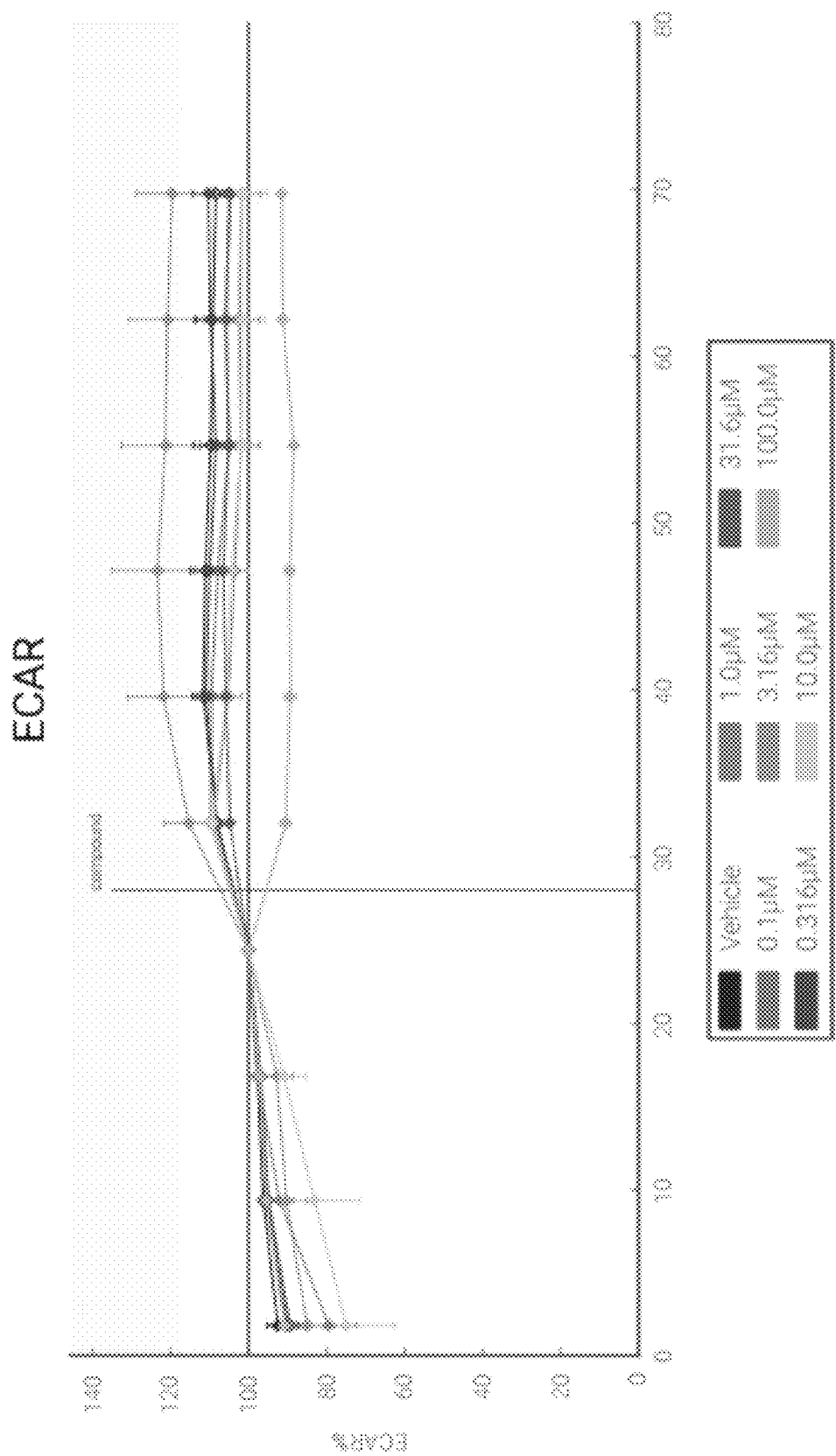
FIG. 25 is a series of graphs showing the effects of a combination of trimetazidine analog 1 and nicotinamide on extracellular acidification rate.
Figure 25:
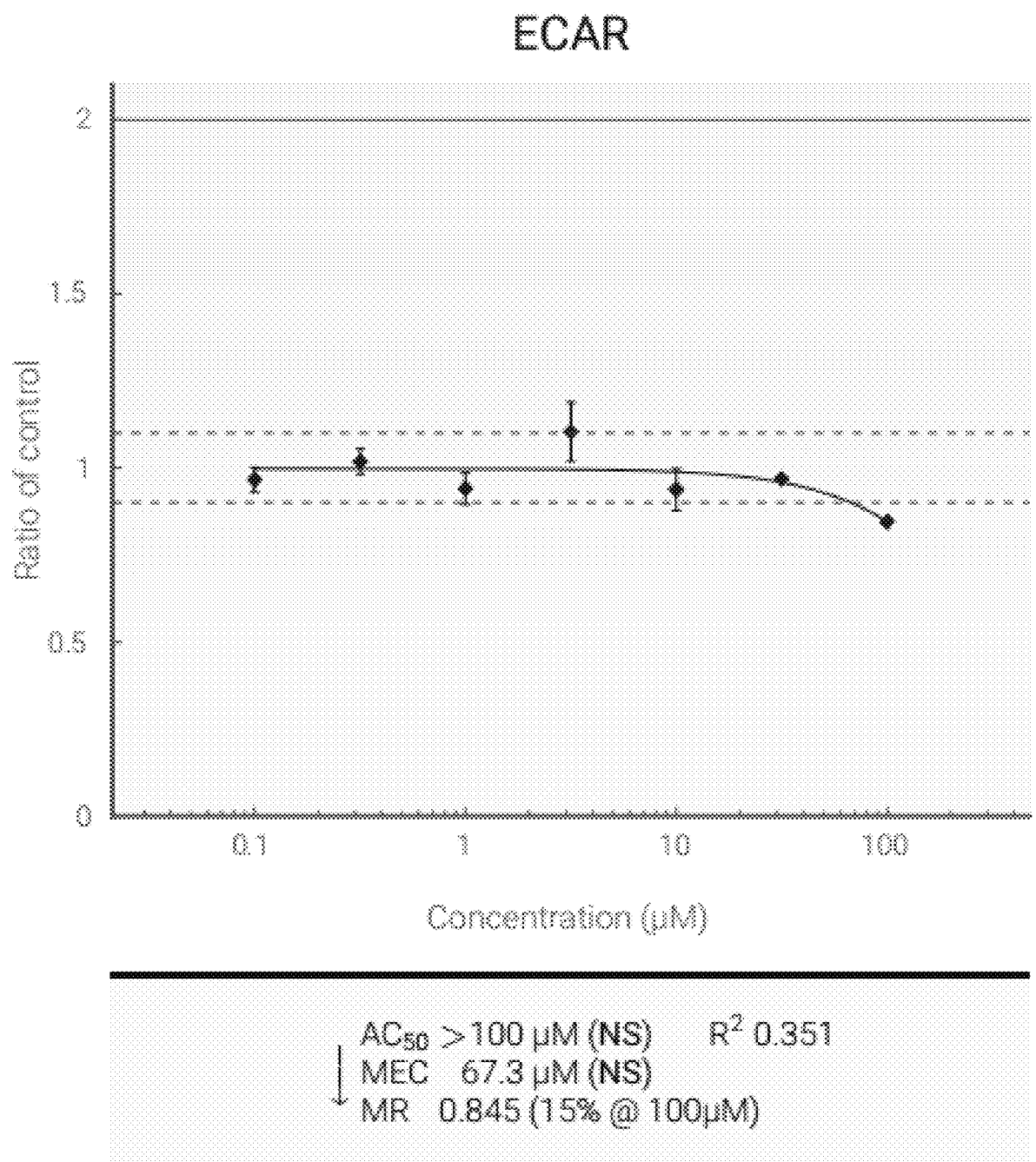

FIG. 25 is a series of graphs showing the effects of a combination of trimetazidine analog 1 and nicotinamide on extracellular acidification rate.

FIG. 26 is a table summarizing the effects of a combination of trimetazidine analog 3 and nicotinamide on various mitochondrial functional parameters.

Figure 27:
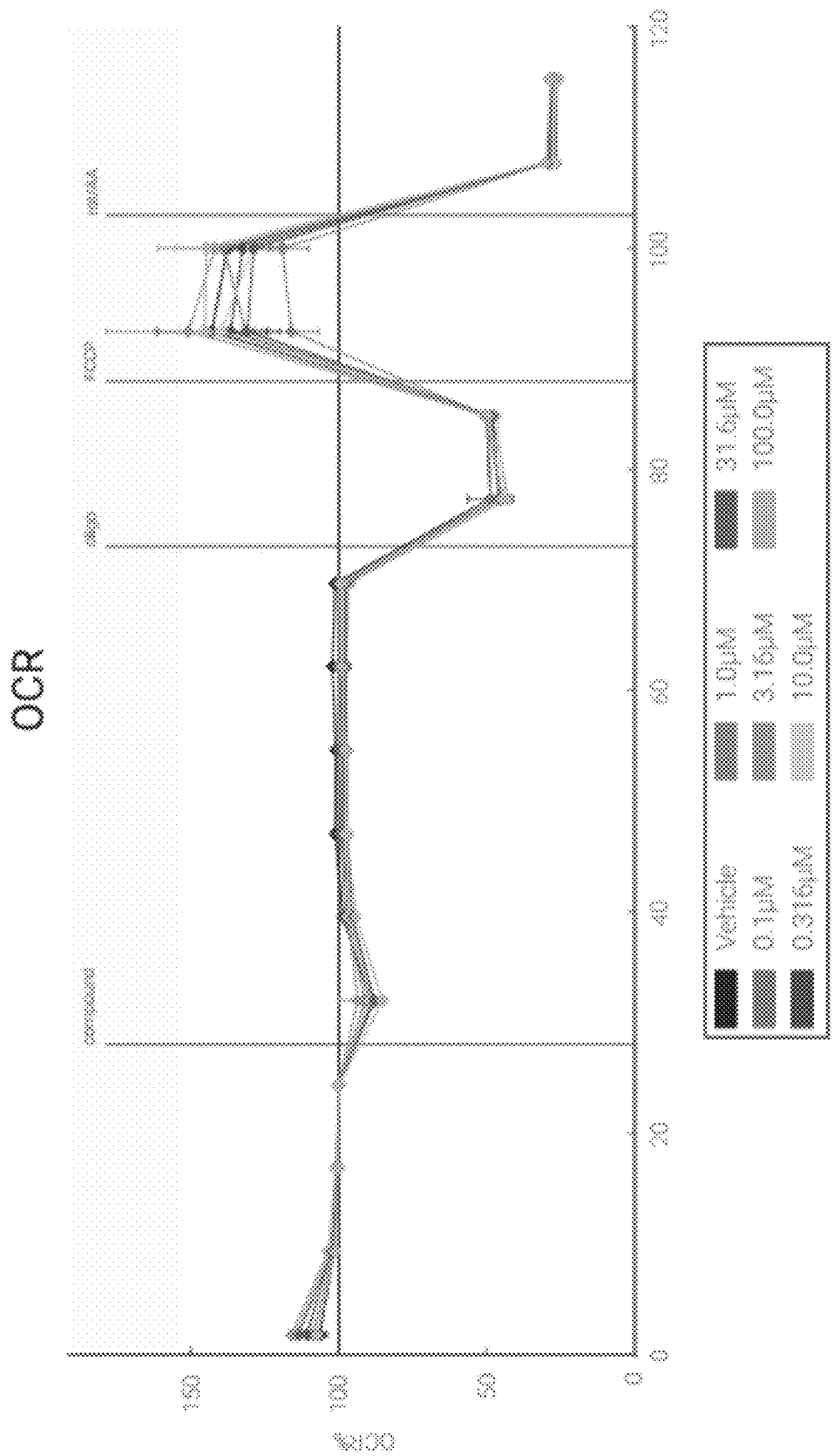
FIG. 27 is a series of graphs showing the effects of a combination of trimetazidine analog 3 and nicotinamide on oxygen consumption rate and reserve capacity.
Figure 27:
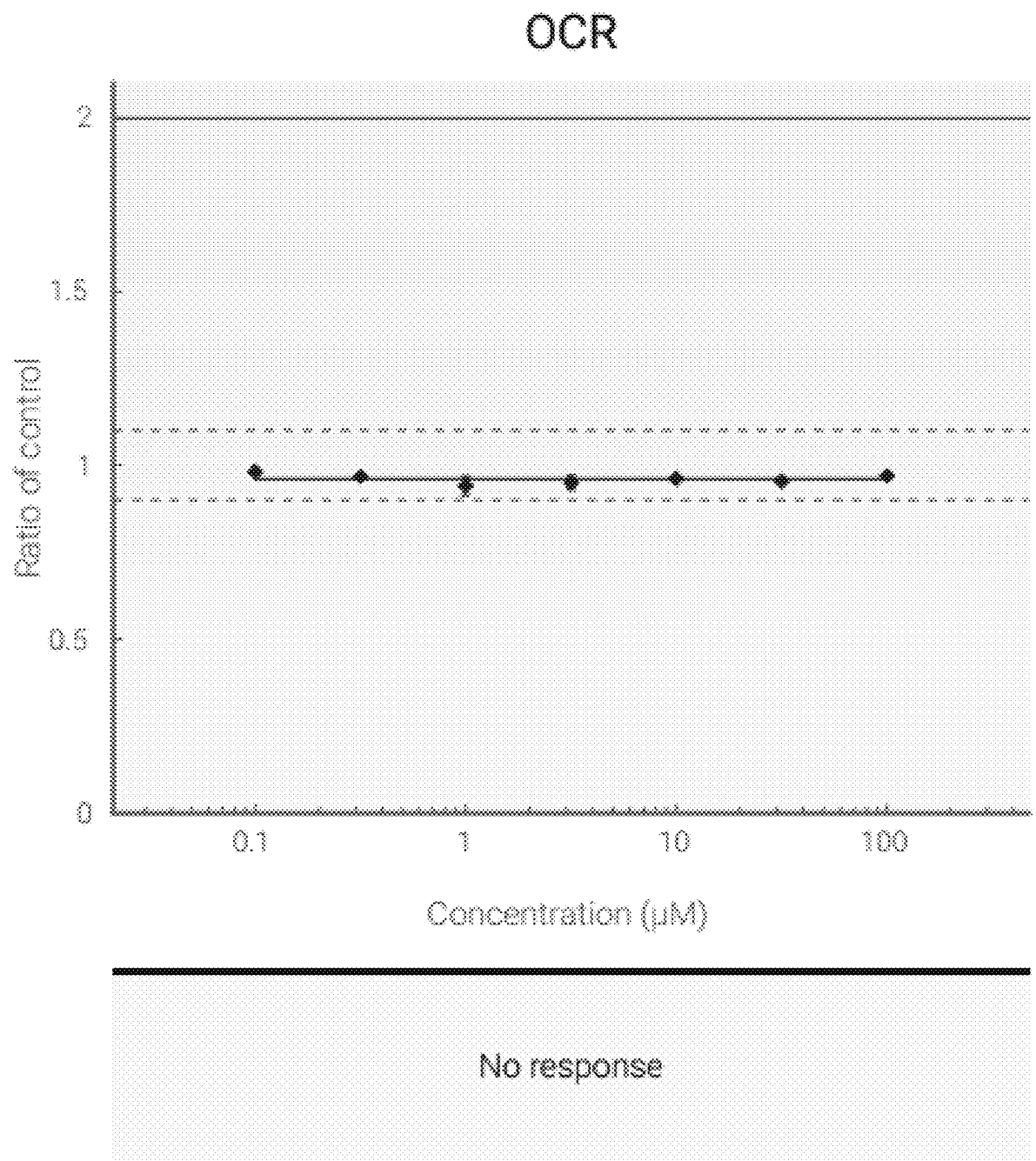
Figure 27:
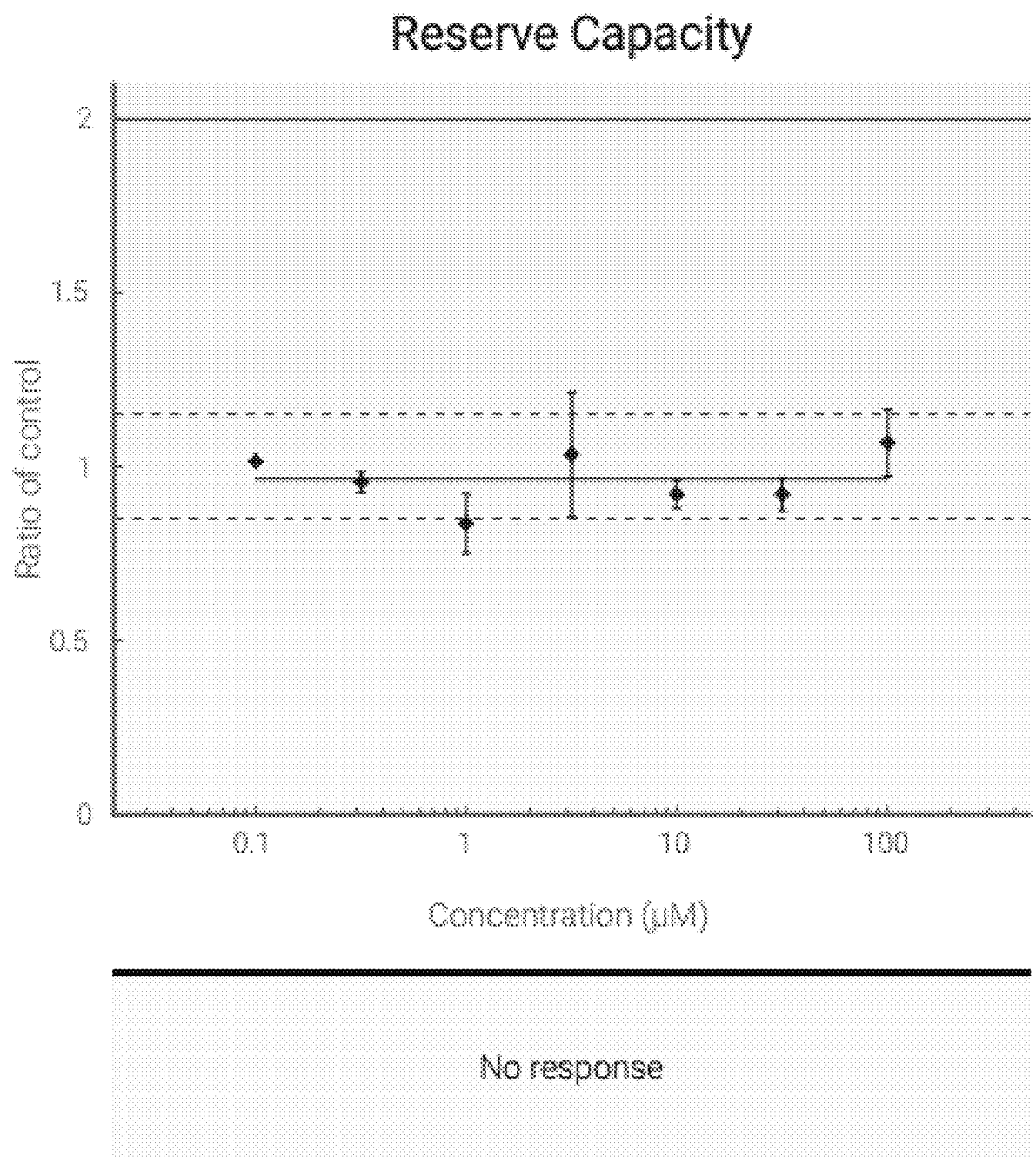

FIG. 27 is a series of graphs showing the effects of a combination of trimetazidine analog 3 and nicotinamide on oxygen consumption rate and reserve capacity.

Figure 28:
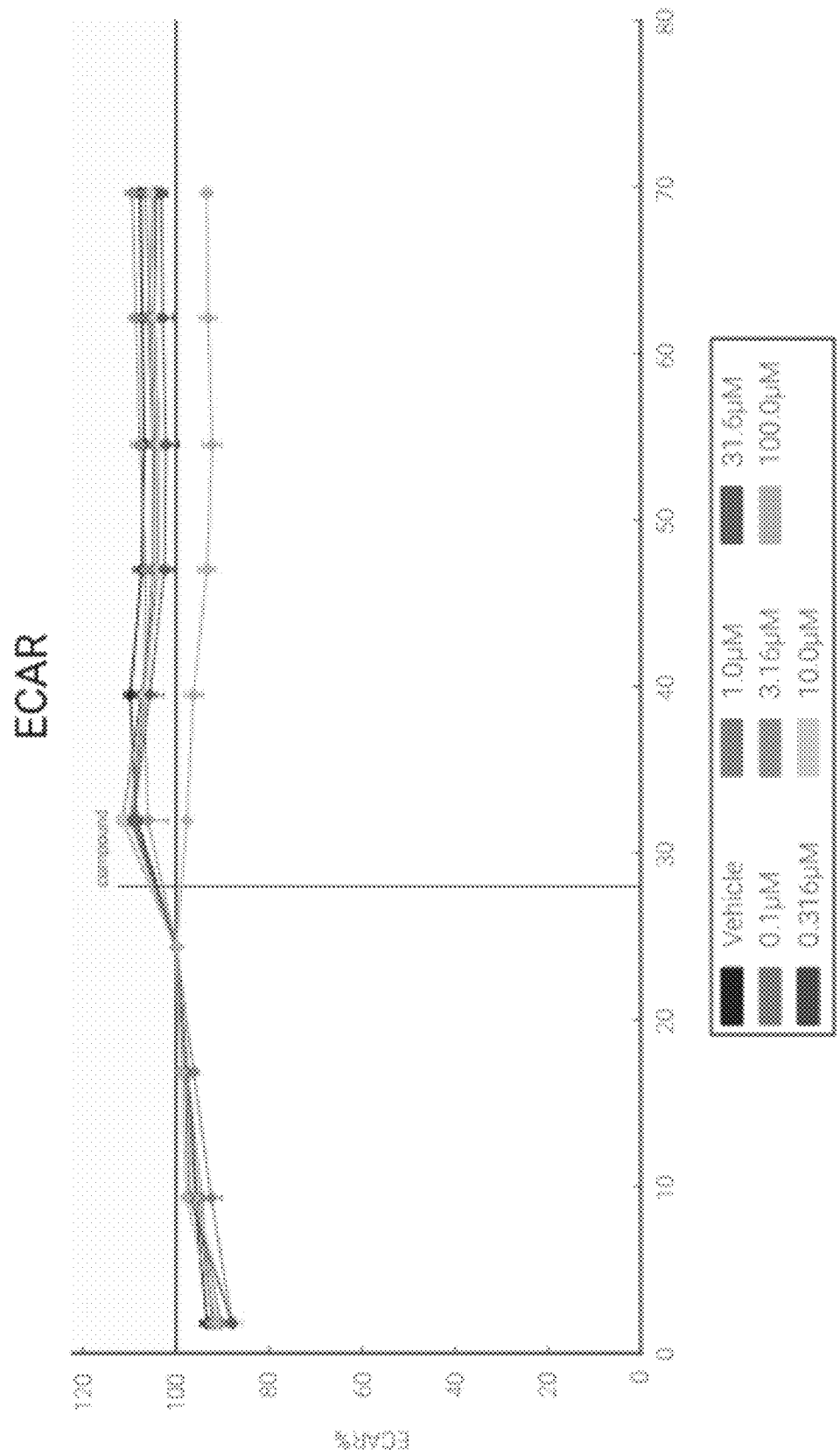
FIG. 28 is a series of graphs showing the effects of a combination of trimetazidine analog 3 and nicotinamide on extracellular acidification rate.
Figure 28:
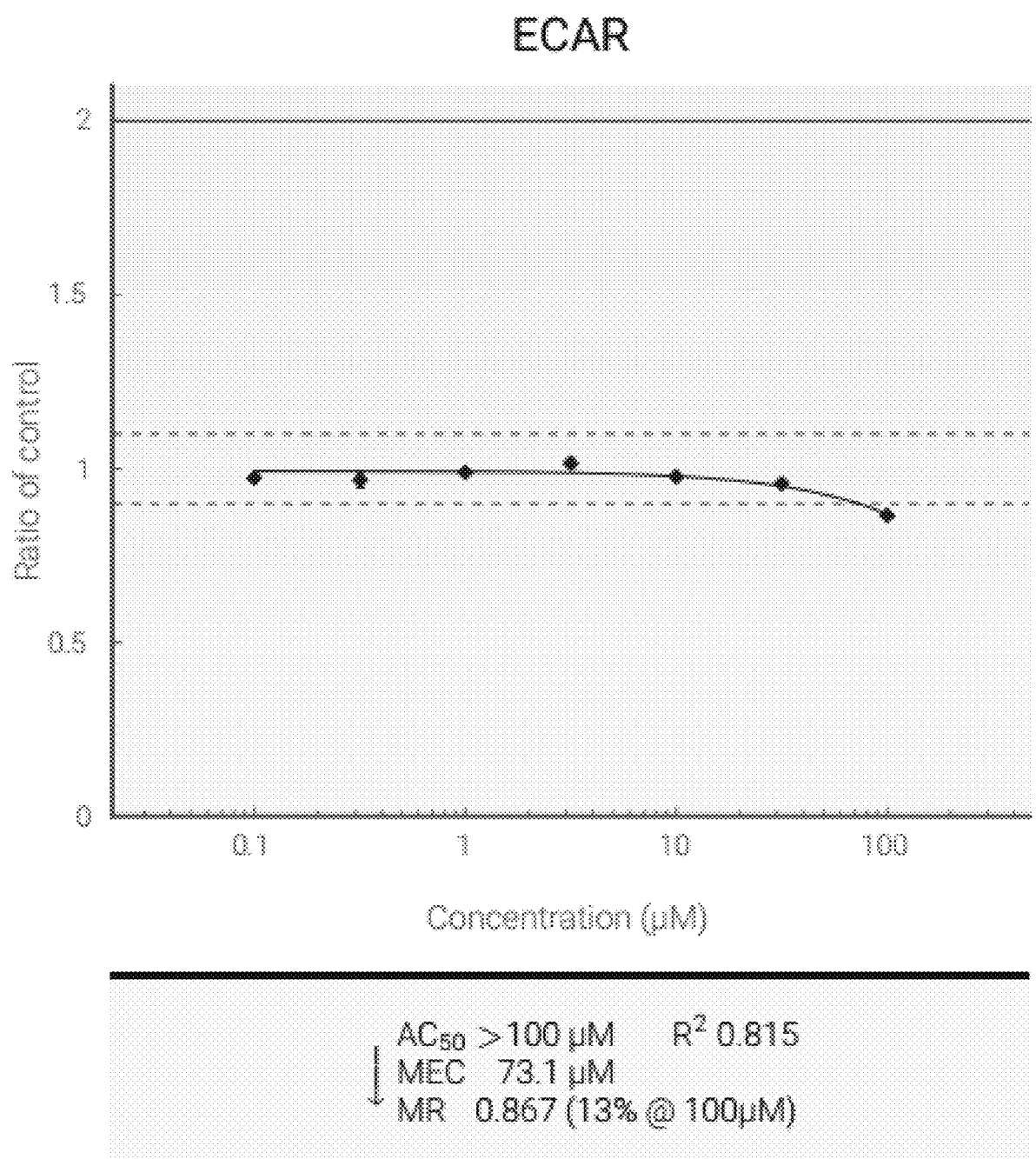

FIG. 28 is a series of graphs showing the effects of a combination of trimetazidine analog 3 and nicotinamide on extracellular acidification rate.

FIG. 29 is a table summarizing the effects of a combination of succinate and nicotinamide on various mitochondrial functional parameters.

Figure 30:
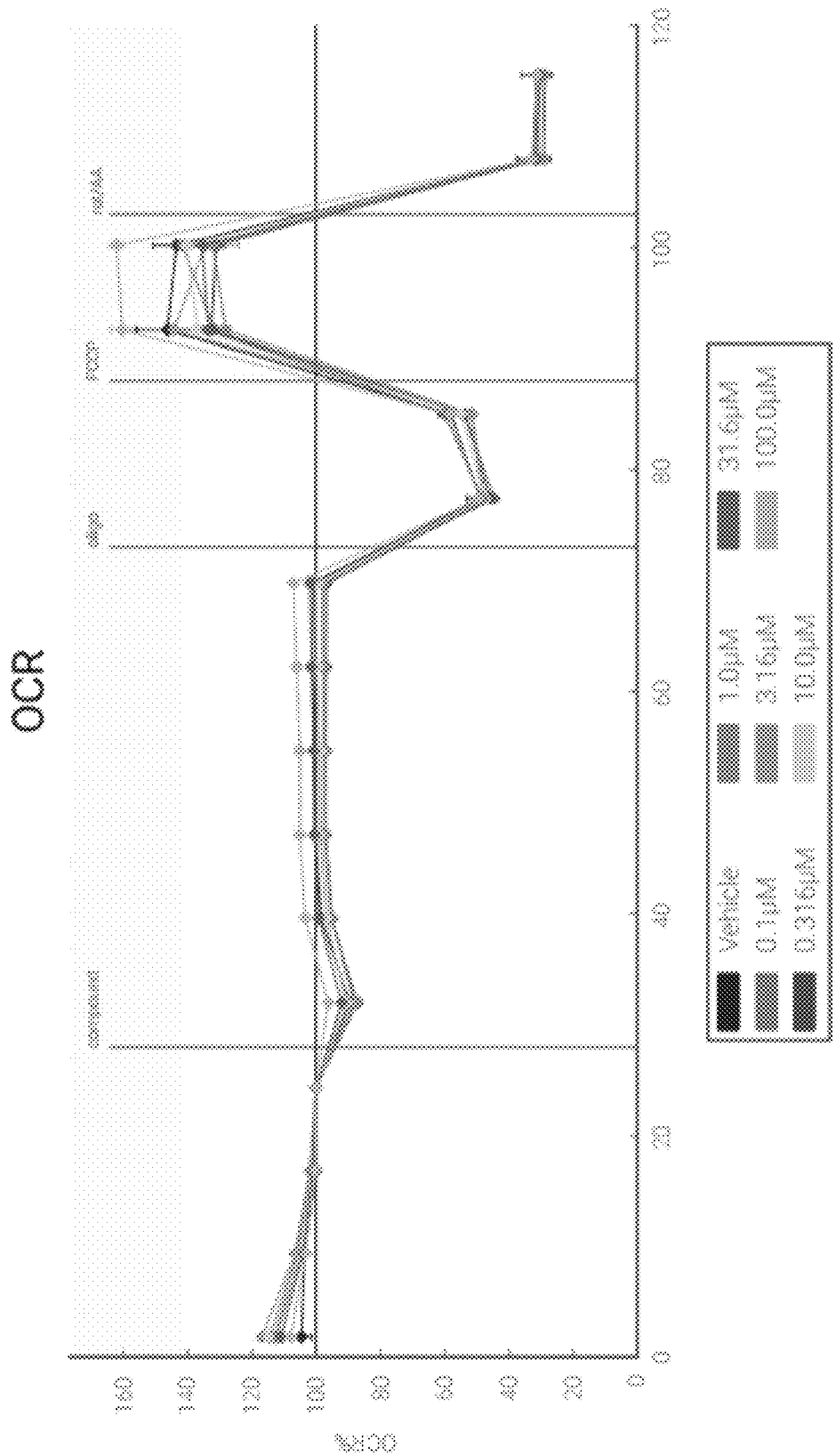
FIG. 30 is a series of graphs showing the effects of a combination of succinate and nicotinamide on oxygen consumption rate and reserve capacity.
Figure 30:
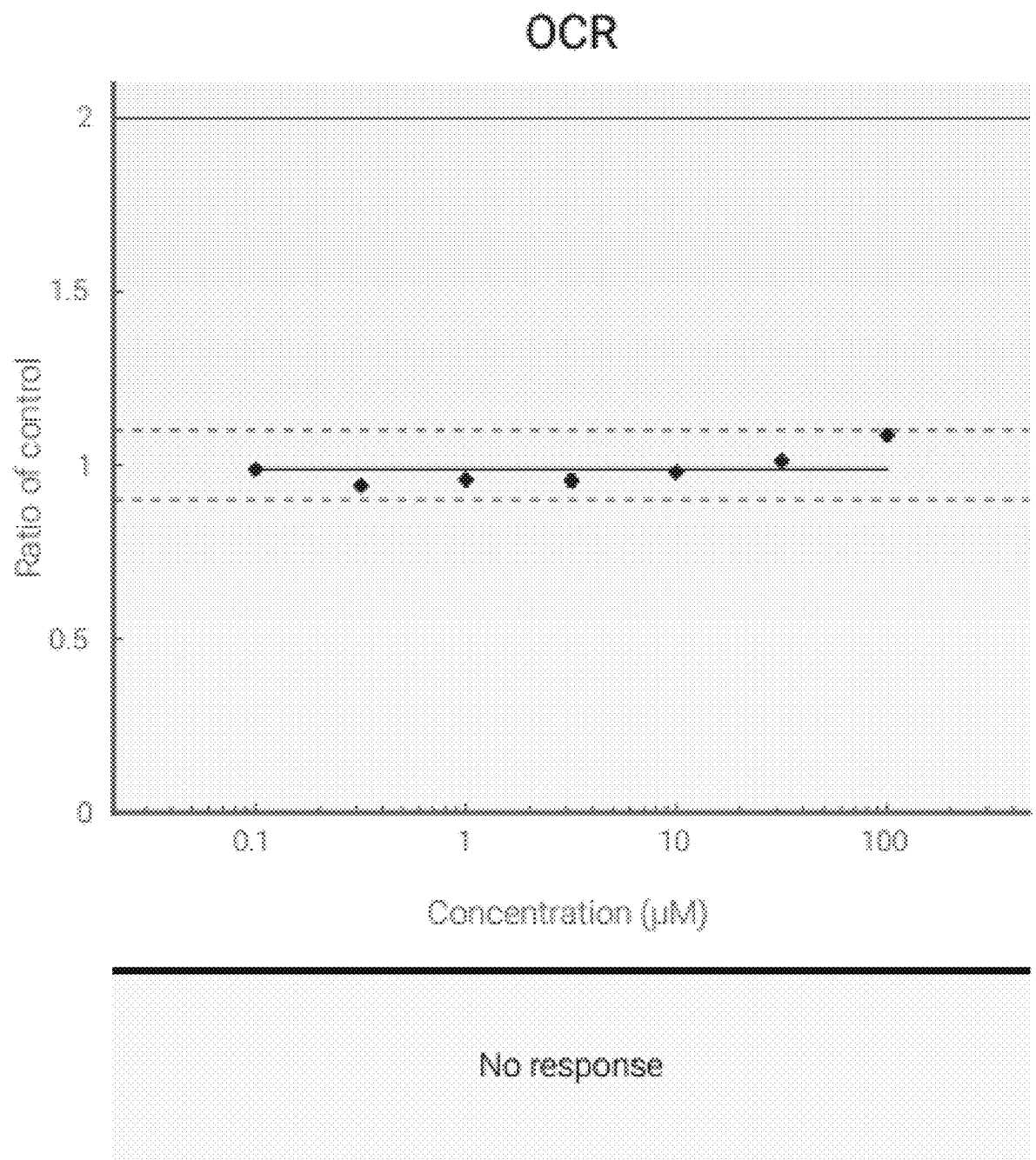
Figure 30:
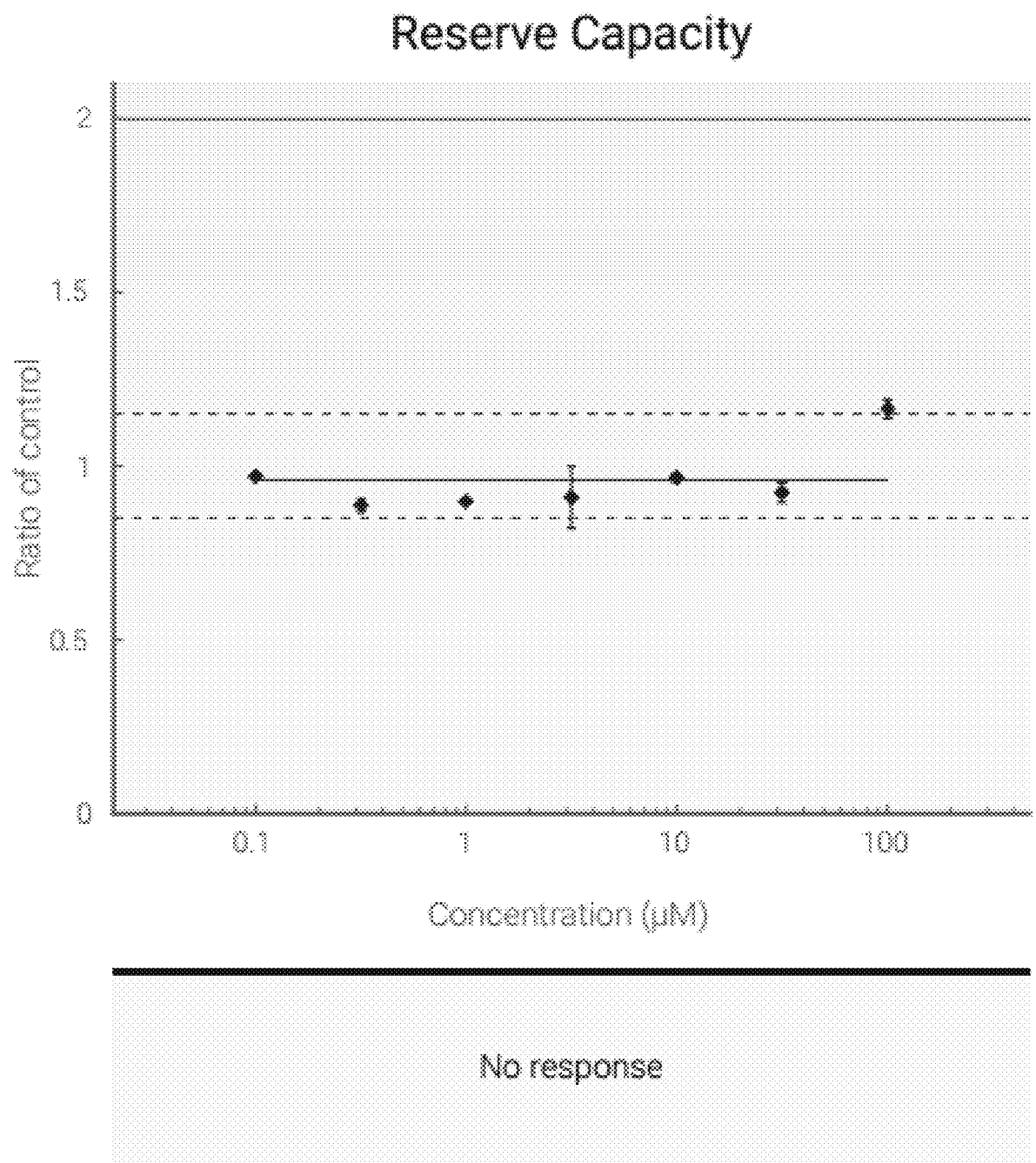

FIG. 30 is a series of graphs showing the effects of a combination of succinate and nicotinamide on oxygen consumption rate and reserve capacity.

Figure 31:
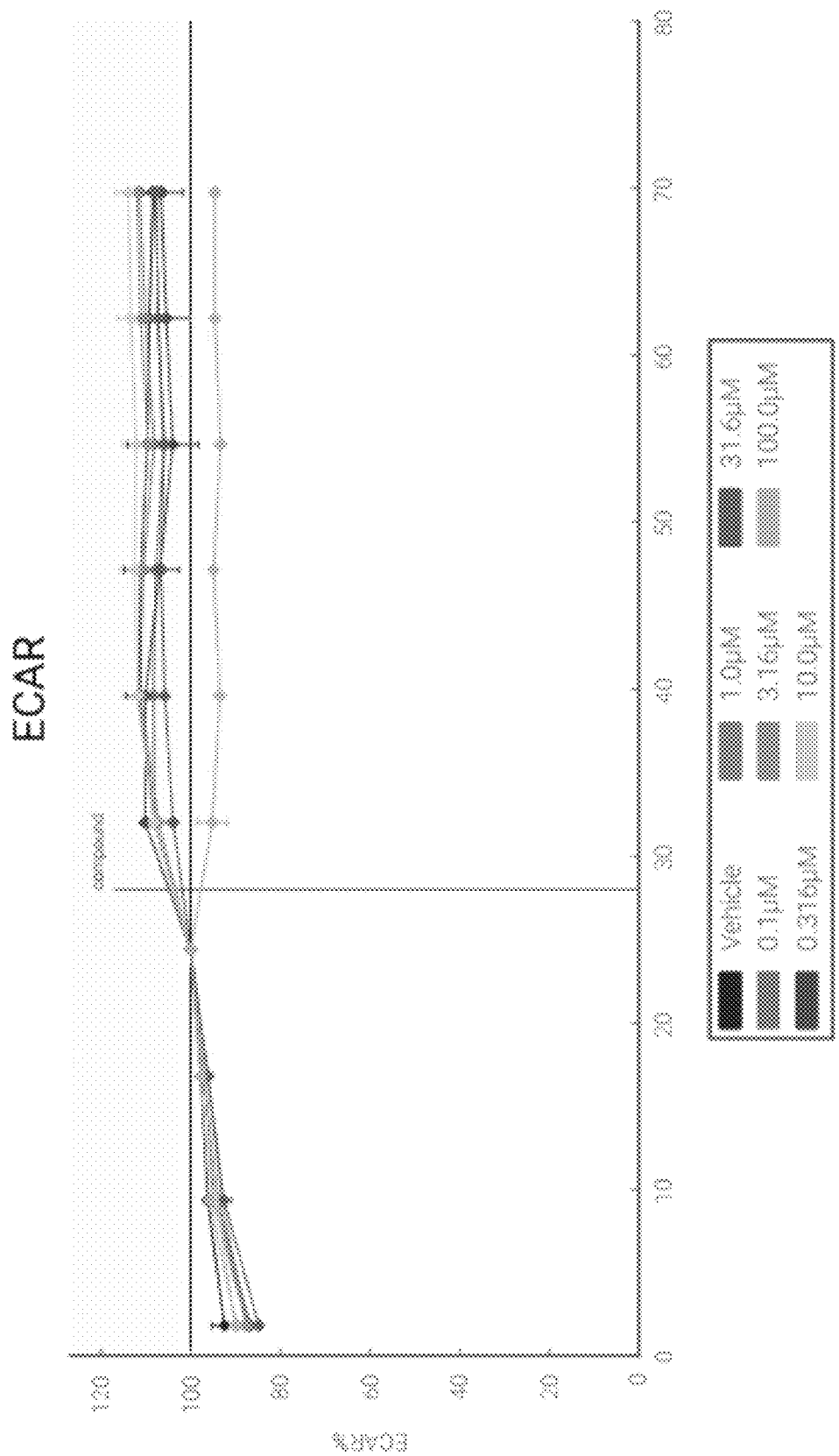
FIG. 31 is a series of graphs showing the effects of a combination of succinate and nicotinamide on extracellular acidification rate.
Figure 31:
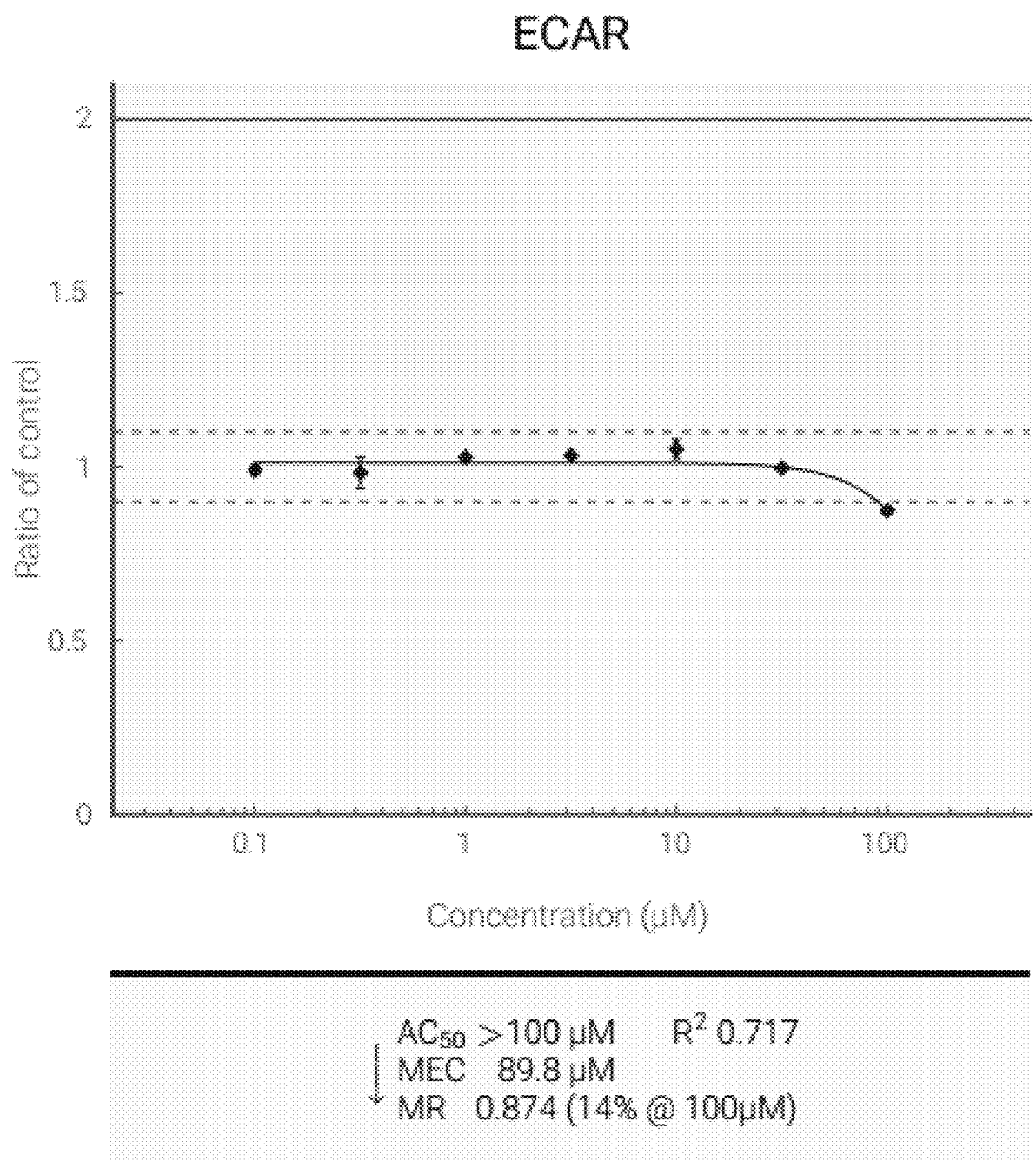

FIG. 31 is a series of graphs showing the effects of a combination of succinate and nicotinamide on extracellular acidification rate.

Effect of Compositions on Coronary Flow, Cardiac Function, and Infarct Size.

The effect of compositions on the coronary flow, cardiac function, and infarct size was analyzed.

Figure 32:
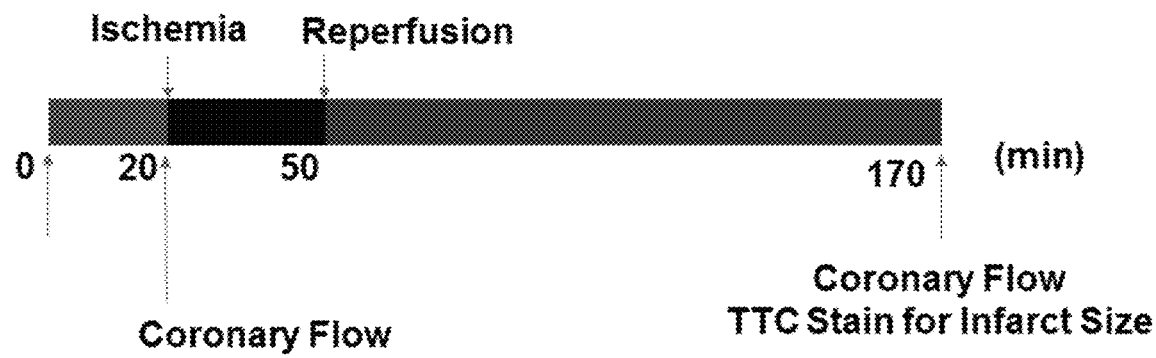
FIG. 32 is a schematic of the ischemia-reperfusion (IR) method used to analyze the effects of compositions of the invention on coronary flow.

FIG. 32 is a schematic of the ischemia-reperfusion (IR) method used to analyze the effects of compositions of the invention on coronary flow, cardiac function, and infarct size. At time 0, mice were given (1) 20 µM trimetazidine (TMZ), (2) 2 µM each of trimetazidine, nicotinamide, and succinate (TNF), (3) 20 µM each of trimetazidine, nicotinamide, and succinate (TNS), or (4) the delivery vehicle (CON). At 20 minutes, ischemia was induced, and coronary flow was analyzed. At 50 minutes, reperfusion was initiated to restore blood flow. At 170 minutes, coronary flow and cardiac function was analyzed, and then the hearts were preserved, sectioned, and infarct size was measured by triphenyltetrazolium chloride (TTC) staining.

Figure 33:
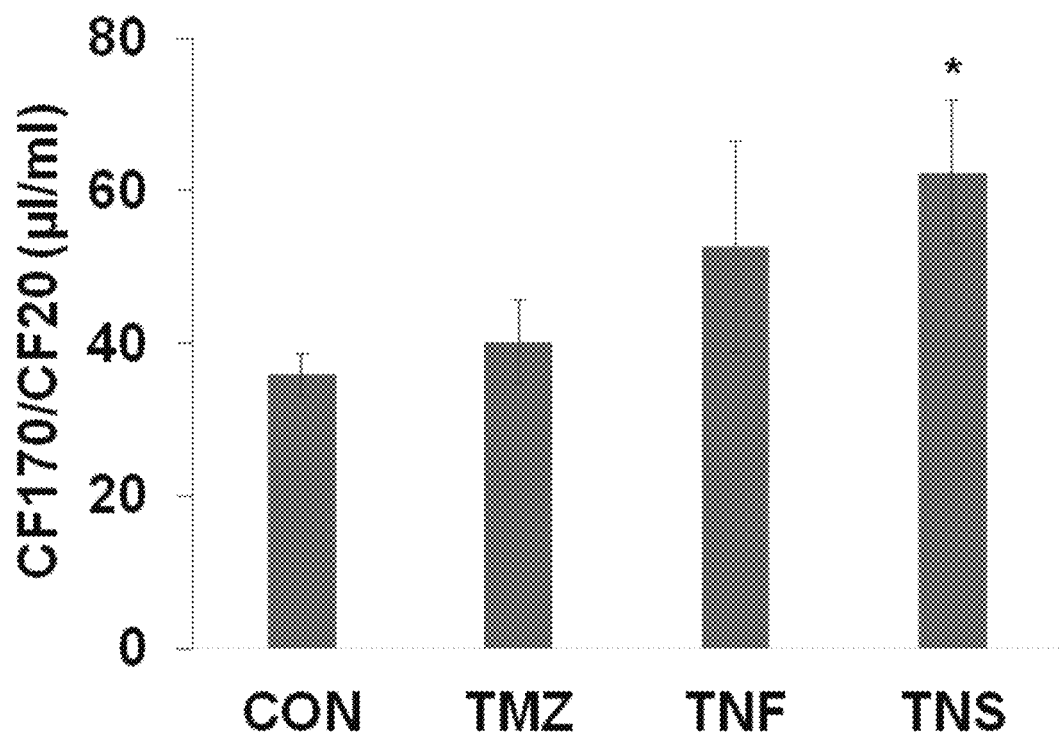
FIG. 33 is a graph of coronary flow of after IR.

FIG. 33 is a graph of coronary flow of after IR. Data is expressed as ratio cardiac flow at 170 minutes to cardiac flow at 20 minutes. TNS treatment preserved coronary flow after IR. Raw data is provided in Tables 1-2.

TABLE 1

| | CF20 (ml/min) | CF170 (ml/min) | CF170/CF20 (ul/ml) |
|---|---|---|---|
| CON11 | 2.31E+00 | 1.11E-01 | 4.81E+01 |
| CON13 | 1.07E+00 | 4.80E-02 | 4.48E+01 |
| CON14 | 8.28E-01 | 4.50E-02 | 5.43E+01 |
| CON9 | 2.11E+00 | 6.96E-02 | 3.30E+01 |
| CON10 | 1.85E+00 | 4.92E-02 | 2.66E+01 |
| CON7 | 1.57E+00 | 5.40E-02 | 3.44E+01 |
| CON8 | 3.22E+00 | 6.78E-02 | 2.11E+01 |
| CON5 | 2.18E+00 | 6.60E-02 | 3.03E+01 |
| CON3 | 2.24E+00 | 7.92E-02 | 3.53E+01 |
| CON4 | 2.22E+00 | 7.84E-02 | 3.53E+01 |
| CON2 | 1.68E+00 | 5.12E-02 | 3.05E+01 |
| MEAN | 1.93E+00 | 6.54E-02 | 3.58E+01 |
| SD | 6.50E-01 | 1.94E-02 | 9.72E+00 |
| SE | 1.96E-01 | 5.86E-03 | 2.93E+00 |
| TTEST | | | |
| TMZ4 | 2.13E+00 | 5.16E-02 | 2.42E+01 |
| TMZ3 | 1.70E+00 | 1.00E-01 | 5.87E+01 |
| TMZ1 | 2.18E+00 | 7.78E-02 | 3.57E+01 |
| TMZ2 | 3.83E+00 | 1.29E-01 | 3.37E+01 |
| TMZ7 | 1.72E+00 | 8.98E-02 | 5.21E+01 |
| TMZ8 | 2.40E+00 | 6.56E-02 | 2.73E+01 |
| TMZ5 | 2.14E+00 | 5.56E-02 | 2.60E+01 |
| TMZ9 | 2.03E+00 | 1.30E-01 | 6.39E+01 |
| MEAN | 2.27E+00 | 8.74E-02 | 4.02E+01 |
| SD | 6.75E-01 | 3.06E-02 | 1.57E+01 |
| SE | 2.39E-01 | 1.08E-02 | 5.56E+00 |
| TTEST | | | |
| TNF1 | 2.24E+00 | 4.80E-02 | 2.14E+01 |
| TNF2 | 2.24E+00 | 3.80E-02 | 1.69E+01 |
| TNF3 | 7.32E-01 | 4.80E-02 | 6.56E+01 |
| TNF4 | 8.20E-01 | 4.90E-02 | 5.98E+01 |
| TNF5 | 1.09E+00 | 2.70E-02 | 2.48E+01 |
| TNF6 | 9.48E-01 | 1.50E-01 | 1.58E+02 |
| TNF7 | 8.08E-01 | 3.70E-02 | 4.58E+01 |
| TNF8 | 1.20E+00 | 4.60E-02 | 3.83E+01 |
| TNF9 | 1.45E+00 | 1.21E-01 | 8.33E+01 |
| TNF10 | 1.20E+00 | 1.52E-02 | 1.27E+01 |
| MEAN | 1.27E+00 | 5.79E-02 | 5.27E+01 |
| SD | 5.56E-01 | 4.28E-02 | 4.37E+01 |
| SE | 1.76E-01 | 1.35E-02 | 1.38E+01 |
| TTEST | 2.21E-02 | 6.06E-01 | 2.26E-01 |
| TNS1 | 1.52E+00 | 4.70E-02 | 3.08E+01 |
| TNS2 | 9.30E-01 | 2.90E-02 | 3.12E+01 |
| TNS3 | 2.24E+00 | 1.67E-01 | 7.46E+01 |
| TNS5 | 5.64E-01 | 5.00E-02 | 8.87E+01 |
| TNS6 | 6.28E-01 | 4.40E-02 | 7.01E+01 |
| TNS7 | 1.08E+00 | 6.40E-02 | 5.95E+01 |

TABLE 1-continued

|  | CF20 (ml/min) | CF170 (ml/min) | CF170/CF20 (ul/ml) |
|---|---|---|---|
| TNS8 | 8.72E−01 | 2.30E−02 | 2.64E+01 |
| TNS9 | 1.18E+00 | 8.50E−02 | 7.23E+01 |
| TNS10 | 1.70E+00 | 1.84E−01 | 1.08E+02 |
| MEAN | 1.19E+00 | 7.70E−02 | 6.24E+01 |
| SD | 5.43E−01 | 5.89E−02 | 2.82E+01 |
| SE | 1.81E−01 | 1.96E−02 | 9.42E+00 |
| TTEST vs TMZ | 1.35E−02 | 5.45E−01 | 8.80E−03 |
|  |  |  | 6.82E−02 |

TABLE 2

|  | CON | TMZ | TNF | TNS |
|---|---|---|---|---|
| MEAN | 36 | 40 | 53 | 62 |
| SD | 10 | 16 | 44 | 28 |
| SE | 3 | 6 | 14 | 9 |

Figure 34:
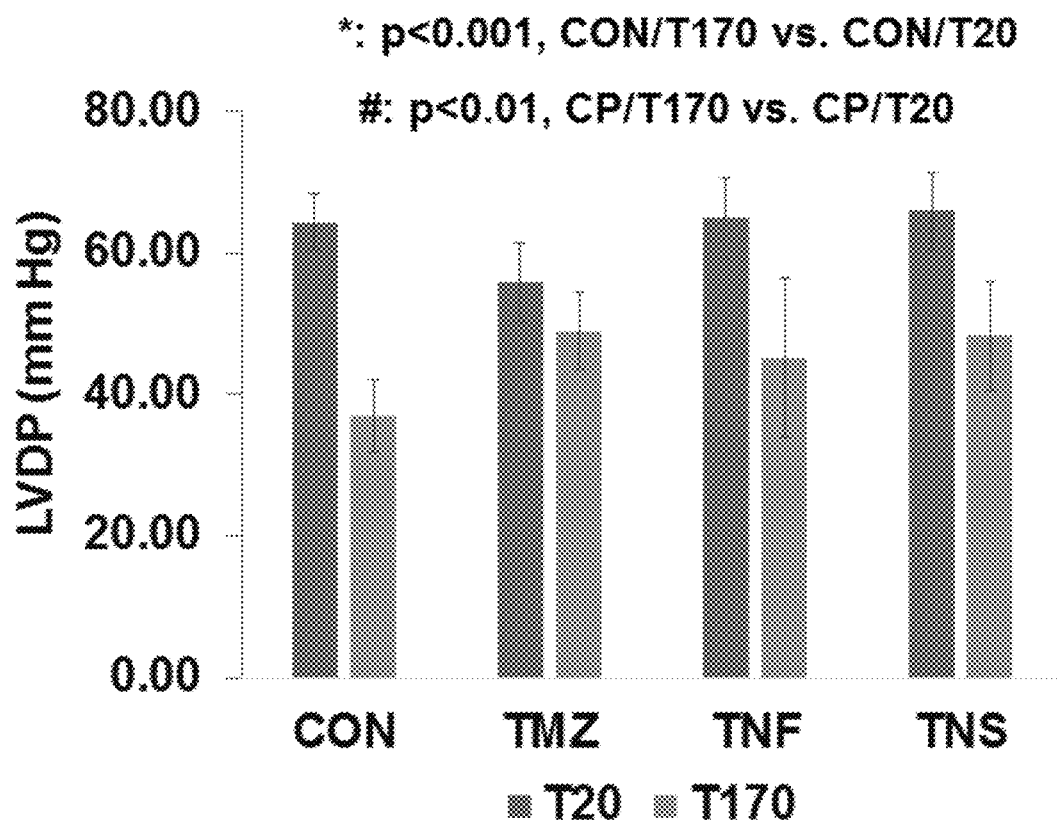
FIG. 34 is graph of left ventricular developed pressure (LVDP) after IR.

FIG. 34 is graph of left ventricular developed pressure (LVDP) after IR. Blue bars indicate LVDP at 20 minutes, and orange bars indicate LVDP at 170 minutes. TMZ, TNS, and TNF treatment prevented a decline in cardiac function after IR. Raw data is provided in Tables 3-6.

TABLE 3

| pre-ischemia | | LVESP | LVEDP | HR | LVDP | LVDP × HR |
|---|---|---|---|---|---|---|
| 5-18-CN | CON11 | 6.61E+01 | 6.20E+00 | 3.28E+02 | 5.99E+01 | 1.97E+04 |
|  | CON12 | 8.15E+01 | 3.73E+00 | 3.56E+02 | 7.78E+01 | 2.77E+04 |
| 6-10-CN | CON13 | 8.00E+01 | −3.74E+00 | 1.37E+02 | 8.37E+01 | 1.15E+04 |
|  | CON14 | 7.28E+01 | 6.12E+00 | 4.54E+02 | 6.67E+01 | 3.03E+04 |
| 5-15-CN | CON9 | 8.07E+01 | 5.00E+00 | 1.42E+02 | 7.57E+01 | 1.08E+04 |
|  | CON10 | 4.91E+01 | 1.15E+00 | 3.21E+02 | 4.80E+01 | 1.54E+04 |
| 5-12-CN | CON7 | 8.55E+01 | 6.35E+00 | 3.05E+02 | 7.91E+01 | 2.42E+04 |
|  | CON8 | 5.06E+01 | 1.68E+00 | 3.04E+02 | 4.90E+01 | 1.49E+04 |
| 5-9-CN | CON5 | 5.45E+01 | 5.63E+00 | 2.75E+02 | 4.89E+01 | 1.35E+04 |
|  | CON6 | 6.37E+01 | 4.31E+00 | 3.08E+02 | 5.94E+01 | 1.83E+04 |
| 5-7-CN | CON3 | 7.32E+01 | 2.70E+00 | 2.40E+02 | 7.05E+01 | 1.69E+04 |
|  | CON4 | 4.91E+01 | 1.65E−01 | 3.14E+02 | 4.89E+01 | 1.54E+04 |
| 5-5-CN | CON1 | 9.48E+01 | 7.96E+00 | 3.04E+02 | 8.68E+01 | 2.64E+04 |
|  | CON2 | 4.69E+01 | 1.64E+00 | 4.02E+02 | 4.67E+01 | 1.88E+04 |
|  | MEAN | 6.77E+01 | 3.39E+00 | 2.99E+02 | 6.44E+01 | 1.88E+04 |
|  | SD | 1.58E+01 | 3.21E+00 | 8.52E+01 | 1.46E+01 | 6.12E+03 |
|  | SE | 4.21E+00 | 8.57E−01 | 2.28E+01 | 3.91E+00 | 1.63E+03 |
|  | TTEST |  |  |  |  | 2.42E−04 |
| 5-14-TMZ | TMZ3 | 7.58E+01 | 6.53E+00 | 2.63E+02 | 6.93E+01 | 1.83E+04 |
|  | TMZ4 | 8.44E+01 | 5.43E+00 | 2.93E+02 | 7.90E+01 | 2.31E+04 |
| 5-11-TMZ | TMZ1 | 7.15E+01 | 6.76E+00 | 1.66E+02 | 6.48E+01 | 1.08E+04 |
|  | TMZ2 | 5.47E+01 | 1.74E+00 | 3.35E+02 | 5.30E+01 | 1.77E+04 |
| 5-8-TMZ | TMZ7 | 6.87E+01 | 3.58E+00 | 3.58E+02 | 6.51E+01 | 2.33E+04 |
|  | TMZ8 | 4.27E+01 | 4.71E+00 | 3.33E+02 | 3.80E+01 | 1.26E+04 |
| 5-6-TMZ | TMZ5 | 3.30E+01 | 4.77E+00 | 3.48E+02 | 2.82E+01 | 9.82E+03 |
|  | TMZ6 | 3.30E+01 | 1.46E+00 | 3.21E+02 | 3.15E+01 | 1.01E+04 |
| 5-4-TMZ | TMZ9 | 6.60E+01 | 7.25E+00 | 2.67E+02 | 5.87E+01 | 1.57E+04 |
|  | TMZ10 | 7.38E+01 | 2.70E+00 | 3.32E+02 | 7.11E+01 | 2.36E+04 |
|  | MEAN | 6.03E+01 | 4.49E+00 | 3.02E+02 | 5.59E+01 | 1.68E+04 |
|  | SD | 1.85E+01 | 2.07E+00 | 5.75E+01 | 1.77E+01 | 5.56E+03 |
|  | SE | 5.84E+00 | 6.56E−01 | 1.82E+01 | 5.58E+00 | 1.76E+03 |
|  |  |  |  |  |  | 3.85E−01 |
| 5-19-TNF | TNF1 | 5.02E+01 | 3.04E+00 | 4.09E+02 | 4.72E+01 | 1.93E+04 |
|  | TNF2 | 4.65E+01 | 1.76E+01 | 2.76E+02 | 4.63E+01 | 1.28E+04 |
| 6-8-TNF | TNF3 | 7.13E+01 | 1.53E+00 | 6.48E+01 | 6.97E+01 | 4.52E+03 |
|  | TNF4 | 9.97E+01 | 4.15E+00 | 1.54E+02 | 9.55E+01 | 1.47E+04 |
| 6-12-TNF | TNF5 | 7.14E+01 | −3.42E+00 | 2.77E+02 | 7.49E+01 | 2.07E+04 |
|  | TNF6 | 8.98E+01 | 8.85E+00 | 3.10E+02 | 8.09E+01 | 2.51E+04 |
| 6-14-TNF | TNF7 | 6.58E+01 | 7.01E+00 | 3.98E+02 | 5.88E+01 | 2.34E+04 |
|  | TNF8 | 5.99E+01 | 1.02E+00 | 2.28E+02 | 5.89E+01 | 1.34E+04 |
| 6-15-TNF | TNF9 | 7.89E+01 | 2.37E−01 | 2.71E+02 | 7.87E+01 | 2.13E+04 |
|  | TNF10 | 4.01E+01 | 1.88E+00 | 3.14E+02 | 3.82E+01 | 1.20E+04 |
|  | MEAN | 6.74E+01 | 2.45E+00 | 2.70E+02 | 6.49E+01 | 1.67E+04 |

TABLE 3-continued

| pre-ischemia | | LVESP | LVEDP | HR | LVDP | LVDP × HR |
|---|---|---|---|---|---|---|
|  | SD | 1.90E+01 | 3.54E+00 | 1.04E+02 | 1.81E+01 | 6.32E+03 |
|  | SE | 6.00E+00 | 1.12E+00 | 3.28E+01 | 5.73E+00 | 2.00E+03 |
|  |  |  |  |  |  | 1.38E−01 |
| 5-20-TNS | TNS1 | 5.59E+01 | 5.23E+00 | 3.33E+02 | 5.07E+01 | 1.69E+04 |
|  | TNS2 | 5.54E+01 | −1.83E+00 | 1.24E+02 | 5.72E+01 | 7.09E+03 |
| 6-7-TNS | TNS3 | 8.78E+01 | 1.53E+00 | 1.64E+02 | 8.63E+01 | 1.42E+04 |
|  | TNS4 | 1.07E+02 | 9.86E+00 | 2.41E+02 | 9.74E+01 | 2.35E+04 |
| 6-9-TNS | TNS5 | 8.97E+01 | 2.34E+00 | 8.35E+01 | 8.74E+01 | 7.29E+03 |
|  | TNS6 | 6.17E+01 | 6.21E+00 | 1.85E+02 | 5.55E+01 | 1.03E+04 |
| 6-13-TNS | TNS7 | 6.62E+01 | 4.14E+00 | 3.36E+02 | 6.21E+01 | 2.09E+04 |
|  | TNS8 | 6.54E+01 | 1.22E+01 | 1.22E+02 | 5.32E+01 | 6.47E+03 |
| 6-15-TNS | TNS9 | 6.16E+01 | 3.64E+00 | 3.45E+02 | 5.80E+01 | 2.00E+04 |
|  | TNS10 | 5.44E+01 | 2.47E+00 | 4.12E+02 | 5.20E+01 | 2.14E+04 |
|  | MEAN | 7.05E+01 | 4.58E+00 | 2.35E+02 | 6.60E+01 | 1.48E+04 |
|  | SD | 1.80E+01 | 4.09E+00 | 1.15E+02 | 1.74E+01 | 6.61E+03 |
|  | SE | 5.69E+00 | 1.29E+00 | 3.63E+01 | 5.49E+00 | 2.09E+03 |
|  |  |  |  |  |  | 7.89E−02 |

TABLE 4

| after 2 h reperfusion | | LVESP | LVEDP | HR | LVDP | LVDP × HR |
|---|---|---|---|---|---|---|
| 5-18-CN | CON11 | 7.78E+01 | 3.68E+01 | 1.18E+02 | 4.10E+01 | 4.82E+03 |
|  | CON12 | 7.07E+01 | 2.23E+01 | 9.23E+01 | 4.84E+01 | 4.47E+03 |
| 6-10-CN | CON13 | 6.48E+01 | 5.54E+01 | 5.72E+02 | 9.39E+00 | 5.38E+03 |
|  | CON14 | 9.54E+01 | 5.64E+01 | 2.08E+02 | 3.90E+01 | 8.12E+03 |
| 5-15-CN | CON9 | 5.18E+01 | 2.71E+01 | 1.75E+02 | 2.47E+01 | 4.33E+03 |
|  | CON10 | 1.10E+02 | 3.13E+01 | 5.76E+01 | 7.84E+01 | 4.51E+03 |
| 5-12-CN | CON7 | 3.93E+01 | 1.42E+01 | 9.11E+01 | 2.51E+01 | 2.29E+03 |
|  | CON8 | 5.29E+01 | 9.48E+00 | 6.07E+01 | 4.34E+01 | 2.64E+03 |
| 5-9-CN | CON5 | 6.56E+01 | 4.89E+01 | 6.50E+01 | 1.67E+01 | 1.09E+03 |
|  | CON6 | 7.44E+01 | 6.56E+01 | 3.78E+01 | 8.81E+00 | 3.33E+02 |
| 5-7-CN | CON3 | 6.35E+01 | 9.99E+00 | 1.15E+02 | 5.35E+01 | 6.18E+03 |
|  | CON4 | 8.76E+01 | 5.34E+01 | 1.06E+02 | 3.43E+01 | 3.65E+03 |
| 5-5-CN | CON1 | 9.29E+01 | 4.38E+01 | 2.61E+02 | 4.91E+01 | 1.28E+04 |
|  | CON2 | 5.18E+01 | 4.43E+01 | 2.57E+02 | 4.74E+01 | 1.22E+04 |
|  | MEAN | 7.13E+01 | 3.42E+01 | 1.58E+02 | 3.71E+01 | 5.20E+03 |
|  | SD | 1.98E+01 | 2.02E+01 | 1.39E+02 | 1.90E+01 | 3.68E+03 |
|  | SE | 5.29E+00 | 5.40E+00 | 3.72E+01 | 5.08E+00 | 9.83E+02 |
|  | TTEST |  |  |  |  |  |
| 5-14-TMZ | TMZ3 | 5.07E+01 | 2.93E+01 | 1.18E+02 | 2.14E+01 | 2.52E+03 |
|  | TMZ4 | 7.66E+01 | 3.31E+01 | 1.19E+02 | 4.34E+01 | 5.15E+03 |
| 5-11-TMZ | TMZ1 | 9.19E+01 | 3.96E+01 | 1.01E+02 | 5.22E+01 | 5.28E+03 |
|  | TMZ2 | 4.77E+01 | 1.80E+01 | 1.51E+02 | 2.97E+01 | 4.49E+03 |
| 5-8-TMZ | TMZ7 | 5.18E+01 | 3.36E+00 | 6.70E+01 | 4.84E+01 | 3.24E+03 |
|  | TMZ8 | 4.86E+01 | 1.87E+00 | 9.22E+01 | 4.67E+01 | 4.31E+03 |
| 5-6-TMZ | TMZ5 | 6.09E+01 | 1.99E+01 | 2.22E+02 | 4.10E+01 | 9.11E+03 |
|  | TMZ6 | 1.09E+02 | 3.21E+01 | 1.70E+02 | 7.65E+01 | 1.30E+04 |
| 5-4-TMZ | TMZ9 | 7.38E+01 | 1.84E+01 | 1.16E+02 | 5.53E+01 | 6.44E+03 |
|  | TMZ10 | 7.61E+01 | 1.77E+00 | 2.38E+02 | 7.43E+01 | 1.77E+04 |
|  | MEAN | 6.86E+01 | 1.97E+01 | 1.39E+02 | 4.89E+01 | 6.82E+03 |
|  | SD | 2.05E+01 | 1.39E+01 | 5.58E+01 | 1.73E+01 | 4.82E+03 |
|  | SE | 6.49E+00 | 4.39E+00 | 1.77E+01 | 5.46E+00 | 1.52E+03 |
| 5-19-TNF | TNF1 | 8.37E+01 | 6.66E+01 | 1.53E+02 | 1.71E+01 | 2.62E+03 |
|  | TNF2 | 6.19E+00 | 5.54E+00 | 2.13E+03 | 6.48E−01 | 1.38E+03 |
| 6-8-TNF | TNF3 | 8.99E+01 | 1.88E+01 | 1.05E+02 | 7.11E+01 | 7.49E+02 |
|  | TNF4 | 6.06E+01 | 1.34E+01 | 8.10E+01 | 4.72E+01 | 3.82E+03 |
| 6-12-TNF | TNF5 | 1.54E+02 | 4.15E+01 | 2.20E+01 | 1.13E+02 | 2.48E+03 |
|  | TNF6 | 1.30E+02 | 4.25E+01 | 3.33E+01 | 8.77E+01 | 2.92E+03 |
| 6-14-TNF | TNF7 | 5.70E+01 | 4.00E+01 | 4.00E+01 | 1.70E+01 | 6.80E+02 |
|  | TNF8 | 3.76E+01 | 1.87E+01 | 5.36E+01 | 1.88E+01 | 1.01E+03 |
| 6-15-TNF | TNF9 | 6.23E+01 | 3.38E+01 | 1.97E+02 | 2.85E+01 | 5.59E+03 |
|  | TNF10 | 7.85E+01 | 2.75E+01 | 7.85E+01 | 5.10E+01 | 4.00E+03 |
|  | MEAN | 7.60E+01 | 3.09E+01 | 2.80E+02 | 4.52E+01 | 2.53E+03 |
|  | SD | 4.28E+01 | 1.79E+01 | 6.54E+02 | 3.59E+01 | 1.62E+03 |
|  | SE | 1.35E+01 | 5.65E+00 | 2.07E+02 | 1.14E+01 | 5.12E+02 |
| 5-20-TNS | TNS1 | 6.47E+01 | 1.78E+01 | 1.04E+02 | 4.69E+01 | 4.88E+03 |
|  | TNS2 | 8.95E+01 | 3.03E+01 | 5.55E+01 | 5.92E+01 | 3.29E+03 |
| 6-7-TNS | TNS3 | 7.79E+01 | 6.34E+01 | 1.28E+02 | 1.45E+01 | 1.85E+03 |
|  | TNS4 | 7.74E+01 | 2.73E+01 | 1.02E+02 | 5.01E+01 | 5.09E+03 |

TABLE 4-continued

| | | LVESP | LVEDP | HR | LVDP | after 2 h reperfusion LVDP × HR |
|---|---|---|---|---|---|---|
| 6-9-TNS | TNS5 | 1.37E+02 | 5.63E+01 | 1.63E+01 | 8.08E+01 | 1.32E+03 |
| | TNS6 | 8.59E+01 | 1.23E+01 | 1.06E+02 | 7.36E+01 | 7.79E+03 |
| 6-13-TNS | TNS7 | 5.76E+01 | 5.16E+01 | 1.35E+02 | 6.00E+00 | 8.07E+02 |
| | TNS8 | 4.96E+01 | 1.53E+01 | 1.22E+02 | 3.43E+01 | 4.20E+03 |
| 6-15-TNS | TNS9 | 9.97E+01 | 3.00E+01 | 7.46E+01 | 6.98E+01 | 5.21E+03 |
| | TNS10 | 4.32E+01 | −4.32E+00 | 7.20E+01 | 4.75E+01 | 3.42E+03 |
| | MEAN | 7.83E+01 | 3.00E+01 | 9.15E+01 | 4.83E+01 | 3.79E+03 |
| | SD | 2.74E+01 | 2.14E+01 | 3.69E+01 | 2.45E+01 | 2.11E+03 |
| | SE | 8.67E+00 | 6.78E+00 | 1.17E+01 | 7.75E+00 | 6.69E+02 |

TABLE 5

| | | pre-ischemia +dp/dtm | −dp/dtm | after 2 h reperfusion | +dp/dtm | −dp/dtm |
|---|---|---|---|---|---|---|
| 5-18-CN | CON11 | 2.60E+03 | −1.82E+03 | CON11 | 1.44E+03 | −8.67E+02 |
| | CON12 | 2.95E+03 | −2.58E+03 | CON12 | 1.63E+03 | −1.07E+03 |
| 6-10-CN | CON13 | 3.10E+03 | −2.42E+03 | CON13 | 2.25E+02 | −2.22E+02 |
| | CON14 | 3.08E+03 | −2.10E+03 | CON14 | 3.44E+02 | −2.87E+02 |
| 5-15-CN | CON9 | 2.28E+03 | −1.38E+03 | CON9 | 9.45E+02 | −5.54E+02 |
| | CON10 | 2.06E+03 | −1.50E+03 | CON10 | 2.29E+03 | −1.75E+03 |
| 5-12-CN | CON7 | 2.71E+03 | −2.10E+03 | CON7 | 2.51E+02 | −2.55E+02 |
| | CON8 | 1.58E+03 | −1.10E+03 | CON8 | 3.63E+02 | −3.05E+02 |
| 5-9-CN | CON5 | 2.17E+03 | −1.50E+03 | CON5 | 2.39E+02 | −2.41E+02 |
| | CON6 | 2.25E+03 | −1.62E+03 | CON6 | 1.47E+02 | −1.49E+02 |
| 5-7-CN | CON3 | 2.63E+03 | −2.06E+03 | CON3 | 1.63E+02 | −1.06E+03 |
| | CON4 | 2.05E+03 | −1.38E+03 | CON4 | 1.10E+02 | −7.03E+02 |
| 5-5-CN | CON1 | 3.17E+03 | −2.37E+03 | CON1 | 1.03E+02 | −1.12E+03 |
| | CON2 | 2.10E+03 | −1.50E+03 | CON2 | 1.75E+02 | −1.27E+03 |
| | MEAN | 2.48E+03 | −1.82E+03 | MEAN | 9.56E+02 | −7.04E+02 |
| | SD | 4.84E+02 | 4.56E+02 | SD | 7.08E+02 | 4.95E+02 |
| | SE | 1.29E+02 | 1.22E+02 | SE | 1.89E+02 | 1.32E+02 |
| | TTEST | | | TTEST | | |
| 5-14-TMZ | TMZ3 | 2.41E+03 | −1.69E+03 | TMZ3 | 4.14E+02 | −3.57E+02 |
| | TMZ4 | 2.77E+03 | −2.26E+03 | TMZ4 | 1.48E+02 | −1.15E+03 |
| 5-11-TMZ | TMZ1 | 1.80E+03 | −1.59E+03 | TMZ1 | 1.38E+02 | −7.45E+02 |
| | TMZ2 | 2.15E+03 | −1.80E+03 | TMZ2 | 1.06E+02 | −6.85E+02 |
| 5-8-TMZ | TMZ7 | 3.40E+03 | −2.59E+03 | TMZ7 | 3.44E+02 | −3.39E+02 |
| | TMZ8 | 1.75E+03 | −1.20E+03 | TMZ8 | 7.36E+02 | −4.28E+02 |
| 5-6-TMZ | TMZ5 | 1.27E+03 | −8.82E+02 | TMZ5 | 1.28E+02 | −8.38E+02 |
| | TMZ6 | 1.24E+03 | −6.59E+02 | TMZ6 | 1.85E+02 | −1.06E+03 |
| 5-4-TMZ | TMZ9 | 1.98E+03 | −1.41E+03 | TMZ9 | 1.13E+02 | −6.38E+02 |
| | TMZ10 | 2.02E+03 | −1.56E+03 | TMZ10 | 1.62E+02 | −9.83E+02 |
| | MEAN | 2.08E+03 | −1.56E+03 | MEAN | 1.13E+02 | −7.22E+02 |
| | SD | 6.58E+02 | 5.81E+02 | SD | 5.01E+02 | 2.90E+02 |
| | SE | 2.08E+02 | 1.84E+02 | SE | 1.58E+02 | 9.16E+01 |
| | | | | | 5.16E−01 | 9.18E−01 |
| 5-19-TNF | TNF1 | 2.67E+03 | −1.49E+03 | TNF1 | 3.86E+02 | −3.75E+02 |
| | TNF2 | 2.85E+03 | −1.44E+03 | TNF2 | 1.46E+02 | −1.43E+02 |
| 6-8-TNF | TNF3 | 1.53E+03 | −7.24E+02 | TNF3 | 2.28E+02 | −2.34E+02 |
| | TNF4 | 3.86E+03 | −2.59E+03 | TNF4 | 2.84E+02 | −2.40E+02 |
| 6-12-TNF | TNF5 | 3.29E+03 | −2.34E+03 | TNF5 | 2.92E+03 | −2.08E+03 |
| | TNF6 | 3.03E+03 | −1.90E+03 | TNF6 | 2.48E+02 | −1.84E+03 |
| 6-14-TNF | TNF7 | 3.22E+03 | −1.62E+03 | TNF7 | 2.53E+02 | −2.48E+02 |
| | TNF8 | 1.74E+03 | −1.12E+03 | TNF8 | 1.53E+02 | −1.52E+02 |
| 6-15-TNF | TNF9 | 2.14E+03 | −2.33E+03 | TNF9 | 1.04E+02 | −6.31E+02 |
| | TNF10 | 1.86E+03 | −9.97E+02 | TNF10 | 2.04E+02 | −1.34E+03 |
| | MEAN | 2.62E+03 | −1.65E+03 | MEAN | 9.93E+02 | −7.29E+02 |
| | SD | 7.71E+02 | 6.26E+02 | SD | 1.08E+03 | 7.43E+02 |
| | SE | 2.44E+02 | 1.98E+02 | SE | 3.41E+02 | 2.35E+02 |
| | | 1.09E−03 | 7.48E−03 | | | |
| 5-20-TNS | TNS1 | 2.37E+03 | −1.60E+03 | TNS1 | 1.79E+03 | −1.12E+03 |
| | TNS2 | 2.87E+03 | −2.53E+03 | TNS2 | 1.84E+03 | −1.30E+03 |
| 6-7-TNS | TNS3 | 4.00E+03 | −2.67E+03 | TNS3 | 2.91E+02 | −3.02E+02 |
| | TNS4 | 3.32E+03 | −2.63E+03 | TNS4 | 1.62E+03 | −1.30E+03 |
| 6-9-TNS | TNS5 | 3.36E+03 | −2.21E+03 | TNS5 | 2.43E+02 | −2.46E+02 |
| | TNS6 | 2.53E+03 | −1.89E+03 | TNS6 | 2.36E+03 | −1.74E+03 |
| 6-13-TNS | TNS7 | 2.92E+03 | −1.75E+03 | TNS7 | 2.49E+02 | −2.47E+02 |
| | TNS8 | 1.12E+03 | −7.42E+02 | TNS8 | 1.29E+03 | −8.50E+02 |

TABLE 5-continued

| | | pre-ischemia +dp/dtm | −dp/dtm | after 2 h reperfusion | +dp/dtm | −dp/dtm |
|---|---|---|---|---|---|---|
| 6-15-TNS | TNS9 | 2.29E+03 | −1.75E+03 | TNS9 | 2.06E+03 | −1.59E+03 |
| | TNS10 | 2.11E+03 | −1.58E+03 | TNS10 | 1.26E+03 | −1.10E+03 |
| | MEAN | 2.69E+03 | −1.94E+03 | MEAN | 1.30E+03 | −9.80E+02 |
| | SD | 7.99E+02 | 5.95E+02 | SD | 7.86E+02 | 5.52E+02 |
| | SE | 2.53E+02 | 1.88E+02 | SE | 2.49E+02 | 1.75E+02 |
| | | 9.96E−04 | 1.55E−03 | | | |

TABLE 6

| | | CON | TMZ | TNF | TNS |
|---|---|---|---|---|---|
| T20 | Mean | 64.36 | 55.86 | 64.90 | 65.96 |
| T20 | SE | 3.91 | 5.58 | 5.73 | 5.49 |
| T170 | Mean | 37.09 | 48.91 | 45.16 | 48.27 |
| T170 | SE | 5.08 | 5.46 | 11.36 | 7.75 |

Figure 35:
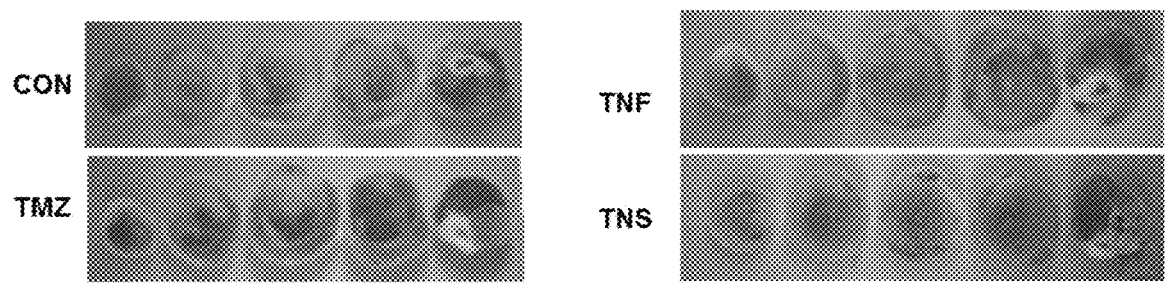
FIG. 35 shows images of TTC-stained heart slices after IR.

FIG. 35 shows images of TTC-stained heart slices after IR. TMZ and TNS treatment decreased infarct size after IR.

Figure 36:
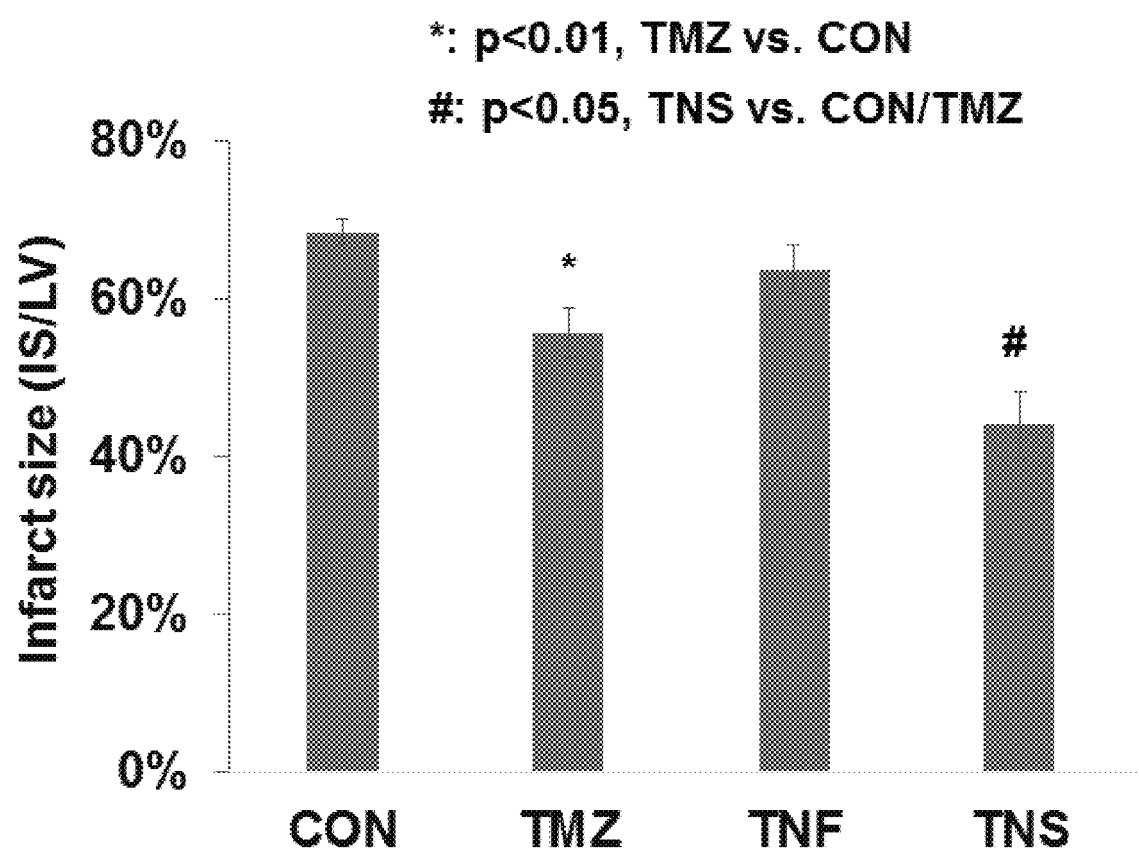
FIG. 36 is graph of infarct size after IR.

FIG. 36 is graph of infarct size after IR. TMZ and TNS treatment decreased infarct size after IR. Raw data is provided in Tables 7-55.

TABLE 7

| CN11 raw values | | |
|---|---|---|
| 1 | Slide11.jpg | 1649 |
| 2 | Slide11.jpg | 10 | 0.06 |
| 3 | Slide11.jpg | 1385 | 8.40 |
| 4 | Slide11.jpg | 2808 | |
| 5 | Slide11.jpg | 104 | 0.81 |
| 6 | Slide11.jpg | 2525 | 19.78 |
| 7 | Slide11.jpg | 3807 | |
| 8 | Slide11.jpg | 1014 | 7.99 |
| 9 | Slide11.jpg | 2207 | 17.39 |
| 10 | Slide11.jpg | 3952 | |
| 11 | Slide11.jpg | 15 | 0.08 |
| 12 | Slide11.jpg | 3300 | 17.54 |
| 13 | Slide11.jpg | 3376 | |
| 14 | Slide11.jpg | 103 | 0.92 |
| 15 | Slide11.jpg | 2816 | 25.02 |
| 16 | Slide11.jpg | 1616 | |
| 17 | Slide11.jpg | 975 | 6.03 |
| 18 | Slide11.jpg | 409 | 2.53 |
| 19 | Slide11.jpg | 2805 | |
| 20 | Slide11.jpg | 819 | 6.42 |
| 21 | Slide11.jpg | 1496 | 11.73 |
| 22 | Slide11.jpg | 3973 | |
| 23 | Slide11.jpg | 1047 | 7.91 |
| 24 | Slide11.jpg | 2465 | 18.61 |
| 25 | Slide11.jpg | 3971 | |
| 26 | Slide11.jpg | 1102 | 5.83 |
| 27 | Slide11.jpg | 2430 | 12.85 |
| 28 | Slide11.jpg | 3516 | |
| 29 | Slide11.jpg | 1919 | 16.37 |
| 30 | Slide11.jpg | 920 | 7.85 |

TABLE 8

| CN11 summary | |
|---|---|
| non-IS | 26.21 |
| IS | 70.86 |
| LV | 97.07 |
| IS/LV | 73% |

TABLE 9

| | CN12 raw values | | |
|---|---|---|---|
| 1 | Slide12.jpg | 1562 | |
| 2 | Slide12.jpg | 1059 | 8.81 |
| 3 | Slide12.jpg | 485 | 4.04 |
| 4 | Slide12.jpg | 2925 | |
| 5 | Slide12.jpg | 260 | 1.78 |
| 6 | Slide12.jpg | 2159 | 14.76 |
| 7 | Slide12.jpg | 3492 | |
| 8 | Slide12.jpg | 263 | 1.88 |
| 9 | Slide12.jpg | 2886 | 20.66 |
| 10 | Slide12.jpg | 4855 | |
| 11 | Slide12.jpg | 1992 | 16.00 |
| 12 | Slide12.jpg | 2292 | 18.41 |
| 13 | Slide12.jpg | 2934 | |
| 14 | Slide12.jpg | 1405 | 6.70 |
| 15 | Slide12.jpg | 914 | 4.36 |
| 16 | Slide12.jpg | 2061 | |
| 17 | Slide12.jpg | 81 | 0.51 |
| 18 | Slide12.jpg | 1704 | 10.75 |
| 19 | Slide12.jpg | 2966 | |
| 20 | Slide12.jpg | 105 | 0.71 |
| 21 | Slide12.jpg | 2810 | 18.95 |
| 22 | Slide12.jpg | 4099 | |
| 23 | Slide12.jpg | 823 | 5.02 |
| 24 | Slide12.jpg | 2350 | 14.33 |
| 25 | Slide12.jpg | 3979 | |
| 26 | Slide12.jpg | 357 | 3.50 |
| 27 | Slide12.jpg | 2787 | 27.32 |
| 28 | Slide12.jpg | 2974 | |
| 29 | Slide12.jpg | 490 | 2.31 |
| 30 | Slide12.jpg | 2112 | 9.94 |

TABLE 10

| CN12 summary | |
|---|---|
| non-IS | 23.61 |
| IS | 71.76 |
| LV | 95.37 |
| IS/LV | 75% |

TABLE 11

| | TNS1 raw values | | |
|---|---|---|---|
| 1 | Slide15.jpg | 1857 | |
| 2 | Slide15.jpg | 58 | 0.28 |
| 3 | Slide15.jpg | 1672 | 8.10 |
| 4 | Slide15.jpg | 3383 | |
| 5 | Slide15.jpg | 901 | 4.53 |
| 6 | Slide15.jpg | 1873 | 9.41 |
| 7 | Slide15.jpg | 3460 | |
| 8 | Slide15.jpg | 1452 | 13.43 |
| 9 | Slide15.jpg | 2272 | 21.01 |
| 10 | Slide15.jpg | 3712 | |
| 11 | Slide15.jpg | 772 | 8.32 |
| 12 | Slide15.jpg | 2422 | 26.10 |
| 13 | Slide15.jpg | 3088 | |
| 14 | Slide15.jpg | 498 | 3.87 |
| 15 | Slide15.jpg | 1733 | 13.47 |
| 16 | Slide15.jpg | 1762 | |
| 17 | Slide15.jpg | 65 | 0.33 |
| 18 | Slide15.jpg | 1626 | 8.31 |
| 19 | Slide15.jpg | 3532 | |
| 20 | Slide15.jpg | 2034 | 9.79 |
| 21 | Slide15.jpg | 1206 | 5.80 |
| 22 | Slide15.jpg | 3411 | |
| 23 | Slide15.jpg | 1752 | 16.44 |
| 24 | Slide15.jpg | 1006 | 9.44 |
| 25 | Slide15.jpg | 4241 | |
| 26 | Slide15.jpg | 2148 | 20.26 |
| 27 | Slide15.jpg | 1101 | 10.38 |
| 28 | Slide15.jpg | 3440 | |
| 29 | Slide15.jpg | 2307 | 16.10 |
| 30 | Slide15.jpg | 165 | 1.15 |

TABLE 12

| TNS1 summary | |
|---|---|
| non-IS | 46.67 |
| IS | 56.59 |
| LV | 103.26 |
| IS/LV | 55% |

TABLE 13

| | TNS2 raw values | | |
|---|---|---|---|
| 1 | Slide16.jpg | 1565 | |
| 2 | Slide16.jpg | 1058 | 7.44 |
| 3 | Slide16.jpg | 145 | 1.02 |
| 4 | Slide16.jpg | 2654 | |
| 5 | Slide16.jpg | 431 | 3.90 |
| 6 | Slide16.jpg | 2043 | 18.47 |
| 7 | Slide16.jpg | 3247 | |
| 8 | Slide16.jpg | 1053 | 8.43 |
| 9 | Slide16.jpg | 1584 | 12.68 |
| 10 | Slide16.jpg | 3892 | |
| 11 | Slide16.jpg | 2391 | 22.73 |
| 12 | Slide16.jpg | 863 | 8.20 |
| 13 | Slide16.jpg | 2505 | |
| 14 | Slide16.jpg | 1488 | 14.85 |
| 15 | Slide16.jpg | 363 | 3.62 |
| 16 | Slide16.jpg | 1526 | |
| 17 | Slide16.jpg | 9 | 0.06 |
| 18 | Slide16.jpg | 1357 | 9.78 |
| 19 | Slide16.jpg | 2337 | |
| 20 | Slide16.jpg | 16 | 0.16 |
| 21 | Slide16.jpg | 1899 | 19.50 |
| 22 | Slide16.jpg | 3558 | |
| 23 | Slide16.jpg | 1453 | 10.62 |
| 24 | Slide16.jpg | 1504 | 10.99 |
| 25 | Slide16.jpg | 4041 | |
| 26 | Slide16.jpg | 517 | 4.73 |
| 27 | Slide16.jpg | 2763 | 25.30 |
| 28 | Slide16.jpg | 2946 | |
| 29 | Slide16.jpg | 631 | 5.35 |
| 30 | Slide16.jpg | 1326 | 11.25 |

TABLE 14

| TNS2 summary | |
|---|---|
| non-IS | 39.14 |
| IS | 60.41 |
| LV | 99.56 |
| IS/LV | 61% |

TABLE 15

| | TNF1 raw values | | |
|---|---|---|---|
| 1 | Slide17.jpg | 1326 | |
| 2 | Slide17.jpg | 63 | 0.24 |
| 3 | Slide17.jpg | 1183 | 4.46 |
| 4 | Slide17.jpg | 3158 | |
| 5 | Slide17.jpg | 825 | 5.49 |
| 6 | Slide17.jpg | 2014 | 13.39 |
| 7 | Slide17.jpg | 4805 | |
| 8 | Slide17.jpg | 1774 | 12.92 |
| 9 | Slide17.jpg | 1722 | 12.54 |

TABLE 15-continued

TNF1 raw values

| | | | |
|---|---|---|---|
| 10 | Slide17.jpg | 4675 | |
| 11 | Slide17.jpg | 1984 | 15.28 |
| 12 | Slide17.jpg | 2470 | 19.02 |
| 13 | Slide17.jpg | 2754 | |
| 14 | Slide17.jpg | 269 | 2.05 |
| 15 | Slide17.jpg | 1377 | 10.50 |
| 16 | Slide17.jpg | 1373 | |
| 17 | Slide17.jpg | 1067 | 3.89 |
| 18 | Slide17.jpg | 43 | 0.16 |
| 19 | Slide17.jpg | 3113 | |
| 20 | Slide17.jpg | 803 | 5.42 |
| 21 | Slide17.jpg | 2008 | 13.55 |
| 22 | Slide17.jpg | 4657 | |
| 23 | Slide17.jpg | 1189 | 8.94 |
| 24 | Slide17.jpg | 2398 | 18.02 |
| 25 | Slide17.jpg | 4607 | |
| 26 | Slide17.jpg | 1256 | 9.81 |
| 27 | Slide17.jpg | 1978 | 15.46 |
| 28 | Slide17.jpg | 2769 | |
| 29 | Slide17.jpg | 2115 | 16.04 |
| 30 | Slide17.jpg | 72 | 0.55 |

TABLE 16

TNF1 summary

| | |
|---|---|
| non-IS | 40.03 |
| IS | 53.82 |
| LV | 93.86 |
| IS/LV | 57% |

TABLE 17

TNF2 raw values

| | | | |
|---|---|---|---|
| 1 | Slide18.jpg | 2133 | |
| 2 | Slide18.jpg | 1861 | 12.21 |
| 3 | Slide18.jpg | 239 | 1.57 |
| 4 | Slide18.jpg | 4037 | |
| 5 | Slide18.jpg | 753 | 5.60 |
| 6 | Slide18.jpg | 2304 | 17.12 |
| 7 | Slide18.jpg | 4663 | |
| 8 | Slide18.jpg | 1548 | 10.62 |
| 9 | Slide18.jpg | 2917 | 20.02 |
| 10 | Slide18.jpg | 5017 | |
| 11 | Slide18.jpg | 2648 | 20.06 |
| 12 | Slide18.jpg | 2480 | 18.78 |
| 13 | Slide18.jpg | 3629 | |
| 14 | Slide18.jpg | 1698 | 13.10 |
| 15 | Slide18.jpg | 348 | 2.69 |
| 16 | Slide18.jpg | 2130 | |
| 17 | Slide18.jpg | 4 | 0.03 |
| 18 | Slide18.jpg | 1988 | 13.07 |
| 19 | Slide18.jpg | 4108 | |
| 20 | Slide18.jpg | 253 | 1.85 |
| 21 | Slide18.jpg | 3796 | 27.72 |
| 22 | Slide18.jpg | 4612 | |
| 23 | Slide18.jpg | 815 | 5.65 |
| 24 | Slide18.jpg | 2427 | 16.84 |
| 25 | Slide18.jpg | 4880 | |
| 26 | Slide18.jpg | 562 | 4.38 |
| 27 | Slide18.jpg | 3535 | 27.53 |
| 28 | Slide18.jpg | 3507 | |
| 29 | Slide18.jpg | 497 | 3.97 |
| 30 | Slide18.jpg | 1837 | 14.67 |

TABLE 18

TNF2 summary

| | |
|---|---|
| non-IS | 38.73 |
| IS | 80.00 |
| LV | 118.73 |
| IS/LV | 73% |

TABLE 19

TNS3 raw values

| | | | |
|---|---|---|---|
| 1 | Slide19.jpg | 1484 | |
| 2 | Slide19.jpg | 923 | 4.98 |
| 3 | Slide19.jpg | 714 | 3.85 |
| 4 | Slide19.jpg | 3124 | |
| 5 | Slide19.jpg | 990 | 6.65 |
| 6 | Slide19.jpg | 1845 | 12.40 |
| 7 | Slide19.jpg | 3414 | |
| 8 | Slide19.jpg | 1282 | 13.89 |
| 9 | Slide19.jpg | 1833 | 19.87 |
| 10 | Slide19.jpg | 3380 | |
| 11 | Slide19.jpg | 2123 | 16.33 |
| 12 | Slide19.jpg | 1042 | 8.02 |
| 13 | Slide19.jpg | 2105 | |
| 14 | Slide19.jpg | 957 | 7.73 |
| 15 | Slide19.jpg | 308 | 2.49 |
| 16 | Slide19.jpg | 1524 | |
| 17 | Slide19.jpg | 10 | 0.05 |
| 18 | Slide19.jpg | 1530 | 8.03 |
| 19 | Slide19.jpg | 2860 | |
| 20 | Slide19.jpg | 13 | 0.10 |
| 21 | Slide19.jpg | 2293 | 16.84 |
| 22 | Slide19.jpg | 3358 | |
| 23 | Slide19.jpg | 960 | 10.58 |
| 24 | Slide19.jpg | 2639 | 29.08 |
| 25 | Slide19.jpg | 2538 | |
| 26 | Slide19.jpg | 296 | 3.03 |
| 27 | Slide19.jpg | 1797 | 18.41 |
| 28 | Slide19.jpg | 1992 | |
| 29 | Slide19.jpg | 1105 | 9.43 |
| 30 | Slide19.jpg | 401 | 3.42 |

TABLE 20

TNS3 summary

| | |
|---|---|
| non-IS | 36.39 |
| IS | 61.20 |
| LV | 97.58 |
| IS/LV | 63% |

TABLE 21

TNS4 raw values

| | | | |
|---|---|---|---|
| 1 | Slide20.jpg | 1524 | |
| 2 | Slide20.jpg | 47 | 0.28 |
| 3 | Slide20.jpg | 1417 | 8.37 |
| 4 | Slide20.jpg | 2478 | |
| 5 | Slide20.jpg | 582 | 5.17 |
| 6 | Slide20.jpg | 1617 | 14.36 |
| 7 | Slide20.jpg | 3284 | |
| 8 | Slide20.jpg | 1226 | 11.20 |
| 9 | Slide20.jpg | 2072 | 18.93 |
| 10 | Slide20.jpg | 3639 | |
| 11 | Slide20.jpg | 771 | 7.20 |
| 12 | Slide20.jpg | 2177 | 20.34 |
| 13 | Slide20.jpg | 3114 | |
| 14 | Slide20.jpg | 491 | 5.36 |
| 15 | Slide20.jpg | 2189 | 23.90 |
| 16 | Slide20.jpg | 1648 | |
| 17 | Slide20.jpg | 1244 | 6.79 |
| 18 | Slide20.jpg | 94 | 0.51 |

TABLE 21-continued

TNS4 raw values

| 19 | Slide20.jpg | 2912 | |
| 20 | Slide20.jpg | 1446 | 10.92 |
| 21 | Slide20.jpg | 1262 | 9.53 |
| 22 | Slide20.jpg | 4073 | |
| 23 | Slide20.jpg | 2350 | 17.31 |
| 24 | Slide20.jpg | 1049 | 7.73 |
| 25 | Slide20.jpg | 3470 | |
| 26 | Slide20.jpg | 2445 | 23.96 |
| 27 | Slide20.jpg | 1052 | 10.31 |
| 28 | Slide20.jpg | 3219 | |
| 29 | Slide20.jpg | 2120 | 22.39 |
| 30 | Slide20.jpg | 32 | 0.34 |

TABLE 22

TNS4 summary

| non-IS | 55.29 |
| IS | 57.16 |
| LV | 112.45 |
| IS/LV | 51% |

TABLE 23

TNF3 raw values

| 1 | Slide21.jpg | 1551 | |
| 2 | Slide21.jpg | 3 | 0.02 |
| 3 | Slide21.jpg | 1502 | 10.65 |
| 4 | Slide21.jpg | 3054 | |
| 5 | Slide21.jpg | 922 | 6.34 |
| 6 | Slide21.jpg | 2049 | 14.09 |
| 7 | Slide21.jpg | 3374 | |
| 8 | Slide21.jpg | 1280 | 12.52 |
| 9 | Slide21.jpg | 1566 | 15.32 |
| 10 | Slide21.jpg | 2799 | |
| 11 | Slide21.jpg | 1476 | 14.77 |
| 12 | Slide21.jpg | 1061 | 10.61 |
| 13 | Slide21.jpg | 2330 | |
| 14 | Slide21.jpg | 398 | 3.25 |
| 15 | Slide21.jpg | 1012 | 8.25 |
| 16 | Slide21.jpg | 1689 | |
| 17 | Slide21.jpg | 7 | 0.05 |
| 18 | Slide21.jpg | 1544 | 10.06 |
| 19 | Slide21.jpg | 2894 | |
| 20 | Slide21.jpg | 361 | 2.62 |
| 21 | Slide21.jpg | 1925 | 13.97 |
| 22 | Slide21.jpg | 3254 | |
| 23 | Slide21.jpg | 1137 | 11.53 |
| 24 | Slide21.jpg | 1267 | 12.85 |
| 25 | Slide21.jpg | 2814 | |
| 26 | Slide21.jpg | 1272 | 12.66 |
| 27 | Slide21.jpg | 1113 | 11.07 |
| 28 | Slide21.jpg | 2821 | |
| 29 | Slide21.jpg | 1438 | 9.69 |
| 30 | Slide21.jpg | 174 | 1.17 |

TABLE 24

TNF3 summary

| non-IS | 36.71 |
| IS | 54.02 |
| LV | 90.74 |
| IS/LV | 60% |

TABLE 25

TNF4 raw values

| 1 | Slide22.jpg | 1354 | |
| 2 | Slide22.jpg | 72 | 0.37 |
| 3 | Slide22.jpg | 1335 | 6.90 |
| 4 | Slide22.jpg | 2892 | |
| 5 | Slide22.jpg | 672 | 3.95 |
| 6 | Slide22.jpg | 2093 | 12.30 |
| 7 | Slide22.jpg | 3414 | |
| 8 | Slide22.jpg | 1342 | 9.83 |
| 9 | Slide22.jpg | 2213 | 16.21 |
| 10 | Slide22.jpg | 3698 | |
| 11 | Slide22.jpg | 1168 | 10.11 |
| 12 | Slide22.jpg | 2317 | 20.05 |
| 13 | Slide22.jpg | 2565 | |
| 14 | Slide22.jpg | 243 | 2.94 |
| 15 | Slide22.jpg | 1398 | 16.90 |
| 16 | Slide22.jpg | 1486 | |
| 17 | Slide22.jpg | 638 | 3.01 |
| 18 | Slide22.jpg | 583 | 2.75 |
| 19 | Slide22.jpg | 2719 | |
| 20 | Slide22.jpg | 26 | 0.16 |
| 21 | Slide22.jpg | 2164 | 13.53 |
| 22 | Slide22.jpg | 3514 | |
| 23 | Slide22.jpg | 568 | 4.04 |
| 24 | Slide22.jpg | 2361 | 16.80 |
| 25 | Slide22.jpg | 3908 | |
| 26 | Slide22.jpg | 1498 | 12.27 |
| 27 | Slide22.jpg | 1805 | 14.78 |
| 28 | Slide22.jpg | 2946 | |
| 29 | Slide22.jpg | 16 | 0.17 |
| 30 | Slide22.jpg | 1969 | 20.72 |

TABLE 26

TNF4 summary

| non-IS | 23.42 |
| IS | 70.46 |
| LV | 93.88 |
| IS/LV | 75% |

TABLE 27

TNS5 raw values

| 1 | Slide23.jpg | 1615 | |
| 2 | Slide23.jpg | 8 | 0.04 |
| 3 | Slide23.jpg | 1571 | 8.75 |
| 4 | Slide23.jpg | 2789 | |
| 5 | Slide23.jpg | 1477 | 11.65 |
| 6 | Slide23.jpg | 1042 | 8.22 |
| 7 | Slide23.jpg | 3558 | |
| 8 | Slide23.jpg | 2026 | 22.21 |
| 9 | Slide23.jpg | 1327 | 14.55 |
| 10 | Slide23.jpg | 3822 | |
| 11 | Slide23.jpg | 1044 | 8.74 |
| 12 | Slide23.jpg | 1590 | 13.31 |
| 13 | Slide23.jpg | 3246 | |
| 14 | Slide23.jpg | 1224 | 8.67 |
| 15 | Slide23.jpg | 705 | 5.00 |
| 16 | Slide23.jpg | 1445 | |
| 17 | Slide23.jpg | 1228 | 7.65 |
| 18 | Slide23.jpg | 200 | 1.25 |
| 19 | Slide23.jpg | 2732 | |
| 20 | Slide23.jpg | 1951 | 15.71 |
| 21 | Slide23.jpg | 782 | 6.30 |
| 22 | Slide23.jpg | 3858 | |
| 23 | Slide23.jpg | 3039 | 30.72 |
| 24 | Slide23.jpg | 400 | 4.04 |
| 25 | Slide23.jpg | 3697 | |
| 26 | Slide23.jpg | 2609 | 22.58 |
| 27 | Slide23.jpg | 943 | 8.16 |
| 28 | Slide23.jpg | 3358 | |

TABLE 27-continued

TNS5 raw values

| | | | |
|---|---|---|---|
| 29 | Slide23.jpg | 1492 | 10.22 |
| 30 | Slide23.jpg | 583 | 3.99 |

TABLE 28

TNS5 summary

| | |
|---|---|
| non-IS | 69.10 |
| IS | 36.78 |
| LV | 105.88 |
| IS/LV | 35% |

TABLE 29

TNS6 raw values

| | | | |
|---|---|---|---|
| 1 | Slide24.jpg | 1216 | |
| 2 | Slide24.jpg | 258 | 1.49 |
| 3 | Slide24.jpg | 770 | 4.43 |
| 4 | Slide24.jpg | 3079 | |
| 5 | Slide24.jpg | 1436 | 10.26 |
| 6 | Slide24.jpg | 1417 | 10.12 |
| 7 | Slide24.jpg | 3677 | |
| 8 | Slide24.jpg | 2085 | 11.34 |
| 9 | Slide24.jpg | 1122 | 6.10 |
| 10 | Slide24.jpg | 3908 | |
| 11 | Slide24.jpg | 2151 | 15.96 |
| 12 | Slide24.jpg | 1415 | 10.50 |
| 13 | Slide24.jpg | 2371 | |
| 14 | Slide24.jpg | 1651 | 14.62 |
| 15 | Slide24.jpg | 495 | 4.38 |
| 16 | Slide24.jpg | 1123 | |
| 17 | Slide24.jpg | 879 | 5.48 |
| 18 | Slide24.jpg | 262 | 1.63 |
| 19 | Slide24.jpg | 3090 | |
| 20 | Slide24.jpg | 1775 | 12.64 |
| 21 | Slide24.jpg | 1121 | 7.98 |
| 22 | Slide24.jpg | 3470 | |
| 23 | Slide24.jpg | 2215 | 12.77 |
| 24 | Slide24.jpg | 1219 | 7.03 |
| 25 | Slide24.jpg | 3666 | |
| 26 | Slide24.jpg | 2524 | 19.97 |
| 27 | Slide24.jpg | 1411 | 11.16 |
| 28 | Slide24.jpg | 2470 | |
| 29 | Slide24.jpg | 1397 | 11.88 |
| 30 | Slide24.jpg | 140 | 1.19 |

TABLE 30

TNS6 summary

| | |
|---|---|
| non-IS | 58.20 |
| IS | 32.27 |
| LV | 90.47 |
| IS/LV | 36% |

TABLE 31

CN13 raw values

| | | | |
|---|---|---|---|
| 1 | Slide25.jpg | 1010 | |
| 2 | Slide25.jpg | 4 | 0.04 |
| 3 | Slide25.jpg | 1006 | 8.96 |
| 4 | Slide25.jpg | 2216 | |
| 5 | Slide25.jpg | 756 | 5.80 |
| 6 | Slide25.jpg | 1708 | 13.10 |
| 7 | Slide25.jpg | 3122 | |
| 8 | Slide25.jpg | 744 | 5.72 |
| 9 | Slide25.jpg | 1674 | 12.87 |
| 10 | Slide25.jpg | 3214 | |
| 11 | Slide25.jpg | 177 | 1.87 |
| 12 | Slide25.jpg | 1678 | 17.75 |
| 13 | Slide25.jpg | 2504 | |
| 14 | Slide25.jpg | 371 | 3.41 |
| 15 | Slide25.jpg | 770 | 7.07 |
| 16 | Slide25.jpg | 940 | |
| 17 | Slide25.jpg | 3 | 0.03 |
| 18 | Slide25.jpg | 902 | 8.64 |
| 19 | Slide25.jpg | 1907 | |
| 20 | Slide25.jpg | 266 | 2.37 |
| 21 | Slide25.jpg | 1439 | 12.83 |
| 22 | Slide25.jpg | 2763 | |
| 23 | Slide25.jpg | 1036 | 9.00 |
| 24 | Slide25.jpg | 1855 | 16.11 |
| 25 | Slide25.jpg | 2930 | |
| 26 | Slide25.jpg | 988 | 11.46 |
| 27 | Slide25.jpg | 1618 | 18.78 |
| 28 | Slide25.jpg | 2498 | |
| 29 | Slide25.jpg | 280 | 2.58 |
| 30 | Slide25.jpg | 1839 | 16.93 |

TABLE 32

CN13 summary

| | |
|---|---|
| non-IS | 21.14 |
| IS | 66.52 |
| LV | 87.66 |
| IS/LV | 76% |

TABLE 33

CN14 raw values

| | | | |
|---|---|---|---|
| 1 | Slide26.jpg | 1387 | |
| 2 | Slide26.jpg | 40 | 0.23 |
| 3 | Slide26.jpg | 1356 | 7.82 |
| 4 | Slide26.jpg | 2994 | |
| 5 | Slide26.jpg | 699 | 4.67 |
| 6 | Slide26.jpg | 1620 | 10.82 |
| 7 | Slide26.jpg | 3017 | |
| 8 | Slide26.jpg | 1087 | 11.89 |
| 9 | Slide26.jpg | 1443 | 15.78 |
| 10 | Slide26.jpg | 2871 | |
| 11 | Slide26.jpg | 2644 | 29.47 |
| 12 | Slide26.jpg | 188 | 2.10 |
| 13 | Slide26.jpg | 2504 | |
| 14 | Slide26.jpg | 7 | 0.05 |
| 15 | Slide26.jpg | 1996 | 13.55 |
| 16 | Slide26.jpg | 1424 | |
| 17 | Slide26.jpg | 490 | 2.75 |
| 18 | Slide26.jpg | 931 | 5.23 |
| 19 | Slide26.jpg | 2926 | |
| 20 | Slide26.jpg | 40 | 0.27 |
| 21 | Slide26.jpg | 2231 | 15.25 |
| 22 | Slide26.jpg | 3248 | |
| 23 | Slide26.jpg | 782 | 7.95 |
| 24 | Slide26.jpg | 2137 | 21.71 |
| 25 | Slide26.jpg | 3401 | |
| 26 | Slide26.jpg | 348 | 3.27 |
| 27 | Slide26.jpg | 2624 | 24.69 |
| 28 | Slide26.jpg | 2079 | |
| 29 | Slide26.jpg | 573 | 4.69 |
| 30 | Slide26.jpg | 1042 | 8.52 |

TABLE 34

| CN14 summary | |
|---|---|
| non-IS | 32.62 |
| IS | 62.74 |
| LV | 95.36 |
| IS/LV | 66% |

TABLE 35

TNF5 raw values

| | | | |
|---|---|---|---|
| 1 | Slide27.jpg | 1504 | |
| 2 | Slide27.jpg | 22 | 0.13 |
| 3 | Slide27.jpg | 1336 | 7.99 |
| 4 | Slide27.jpg | 2786 | |
| 5 | Slide27.jpg | 390 | 3.22 |
| 6 | Slide27.jpg | 1956 | 16.15 |
| 7 | Slide27.jpg | 3792 | |
| 8 | Slide27.jpg | 1444 | 10.66 |
| 9 | Slide27.jpg | 2232 | 16.48 |
| 10 | Slide27.jpg | 3470 | |
| 11 | Slide27.jpg | 587 | 5.41 |
| 12 | Slide27.jpg | 2824 | 26.04 |
| 13 | Slide27.jpg | 3002 | |
| 14 | Slide27.jpg | 2361 | 16.52 |
| 15 | Slide27.jpg | 1329 | 9.30 |
| 16 | Slide27.jpg | 1666 | |
| 17 | Slide27.jpg | 274 | 1.48 |
| 18 | Slide27.jpg | 1024 | 5.53 |
| 19 | Slide27.jpg | 2735 | |
| 20 | Slide27.jpg | 9 | 0.08 |
| 21 | Slide27.jpg | 2897 | 24.36 |
| 22 | Slide27.jpg | 3575 | |
| 23 | Slide27.jpg | 1217 | 9.53 |
| 24 | Slide27.jpg | 2163 | 16.94 |
| 25 | Slide27.jpg | 3350 | |
| 26 | Slide27.jpg | 997 | 9.52 |
| 27 | Slide27.jpg | 1812 | 17.31 |
| 28 | Slide27.jpg | 3022 | |
| 29 | Slide27.jpg | 12 | 0.08 |
| 30 | Slide27.jpg | 1778 | 12.36 |

TABLE 36

| TNF5 summary | |
|---|---|
| non-IS | 28.32 |
| IS | 76.23 |
| LV | 104.55 |
| IS/LV | 73% |

TABLE 37

TNF6 raw values

| | | | |
|---|---|---|---|
| 1 | Slide28.jpg | 1114 | |
| 2 | Slide28.jpg | 62 | 0.45 |
| 3 | Slide28.jpg | 879 | 6.31 |
| 4 | Slide28.jpg | 2858 | |
| 5 | Slide28.jpg | 459 | 3.85 |
| 6 | Slide28.jpg | 1713 | 14.38 |
| 7 | Slide28.jpg | 3625 | |
| 8 | Slide28.jpg | 369 | 3.56 |
| 9 | Slide28.jpg | 2924 | 28.23 |
| 10 | Slide28.jpg | 3948 | |
| 11 | Slide28.jpg | 511 | 4.27 |
| 12 | Slide28.jpg | 2866 | 23.96 |
| 13 | Slide28.jpg | 3135 | |
| 14 | Slide28.jpg | 386 | 3.08 |
| 15 | Slide28.jpg | 1447 | 11.54 |
| 16 | Slide28.jpg | 1126 | |
| 17 | Slide28.jpg | 10 | 0.07 |
| 18 | Slide28.jpg | 1043 | 7.41 |

TABLE 37-continued

TNF6 raw values

| | | | |
|---|---|---|---|
| 19 | Slide28.jpg | 3156 | |
| 20 | Slide28.jpg | 160 | 1.22 |
| 21 | Slide28.jpg | 3062 | 23.29 |
| 22 | Slide28.jpg | 3790 | |
| 23 | Slide28.jpg | 827 | 7.64 |
| 24 | Slide28.jpg | 2644 | 24.42 |
| 25 | Slide28.jpg | 3618 | |
| 26 | Slide28.jpg | 1607 | 14.66 |
| 27 | Slide28.jpg | 2452 | 22.36 |
| 28 | Slide28.jpg | 3440 | |
| 29 | Slide28.jpg | 1023 | 7.43 |
| 30 | Slide28.jpg | 1770 | 12.86 |

TABLE 38

| TNF6 summary | |
|---|---|
| non-IS | 23.11 |
| IS | 87.38 |
| LV | 110.50 |
| IS/LV | 79% |

TABLE 39

TNS7 raw values

| | | | |
|---|---|---|---|
| 1 | Slide29.jpg | 1713 | |
| 2 | Slide29.jpg | 607 | 4.61 |
| 3 | Slide29.jpg | 782 | 5.93 |
| 4 | Slide29.jpg | 2484 | |
| 5 | Slide29.jpg | 195 | 1.88 |
| 6 | Slide29.jpg | 1842 | 17.80 |
| 7 | Slide29.jpg | 2807 | |
| 8 | Slide29.jpg | 1568 | 12.29 |
| 9 | Slide29.jpg | 380 | 2.98 |
| 10 | Slide29.jpg | 3271 | |
| 11 | Slide29.jpg | 2187 | 20.06 |
| 12 | Slide29.jpg | 350 | 3.21 |
| 13 | Slide29.jpg | 2309 | |
| 14 | Slide29.jpg | 610 | 5.55 |
| 15 | Slide29.jpg | 1008 | 9.17 |
| 16 | Slide29.jpg | 1923 | |
| 17 | Slide29.jpg | 865 | 5.85 |
| 18 | Slide29.jpg | 631 | 4.27 |
| 19 | Slide29.jpg | 3033 | |
| 20 | Slide29.jpg | 1501 | 11.88 |
| 21 | Slide29.jpg | 780 | 6.17 |
| 22 | Slide29.jpg | 3287 | |
| 23 | Slide29.jpg | 2214 | 14.82 |
| 24 | Slide29.jpg | 456 | 3.05 |
| 25 | Slide29.jpg | 3395 | |
| 26 | Slide29.jpg | 2398 | 21.19 |
| 27 | Slide29.jpg | 287 | 2.54 |
| 28 | Slide29.jpg | 2969 | |
| 29 | Slide29.jpg | 1647 | 11.65 |
| 30 | Slide29.jpg | 67 | 0.47 |

TABLE 40

| TNS7 summary | |
|---|---|
| non-IS | 54.88 |
| IS | 27.79 |
| LV | 82.68 |
| IS/LV | 34% |

TABLE 41

TNS8 raw values

| | | | |
|---|---|---|---|
| 1 | Slide30.jpg | 1123 | |
| 2 | Slide30.jpg | 11 | 0.05 |
| 3 | Slide30.jpg | 988 | 4.40 |
| 4 | Slide30.jpg | 2352 | |
| 5 | Slide30.jpg | 279 | 2.25 |
| 6 | Slide30.jpg | 2001 | 16.16 |
| 7 | Slide30.jpg | 3274 | |
| 8 | Slide30.jpg | 1085 | 7.29 |
| 9 | Slide30.jpg | 1821 | 12.24 |
| 10 | Slide30.jpg | 3333 | |
| 11 | Slide30.jpg | 2048 | 17.20 |
| 12 | Slide30.jpg | 838 | 7.04 |
| 13 | Slide30.jpg | 2240 | |
| 14 | Slide30.jpg | 793 | 7.08 |
| 15 | Slide30.jpg | 840 | 7.50 |
| 16 | Slide30.jpg | 914 | |
| 17 | Slide30.jpg | 866 | 4.74 |
| 18 | Slide30.jpg | 64 | 0.35 |
| 19 | Slide30.jpg | 2811 | |
| 20 | Slide30.jpg | 397 | 2.68 |
| 21 | Slide30.jpg | 2135 | 14.43 |
| 22 | Slide30.jpg | 3378 | |
| 23 | Slide30.jpg | 588 | 3.83 |
| 24 | Slide30.jpg | 2250 | 14.65 |
| 25 | Slide30.jpg | 3241 | |
| 26 | Slide30.jpg | 2671 | 23.08 |
| 27 | Slide30.jpg | 287 | 2.48 |
| 28 | Slide30.jpg | 2697 | |
| 29 | Slide30.jpg | 1247 | 9.25 |
| 30 | Slide30.jpg | 23 | 0.17 |

TABLE 42

TNS8 summary

| | |
|---|---|
| non-IS | 38.73 |
| IS | 39.71 |
| LV | 78.44 |
| IS/LV | 51% |

TABLE 43

TNF7 raw values

| | | | |
|---|---|---|---|
| 1 | Slide31.jpg | 1733 | |
| 2 | Slide31.jpg | 15 | 0.06 |
| 3 | Slide31.jpg | 1704 | 6.88 |
| 4 | Slide31.jpg | 3401 | |
| 5 | Slide31.jpg | 719 | 3.38 |
| 6 | Slide31.jpg | 2216 | 10.43 |
| 7 | Slide31.jpg | 3789 | |
| 8 | Slide31.jpg | 917 | 7.02 |
| 9 | Slide31.jpg | 2163 | 16.56 |
| 10 | Slide31.jpg | 4149 | |
| 11 | Slide31.jpg | 719 | 5.03 |
| 12 | Slide31.jpg | 3423 | 23.93 |
| 13 | Slide31.jpg | 3309 | |
| 14 | Slide31.jpg | 1479 | 8.49 |
| 15 | Slide31.jpg | 1771 | 10.17 |
| 16 | Slide31.jpg | 1777 | |
| 17 | Slide31.jpg | 1049 | 4.13 |
| 18 | Slide31.jpg | 678 | 2.67 |
| 19 | Slide31.jpg | 3117 | |
| 20 | Slide31.jpg | 221 | 1.13 |
| 21 | Slide31.jpg | 2281 | 11.71 |
| 22 | Slide31.jpg | 3970 | |
| 23 | Slide31.jpg | 2416 | 17.65 |
| 24 | Slide31.jpg | 796 | 5.81 |
| 25 | Slide31.jpg | 4354 | |
| 26 | Slide31.jpg | 3291 | 21.92 |
| 27 | Slide31.jpg | 697 | 4.64 |
| 28 | Slide31.jpg | 3316 | |

TABLE 43-continued

TNF7 raw values

| | | | |
|---|---|---|---|
| 29 | Slide31.jpg | 2414 | 13.83 |
| 30 | Slide31.jpg | 62 | 0.36 |

TABLE 44

TNF7 summary

| | |
|---|---|
| non-IS | 41.32 |
| IS | 46.57 |
| LV | 87.90 |
| IS/LV | 53% |

TABLE 45

TNF8 raw values

| | | | |
|---|---|---|---|
| 1 | Slide32.jpg | 1553 | |
| 2 | Slide32.jpg | 572 | 2.58 |
| 3 | Slide32.jpg | 873 | 3.93 |
| 4 | Slide32.jpg | 3334 | |
| 5 | Slide32.jpg | 1084 | 5.53 |
| 6 | Slide32.jpg | 1525 | 7.78 |
| 7 | Slide32.jpg | 4166 | |
| 8 | Slide32.jpg | 2437 | 12.87 |
| 9 | Slide32.jpg | 1557 | 8.22 |
| 10 | Slide32.jpg | 4558 | |
| 11 | Slide32.jpg | 2698 | 20.13 |
| 12 | Slide32.jpg | 1306 | 9.74 |
| 13 | Slide32.jpg | 3405 | |
| 14 | Slide32.jpg | 2991 | 25.47 |
| 15 | Slide32.jpg | 51 | 0.43 |
| 16 | Slide32.jpg | 1543 | |
| 17 | Slide32.jpg | 3 | 0.01 |
| 18 | Slide32.jpg | 1407 | 6.38 |
| 19 | Slide32.jpg | 3359 | |
| 20 | Slide32.jpg | 581 | 2.94 |
| 21 | Slide32.jpg | 2011 | 10.18 |
| 22 | Slide32.jpg | 3986 | |
| 23 | Slide32.jpg | 202 | 1.11 |
| 24 | Slide32.jpg | 3788 | 20.91 |
| 25 | Slide32.jpg | 4684 | |
| 26 | Slide32.jpg | 425 | 3.08 |
| 27 | Slide32.jpg | 3308 | 24.01 |
| 28 | Slide32.jpg | 3498 | |
| 29 | Slide32.jpg | 920 | 7.63 |
| 30 | Slide32.jpg | 1731 | 14.35 |

TABLE 46

TNF8 summary

| | |
|---|---|
| non-IS | 40.68 |
| IS | 52.97 |
| LV | 93.65 |
| IS/LV | 57% |

TABLE 47

TNS9 raw values

| | | | |
|---|---|---|---|
| 1 | Slide33.jpg | 2637 | |
| 2 | Slide33.jpg | 14 | 0.06 |
| 3 | Slide33.jpg | 2081 | 9.47 |
| 4 | Slide33.jpg | 4101 | |
| 5 | Slide33.jpg | 1571 | 7.28 |
| 6 | Slide33.jpg | 1516 | 7.02 |
| 7 | Slide33.jpg | 4527 | |
| 8 | Slide33.jpg | 2519 | 18.36 |
| 9 | Slide33.jpg | 1555 | 11.34 |

TABLE 47-continued

TNS9 raw values

| | | | |
|---|---|---|---|
| 10 | Slide33.jpg | 3326 | |
| 11 | Slide33.jpg | 3188 | 19.17 |
| 12 | Slide33.jpg | 27 | 0.16 |
| 13 | Slide33.jpg | 2336 | |
| 14 | Slide33.jpg | 1885 | 9.68 |
| 15 | Slide33.jpg | 240 | 1.23 |
| 16 | Slide33.jpg | 2343 | |
| 17 | Slide33.jpg | 2027 | 10.38 |
| 18 | Slide33.jpg | 21 | 0.11 |
| 19 | Slide33.jpg | 3393 | |
| 20 | Slide33.jpg | 1928 | 10.80 |
| 21 | Slide33.jpg | 945 | 5.29 |
| 22 | Slide33.jpg | 4425 | |
| 23 | Slide33.jpg | 2984 | 22.25 |
| 24 | Slide33.jpg | 637 | 4.75 |
| 25 | Slide33.jpg | 3063 | |
| 26 | Slide33.jpg | 773 | 5.05 |
| 27 | Slide33.jpg | 1885 | 12.31 |
| 28 | Slide33.jpg | 2324 | |
| 29 | Slide33.jpg | 1390 | 7.18 |
| 30 | Slide33.jpg | 9 | 0.05 |

TABLE 48

TNS9 summary

| | |
|---|---|
| non-IS | 55.11 |
| IS | 25.86 |
| LV | 80.97 |
| IS/LV | 32% |

TABLE 49

TNS10 raw values

| | | | |
|---|---|---|---|
| 1 | Slide34.jpg | 1775 | |
| 2 | Slide34.jpg | 1082 | 4.88 |
| 3 | Slide34.jpg | 348 | 1.57 |
| 4 | Slide34.jpg | 3607 | |
| 5 | Slide34.jpg | 1823 | 11.12 |
| 6 | Slide34.jpg | 1483 | 9.05 |
| 7 | Slide34.jpg | 4313 | |
| 8 | Slide34.jpg | 1087 | 6.80 |
| 9 | Slide34.jpg | 2173 | 13.60 |
| 10 | Slide34.jpg | 4275 | |
| 11 | Slide34.jpg | 2471 | 15.03 |
| 12 | Slide34.jpg | 1734 | 10.55 |
| 13 | Slide34.jpg | 2864 | |
| 14 | Slide34.jpg | 2424 | 18.62 |
| 15 | Slide34.jpg | 43 | 0.33 |
| 16 | Slide34.jpg | 1601 | |
| 17 | Slide34.jpg | 1600 | 8.00 |
| 18 | Slide34.jpg | 16 | 0.08 |
| 19 | Slide34.jpg | 3486 | |
| 20 | Slide34.jpg | 933 | 5.89 |
| 21 | Slide34.jpg | 935 | 5.90 |
| 22 | Slide34.jpg | 4312 | |
| 23 | Slide34.jpg | 3250 | 20.35 |
| 24 | Slide34.jpg | 722 | 4.52 |
| 25 | Slide34.jpg | 4178 | |
| 26 | Slide34.jpg | 3996 | 24.87 |
| 27 | Slide34.jpg | 231 | 1.44 |
| 28 | Slide34.jpg | 3046 | |
| 29 | Slide34.jpg | 2854 | 20.61 |
| 30 | Slide34.jpg | 39 | 0.28 |

TABLE 50

TNS10 summary

| | |
|---|---|
| non-IS | 68.08 |
| IS | 23.66 |
| LV | 91.74 |
| IS/LV | 26% |

TABLE 51

TNF9 raw values

| | | | |
|---|---|---|---|
| 1 | Slide35.jpg | 1737 | |
| 2 | Slide35.jpg | 841 | 2.91 |
| 3 | Slide35.jpg | 788 | 2.72 |
| 4 | Slide35.jpg | 3368 | |
| 5 | Slide35.jpg | 1416 | 7.99 |
| 6 | Slide35.jpg | 1230 | 6.94 |
| 7 | Slide35.jpg | 4474 | |
| 8 | Slide35.jpg | 1046 | 8.18 |
| 9 | Slide35.jpg | 3356 | 26.25 |
| 10 | Slide35.jpg | 4877 | |
| 11 | Slide35.jpg | 1303 | 6.68 |
| 12 | Slide35.jpg | 3142 | 16.11 |
| 13 | Slide35.jpg | 3803 | |
| 14 | Slide35.jpg | 2906 | 16.81 |
| 15 | Slide35.jpg | 15 | 0.09 |
| 16 | Slide35.jpg | 1719 | |
| 17 | Slide35.jpg | 8 | 0.03 |
| 18 | Slide35.jpg | 1545 | 5.39 |
| 19 | Slide35.jpg | 3500 | |
| 20 | Slide35.jpg | 9 | 0.05 |
| 21 | Slide35.jpg | 3382 | 18.36 |
| 22 | Slide35.jpg | 4790 | |
| 23 | Slide35.jpg | 9 | 0.07 |
| 24 | Slide35.jpg | 4476 | 32.71 |
| 25 | Slide35.jpg | 4213 | |
| 26 | Slide35.jpg | 1798 | 10.67 |
| 27 | Slide35.jpg | 2840 | 16.85 |
| 28 | Slide35.jpg | 3714 | |
| 29 | Slide35.jpg | 2917 | 17.28 |
| 30 | Slide35.jpg | 342 | 2.03 |

TABLE 52

TNF9 summary

| | |
|---|---|
| non-IS | 35.33 |
| IS | 63.72 |
| LV | 99.05 |
| IS/LV | 64% |

TABLE 53

TNF10 raw values

| | | | |
|---|---|---|---|
| 1 | Slide36.jpg | 2294 | |
| 2 | Slide36.jpg | 14 | 0.08 |
| 3 | Slide36.jpg | 2183 | 12.37 |
| 4 | Slide36.jpg | 4093 | |
| 5 | Slide36.jpg | 189 | 1.34 |
| 6 | Slide36.jpg | 3572 | 25.31 |
| 7 | Slide36.jpg | 4330 | |
| 8 | Slide36.jpg | 829 | 9.38 |
| 9 | Slide36.jpg | 2710 | 30.67 |
| 10 | Slide36.jpg | 2189 | |
| 11 | Slide36.jpg | 185 | 1.18 |
| 12 | Slide36.jpg | 1581 | 10.11 |
| 13 | Slide36.jpg | 1961 | |
| 14 | Slide36.jpg | 344 | 1.40 |
| 15 | Slide36.jpg | 1293 | 5.27 |
| 16 | Slide36.jpg | 2188 | |
| 17 | Slide36.jpg | 1766 | 10.49 |
| 18 | Slide36.jpg | 382 | 2.27 |

TABLE 53-continued

TNF10 raw values

| 19 | Slide36.jpg | 4243 | |
|----|-------------|------|-------|
| 20 | Slide36.jpg | 2206 | 15.08 |
| 21 | Slide36.jpg | 1246 | 8.52 |
| 22 | Slide36.jpg | 4883 | |
| 23 | Slide36.jpg | 3763 | 37.76 |
| 24 | Slide36.jpg | 583  | 5.85 |
| 25 | Slide36.jpg | 2162 | |
| 26 | Slide36.jpg | 2025 | 13.11 |
| 27 | Slide36.jpg | 18   | 0.12 |
| 28 | Slide36.jpg | 2558 | |
| 29 | Slide36.jpg | 1179 | 3.69 |
| 30 | Slide36.jpg | 615  | 1.92 |

TABLE 54

TNF10 summary

| non-IS | 46.76 |
|--------|-------|
| IS     | 51.20 |
| LV     | 97.96 |
| IS/LV  | 52%   |

TABLE 55

Composite image data

| | IS/LV | | IS/LV | | IS/LV | | IS/LV |
|---|---|---|---|---|---|---|---|
| CON7 | 70% | TMZ3 | 64% | TNF1 | 57% | TNF1 | 55% |
| CON5 | 65% | TMZ1 | 68% | TNF2 | 67% | TNF2 | 61% |
| CON6 | 75% | TMZ2 | 60% | TNF3 | 60% | TNF3 | 63% |
| CON4 | 65% | TMZ7 | 43% | TNF4 | 75% | TNF4 | 51% |
| CON3 | 64% | TMZ8 | 51% | TNF5 | 73% | TNF5 | 35% |
| CON1 | 77% | TMZ5 | 58% | TNF6 | 79% | TNF6 | 36% |
| CON2 | 55% | TMZ6 | 49% | TNF7 | 53% | TNF7 | 34% |
| CON8 | 68% | TMZ9 | 44% | TNF8 | 57% | TNF8 | 51% |
| CON9 | 67% | TMZ10 | 49% | TNF9 | 64% | TNF9 | 31% |
| CON10 | 62% | TMZ4 | 71% | TNF10 | 52% | TNS10 | 26% |
| CON11 | 73% | | | | | | |
| CON12 | 75% | | | | | | |
| CON13 | 76% | | | | | | |
| CON14 | 66% | | | | | | |
| Mean | 68% | Mean | 56% | Mean | 64% | Mean | 44% |
| SD | 6% | SD | 10% | SD | 10% | SD | 13% |
| SE | 2% | SE | 3% | SE | 3% | SE | 4% |
| TTEST | | | 8.77E-04 | | 1.61E-01 | | 4.79E-06 |
| | | | | | | TMZ/TNS | 4.00E-02 |

The results show that a combination of trimetazidine, nicotinamide, and succinate at 20 µM preserved coronary flow and cardiac functional recovery and decreased infarct size in isolated hearts after ischemia-reperfusion. This combination was more effective in decreasing infarct size than TMZ alone. A combination of trimetazidine, nicotinamide, and succinate at 2 µM did not appear to decrease myocardial ischemia-reperfusion injury.

This study suggested that the combination of trimetazidine, nicotinamide, and succinate at 20 µM generated better protection against ischemia-reperfusion injury in Langendorff system.

Figure 37:
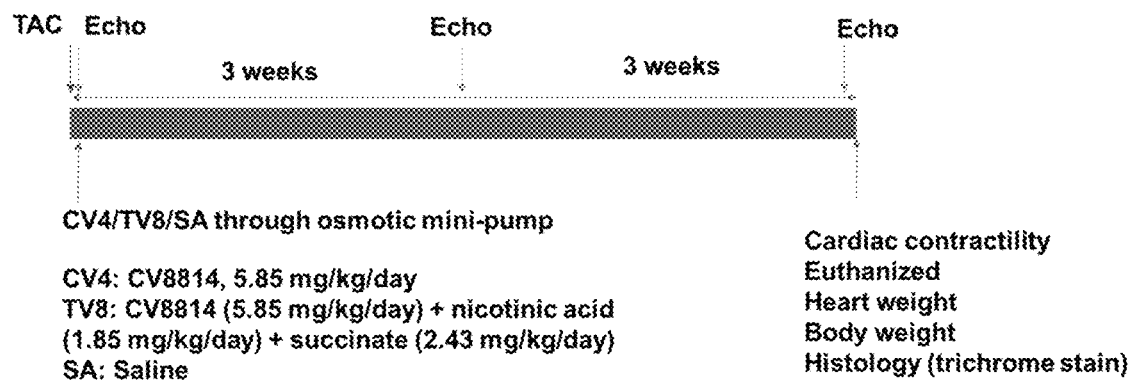
FIG. 37 is a schematic of the method used to analyze the effects of compositions of the invention on cardiac function.

FIG. 37 is a schematic of the method used to analyze the effects of compositions of the invention on cardiac function. Following transverse aortic constriction (TAC) or a sham procedure, mice were given one of the following via an osmotic mini-pump: CV8814 at 5.85 mg/kg/day (CV4); CV8814 at 5.85 mg/kg/day, nicotinic acid at 1.85 mg/kg/day, and succinate at 2.43 mg/kg/day (TV8); or saline (SA). Echocardiograms were measured immediately following TAC, three weeks after TAC, and 6 weeks after TAC. Mice were sacrificed at 6 weeks, and tissues were analyzed.

Figure 38:
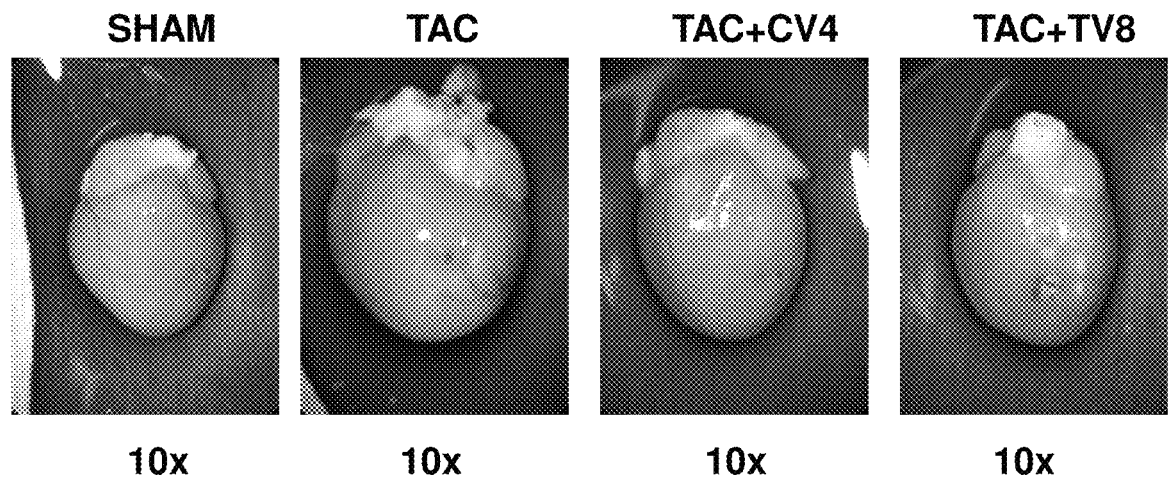
FIG. 38 shows hearts from mice six weeks after transverse aortic constriction.

FIG. 38 shows hearts from mice six weeks after a sham procedure (SHAM), TAC followed by saline administration (TAC), TAC followed by CV4 administration (CV4), or TAC followed by TV8 administration.

Figure 39:
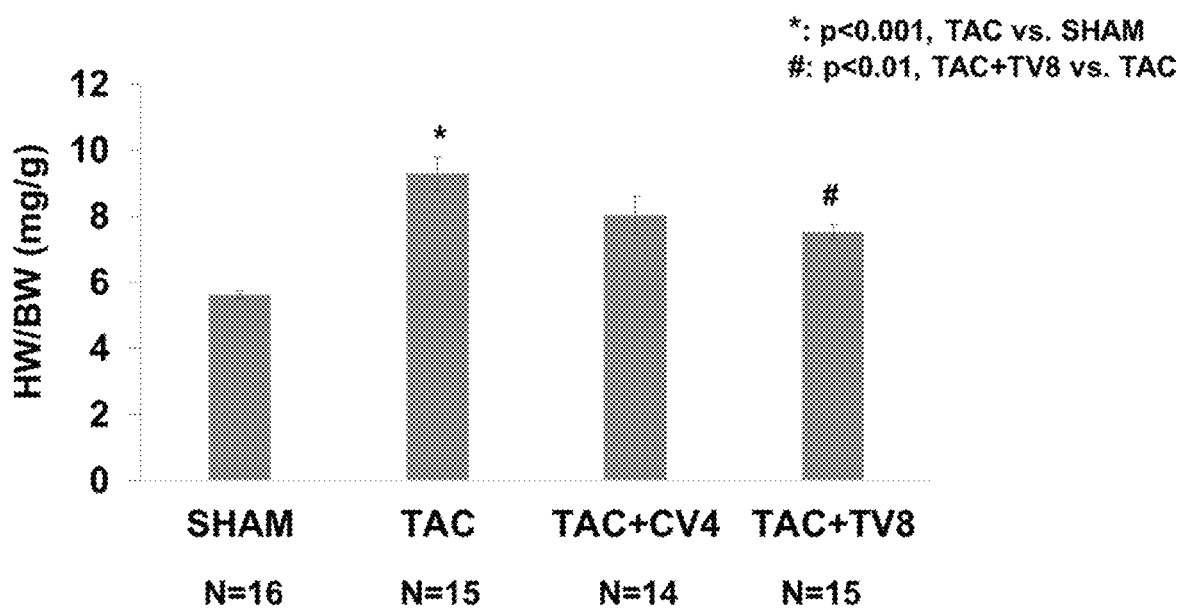
FIG. 39 is of graph of heart weight relative to body weight six weeks after transverse aortic constriction.

FIG. 39 is of graph of heart weight relative to body weight six weeks after transverse aortic constriction. Treatments are as indicated in relation to FIG. 38.

Figure 40:
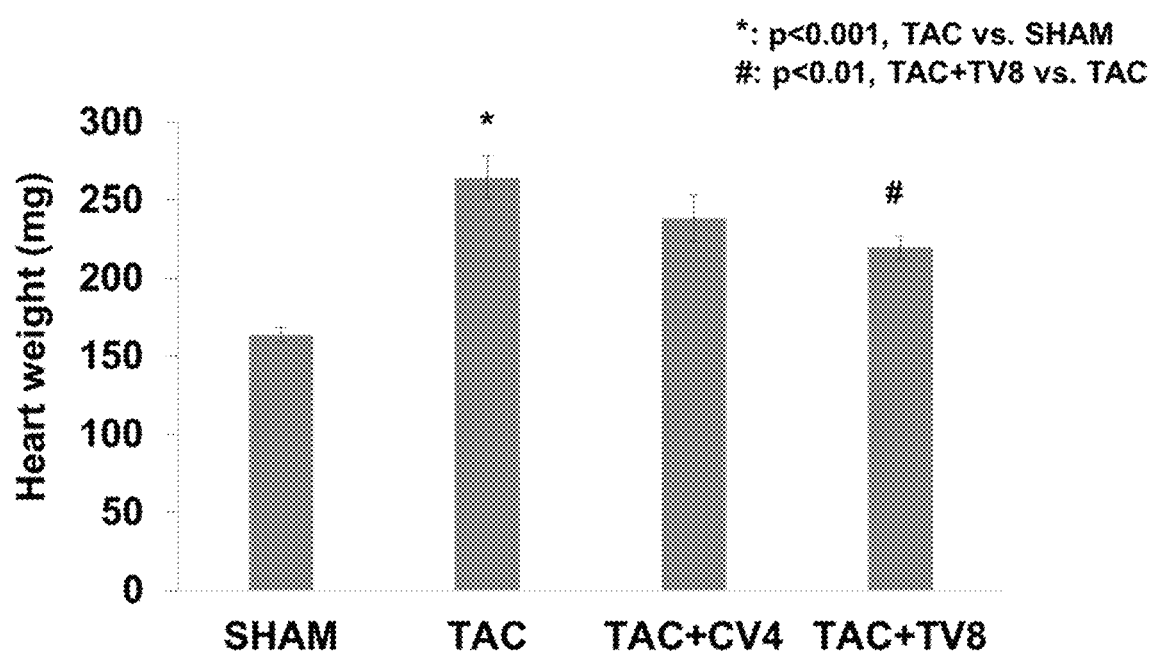
FIG. 40 is graph of heart weight six weeks after transverse aortic constriction.

FIG. 40 is graph of heart weight six weeks after transverse aortic constriction. Treatments are as indicated to FIG. 38.

Figure 41:
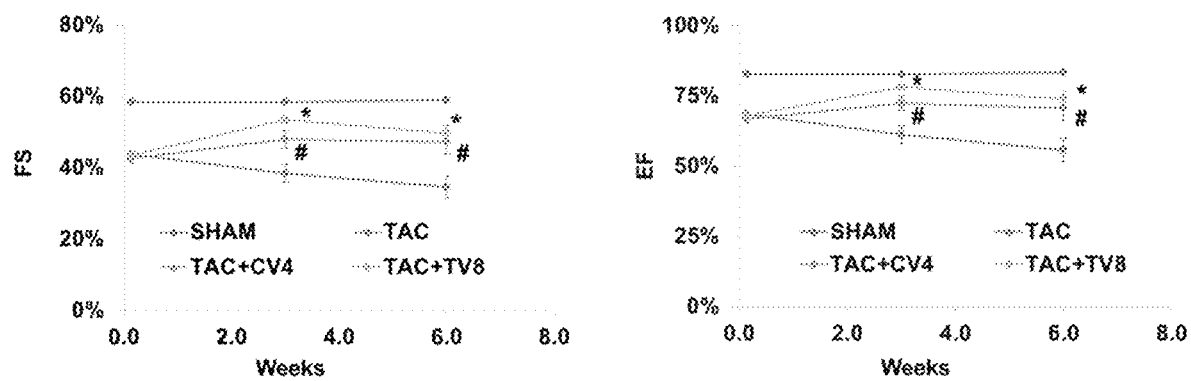
FIG. 41 shows graphs of fractional shortening (FS) and ejection fraction (EF) at indicated time points after transverse aortic constriction.

FIG. 41 shows graphs of fractional shortening (FS) and ejection fraction (EF) at indicated time points after transverse aortic constriction. Treatments are as indicated in relation to FIG. 38.

Figure 42:
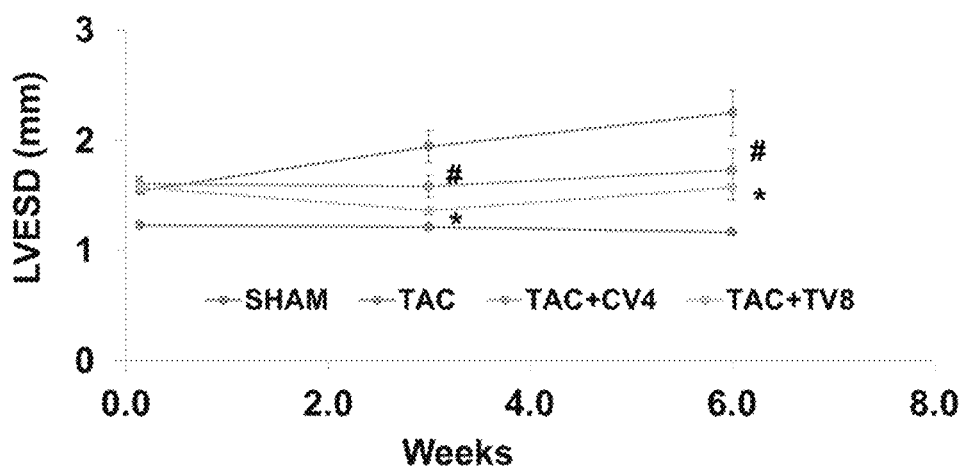
FIG. 42 is a graph of left ventricular end-systolic diameter at indicated time points after transverse aortic constriction.

FIG. 42 is a graph of left ventricular end-systolic diameter at indicated time points after transverse aortic constriction. Treatments are as indicated in relation to FIG. 38.

Figure 43:
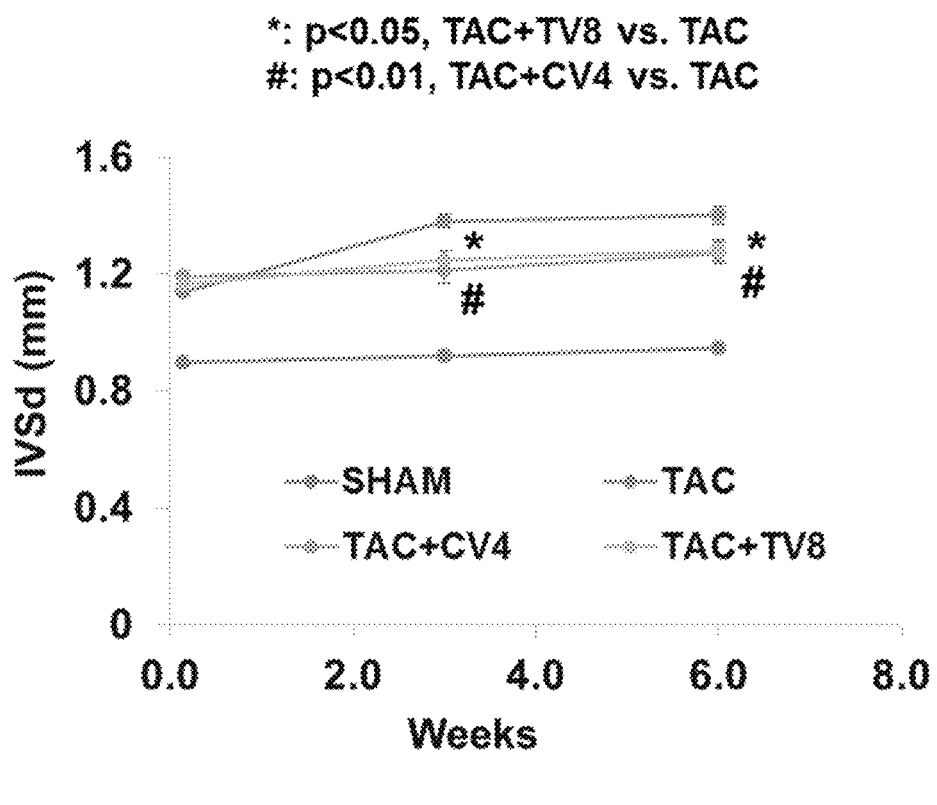
FIG. 43 is a graph of intraventricular septal dimension at indicated time points after transverse aortic constriction.

FIG. 43 is a graph of intraventricular septal dimension at indicated time points after transverse aortic constriction. Treatments are as indicated in relation to FIG. 38.

Figure 44:
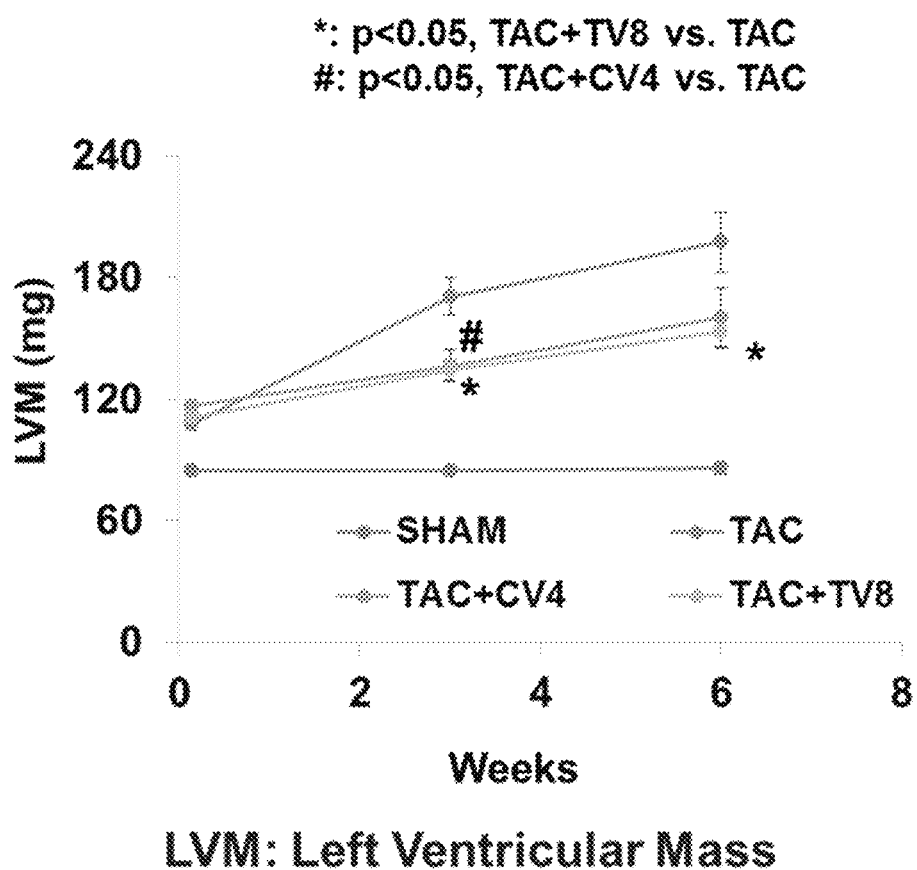
FIG. 44 is a graph of left ventricular mass at indicated time points after transverse aortic constriction.

FIG. 44 is a graph of left ventricular mass at indicated time points after transverse aortic constriction. Treatments are as indicated in relation to FIG. 38.

Figure 45:
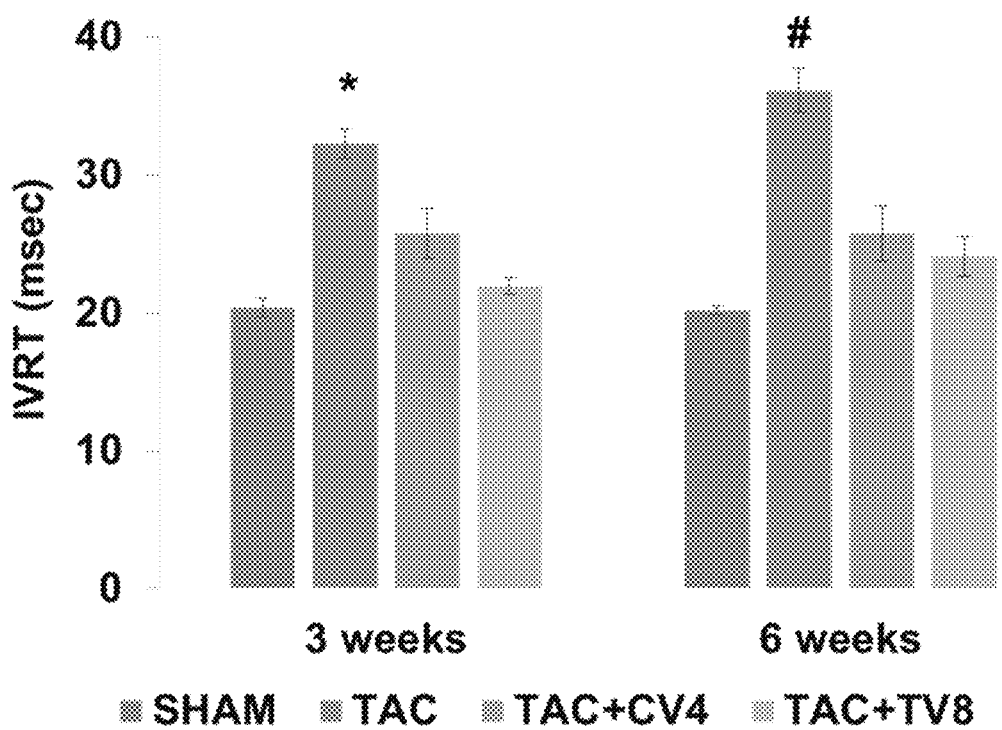
FIG. 45 is a graph of isovolumic relaxation time at indicated time points after transverse aortic constriction.

FIG. 45 is a graph of isovolumic relaxation time at indicated time points after transverse aortic constriction. Treatments are as indicated in relation to FIG. 38.

Figure 46:
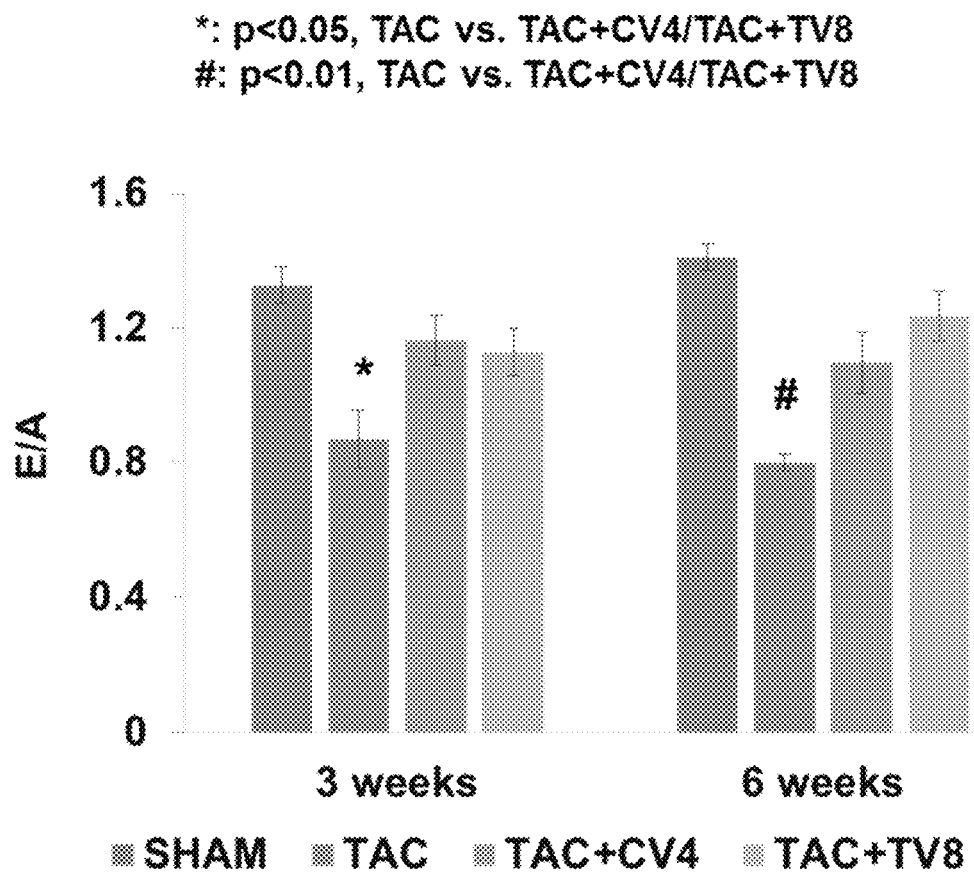
FIG. 46 is a graph of the ratio peak velocity flow in early diastole vs. late diastole at indicated time points after transverse aortic constriction.

FIG. 46 is a graph of the ratio peak velocity flow in early diastole vs. late diastole at indicated time points after transverse aortic constriction. Treatments are as indicated in relation to FIG. 38.

Figure 47:
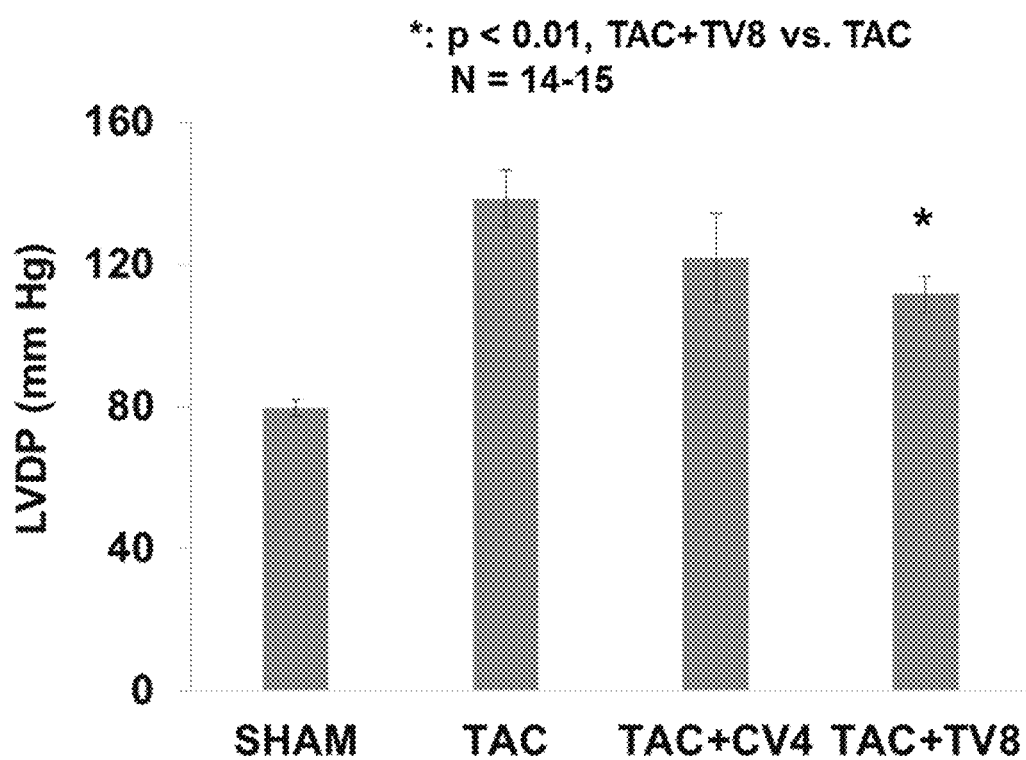
FIG. 47 is a graph of left ventricular developed pressure at six weeks after transverse aortic constriction.

FIG. 47 is a graph of left ventricular developed pressure at six weeks after transverse aortic constriction. Treatments are as indicated in relation to FIG. 38.

Figure 48:
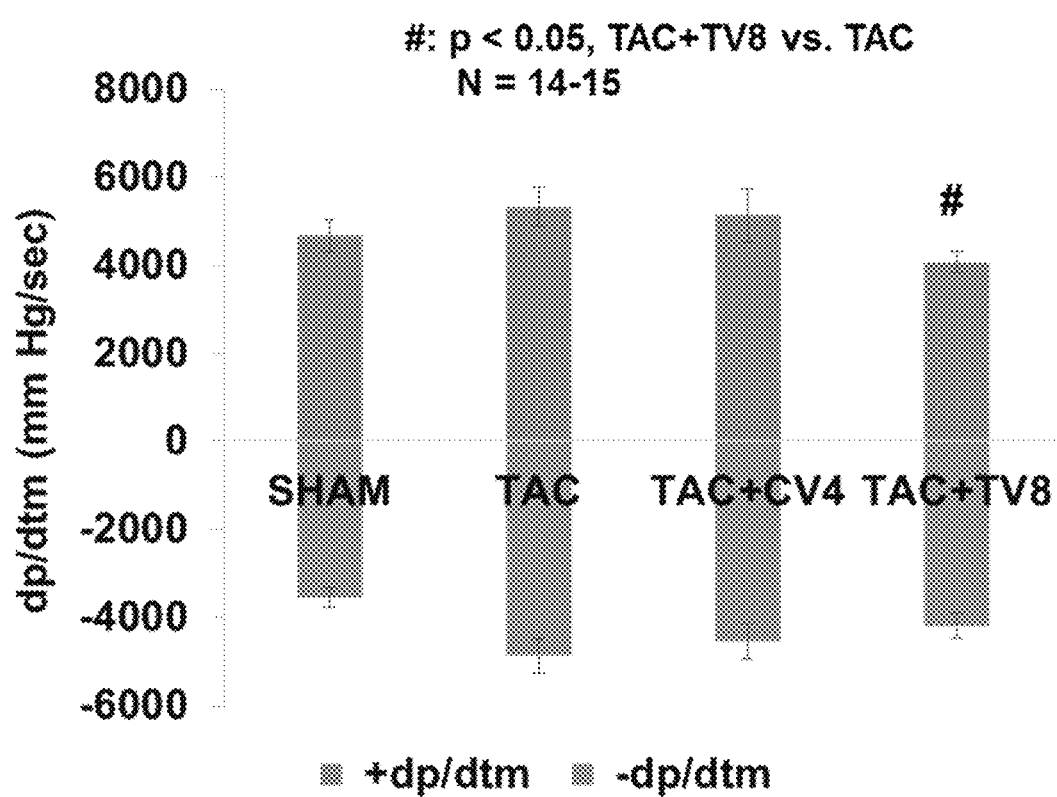
FIG. 48 is a graph of the rate of left ventricle pressure rise at six weeks after transverse aortic constriction.

FIG. 48 is a graph of the rate of left ventricle pressure rise at six weeks after transverse aortic constriction. Treatments are as indicated in relation to FIG. 38.

Chemical Synthesis Schemes.

Compounds of the invention include 2-(4-(2,3,4-trimethoxybenzyl)piperazin-1-yl)ethan-1-ol (referred to herein as CV8814) and 2-(4-(2,3,4-trimethoxybenzyl)piperazin-1-yl)ethyl nicotinate (referred to herein as CV-8972). These compounds may be synthesized according to the following scheme:

Stage 1:

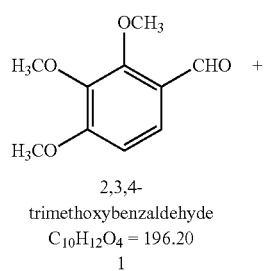

2,3,4-trimethoxybenzaldehyde
$C_{10}H_{12}O_4 = 196.20$
1

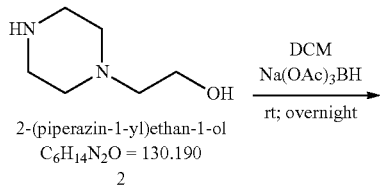

2-(piperazin-1-yl)ethan-1-ol
$C_6H_{14}N_2O = 130.190$
2

DCM
Na(OAc)$_3$BH
rt; overnight

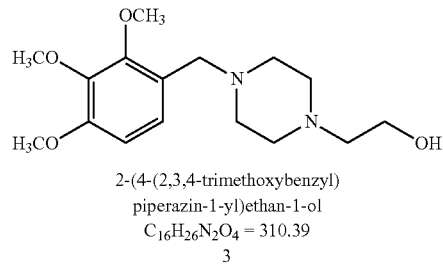

2-(4-(2,3,4-trimethoxybenzyl)piperazin-1-yl)ethan-1-ol
$C_{16}H_{26}N_2O_4 = 310.39$
3

Ethylacetate + MTBE, 4M HCl Dioxane

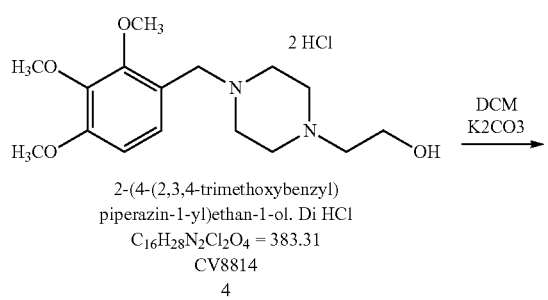

2-(4-(2,3,4-trimethoxybenzyl)piperazin-1-yl)ethan-1-ol. Di HCl
$C_{16}H_{28}N_2Cl_2O_4 = 383.31$
CV8814
4

Stage 2:

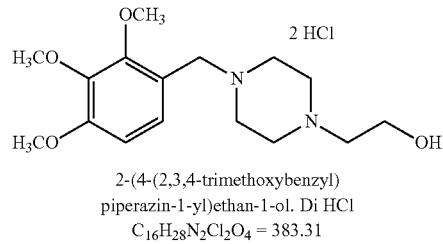

2-(4-(2,3,4-trimethoxybenzyl)piperazin-1-yl)ethan-1-ol. Di HCl
$C_{16}H_{28}N_2Cl_2O_4 = 383.31$
CV8814
4

-continued

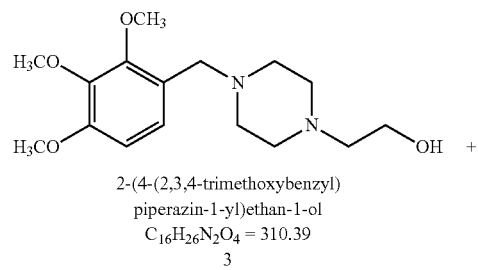

2-(4-(2,3,4-trimethoxybenzyl)piperazin-1-yl)ethan-1-ol
$C_{16}H_{26}N_2O_4 = 310.39$
3

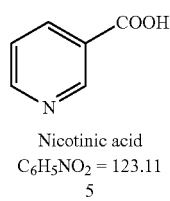

Nicotinic acid
$C_6H_5NO_2 = 123.11$
5

DCM
EDCl
DMAP

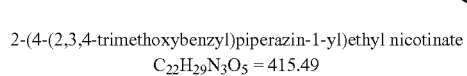

2-(4-(2,3,4-trimethoxybenzyl)piperazin-1-yl)ethyl nicotinate
$C_{22}H_{29}N_3O_5 = 415.49$
6

Stage 3:

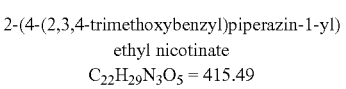

2-(4-(2,3,4-trimethoxybenzyl)piperazin-1-yl)ethyl nicotinate
$C_{22}H_{29}N_3O_5 = 415.49$
6

MTBE
4M HCl Dioxane

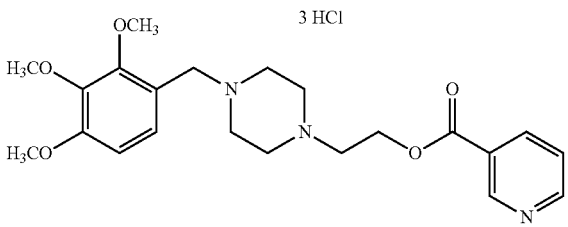

2-(4-(2,3,4-trimethoxybenzyl)piperazin-1-yl)ethyl nicotinate.
3HCl $C_{21}H_{32}Cl_3N_3O_4 \cdot 3HCl = 524.86$
CV8972

DCM
K$_2$CO$_3$

The product was converted to the desired polymorph by recrystallization. The percentage of water and the ratio of methanol:methyl ethyl ketone (MEK) were varied in different batches using 2.5 g of product.

In batch MBA 25, 5% water w/r/t total volume of solvent (23 volumes) containing 30% methanol:70% MEK was used for precipitation. The yield was 67% of monohydrate of CV-8972. Water content was determined by KF to be 3.46%.

In batch MBA 26, 1.33% water w/r/t total volume of solvent (30 volumes) containing 20% methanol:80% MEK was used for precipitation. The yield was 86.5% of monohydrate of CV-8972. Water content was determined by KF to be 4.0%. The product was dried under vacuum at 40° C. for 24 hours to decrease water content to 3.75%.

In batch MBA 27, 3% water w/r/t total volume of solvent (32 volumes) containing 22% methanol:78% MEK was used for precipitation. The yield was 87.22% of monohydrate of CV-8972. Water content was determined by KF to be 3.93% after 18 hours of drying at room temperature under vacuum. The product was further dried under vacuum at 40° C. for 24 hours to decrease water content to 3.54%.

In other batches, the ratio and total volume of solvent were held constant at 20% methanol:80% MEK and 30 volumes in batches using 2.5 g of product, and only the percentage of water was varied.

In batch MBA 29, 1.0 equivalent of water was added. Material was isolated and dried under vacuum at 40° C. for 24 hours. Water content was determined by KF to be 0.89%, showing that the monohydrate form was not forming stoichiometrically.

In batch MBA 30, 3% water was added. Material was isolated and dried under vacuum at 40° C. for 24 hours. Water content was determined by KF to be 3.51%, showing that monohydrate is forming with addition of excess water.

In batch MBA 31, 5% water was added. Material was isolated and dried under vacuum at 40° C. for 24 hours. Water content was determined by KF to be 3.30%, showing that monohydrate is forming with addition of excess water.

Results are summarized in Table 56.

TABLE 56

| Sample | Water percentage theoretical (for monohydrate preparation) | KF result (% of water) | KF result (Sample after drying at 40° C. for 24 hours) | Amount of Water used for reaction (based on total volume) | Ratio of MeOH:MEK | Total Volume | Yield obtained (%) | Drying Time (hr) | Drying temperature (° C.) |
|---|---|---|---|---|---|---|---|---|---|
| 289-MBA-25 | 3.32% | 3.46 | — | 5% | 30-70 | 23 vol | 67.6 | 24 | 22 |
| 289-MBA-26 | 3.32% | 4.00 | 3.75 | 1.33% | 20-80 | 30 vol | 86.5 | 19 | 23 |
| 289-MBA-27 | 3.32% | 3.93 | 3.54 | 3% | 22-78 | 32 vol | 87.22 | 18 | 23 |
| 289-MBA-29 | 3.32% | — | 0.89 | 1.0 eq based on input weight | 20-80 | 30 vol | 84 | 24 | 40 |
| 289-MBA-30 | 3.32% | — | 3.51 | 3% | 20-80 | 30 vol | 90 | 24 | 40 |
| 289-MBA-31 | 3.32% | — | 3.30 | 5% | 20-80 | 30 vol | 81 | 24 | 40 |

Metabolism of Compounds in Dogs

The metabolism of various compounds was analyzed in dogs.

Figure 49:
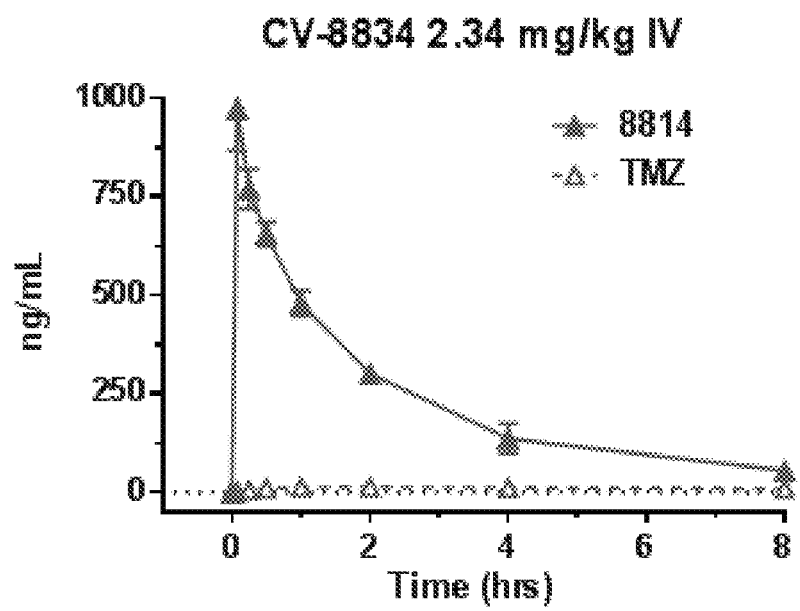
FIG. 49 is a graph showing levels of CV-8814 and trimetazidine after intravenous administration of CV-8834.

FIG. 49 is a graph showing levels of CV-8814 (solid triangles, solid lines) and trimetazidine (open triangles, dashed lines) after intravenous administration of CV-8834 at 2.34 mg/kg. CV-8834 is a compound of formula (II) in which y=1.

Figure 50:
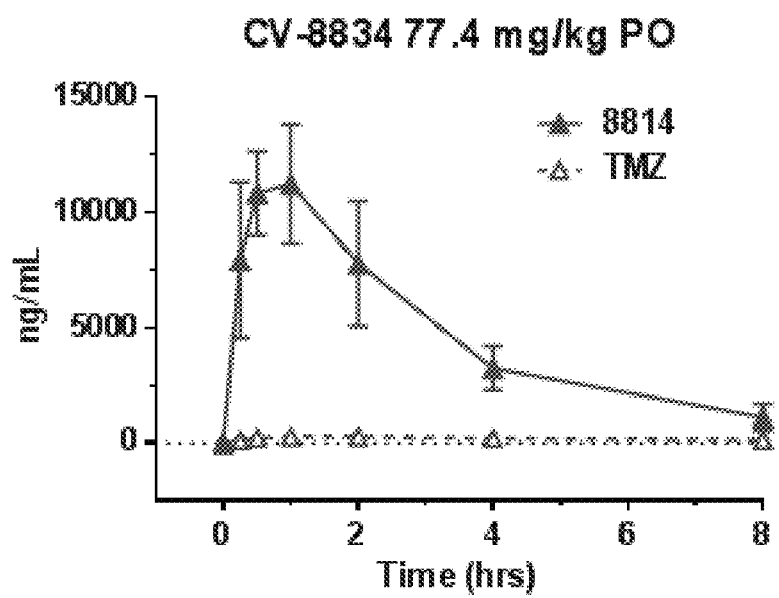
FIG. 50 is a graph showing levels of CV-8814 and trimetazidine after oral administration of CV-8834.

FIG. 50 is a graph showing levels of CV-8814 (solid triangles, solid lines) and trimetazidine (open triangles, dashed lines) after oral administration of CV-8834 at 77.4 mg/kg.

Figure 51:
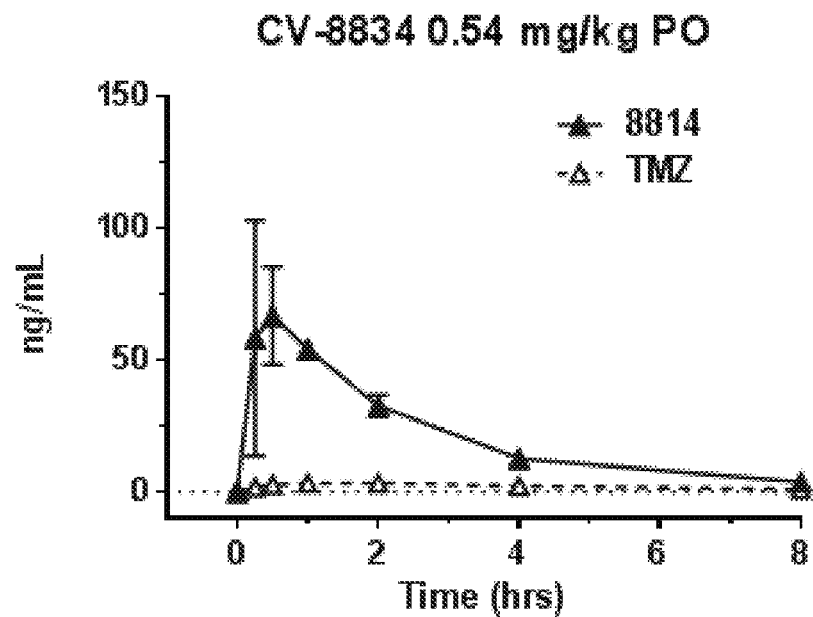
FIG. 51 is a graph showing levels of CV-8814 and trimetazidine after oral administration of CV-8834.

FIG. 51 is a graph showing levels of CV-8814 (solid triangles, solid lines) and trimetazidine (open triangles, dashed lines) after oral administration of CV-8834 at 0.54 mg/kg.

Figure 52:
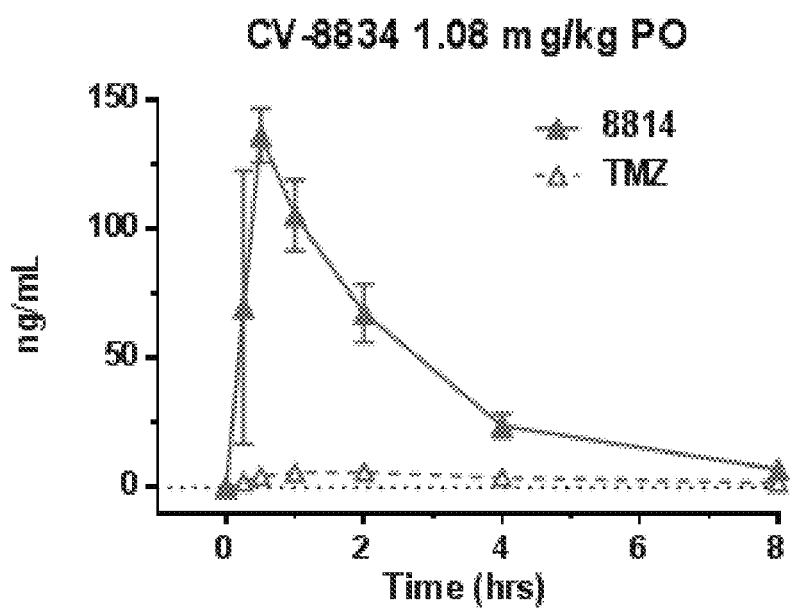
FIG. 52 is a graph showing levels of CV-8814 and trimetazidine after oral administration of CV-8834.

FIG. 52 is a graph showing levels of CV-8814 (solid triangles, solid lines) and trimetazidine (open triangles, dashed lines) after oral administration of CV-8834 at 1.08 mg/kg.

Figure 53:
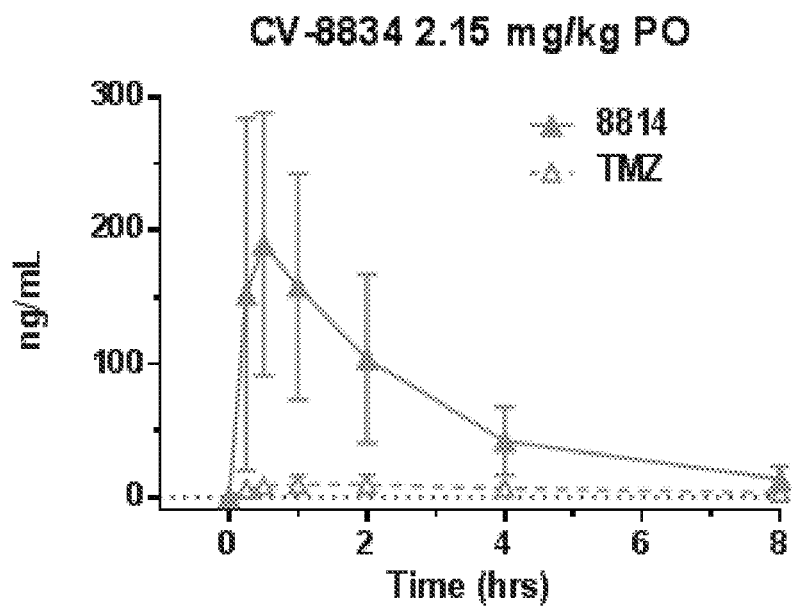
FIG. 53 is a graph showing levels of CV-8814 and trimetazidine after oral administration of CV-8834.

FIG. 53 is a graph showing levels of CV-8814 (solid triangles, solid lines) and trimetazidine (open triangles, dashed lines) after oral administration of CV-8834 at 2.15 mg/kg.

Data from FIGS. 48-53 is summarized in Table 57.

TABLE 57

| Compound | Route of admin. | Dose (mg/kg) | Analyte | $T_{max}$ (hours) | $C_{max}$ (ng/mL) | $AUC_{0-8}$ (ng × hr/mL) | % F |
|---|---|---|---|---|---|---|---|
| CV-8834 | PO | 77.4 | 8814 | 0.75 | 12100 | 38050 | 69 |
| CV-8834 | PO | 77.4 | TMZ | 1.67 | 288 | 1600 | 72 |
| CV-8834 | IV | 2.34 | 8814 | 0.083 | 974 | 1668 | — |
| CV-8834 | IV | 2.34 | TMZ | 2.67 | 13.4 | 66.7 | — |
| CV-8834 | PO | 0.54 | 8814 | 0.5 | 74.0 | 175 | 45 |
| CV-8834 | PO | 0.54 | TMZ | 1.17 | 3.63 | 17.6 | >100 |
| CV-8834 | PO | 1.08 | 8814 | 0.5 | 136 | 335 | 44 |
| CV-8834 | PO | 1.08 | TMZ | 0.866 | 6.19 | 30.4 | 99 |
| CV-8834 | PO | 2.15 | 8814 | 0.583 | 199 | 536 | 35 |
| CV-8834 | PO | 2.15 | TMZ | 1.17 | 9.80 | 51.6 | 84 |

Figure 54:
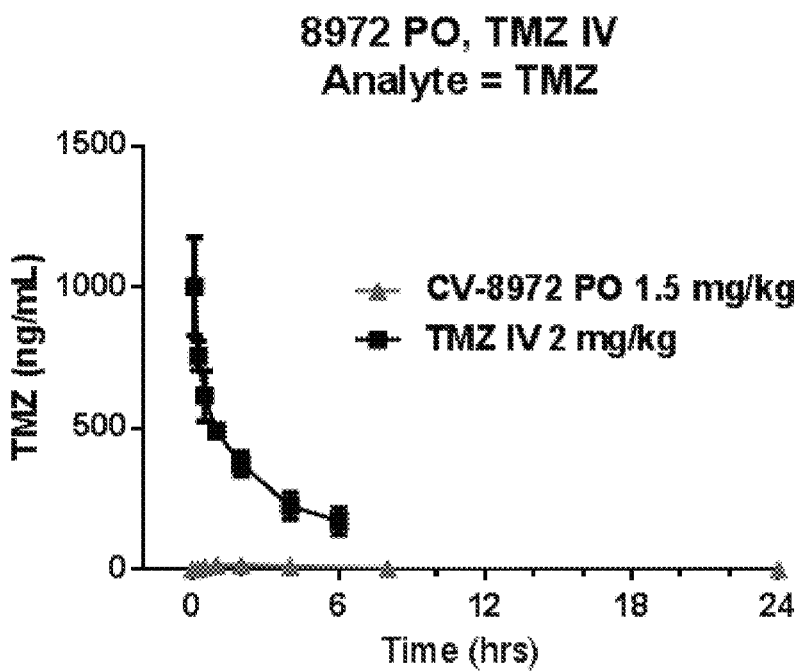
FIG. 54 is a graph showing levels of trimetazidine after oral administration of CV-8972 or intravenous administration of trimetazidine.

FIG. 54 is a graph showing levels of trimetazidine after oral administration of CV-8972 at 1.5 mg/kg (triangles) or intravenous administration of trimetazidine at 2 mg/kg (squares).

Figure 55:
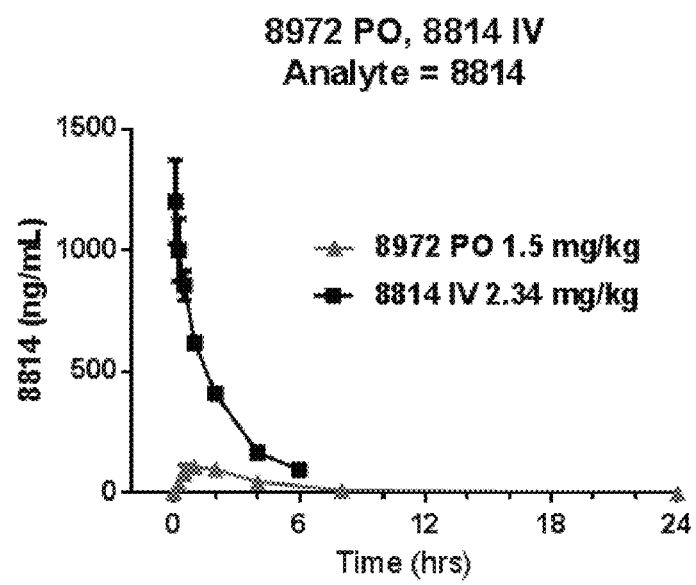
FIG. 55 is a graph showing levels of CV-8814 after oral administration of CV-8972 or intravenous administration of CV-8814.

FIG. 55 is a graph showing levels of CV-8814 after oral administration of CV-8972 at 1.5 mg/kg (triangles) or intravenous administration of CV-8814 at 2.34 mg/kg (squares).

Figure 56:
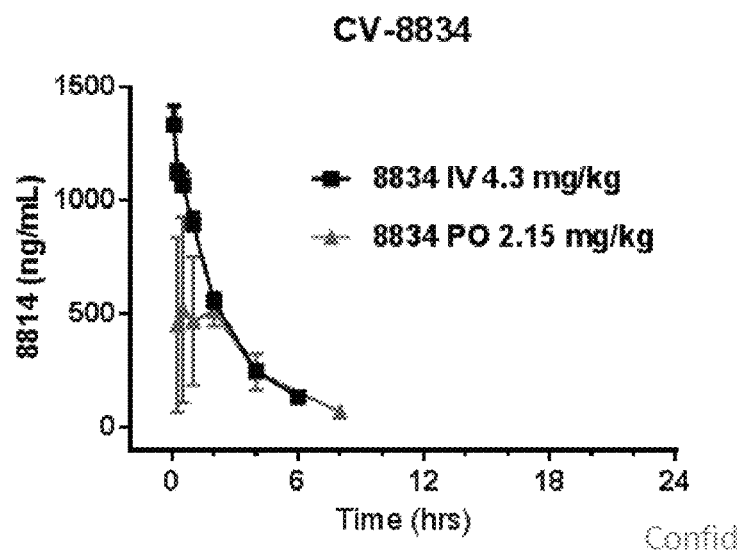
FIG. 56 is a graph showing levels of CV-8814 after intravenous administration of CV-8834 or oral administration of CV-8834.

FIG. 56 is a graph showing levels of CV-8814 after intravenous administration of CV-8834 at 4.3 mg/kg (squares) or oral administration of CV-8834 at 2.15 mg/kg (triangles).

Figure 57:
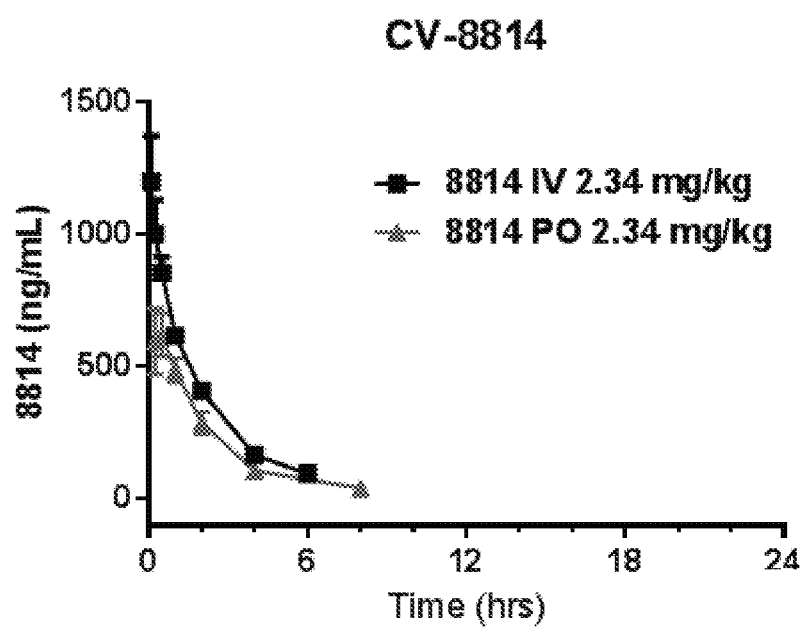
FIG. 57 is a graph showing levels of CV-8814 after intravenous administration of CV-8814 or oral administration of CV-8814.

FIG. 57 is a graph showing levels of CV-8814 after intravenous administration of CV-8814 at 2.34 mg/kg (squares) or oral administration of CV-8814 at 2.34 mg/kg (triangles).

Data from FIGS. 54-57 is summarized in Table 58.

TABLE 58

| Compound | Route of admin. | Dose (mg/kg) | Vehicle | Fasted | Analyte | $T_{max}$ (hours) | $C_{max}$ (ng/mL) | $AUC_{0-24}$ (ng × hr/mL) | % F |
|---|---|---|---|---|---|---|---|---|---|
| CV-8972 | PO | 1.5 | — | — | TMZ | 2.0 | 17.0 | 117 | 4.3% |
| TMZ | IV | 2 | 0.9% NaCl | 8 hrs | TMZ | 0.083 | 1002 | 3612 | — |
| CV-8972 | PO | 1.5 | — | — | 8814 | 1.125 | 108 | 534 | 27% |
| CV-8814 | IV | 2.34 | 0.9% NaCl | 8 hrs | 8814 | 0.083 | 1200 | 3059 | — |
| CV-8834 | PO | 4.3 | 0.9% NaCl | 8 hrs | 8814 | 1.0 | 692 | 2871 | 69% |
| CV-8834 | IV | 4.3 | 0.9% NaCl | 8 hrs | 8814 | 0.083 | 1333 | 4154 | — |
| CV-8834 | PO | 4.3 | 0.9% NaCl | 8 hrs | 8814 | 1.0 | 692 | 2871 | 51% |
| CV-8814 | IV | 2.34 | 0.9% NaCl | 8 hrs | 8814 | 0.083 | 1200 | 3059 | — |
| CV-8814 | PO | 2.34 | 0.9% NaCl | 8 hrs | 8814 | 0.333 | 672 | 1919 | 63% |
| CV-8814 | IV | 2.34 | 0.9% NaCl | 8 hrs | 8814 | 0.083 | 1200 | 3059 | — |

Effect of CV-8814 on Enzyme Activity

The effect of CV-8814 on the activity of various enzymes was analyzed in in vitro assays. Enzyme activity was assayed in the presence of 10 µM CV-8814 using conditions of time, temperature, substrate, and buffer that were optimized for each enzyme based on published literature. Inhibition of 50% or greater was not observed for any of the following enzymes: ATPase, $Na^+/K^+$, pig heart; Cholinesterase, Acetyl, ACES, human; Cyclooxygenase COX-1, human; Cyclooxygenase COX-2, human; Monoamine Oxidase MAO-A, human; Monoamine Oxidase MAO-B, human; Peptidase, Angiotensin Converting Enzyme, rabbit; Peptidase, CTSG (Cathepsin G), human; Phosphodiesterase PDE3, human; Phosphodiesterase PDE4, human; Protein Serine/Threonine Kinase, PKC, Non-selective, rat; Protein Tyrosine Kinase, Insulin Receptor, human; Protein Tyrosine Kinase, LCK, human; Adenosine A1, human; Adenosine $A_{2A}$, human; Adrenergic $\alpha_{1A}$, rat; Adrenergic $\alpha_{1B}$, rat; Adrenergic $\alpha_{1D}$, human; Adrenergic $\alpha_{2A}$, human; Adrenergic $\alpha_{2B}$, human; Adrenergic $\beta_1$, human; Adrenergic $\beta_2$, human; Androgen (Testosterone), human; Angiotensin $AT_1$, human; Bradykinin $B_2$, human; Calcium Channel L-Type, Benzothiazepine, rat; Calcium Channel L-Type, Dihydropyridine, rat; Calcium Channel L-Type, Phenylalkylamine, rat; Calcium Channel N-Type, rat; Cannabinoid $CB_1$, human; Cannabinoid $CB_2$, human; Chemokine CCR1, human; Chemokine CXCR2 (IL-$8R_B$), human; Cholecystokinin $CCK_1$ ($CCK_A$), human; Cholecystokinin $CCK_2$ ($CCK_B$), human; Dopamine $D_1$, human; Dopamine $D_{2L}$, human; Dopamine $D_{2S}$, human; Endothelin $ET_A$, human; Estrogen ERα, human; $GABA_A$, Chloride Channel, TBOB, rat; $GABA_A$, Flunitrazepam, Central, rat; $GABA_A$, Ro-15-1788, Hippocampus, rat; $GABA_{B1A}$, human; Glucocorticoid, human; Glutamate, AMPA, rat; Glutamate, Kainate, rat; Glutamate, Metabotropic, mGlu5, human; Glutamate, NMDA, Agonism, rat; Glutamate, NMDA, Glycine, rat; Glutamate, NMDA, Phencyclidine, rat; Glutamate, NMDA, Polyamine, rat; Glycine, Strychnine-Sensitive, rat; Histamine $H_1$, human; Histamine $H_2$, human; Melanocortin $MC_1$, human; Melanocortin $MC_4$, human; Muscarinic $M_1$, human; Muscarinic $M_2$, human; Muscarinic $M_3$, human; Muscarinic $M_4$, human; Neuropeptide Y $Y_1$, human; Nicotinic Acetylcholine, human; Nicotinic Acetylcholine al, Bungarotoxin, human; Opiate $\delta_1$ (OP1, DOP), human; Opiate κ (OP2, KOP), human; Opiate µ (OP3, MOP), human; Platelet Activating Factor (PAF), human; Potassium Channel [KATP], hamster; Potassium Channel hERG, human; PPARγ, human; Progesterone PR-B, human; Serotonin (5-Hydroxytryptamine) 5-$HT_{1A}$, human; Serotonin (5-Hydroxytryptamine) 5-$HT_{1B}$, human; Serotonin (5-Hydroxytryptamine) 5-$HT_{2A}$, human; Serotonin (5-Hydroxytryptamine) 5-$HT_{2B}$, human; Serotonin (5-Hydroxytryptamine) 5-$HT_{2C}$, human; Serotonin (5-Hydroxytryptamine) 5-$HT_3$, human; Sodium Channel, Site 2, rat; Tachykinin $NK_1$, human; Transporter, Adenosine, guinea pig; Transporter, Dopamine (DAT), human; Transporter, GABA, rat; Transporter, Norepinephrine (NET), human; Transporter, Serotonin (5-Hydroxytryptamine) (SERT), human; and Vasopressin $V_{1A}$, human.

Analysis of CV-8972 Batch Properties

CV-8972 (2-(4-(2,3,4-trimethoxybenzyl)piperazin-1-yl) ethyl nicotinate, HCl salt, monohydrate) was prepared and analyzed. The batch was determined to be 99.62% pure by HPLC.

Figure 58:
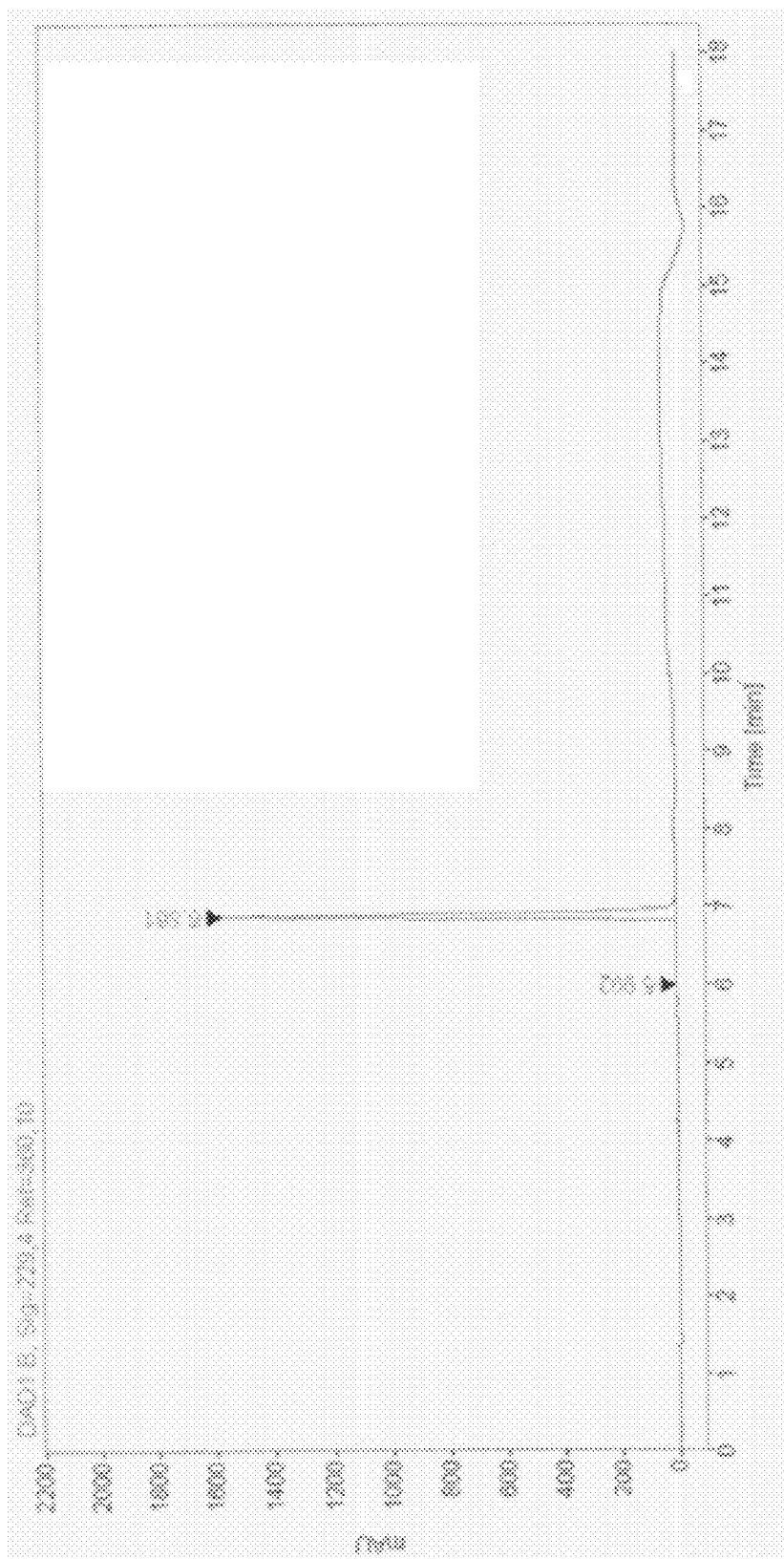
FIG. 58 is a graph showing the HPLC elution profile of a batch of CV-8972.

FIG. 58 is a graph showing the HPLC elution profile of a batch of CV-8972.

Figure 59:
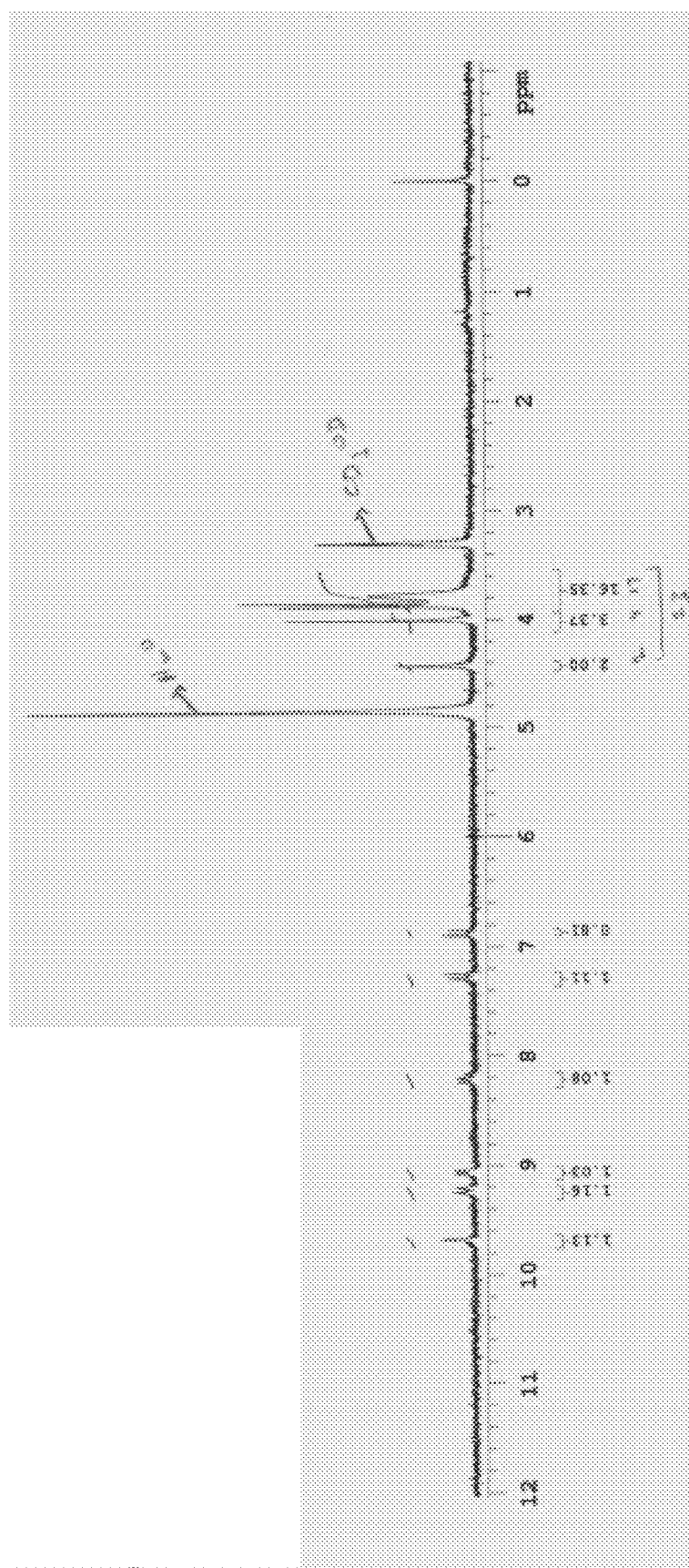
FIG. 59 is a graph showing analysis of molecular species present in a batch of CV-8972.

FIG. 59 is a graph showing analysis of molecular species present in a batch of CV-8972.

Figure 60:
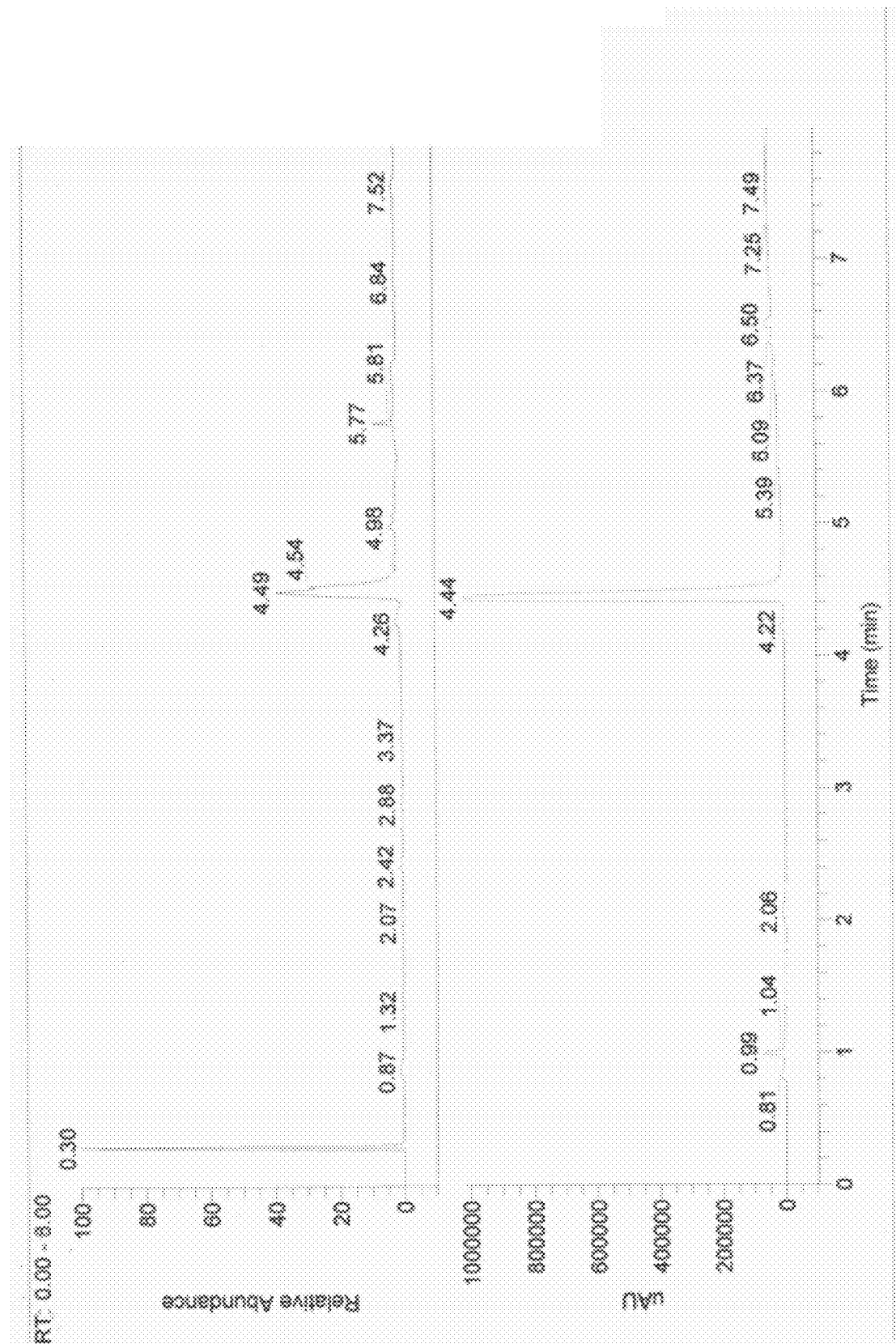
FIG. 60 is a pair of graphs showing HPLC elution profiles of molecular species present in a batch of CV-8972.

FIG. 60 is a pair of graphs showing HPLC elution profiles of molecular species present in a batch of CV-8972.

Figure 61:
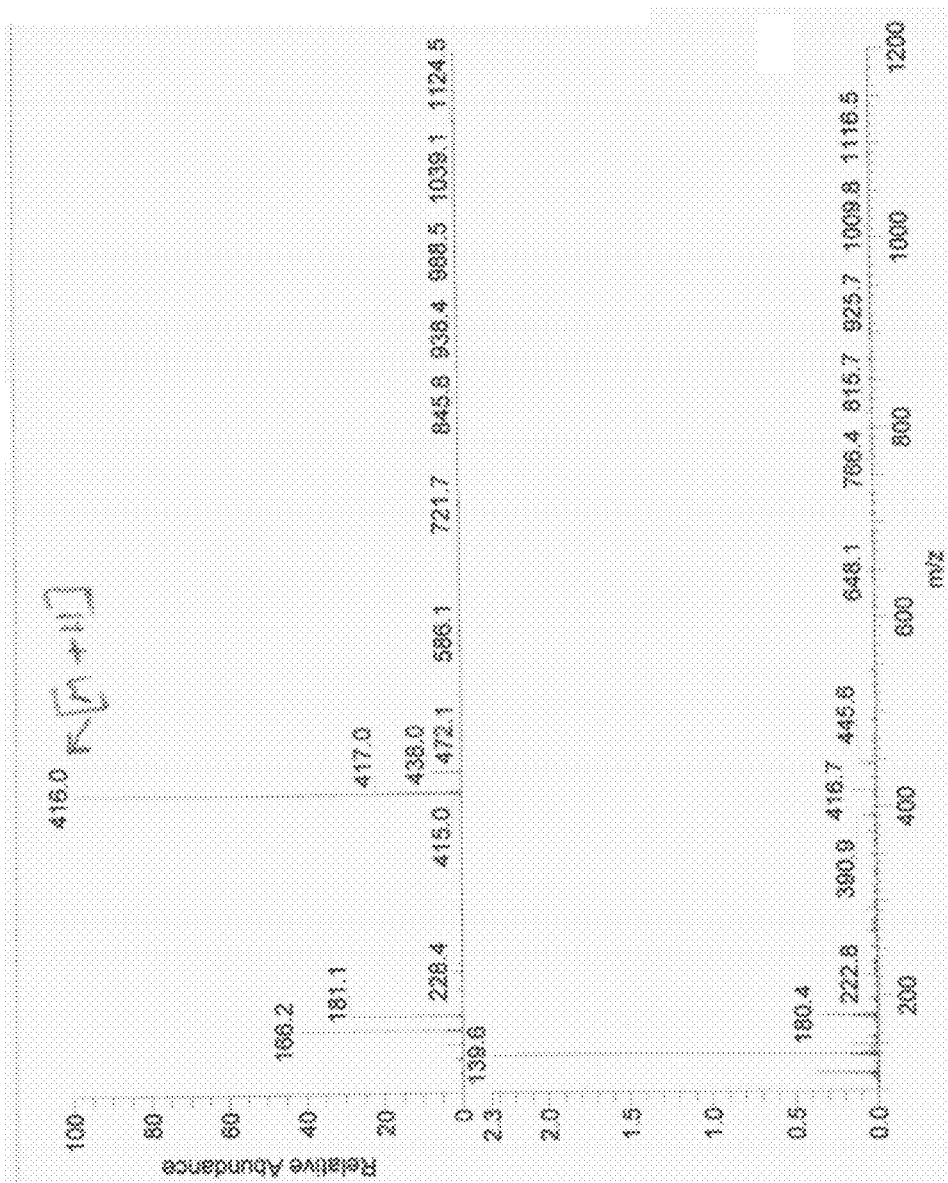
FIG. 61 is a pair of graphs showing HPLC elution profiles of molecular species present in a batch of CV-8972.

FIG. 61 is a pair of graphs showing HPLC elution profiles of molecular species present in a batch of CV-8972.

Figure 62:
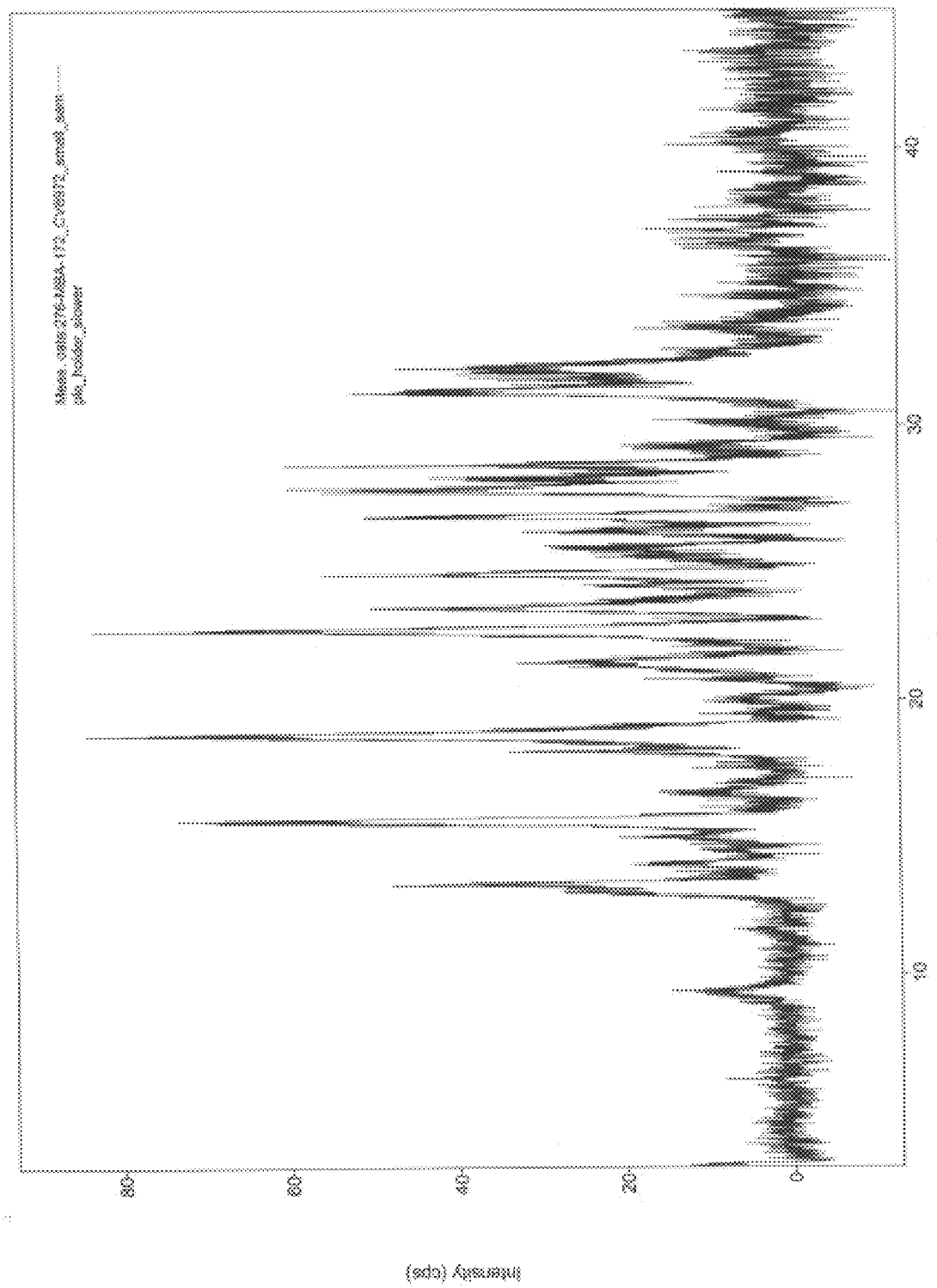
FIG. 62 is a graph showing X-ray powder diffraction analysis of a batch of CV-8972.

FIG. 62 is a graph showing X-ray powder diffraction analysis of a batch of CV-8972.

Figure 63:
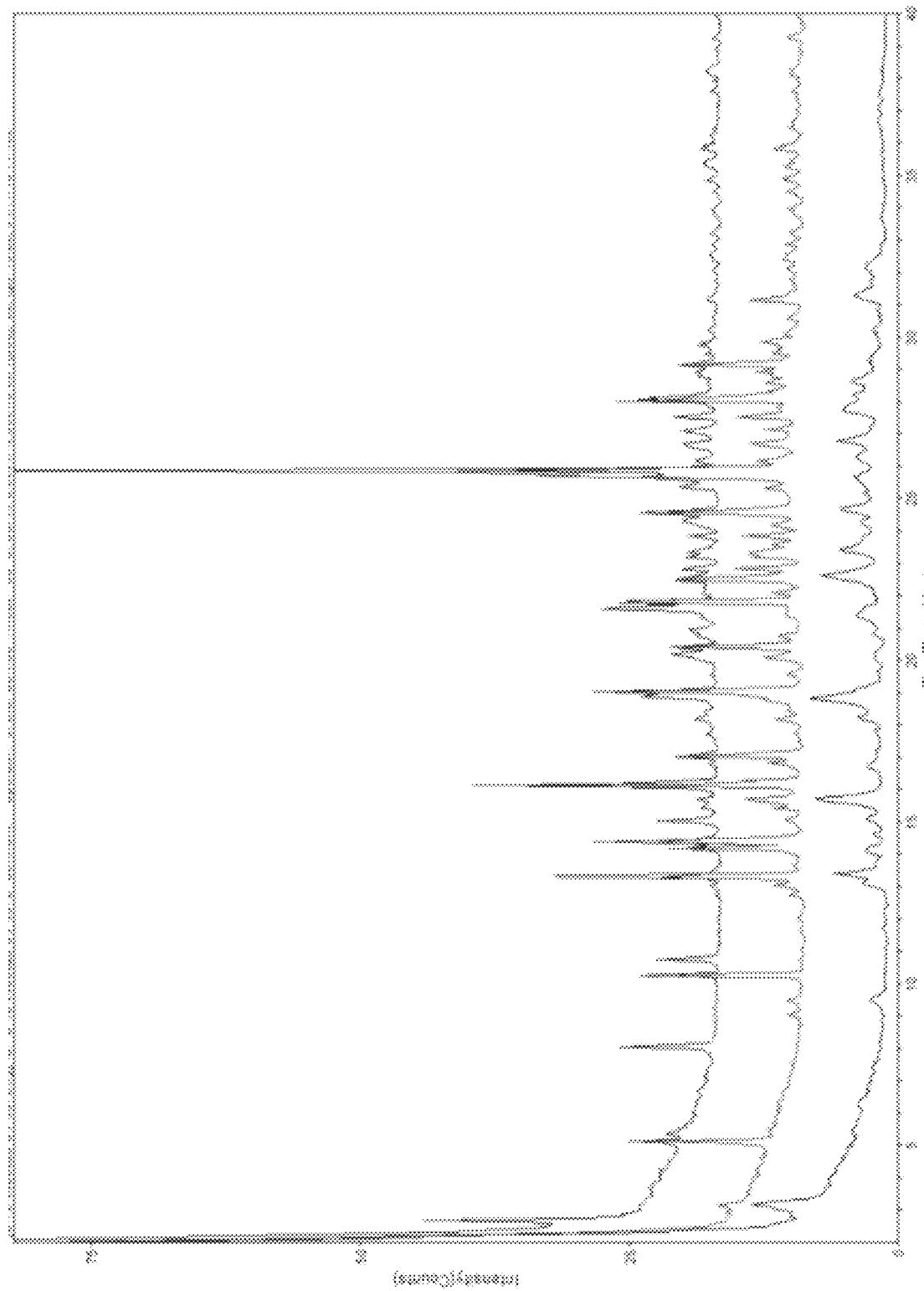
FIG. 63 is a graph showing X-ray powder diffraction analysis of batches of CV-8972.

FIG. 63 is a graph showing X-ray powder diffraction analysis of batches of CV-8972. Batch 289-MBA-15-A, shown in blue, contains form B of CV-8972, batch 276-MBA-172, shown in black contains form A of CV-8972, and batch 289-MBA-16, shown in red, contains a mixture of forms A and B.

Figure 64:
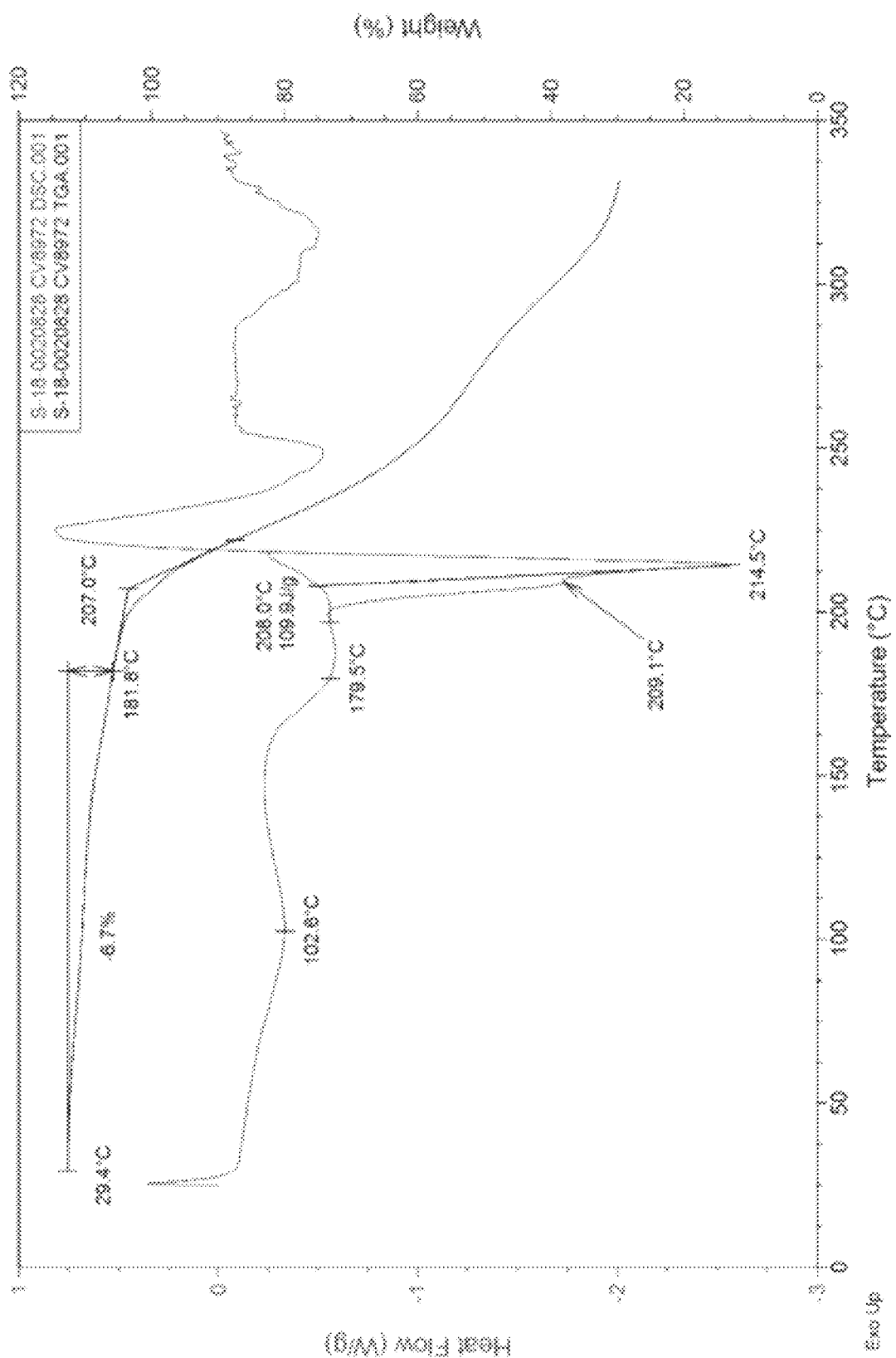
FIG. 64 is a graph showing differential scanning calorimetry and thermal gravimetric analysis of a batch of CV-8972.

FIG. 64 is a graph showing differential scanning calorimetry and thermal gravimetric analysis of batch 276-MBA-172 of CV-8972.

Figure 65:
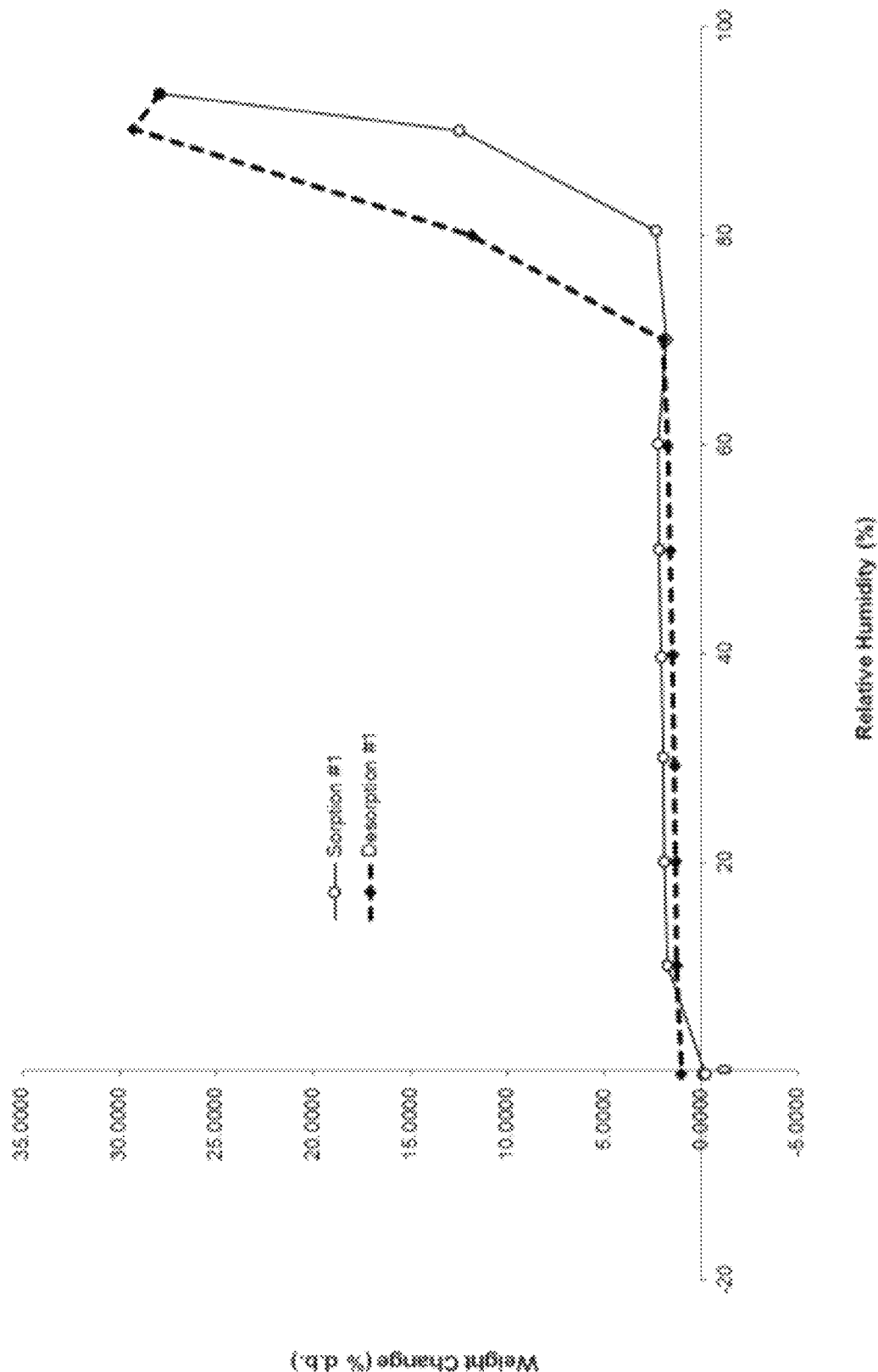
FIG. 65 is a graph showing dynamic vapor sorption (DVS) of a batch of CV-8972.

FIG. 65 is a graph showing dynamic vapor sorption (DVS) of batch 276-MBA-172 of CV-8972.

Figure 66:
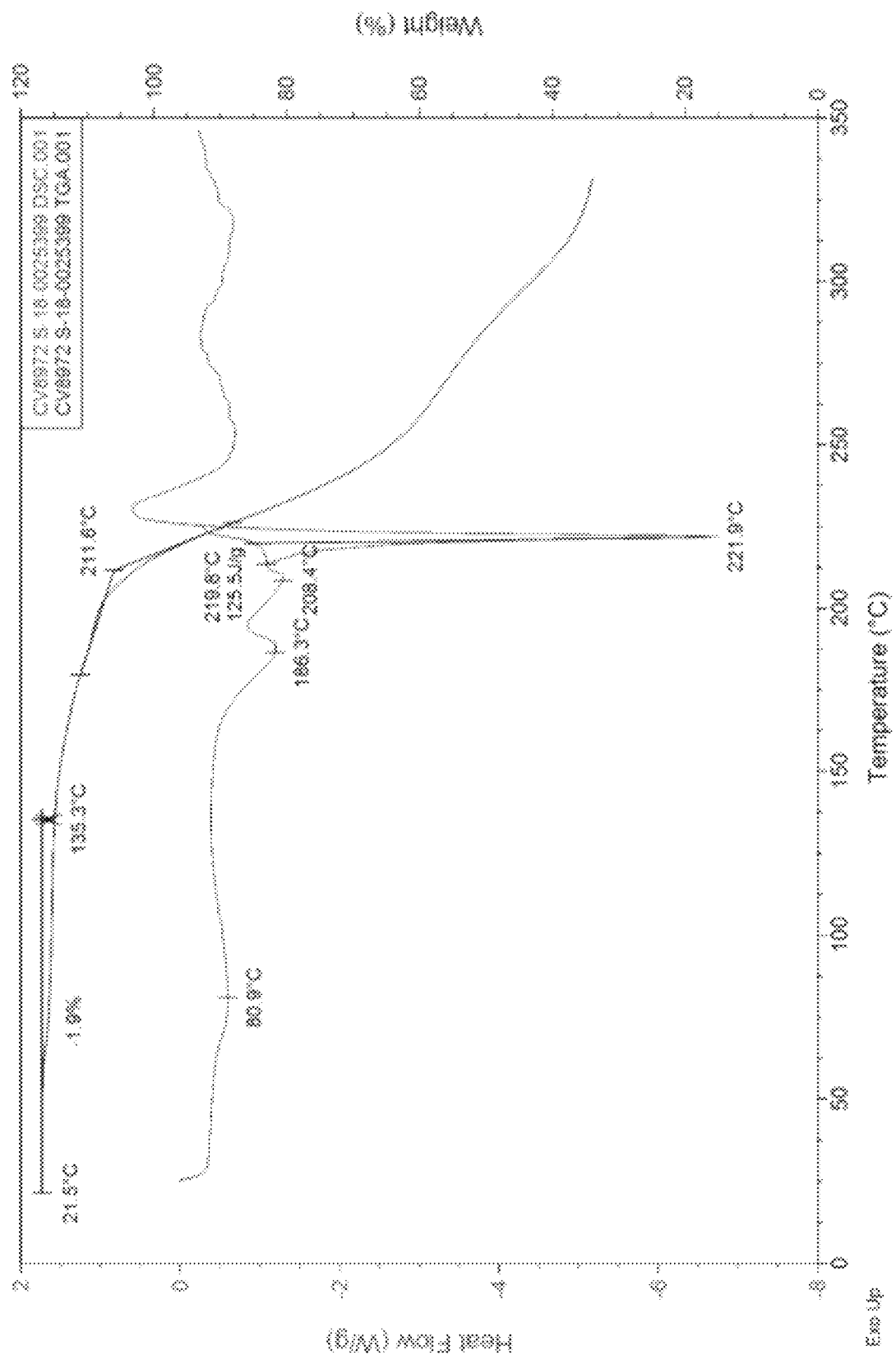
FIG. 66 is a graph showing differential scanning calorimetry and thermal gravimetric analysis of a batch of CV-8972.

FIG. 66 is a graph showing differential scanning calorimetry and thermal gravimetric analysis of batch 289-MBA-15-A of CV-8972.

Figure 67:
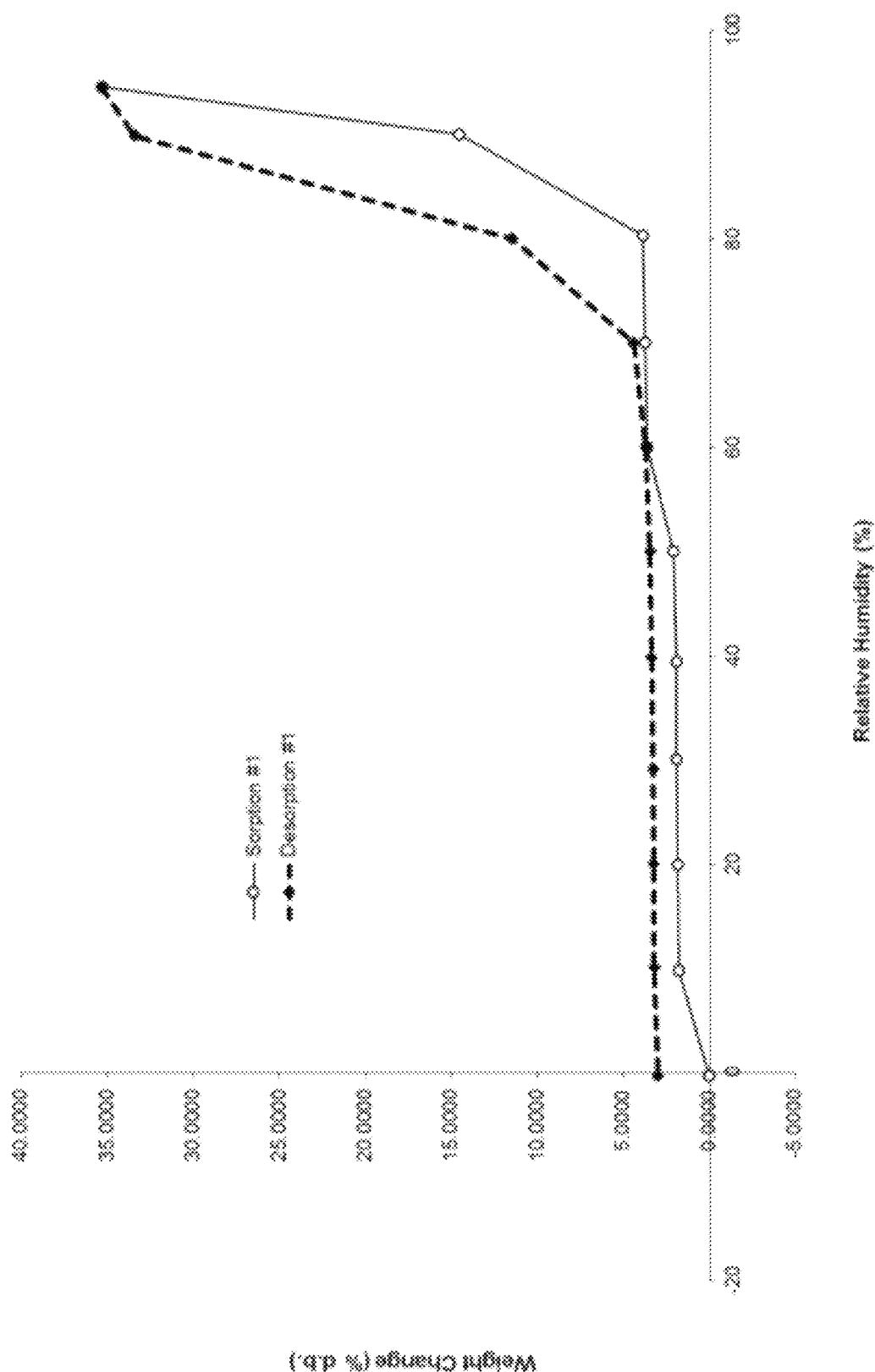
FIG. 67 is a graph showing dynamic vapor sorption (DVS) of a batch of CV-8972.

FIG. 67 is a graph showing dynamic vapor sorption (DVS) of batch 289-MBA-15-A of CV-8972.

Figure 68:
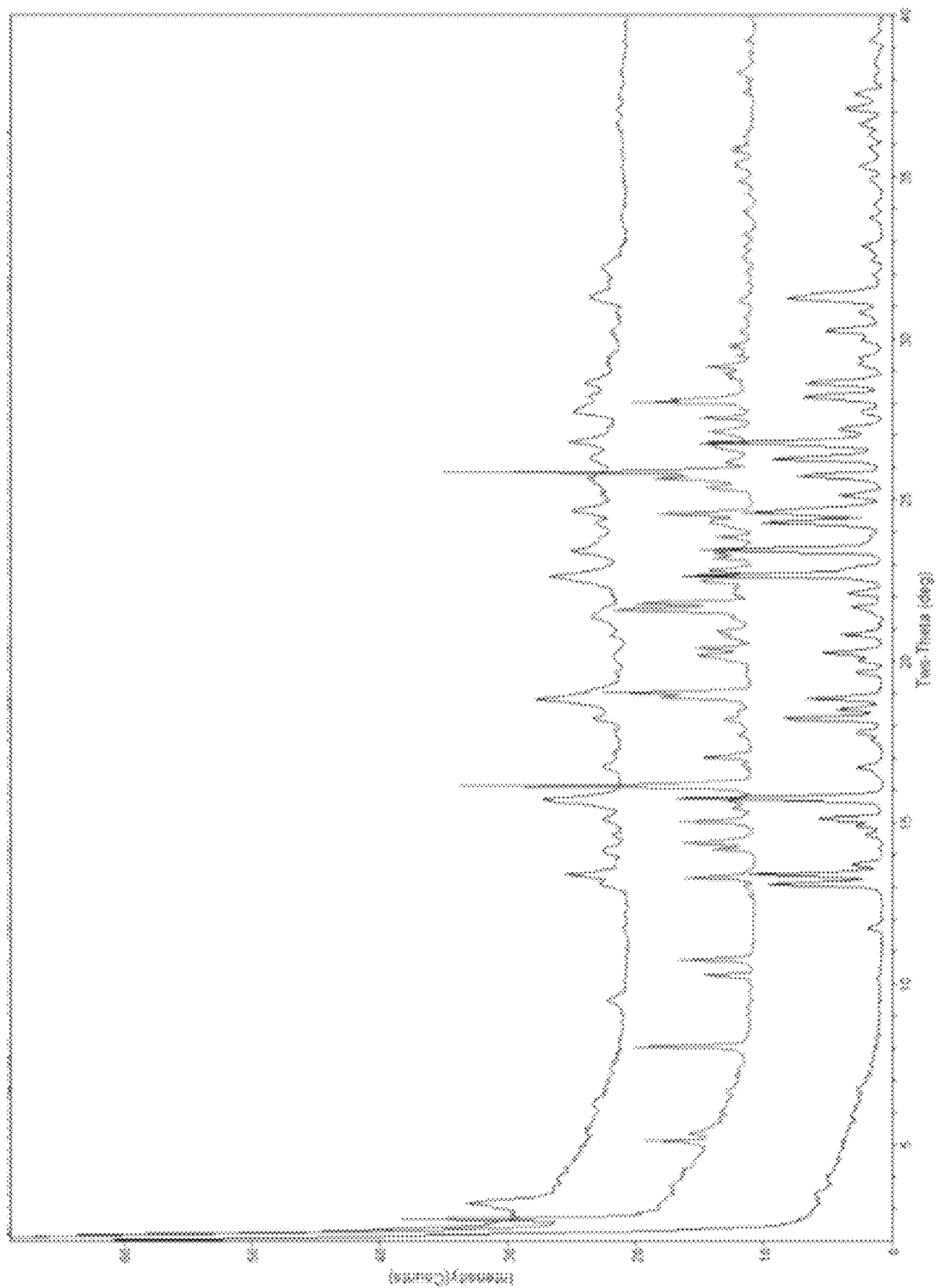
FIG. 68 is a graph showing X-ray powder diffraction analysis of samples of CV-8972.

FIG. 68 is a graph showing X-ray powder diffraction analysis of samples of CV-8972. A pre-DVS sample from batch 276-MBA-172 is shown in blue, a pre-DVS sample from batch 289-MBA-15-A is shown in red, and a post-DVS sample from batch 289-MBA-15-A is shown in black.

Figure 69:
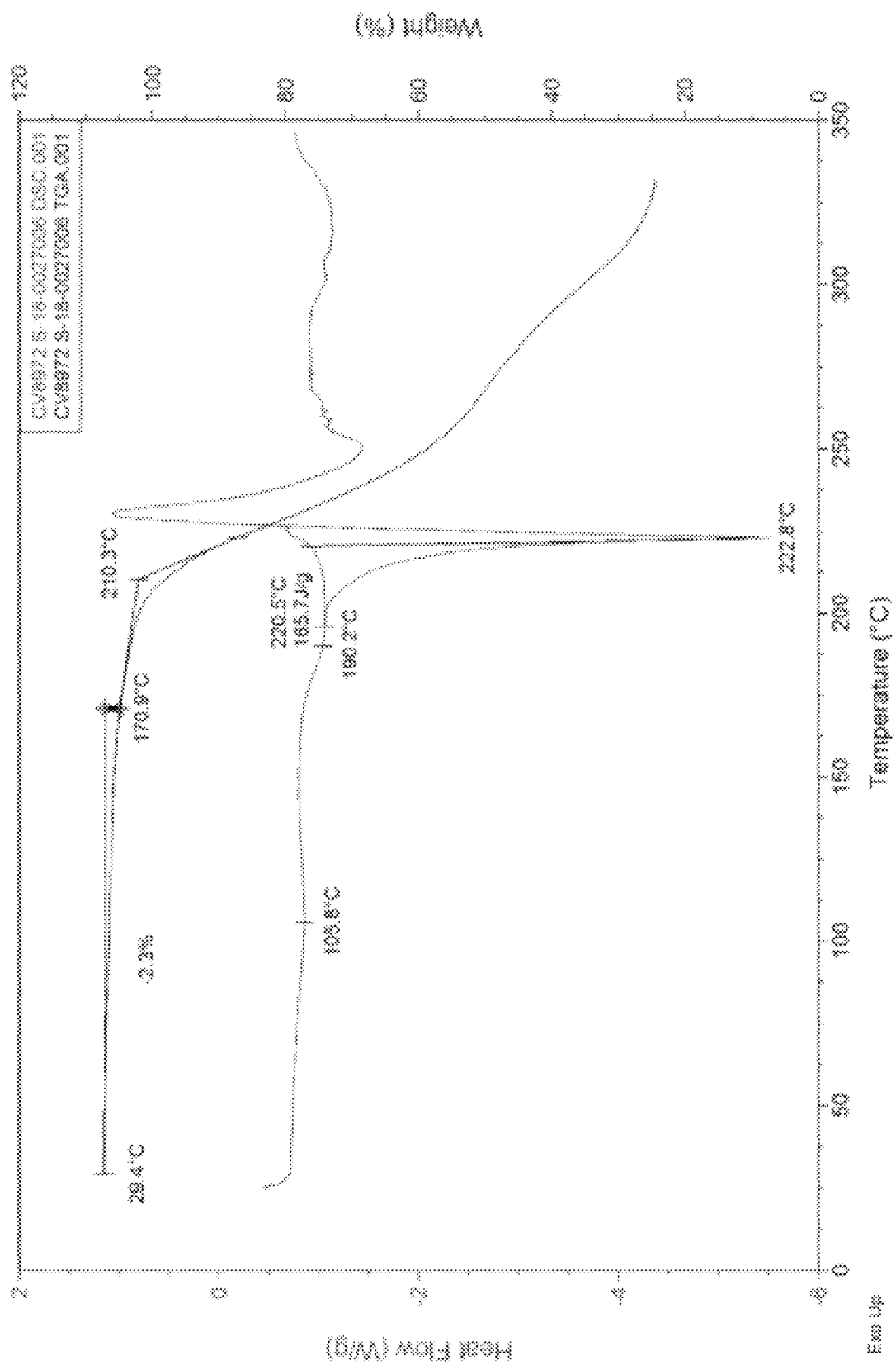
FIG. 69 is a graph showing differential scanning calorimetry and thermal gravimetric analysis of a batch of CV-8972.

FIG. 69 is a graph showing differential scanning calorimetry and thermal gravimetric analysis of batch 289-MBA-16 of CV-8972.

Figure 70:
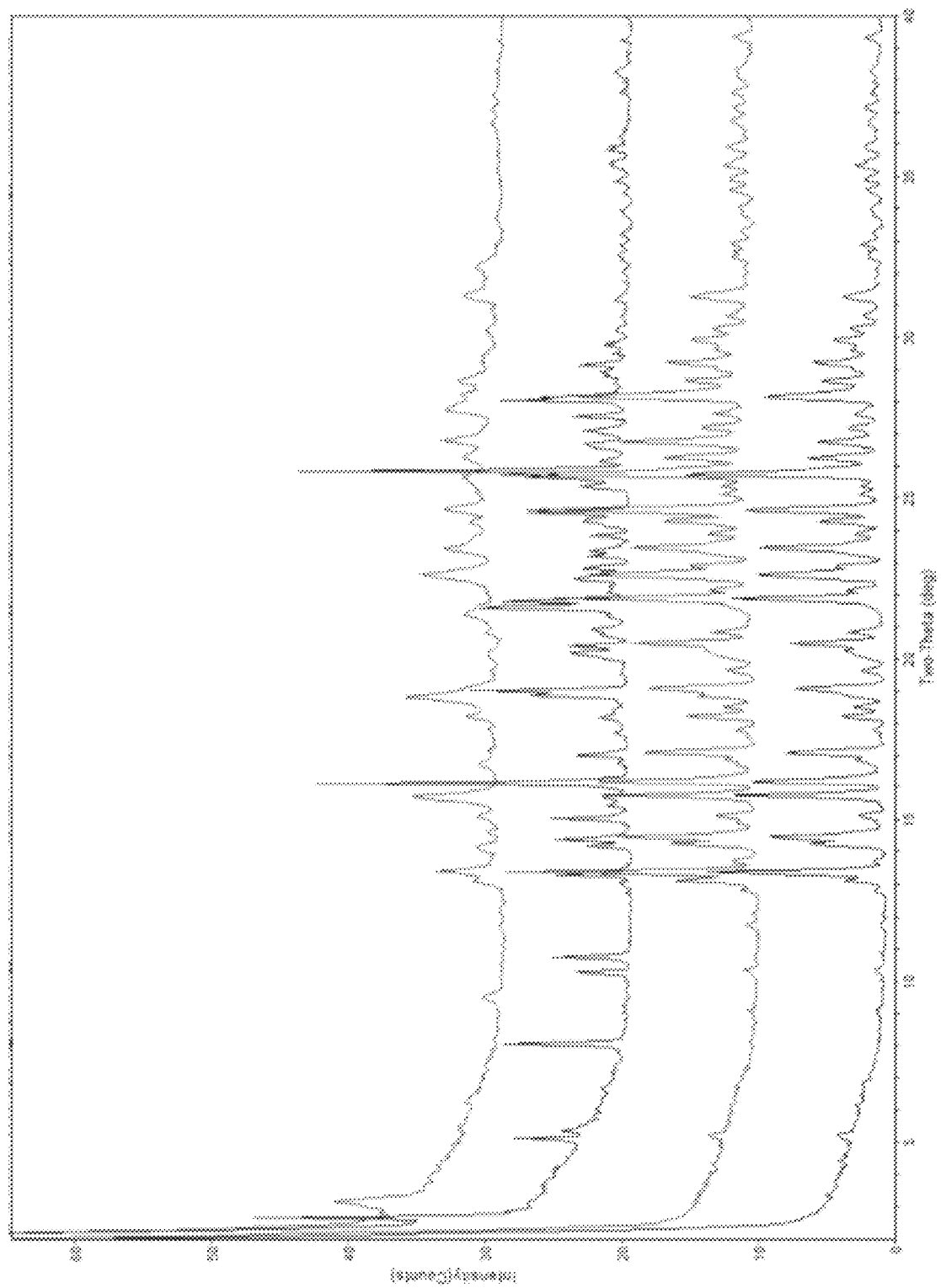
FIG. 70 is a graph showing X-ray powder diffraction analysis of samples of CV-8972.

FIG. 70 is a graph showing X-ray powder diffraction analysis of samples of CV-8972. Form B is shown in green, form A is shown in blue, a sample from an ethanol slurry of batch 289-MBA-15-A is shown in red, and a sample from an ethanol slurry of batch 289-MBA-16 is shown in black.

The stability of CV-8972 was analyzed.

Samples from batch 289-MBA-15-A (containing form B) were added to various solvents, incubated under various conditions, and analyzed by X-ray powder diffraction. Results are summarized in Table 59.

TABLE 59

| Solvent | Conditions | XRPD results |
|---|---|---|
| EtOH | Slurry, RT, 3 d | Form A + Form B |
| MeOH/H2O (95:5) $A_w$ = 0.16 | Slurry, RT, 5 d | Form A |
| IPA/H2O (98:2) $A_w$ = 0.26 | Slurry, RT, 5 d | Form A |
| MeOH/H2O (80:20) $A_w$ = 0.48 | Slurry, RT, 5 d | Form A |
| EtOH/H2O (90:10) $A_w$ = 0.52 | Slurry, RT, 5 d | Form A |
| IPA/H2O (90:10) $A_w$ = 0.67 | Slurry, RT, 5 d | Form A |

TABLE 59-continued

| Solvent | Conditions | XRPD results |
|---|---|---|
| Acetone/H2O (90:10) $A_w$ = 0.72 | Slurry, RT, 5 d | Form A |
| ACN/H2O (90:10) $A_w$ = 0.83 | Slurry, RT, 5 d | Form A |
| EtOAc/H2O (97:3) $A_w$ = 0.94 | Slurry, RT, 5 d | Form A |
| MeOH | Slurry, RT, 5 d | Form A + Form B |
| EtOAc | Slurry, RT, 5 d | Form A + Form B |
| MEK | Slurry, RT, 5 d | Form A |
| — | 100° C., 20 minutes | Form B, shifted with minor Form A |
| EtOH | CC from 60° C. | Form C + minor Form A |

Samples from batch 289-MBA-16 (containing forms A and B) were added to various solvents, incubated under various conditions, and analyzed by X-ray powder diffraction. Results are summarized in Table 60.

TABLE 60

| Solvent | Conditions | XRPD results |
|---|---|---|
| EtOH | Slurry, RT, 3 d | Form A + Form B |
| MeOH | Vapor diffusion w/MTBE | Form A |
| EtOAc | Attempted to dissolve at ~60° C., solids remained, cooled slowly to RT, let stir at RT from 60° C. | Form A + Form B |

Figure 71:
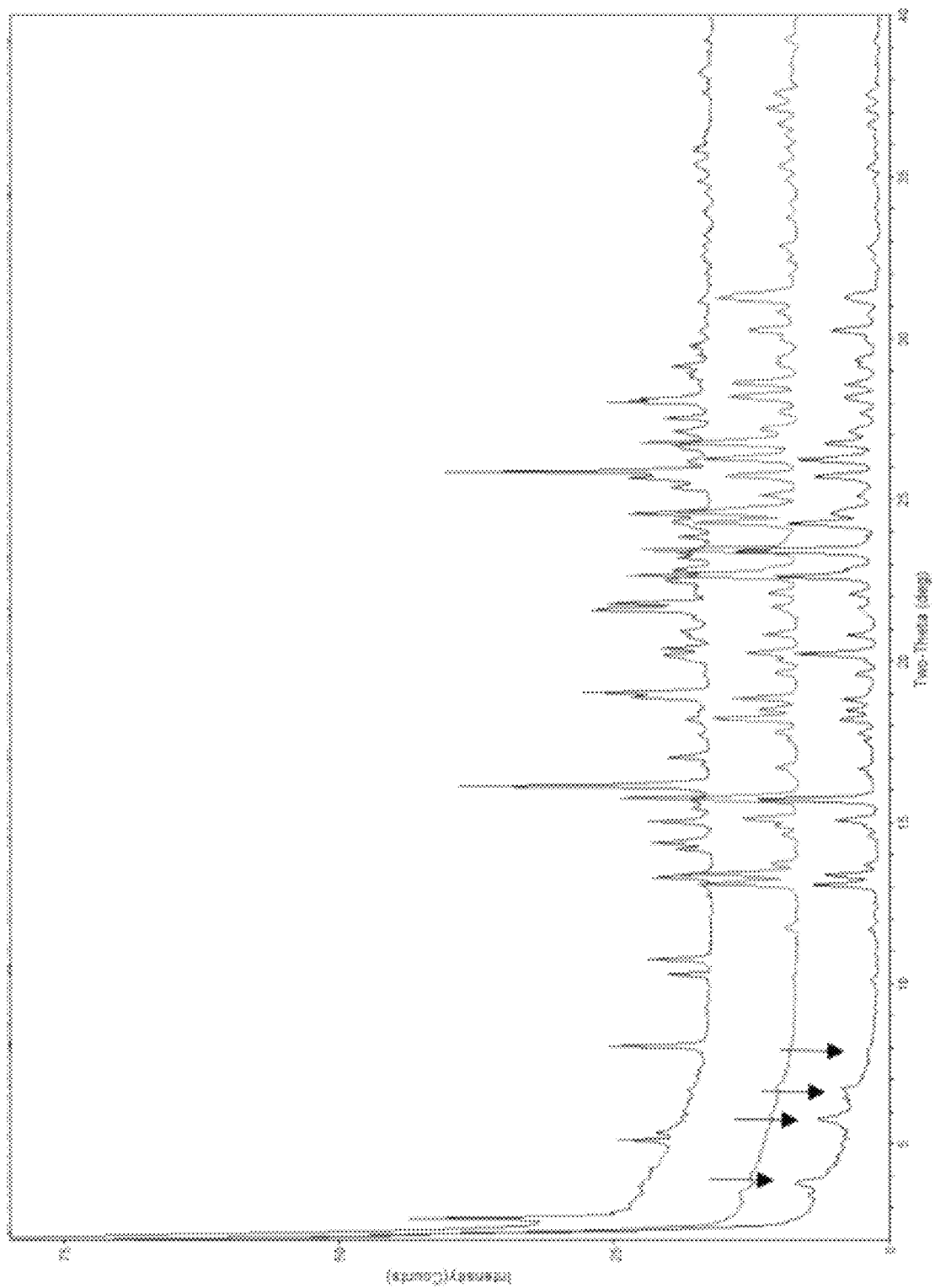
FIG. 71 is a graph showing X-ray powder diffraction analysis of samples of CV-8972.

FIG. 71 is a graph showing X-ray powder diffraction analysis of samples of CV-8972. A sample containing form B is shown in blue, a sample containing form A is shown in red, and a sample containing a mixture of forms A and C is shown in black.

The stability of CV-8972 was analyzed. Aqueous samples containing CV-8972 at different concentrations and pH were incubated for various periods and analyzed. Results are shown in Table 61.

TABLE 61

| Sample | Time (hrs) | PH | Retention Time | | | | | Decrease in purity of CV-8972 between time points |
|---|---|---|---|---|---|---|---|---|
| | | | 2.2 | 2.6 | 4.2 | 4.7 | 5.6 | |
| 276-MBA-172 | 0 | 6.6 | 3.39 | 0.6 | 0.23 | 0.54 | 95.24 | |
| 10 mg/mL | 1 | 6.8 | 4.81 | 0.81 | 0.23 | 0.73 | 93.43 | 1.81 |
| pH 6 (Form A) | 4 | 6.8 | 5.72 | 0.9 | 0.21 | 0.83 | 91.82 | 1.61 |
| | 6 | 6.7 | 6.45 | 0.81 | ND | 0.93 | 91.8 | 0.02 |
| | 22 | 6.7 | 7.38 | 1.54 | 0.13 | 1.11 | 89.66 | 2.14 |
| 276-MBA-172 | 0 | 6.1 | ND | ND | 1.29 | ND | 98.01 | |
| 2 mg/mL pH 6 | 1 | 6.1 | 1.5 | ND | 1.28 | ND | 97.22 | 0.79 |
| (Form A) | 4 | 6.1 | 2.03 | ND | 0.95 | ND | 97.01 | 0.21 |
| | 6 | 6.1 | 2.47 | ND | 1.02 | ND | 96.51 | 0.5 |
| | 22 | 6.1 | | | | | | |
| 289-MBA-15-A | 0 | 6 | 3.3 | 0.6 | 0.26 | 0.48 | 95.36 | |
| 10 mg/mL pH 6 | 1 | 6.1 | 3.76 | 0.65 | 0.25 | 0.53 | 94.81 | 0.55 |
| (Form B) | 4 | 6 | 3.97 | 0.59 | 0.19 | 0.56 | 94.69 | 0.12 |
| | 6 | 5.9 | 4.3 | 0.54 | 0.17 | 0.6 | 94.39 | 0.3 |
| | 22 | 5.9 | 4.53 | 0.69 | 0.19 | 0.65 | 93.93 | 0.46 |
| 289-MBA-15-A | 0 | 6.9 | 1.33 | ND | 1.19 | ND | 97.48 | |
| 2 mg/mL pH 6 | 1 | 6.9 | 3.73 | ND | 1.17 | ND | 95.1 | 2.38 |
| (Form B) | 4 | 6.8 | 5.25 | 0.67 | 0.84 | 0.79 | 92.45 | 2.65 |
| | 6 | 6.8 | 6.63 | 0.9 | 0.83 | 0.99 | 90.65 | 1.8 |
| | 22 | 6.7 | 7.72 | 1.13 | 0.86 | 1.14 | 89.15 | 1.5 |
| 276-MBA-172 | 0 | 7.1 | 5.9 | 0.94 | 0.22 | 0.78 | 92.85 | |
| 10 mg/mL pH 7 | 1 | 7.2 | 8.12 | 1.45 | 0.21 | 1.17 | 89.05 | 3.8 |
| (Form A) | 4 | 7.1 | 10.14 | 1.48 | 0.13 | 1.46 | 86.8 | 2.25 |
| | 6 | 7.1 | 11.63 | 1.78 | 0.13 | 1.67 | 84.79 | 2.01 |
| | 22 | 7 | | | | | | |

TABLE 61-continued

| Sample | Time (hrs) | PH | Retention Time 2.2 | 2.6 | 4.2 | 4.7 | 5.6 | Decrease in purity of CV-8972 between time points |
|---|---|---|---|---|---|---|---|---|
| 276-MBA-172 | 0 | 6.7 | 1.42 | ND | 1.05 | ND | 97.53 | |
| 2 mg/mL pH 7 | 1 | 6.8 | 3.31 | ND | 1.06 | 0.57 | 95.06 | 2.47 |
| (Form A) | 4 | 6.7 | 4.21 | 0.58 | 0.82 | 0.69 | 93.7 | 1.36 |
| | 6 | 6.7 | 5.63 | 0.67 | 0.74 | 0.85 | 92.12 | 1.58 |
| | 22 | 6.8 | 6.26 | 0.85 | 0.85 | 0.98 | 91.07 | 1.05 |
| 289-MBA-15-A | 0 | 7.4 | 6.2 | 1.16 | 0.27 | 0.87 | 91.5 | |
| 10 mg/mL pH 7 | 1 | 7.4 | 10.47 | 1.65 | 0.25 | 1.44 | 86.18 | 5.32 |
| (Form B) | 4 | 7.4 | 13.64 | 1.93 | 0.19 | 1.89 | 82.36 | 3.82 |
| | 6 | 7.3 | 15.66 | 2.57 | 0.2 | 0.2 | 79.37 | 2.99 |
| | 22 | 7.1 | | | | | | |
| 289-MBA-15-A | 0 | 6.5 | 1.62 | ND | 0.9 | ND | 97.48 | |
| 2 mg/mL pH 7 | 1 | 6.6 | 3.16 | ND | 0.89 | 0.49 | 95.46 | 2.02 |
| (Form B) | 4 | 6.5 | 4.27 | 0.53 | 0.66 | 0.62 | 93.92 | 1.54 |
| | 6 | 6.5 | | | | | | |
| | 22 | 6.5 | | | | | | |

Samples from batch S-18-0030513 (containing form A) were added to various solvents, incubated under various conditions, and analyzed by X-ray powder diffraction. Results are summarized in Table 62.

TABLE 62

| Solvent | Conditions | XRPD results |
|---|---|---|
| CHCl3 | Slurry, RT | Form A |
| EtOAc | Slurry, RT | Form A |
| THF | Slurry, RT | Form A |
| — | VO, RT | Form A |
| — | 80° C., 20 minutes | Form A with slight peak shifting |
| — | 100° C., 20 minutes | Form B + Form A, shifted |
| — | 97% RH Stress of Form A dried at 80° C. for 20 min | Form A |
| EtOH | Crash cool from 70° C. | Form A + Form C |
| MEK/H2O 99:1 | Slow cool from 70° C. | Form A |

Samples from batch 289-MBA-16 (containing forms A and B) were added to various solvents, incubated under various conditions, and analyzed by X-ray powder diffraction. Results are summarized in Table 63.

TABLE 63

| Solvent | Conditions | XRPD results |
|---|---|---|
| EtOH | Slurry, RT, 3 d | Form A + Form B |
| MeOH | VD w/MTBE | Form A |
| EtOAc | SC from 60° C. | Form A + Form B |
| THF | SC from 60° C. | Form B |
| EtOH | SC from 60° C. | Form A + Form C |
| MeOH/H2O | (95:5) Slurry, overnight, 1 g scale | Form A |

Figure 72:
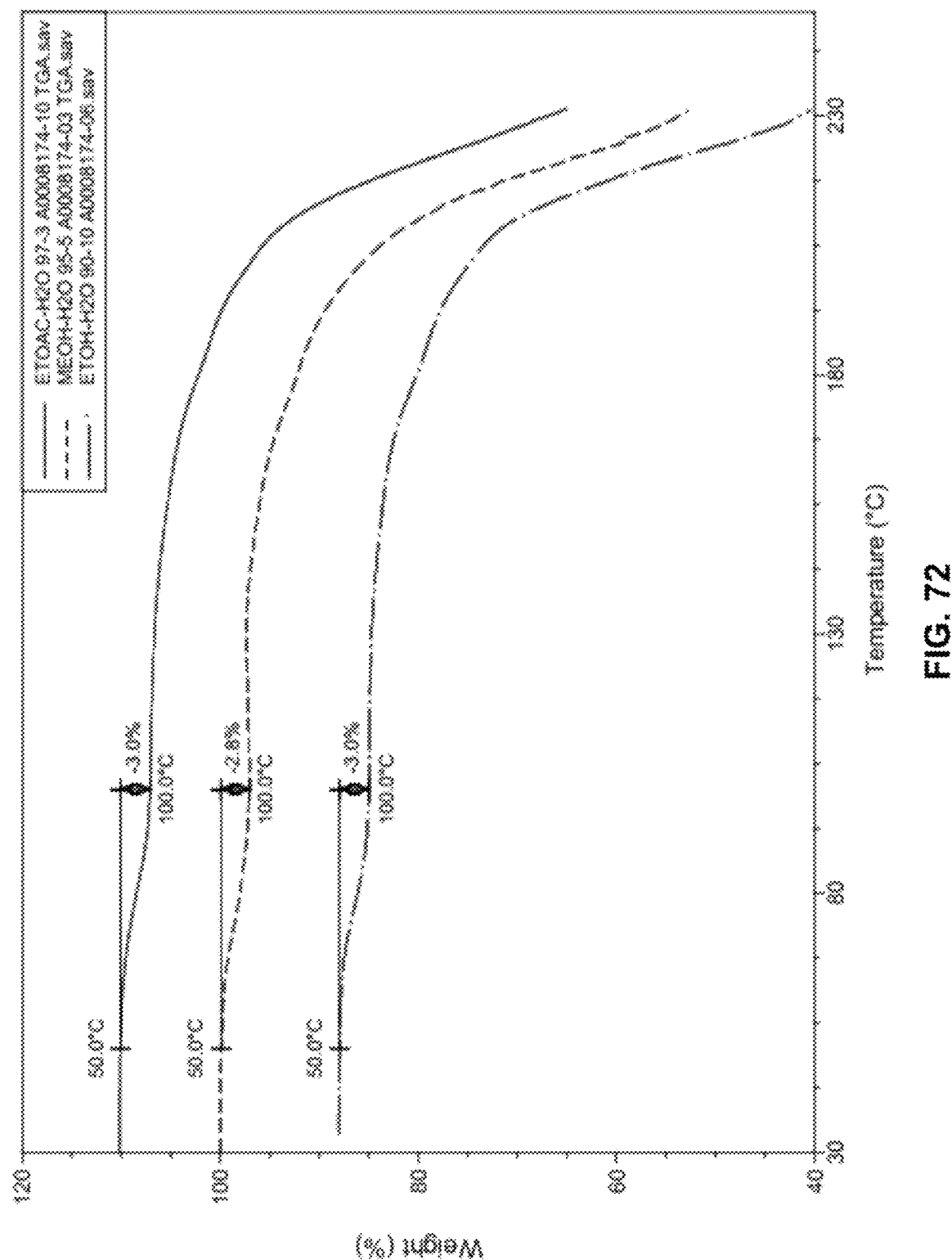
FIG. 72 is a graph showing differential scanning calorimetry and thermal gravimetric analysis of samples containing form A of CV-8972.

FIG. 72 is a graph showing differential scanning calorimetry and thermal gravimetric analysis of samples containing form A of CV-8972. A sample from an ethanol acetate-water slurry is shown with solid lines, a sample from a methanol-water slurry is shown with regularly-dashed lines, and a sample from an ethanol-water slurry is shown with dashed-dotted lines.

Figure 73:
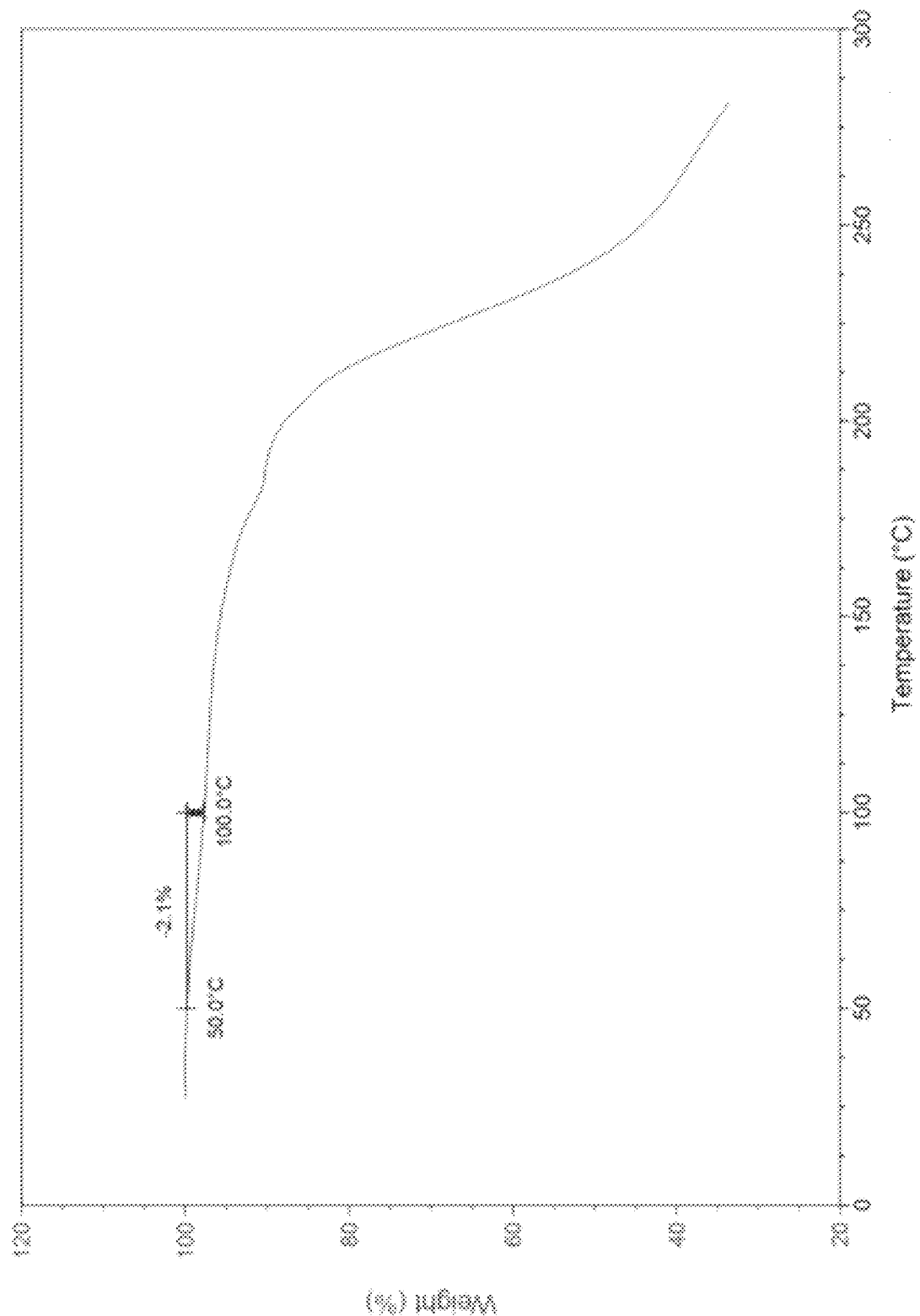
FIG. 73 is a graph showing differential scanning calorimetry and thermal gravimetric analysis of a sample containing form A of CV-8972.

FIG. 73 is a graph showing differential scanning calorimetry and thermal gravimetric analysis of a sample containing form A of CV-8972. Prior to analysis, the sample was dried at 100° C. for 20 minutes.

Samples containing form A of CV-8972 were analyzed for stability in response to humidity. Samples were incubated at 40° C., 75% relative humidity for various periods and analyzed. Results are shown in Table 64.

TABLE 64

| Time (days) | Retention Time 1.9 | 3.9 | 4.5 | 5.4 |
|---|---|---|---|---|
| 0 | ND | 1.16 | ND | 98.84 |
| 1 | ND | 0.68 | ND | 99.32 |
| 7 | 0.63 | 0.14 | 0.12 | 99.12 |

Form A of CV-8972 were analyzed for stability in aqueous solution. Aqueous samples containing CV-8972 at different concentrations and pH were incubated for various periods and analyzed. Results are shown in Table 65.

TABLE 65

| Concentration of CV-8972 | Time (hrs) | Retention Time 1.9 | 2.2 | 3.9 | 4.5 | 5.4 | % change from t0 of RT 5.4 |
|---|---|---|---|---|---|---|---|
| 21 mg/mL, | 0 | ND | ND | 1.12 | ND | 98.88 | — |
| Initial pH = 2.0 | 1 | 1.03 | ND | 0.94 | ND | 98.03 | −0.86 |
| | 2 | 1.9 | ND | 1 | ND | 97.11 | −1.79 |
| | 6 | 5.25 | 0.83 | 0.96 | 0.78 | 92.18 | −6.78 |
| 12.5 mg/mL, | 0 | ND | ND | 1.79 | ND | 98.21 | — |
| Initial pH = 2.1 | 1 | 1.38 | ND | 1.41 | ND | 97.21 | −1.02 |
| | 2 | 2.43 | ND | 1.67 | ND | 95.9 | −2.35 |
| | 6 | 6.59 | 1.04 | 1.74 | 1.04 | 89.58 | −8.79 |
| 4.2 mg/mL, | 0 | ND | ND | 5.35 | ND | 94.65 | — |
| Initial pH = 2.3 | 1 | ND | ND | 4.02 | ND | 95.98 | 1.41 |
| | 2 | 3.72 | ND | 5.09 | ND | 91.19 | −3.66 |
| | 6 | 9.71 | ND | 5.3 | ND | 84.99 | −10.21 |

The amount of CV-8972 present in various dosing compositions was analyzed. Results are shown in Table 66.

TABLE 66

| Target Dose (mg/mL) | Vol. API soln. (mL) | Mass CV8972 (mg) | Initial pH API soln. | Vol. 1N NaOH (mL) | Total vol. base soln. (mL) | pH after base soln. addn. | Vol. addl. 1N NaOH added (mL) | Final Dose (mg/mL) |
|---|---|---|---|---|---|---|---|---|
| 10 | 30 | 779.06 | 2.0 | 2.07 | 30 | 3.6 | 0.7 | 9.92 |
| 2 | 30 | 157.38 | 2.4 | 0.19 | 30 | 2.8 | 0.35 | 2.02 |
| 10 | 50 | 777.05 | 2.1 | 2.77 | 10 | 6.2 | — | 10.01 |
| 2 | 50 | 142.08 | 2.5 | 0.99 | 10 | 3.0 | 0.3 | 1.82 |

Brain-to-Plasma Ratio of Compounds In Vivo

The brain-to-plasma ratio of trimetazidine and CV-8814 was analyzed after intravenous administration of the compounds to rats. Dosing solutions were analyzed by liquid chromatography tandem mass spectrometry (LC-MS/MS). Results are shown in Table 67.

TABLE 67

| Test Article | Route of Administration | Vehicle | Nominal Dosing Conc. (mg/mL) | Measured Dosing Solution Conc. (mg/mL) | % of Nominal |
|---|---|---|---|---|---|
| TMZ | IV | Normal Saline* | 1.0 | 1.14 | 114 |
| CV-8814 | IV | Normal Saline* | 0.585 | 0.668 | 114 |

The concentrations of compounds in the brain and plasma were analyzed 2 hours after administering compounds at 1 mg/kg to rats. Results from trimetazidine-treated rats are shown in Table 68. Results from CV-8814-treated rats are shown in Table 69.

TABLE 68

| TMZ-treated rats | | | |
|---|---|---|---|
| | Rat# | | |
| | 11 | 12 | 13 |
| Brain Weight (g) | 1.781 | 1.775 | 1.883 |
| Brain Homogenate Volume (mL) | 8.91 | 8.88 | 9.42 |
| Brain Homogenate Conc. (ng/mL) | 7.08 | 7.35 | 7.90 |
| Brain Tissue Conc. (ng/g) | 35.4 | 36.8 | 39.5 |
| Plasma Conc. (ng/g)[1] | 22.7 | 14.0 | 14.1 |
| B:P Ratio | 1.56 | 2.63 | 2.80 |

TABLE 69

| CV-8814-treated rats | | | |
|---|---|---|---|
| | Rat# | | |
| | 14 | 15 | 16 |
| Brain Weight (g) | 1.857 | 1.902 | 2.026 |
| Brain Homogenate Volume (mL) | 9.29 | 9.51 | 10.1 |
| Brain Homogenate Conc. (ng/mL) | 4.01 | 4.21 | 4.74 |
| Brain Tissue Conc. (ng/g) | 20.1 | 21.1 | 24 |
| Plasma Conc. (ng/g)[1] | 19.3 | 17.0 | 14.0 |
| B:P Ratio | 1.04 | 1.24 | 1.693 |

The average B:P ratio for trimetazidine-treated rats was 2.33±0.672. The average B:P ratio for trimetazidine-treated rats was 1.32±0.335.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A pharmaceutical composition comprising a controlled-release formulation of a compound represented by formula (X):

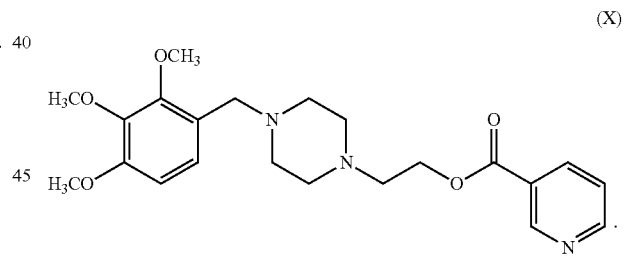

2. The pharmaceutical composition of claim 1, wherein the controlled-release formulation comprises the compound in a therapeutically effective amount to increase cardiac efficiency in a subject.

3. The pharmaceutical composition of claim 2, wherein the controlled-release formulation is formulated for oral administration.

4. The pharmaceutical composition of claim 3, wherein the controlled-release formulation comprises a format selected from the group consisting of a tablet, troche, lozenge, aqueous suspension, oily suspension, emulsion, hard capsule, soft capsule, and syrup.

* * * * *